US010729784B2

(12) United States Patent
Sahin et al.

(10) Patent No.: US 10,729,784 B2
(45) Date of Patent: Aug. 4, 2020

(54) METHOD FOR CELLULAR RNA EXPRESSION

(71) Applicants: TRON TRANSLATIONALE ONKOLOGIE AN DER UNIVERSITATSMEDIZIN DER JOHANNES GUTENBERG-UNIVERSITAT MAINZ gGMBH, Mainz (DE); BIONTECH RNA PHARMACEUTICALS GMBH, Mainz (DE)

(72) Inventors: Ugur Sahin, Mainz (DE); Tim Beissert, Gross-Gerau (DE); Marco Poleganov, Frankfurt (DE); Stephanie Herz, Kasel (DE); Lars Koste, Mainz (DE)

(73) Assignees: TRON TRANSLATIONALE ONKOLOGIE AN DER UNIVERSITATSM, Mainz (DE); BIONTECH RNA PHARMACEUTICALS GMBH, Mainz (DE)

( * ) Notice: Subject to any disclaimer, the term of this patent is extended or adjusted under 35 U.S.C. 154(b) by 0 days.

(21) Appl. No.: 16/245,353

(22) Filed: Jan. 11, 2019

(65) Prior Publication Data

US 2019/0269793 A1 Sep. 5, 2019

Related U.S. Application Data

(60) Division of application No. 14/706,228, filed on May 7, 2015, now Pat. No. 10,207,009, which is a (Continued)

(51) Int. Cl.
*C12N 15/00* (2006.01)
*A61K 48/00* (2006.01)
(Continued)

(52) U.S. Cl.
CPC ............ *A61K 48/00* (2013.01); *A61K 31/429* (2013.01); *A61K 31/52* (2013.01); *A61K 38/162* (2013.01);
(Continued)

(58) Field of Classification Search
None
See application file for complete search history.

(56) References Cited

U.S. PATENT DOCUMENTS

| | | | |
|---|---|---|---|
| 2012/0046346 | A1 | 2/2012 | Rossi et al. |
| 2014/0227300 | A1 | 8/2014 | Chin et al. |
| 2014/0328825 | A1 | 11/2014 | Meis et al. |

FOREIGN PATENT DOCUMENTS

| | | | |
|---|---|---|---|
| WO | WO2011/015347 | A1 | 2/2011 |
| WO | WO2012/072096 | A1 | 6/2012 |

OTHER PUBLICATIONS

Liu et al., "Yamanaka factors critically regulate the developmental signaling network in mouse embryonic stem cells," Cell Research 18: 1177-1189 (Year: 2008).*

(Continued)

*Primary Examiner* — M Franco G Salvoza
(74) *Attorney, Agent, or Firm* — Joseph C. Zucchero; Carolyn S. Elmore; Elmore Patent Law Group, P.C.

(57) ABSTRACT

The present invention relates to expressing RNA in cells and, in particular, enhancing viability of cells in which RNA is to be expressed. Specifically, the present invention provides methods for expressing RNA in cells comprising the steps of preventing engagement of IFN receptor by extracellular IFN and inhibiting intracellular IFN signalling in the (Continued)

cells. Thus, preventing engagement of IFN receptor by extracellular IFN and inhibiting intracellular IFN signalling in the cells allows repetitive transfer of RNA into the cells.

19 Claims, 36 Drawing Sheets

Specification includes a Sequence Listing.

Related U.S. Application Data continuation of application No. PCT/EP2013/003362, filed on Nov. 7, 2013, which is a continuation of application No. PCT/EP2013/002234, filed on Jul. 29, 2013, and a continuation of application No. PCT/EP2012/004673, filed on Nov. 9, 2012.

(51) Int. Cl.

| | |
|---|---|
| ***A61K 31/52*** | (2006.01) |
| ***A61K 31/429*** | (2006.01) |
| ***A61K 38/16*** | (2006.01) |
| ***C12N 13/00*** | (2006.01) |
| ***C12N 5/074*** | (2010.01) |
| *C12P 21/04* | (2006.01) |

(52) U.S. Cl.

CPC .......... *C12N 5/0696* (2013.01); *C12N 13/00* (2013.01); *C12N 2501/24* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2501/65* (2013.01); *C12N 2501/727* (2013.01); *C12N 2506/1307* (2013.01); *C12N 2510/00* (2013.01)

(56) References Cited

OTHER PUBLICATIONS

Leonardo et al., "The functions of microRNAs in pluripotency and reprogramming," Nat Cell Biol 14(11): 1114-1121 (Year: 2012).*
Angel, et al., "Innate Immune Suppression Enables Frequent Transfection with RNA Encoding Reprogramming Proteins", PLoS One 5(7): e11756, 2010.
Carroll, et al., "Recombinant vaccinia virus K3L gene product prevents activation of double-stranded RNA-dependent, initiation factor 2 alpha-specific protein kinase", J. Biol. Chem. 268(17), 1993, 12837-42.
Chen, et al., "Rhinovirus induces airway epithelial gene expression through double-stranded RNA and IFN-dependent pathways", American Journal of Respiratory Cell and Molecular Biology, 34(2), 2006, 192-203.
Dave, R. et al., "siRNA Targeting Vaccinia Virus Double-Stranded RNA Binding Protein [E3L] Exerts Potent Antiviral Effects", Virology, 348, 2006, 489-497.
Drews, et al., "The cytotoxic and immunogenic hurdles associated with non-viral mRNA-mediated reprogramming of human fibroblasts", Biomaterials, 33, 2012, 4059-4068.
Garcia-Sastre, et al., "Type 1 interferons and the virus-host relationship:a lesson in detente", Science, 312(5775), 2006, 879-882.
Kuhn, et al., "mRNA as a Versatile Tool for Exogenous Protein Expression", Current Gene Therapy, 12, 2012, 347-361.
Kuhn, A. et al., "Phosphorothioate cap analogs increase stability and translational efficiency of RNA vaccines in immature dendritic cells and induce superior immune responses in vivo", Gene Therapy, 17, 2010, 961-971.
Nishikawa, et al., "The promise of human induced pluripotent stem cells for research and therapy", Nature Reviews, 9, 2008, 725-729.
Plews, et al., "Activation of Pluripotency Genes in Human Fibroblast Cells by a Novel mRNA Based Approach", PLoS One, 5(12):e14397, 2010.
Robinton, et al., "The promise of induced pluripotent stem cells in research and therapy", Nature, 481(7381), 2012, 295-305.
Tavernier, et al., "Activation of pluripotency-associated genes in mouse embryonic fibroblasts by non-viral transfection with in vitro-derived MRNAs encoding Oct4, Sox2, Klf4 and cMyc", Biomaterials, 33, 2012, 412-417.
Warren, et al., "Highly efficient reprogramming to pluripotency and directed differentiation of human cells with synthetic modified mRNA", Cell Stem Cell, 7(5), 2010, 618-630.
White, et al., "The amino terminus of the vaccinia virus E3 protein is neccessary to inhibit the interferon response", J. of Virol., vol. 86, No. 10, 2012, 5895-5904.
Yakubov, et al., "Reprogamming of human fibroblasts to pluripotent stem cells using mRNA of four transcription factors", Biochemical and Biophysical Research Communications, 394, 2010, 189-193.
Zhang, et al., "Protein Kinase PKR Plays a Stimulus- and Virus-Dependent Role in Apoptotic Death and Virus Multiplication in Human Cells", Journal of Virology, vol. 81, No. 15, 2007, 8192-8200.

* cited by examiner

A

SEQUENCE LISTING

<160> NUMBER OF SEQ ID NOS: 30

<210> SEQ ID NO 1
<211> LENGTH: 1411
<212> TYPE: DNA
<213> ORGANISM: Homo sapiens -continued

<400> SEQUENCE: 1

```
ccttcgcaag ccctcatttc accaggcccc cggcttgggg cgccttcctt ccccatggcg     60
ggacacctgg cttcggattt cgccttctcg ccccctccag gtggtggagg tgatgggcca    120
ggggggccgg agccgggctg ggttgatcct cggacctggc taagcttcca aggccctcct    180
ggagggccag gaatcgggcc gggggttggg ccaggctctg aggtgtgggg gattccccca    240
tgccccccgc cgtatgagtt ctgtgggggg atggcgtact gtgggcccca ggttggagtg    300
gggctagtgc cccaaggcgg cttggagacc tctcagcctg agggcgaagc aggagtcggg    360
gtggagagca actccgatgg ggcctccccg gagccctgca ccgtcacccc tggtgccgtg    420
aagctggaga aggagaagct ggagcaaaac ccggaggagt cccaggacat caaagctctg    480
cagaaagaac tcgagcaatt tgccaagctc ctgaagcaga agaggatcac cctgggatat    540
acacaggccg atgtggggct caccctgggg gttctatttg ggaaggtatt cagccaaacg    600
accatctgcc gctttgaggc tctgcagctt agcttcaaga acatgtgtaa gctgcggccc    660
ttgctgcaga agtgggtgga ggaagctgac aacaatgaaa atcttcagga gatatgcaaa    720
gcagaaaccc tcgtgcaggc ccgaaagaga aagcgaacca gtatcgagaa ccgagtgaga    780
ggcaacctgg agaatttgtt cctgcagtgc ccgaaaccca cactgcagca gatcagccac    840
atcgcccagc agcttgggct cgagaaggat gtggtccgag tgtggttctg taaccggcgc    900
cagaagggca agcgatcaag cagcgactat gcacaacgag aggattttga ggctgctggg    960
tctcctttct caggggggacc agtgtccttt cctctggccc cagggcccca ttttggtacc   1020
ccaggctatg ggagccctca cttcactgca ctgtactcct cggtcccttt ccctgagggg   1080
gaagcctttc cccctgtctc cgtcaccact ctgggctctc ccatgcattc aaactgaggt   1140
gcctgccctt ctaggaatgg gggacagggg gaggggagga gctagggaaa gaaaacctgg   1200
agtttgtgcc agggtttttg ggattaagtt cttcattcac taaggaagga attgggaaca   1260
caaagggtgg gggcagggga gtttggggca actggttgga gggaaggtga agttcaatga   1320
tgctcttgat tttaatccca catcatgtat cacttttttc ttaaataaag aagcctggga   1380
cacagtagat agacacactt aaaaaaaaaa a                                   1411
```

<210> SEQ ID NO 2
<211> LENGTH: 360
<212> TYPE: PRT
<213> ORGANISM: Homo sapiens

<400> SEQUENCE: 2

```
Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110
```

-continued

```
Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
    210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
        275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
        355                 360


<210> SEQ ID NO 3
<211> LENGTH: 1085
<212> TYPE: DNA
<213> ORGANISM: Homo sapiens

<400> SEQUENCE: 3

cacagcgccc gcatgtacaa catgatggag acggagctga agccgccggg cccgcagcaa      60

acttcggggg gcggcggcgg caactccacc gcggcggcgg ccggcggcaa ccagaaaaac     120

agcccggacc gcgtcaagcg gcccatgaat gccttcatgg tgtggtcccg cgggcagcgg     180

cgcaagatgg cccaggagaa ccccaagatg cacaactcgg agatcagcaa gcgcctgggc     240

gccgagtgga aacttttgtc ggagacggag aagcggccgt tcatcgacga ggctaagcgg     300

ctgcgagcgc tgcacatgaa ggagcacccg gattataaat accggccccg gcggaaaacc     360

aagacgctca tgaagaagga taagtacacg ctgcccggcg ggctgctggc ccccggcggc     420

aatagcatgg cgagcggggt cggggtgggc gccggcctgg gcgcgggcgt gaaccagcgc     480

atggacagtt acgcgcacat gaacggctgg agcaacggca gctacagcat gatgcaggac     540

cagctgggct acccgcagca cccgggcctc aatgcgcacg gcgcagcgca gatgcagccc     600

atgcaccgct acgacgtgag cgccctgcag tacaactcca tgaccagctc gcagacctac     660

atgaacggct cgcccaccta cagcatgtcc tactcgcagc agggcacccc tggcatggct     720
```

```
cttggctcca tgggttcggt ggtcaagtcc gaggccagct ccagcccccc tgtggttacc    780

tcttcctccc actccagggc gccctgccag gccggggacc tccgggacat gatcagcatg    840

tatctccccg gcgccgaggt gccggaaccc gccgccccca gcagacttca catgtcccag    900

cactaccaga gcggcccggt gcccggcacg gccattaacg gcacactgcc cctctcacac    960

atgtgagggc cggacagcga actggagggg ggagaaattt tcaaagaaaa acgagggaaa   1020

tgggaggggt gcaaaagagg agagtaagaa acagcatgga gaaaacccgg tacgctcaaa   1080

aaaaa                                                               1085


<210> SEQ ID NO 4
<211> LENGTH: 317
<212> TYPE: PRT
<213> ORGANISM: Homo sapiens

<400> SEQUENCE: 4

Met Tyr Asn Met Met Glu Thr Glu Leu Lys Pro Pro Gly Pro Gln Gln
1               5                   10                  15

Thr Ser Gly Gly Gly Gly Gly Asn Ser Thr Ala Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
        275                 280                 285

Pro Ser Arg Leu His Met Ser Gln His Tyr Gln Ser Gly Pro Val Pro
    290                 295                 300
```

-continued

Gly Thr Ala Ile Asn Gly Thr Leu Pro Leu Ser His Met
305 310 315

<210> SEQ ID NO 5
<211> LENGTH: 2098
<212> TYPE: DNA
<213> ORGANISM: Homo sapiens

<400> SEQUENCE: 5
attataaatc tagagactcc aggattttaa cgttctgctg gactgagctg gttgcctcat 60
gttattatgc aggcaactca ctttatccca atttcttgat acttttcctt ctggaggtcc 120
tatttctcta acatcttcca gaaaagtctt aaagctgcct taaccttttt tccagtccac 180
ctcttaaatt ttttcctcct cttcctctat actaacatga gtgtggatcc agcttgtccc 240
caaagcttgc cttgctttga agcatccgac tgtaaagaat cttcacctat gcctgtgatt 300
tgtgggcctg aagaaaacta tccatccttg caaatgtctt ctgctgagat gcctcacacg 360
gagactgtct ctcctcttcc ttcctccatg gatctgctta ttcaggacag ccctgattct 420
tccaccagtc ccaaaggcaa acaacccact tctgcagaga agagtgtcgc aaaaaaggaa 480
gacaaggtcc cggtcaagaa acagaagacc agaactgtgt tctcttccac ccagctgtgt 540
gtactcaatg atagatttca gagacagaaa tacctcagcc tccagcagat gcaagaactc 600
tccaacatcc tgaacctcag ctacaaacag gtgaagacct ggttccagaa ccagagaatg 660
aaatctaaga ggtggcagaa aaacaactgg ccgaagaata gcaatggtgt gacgcagaag 720
gcctcagcac ctacctaccc cagcctttac tcttcctacc accagggatg cctggtgaac 780
ccgactggga accttccaat gtggagcaac cagacctgga acaattcaac ctggagcaac 840
cagacccaga acatccagtc ctggagcaac cactcctgga acactcagac ctggtgcacc 900
caatcctgga acaatcaggc ctggaacagt cccttctata actgtggaga ggaatctctg 960
cagtcctgca tgcagttcca gccaaattct cctgccagtg acttggaggc tgccttggaa 1020
gctgctgggg aaggccttaa tgtaatacag cagaccacta ggtattttag tactccacaa 1080
accatggatt tattcctaaa ctactccatg aacatgcaac ctgaagacgt gtgaagatga 1140
gtgaaactga tattactcaa tttcagtctg gacactggct gaatccttcc tctcccctcc 1200
tcccatccct cataggattt ttcttgtttg gaaaccacgt gttctggttt ccatgatgcc 1260
catccagtca atctcatgga gggtggagta tggttggagc ctaatcagcg aggtttcttt 1320
tttttttttt ttcctattgg atcttcctgg agaaaatact tttttttttt tttttttga 1380 aacggagtct tgctctgtcg cccaggctgg agtgcagtgg cgcggtcttg gctcactgca 1440
agctccgtct cccgggttca cgccattctc ctgcctcagc ctcccgagca gctgggacta 1500
caggcgcccg ccacctcgcc cggctaatat tttgtatttt tagtagagac ggggtttcac 1560
tgtgttagcc aggatggtct cgatctcctg accttgtgat ccacccgcct cggcctccct 1620
aacagctggg atttacaggc gtgagccacc gcgccctgcc tagaaaagac attttaataa 1680
ccttggctgc cgtctctggc tatagataag tagatctaat actagtttgg atatctttag 1740
ggtttagaat ctaacctcaa gaataagaaa tacaagtaca aattggtgat gaagatgtat 1800
tcgtattgtt tgggattggg aggctttgct tattttttaa aaactattga ggtaaagggt 1860
taagctgtaa catacttaat tgatttctta ccgtttttgg ctctgttttg ctatatcccc 1920
taatttgttg gttgtgctaa tctttgtaga aagaggtctc gtatttgctg catcgtaatg 1980
acatgagtac tgctttagtt ggtttaagtt caaatgaatg aaacaactat ttttccttta 2040

```
gttgatttta ccctgatttc accgagtgtt tcaatgagta aatatacagc ttaaacat     2098


<210> SEQ ID NO 6
<211> LENGTH: 305
<212> TYPE: PRT
<213> ORGANISM: Homo sapiens

<400> SEQUENCE: 6

Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Lys Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110

Arg Phe Gln Arg Gln Lys Tyr Leu Ser Leu Gln Gln Met Gln Glu Leu
        115                 120                 125

Ser Asn Ile Leu Asn Leu Ser Tyr Lys Gln Val Lys Thr Trp Phe Gln
    130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
        195                 200                 205

Gln Thr Gln Asn Ile Gln Ser Trp Ser Asn His Ser Trp Asn Thr Gln
    210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                245                 250                 255

Asn Ser Pro Ala Ser Asp Leu Glu Ala Ala Leu Glu Ala Ala Gly Glu
            260                 265                 270

Gly Leu Asn Val Ile Gln Gln Thr Thr Arg Tyr Phe Ser Thr Pro Gln
        275                 280                 285

Thr Met Asp Leu Phe Leu Asn Tyr Ser Met Asn Met Gln Pro Glu Asp
    290                 295                 300

Val
305


<210> SEQ ID NO 7
<211> LENGTH: 780
<212> TYPE: DNA
<213> ORGANISM: Homo sapiens

<400> SEQUENCE: 7
```

```
gtgcggggga agatgtagca gcttcttctc cgaaccaacc ctttgccttc ggacttctcc      60

ggggccagca gccgcccgac caggggcccg gggccacggg ctcagccgac gaccatgggc     120

tccgtgtcca accagcagtt tgcaggtggc tgcgccaagg cggcagaaga ggcgcccgag     180

gaggcgccgg aggacgcggc ccgggcggcg gacgagcctc agctgctgca cggtgcgggc     240

atctgtaagt ggttcaacgt gcgcatgggg ttcggcttcc tgtccatgac cgcccgcgcc     300

ggggtcgcgc tcgacccccc agtggatgtc tttgtgcacc agagtaagct gcacatggaa     360

gggttccgga gcttgaagga gggtgaggca gtggagttca cctttaagaa gtcagccaag     420

ggtctggaat ccatccgtgt caccggacct ggtggagtat tctgtattgg gagtgagagg     480

cggccaaaag gaaagagcat gcagaagcgc agatcaaaag gagacaggtg ctacaactgt     540

ggaggtctag atcatcatgc caaggaatgc aagctgccac cccagcccaa gaagtgccac     600

ttctgccaga gcatcagcca tatggtagcc tcatgtccgc tgaaggccca gcagggccct     660

agtgcacagg gaaagccaac ctactttcga gaggaagaag aagaaatcca cagccctacc     720

ctgctcccgg aggcacagaa ttgagccaca atgggtgggg gctattcttt tgctatcagg     780
```

<210> SEQ ID NO 8
<211> LENGTH: 209
<212> TYPE: PRT
<213> ORGANISM: Homo sapiens

<400> SEQUENCE: 8

```
Met Gly Ser Val Ser Asn Gln Gln Phe Ala Gly Gly Cys Ala Lys Ala
1               5                   10                  15

Ala Glu Glu Ala Pro Glu Glu Ala Pro Glu Asp Ala Ala Arg Ala Ala
            20                  25                  30

Asp Glu Pro Gln Leu Leu His Gly Ala Gly Ile Cys Lys Trp Phe Asn
        35                  40                  45

Val Arg Met Gly Phe Gly Phe Leu Ser Met Thr Ala Arg Ala Gly Val
    50                  55                  60

Ala Leu Asp Pro Pro Val Asp Val Phe Val His Gln Ser Lys Leu His
65                  70                  75                  80

Met Glu Gly Phe Arg Ser Leu Lys Glu Gly Glu Ala Val Glu Phe Thr
                85                  90                  95

Phe Lys Lys Ser Ala Lys Gly Leu Glu Ser Ile Arg Val Thr Gly Pro
            100                 105                 110

Gly Gly Val Phe Cys Ile Gly Ser Glu Arg Arg Pro Lys Gly Lys Ser
        115                 120                 125

Met Gln Lys Arg Arg Ser Lys Gly Asp Arg Cys Tyr Asn Cys Gly Gly
    130                 135                 140

Leu Asp His His Ala Lys Glu Cys Lys Leu Pro Pro Gln Pro Lys Lys
145                 150                 155                 160

Cys His Phe Cys Gln Ser Ile Ser His Met Val Ala Ser Cys Pro Leu
                165                 170                 175

Lys Ala Gln Gln Gly Pro Ser Ala Gln Gly Lys Pro Thr Tyr Phe Arg
            180                 185                 190

Glu Glu Glu Glu Glu Ile His Ser Pro Thr Leu Leu Pro Glu Ala Gln
        195                 200                 205

Asn
```

<210> SEQ ID NO 9
<211> LENGTH: 2639
<212> TYPE: DNA

<213> ORGANISM: Homo sapiens

<400> SEQUENCE: 9
tcgaggcgac cgcgacagtg gtgggggacg ctgctgagtg gaagagagcg cagcccggcc 60
accggaccta cttactcgcc ttgctgattg tctatttttg cgtttacaac ttttctaaga 120
acttttgtat acaaaggaac tttttaaaaa agacgcttcc aagttatatt taatccaaag 180
aagaaggatc tcggccaatt tggggttttg ggttttggct tcgtttcttc tcttcgttga 240
ctttggggtt caggtgcccc agctgcttcg ggctgccgag gaccttctgg gcccccacat 300
taatgaggca gccacctggc gagtctgaca tggctgtcag cgacgcgctg ctcccatctt 360
tctccacgtt cgcgtctggc ccggcgggaa gggagaagac actgcgtcaa gcaggtgccc 420
cgaataaccg ctggcgggag gagctctccc acatgaagcg acttccccca gtgcttcccg 480
gccgccccta tgacctggcg gcggcgaccg tggccacaga cctggagagc ggcggagccg 540
gtgcggcttg cggcggtagc aacctggcgc ccctacctcg gagagagacc gaggagttca 600
acgatctcct ggacctggac tttattctct ccaattcgct gacccatcct ccggagtcag 660
tggccgccac cgtgtcctcg tcagcgtcag cctcctcttc gtcgtcgccg tcgagcagcg 720
gccctgccag cgcgccctcc acctgcagct tcacctatcc gatccgggcc gggaacgacc 780
cgggcgtggc gccgggcggc acgggcggag gcctcctcta tggcagggag tccgctcccc 840
ctccgacggc tcccttcaac ctggcggaca tcaacgacgt gagcccctcg ggcggcttcg 900
tggccgagct cctgcggcca gaattggacc cggtgtacat tccgccgcag cagccgcagc 960
cgccaggtgg cgggctgatg ggcaagttcg tgctgaaggc gtcgctgagc gcccctggca 1020
gcgagtacgg cagcccgtcg gtcatcagcg tcagcaaagg cagccctgac ggcagccacc 1080
cggtggtggt ggcgccctac aacggcgggc cgccgcgcac gtgccccaag atcaagcagg 1140
aggcggtctc ttcgtgcacc cacttgggcg ctggaccccc tctcagcaat ggccaccggc 1200
cggctgcaca cgacttcccc ctggggcggc agctccccag caggactacc ccgaccctgg 1260
gtcttgagga agtgctgagc agcagggact gtcaccctgc cctgccgctt cctcccggct 1320
tccatcccca cccggggccc aattacccat ccttcctgcc cgatcagatg cagccgcaag 1380
tcccgccgct ccattaccaa gagctcatgc cacccggttc ctgcatgcca gaggagccca 1440
agccaaagag gggaagacga tcgtggcccc ggaaaaggac cgccacccac acttgtgatt 1500
acgcgggctg cggcaaaacc tacacaaaga gttcccatct caaggcacac ctgcgaaccc 1560
acacaggtga gaaaccttac cactgtgact gggacggctg tggatggaaa ttcgcccgct 1620
cagatgaact gaccaggcac taccgtaaac acacggggca ccgcccgttc cagtgccaaa 1680
aatgcgaccg agcattttcc aggtcggacc acctcgcctt acacatgaag aggcattttt 1740
aaatcccaga cagtggatat gacccacact gccagaagag aattcagtat tttttacttt 1800
tcacactgtc ttcccgatga gggaaggagc ccagccagaa agcactacaa tcatggtcaa 1860
gttcccaact gagtcatctt gtgagtggat aatcaggaaa aatgaggaat ccaaaagaca 1920
aaaatcaaag aacagatggg gtctgtgact ggatcttcta tcattccaat tctaaatccg 1980
acttgaatat tcctggactt acaaaatgcc aagggggtga ctggaagttg tggatatcag 2040
ggtataaatt atatccgtga gttgggggag ggaagaccag aattcccttg aattgtgtat 2100
tgatgcaata taagcataaa agatcacctt gtattctctt taccttctaa aagccattat 2160
tatgatgtta gaagaagagg aagaaattca ggtacagaaa acatgtttaa atagcctaaa 2220
tgatggtgct tggtgagtct tggttctaaa ggtaccaaac aaggaagcca aagttttcaa 2280

-continued actgctgcat actttgacaa ggaaaatcta tatttgtctt ccgatcaaca tttatgacct 2340
aagtcaggta atatacctgg tttacttctt tagcattttt atgcagacag tctgttatgc 2400
actgtggttt cagatgtgca ataatttgta caatggttta ttcccaagta tgccttaagc 2460
agaacaaatg tgtttttcta tatagttcct tgccttaata aatatgtaat ataaatttaa 2520
gcaaacgtct attttgtata tttgtaaact acaaagtaaa atgaacattt tgtggagttt 2580
gtattttgca tactcaaggt gagaattaag ttttaaataa acctataata ttttatctg 2639

<210> SEQ ID NO 10
<211> LENGTH: 470
<212> TYPE: PRT
<213> ORGANISM: Homo sapiens

<400> SEQUENCE: 10

Met Ala Val Ser Asp Ala Leu Leu Pro Ser Phe Ser Thr Phe Ala Ser
1 5 10 15

Gly Pro Ala Gly Arg Glu Lys Thr Leu Arg Gln Ala Gly Ala Pro Asn
20 25 30

Asn Arg Trp Arg Glu Glu Leu Ser His Met Lys Arg Leu Pro Pro Val
35 40 45

Leu Pro Gly Arg Pro Tyr Asp Leu Ala Ala Ala Thr Val Ala Thr Asp
50 55 60

Leu Glu Ser Gly Gly Ala Gly Ala Ala Cys Gly Gly Ser Asn Leu Ala
65 70 75 80

Pro Leu Pro Arg Arg Glu Thr Glu Glu Phe Asn Asp Leu Leu Asp Leu
85 90 95

Asp Phe Ile Leu Ser Asn Ser Leu Thr His Pro Pro Glu Ser Val Ala
100 105 110

Ala Thr Val Ser Ser Ser Ala Ser Ala Ser Ser Ser Ser Ser Pro Ser
115 120 125

Ser Ser Gly Pro Ala Ser Ala Pro Ser Thr Cys Ser Phe Thr Tyr Pro
130 135 140

Ile Arg Ala Gly Asn Asp Pro Gly Val Ala Pro Gly Gly Thr Gly Gly
145 150 155 160

Gly Leu Leu Tyr Gly Arg Glu Ser Ala Pro Pro Pro Thr Ala Pro Phe
165 170 175

Asn Leu Ala Asp Ile Asn Asp Val Ser Pro Ser Gly Gly Phe Val Ala
180 185 190

Glu Leu Leu Arg Pro Glu Leu Asp Pro Val Tyr Ile Pro Pro Gln Gln
195 200 205

Pro Gln Pro Pro Gly Gly Gly Leu Met Gly Lys Phe Val Leu Lys Ala
210 215 220

Ser Leu Ser Ala Pro Gly Ser Glu Tyr Gly Ser Pro Ser Val Ile Ser
225 230 235 240

Val Ser Lys Gly Ser Pro Asp Gly Ser His Pro Val Val Val Ala Pro
245 250 255

Tyr Asn Gly Gly Pro Pro Arg Thr Cys Pro Lys Ile Lys Gln Glu Ala
260 265 270

Val Ser Ser Cys Thr His Leu Gly Ala Gly Pro Pro Leu Ser Asn Gly
275 280 285

His Arg Pro Ala Ala His Asp Phe Pro Leu Gly Arg Gln Leu Pro Ser
290 295 300

Arg Thr Thr Pro Thr Leu Gly Leu Glu Glu Val Leu Ser Ser Arg Asp

-continued

```
305                 310                 315                 320

Cys His Pro Ala Leu Pro Leu Pro Pro Gly Phe His Pro His Pro Gly
                325                 330                 335

Pro Asn Tyr Pro Ser Phe Leu Pro Asp Gln Met Gln Pro Gln Val Pro
            340                 345                 350

Pro Leu His Tyr Gln Glu Leu Met Pro Pro Gly Ser Cys Met Pro Glu
        355                 360                 365

Glu Pro Lys Pro Lys Arg Gly Arg Arg Ser Trp Pro Arg Lys Arg Thr
    370                 375                 380

Ala Thr His Thr Cys Asp Tyr Ala Gly Cys Gly Lys Thr Tyr Thr Lys
385                 390                 395                 400

Ser Ser His Leu Lys Ala His Leu Arg Thr His Thr Gly Glu Lys Pro
                405                 410                 415

Tyr His Cys Asp Trp Asp Gly Cys Gly Trp Lys Phe Ala Arg Ser Asp
            420                 425                 430

Glu Leu Thr Arg His Tyr Arg Lys His Thr Gly His Arg Pro Phe Gln
        435                 440                 445

Cys Gln Lys Cys Asp Arg Ala Phe Ser Arg Ser Asp His Leu Ala Leu
    450                 455                 460

His Met Lys Arg His Phe
465                 470


<210> SEQ ID NO 11
<211> LENGTH: 2377
<212> TYPE: DNA
<213> ORGANISM: Homo sapiens

<400> SEQUENCE: 11

acccccgagc tgtgctgctc gcggccgcca ccgccgggcc ccggccgtcc ctggctcccc      60

tcctgcctcg agaagggcag ggcttctcag aggcttggcg ggaaaaagaa cggagggagg     120

gatcgcgctg agtataaaag ccggttttcg gggctttatc taactcgctg tagtaattcc     180

agcgagaggc agagggagcg agcgggcggc cggctagggt ggaagagccg ggcgagcaga     240

gctgcgctgc gggcgtcctg ggaagggaga tccggagcga atagggggct tcgcctctgg     300

cccagccctc ccgctgatcc cccagccagc ggtccgcaac ccttgccgca tccacgaaac     360

tttgcccata gcagcgggcg ggcactttgc actggaactt acaacacccg agcaaggacg     420

cgactctccc gacgcgggga ggctattctg cccatttggg gacacttccc cgccgctgcc     480

aggacccgct tctctgaaag gctctccttg cagctgctta gacgctggat ttttttcggg     540

tagtggaaaa ccagcagcct cccgcgacga tgcccctcaa cgttagcttc accaacagga     600

actatgacct cgactacgac tcggtgcagc cgtatttcta ctgcgacgag gaggagaact     660

tctaccagca gcagcagcag agcgagctgc agcccccggc gcccagcgag gatatctgga     720

agaaattcga gctgctgccc accccgcccc tgtcccctag ccgccgctcc gggctctgct     780

cgccctccta cgttgcggtc acacccttct cccttcgggg agacaacgac ggcggtggcg     840

ggagcttctc cacggccgac cagctggaga tggtgaccga gctgctggga ggagacatgg     900

tgaaccagag tttcatctgc gacccggacg acgagacctt catcaaaaac atcatcatcc     960

aggactgtat gtggagcggc ttctcggccg ccgccaagct cgtctcagag aagctggcct    1020

cctaccaggc tgcgcgcaaa gacagcggca gcccgaaccc cgcccgcggc cacagcgtct    1080

gctccacctc cagcttgtac ctgcaggatc tgagcgccgc cgcctcagag tgcatcgacc    1140

cctcggtggt cttcccctac cctctcaacg acagcagctc gcccaagtcc tgcgcctcgc    1200
```

aagactccag cgccttctct ccgtcctcgg attctctgct ctcctcgacg gagtcctccc 1260
cgcagggcag ccccgagccc ctggtgctcc atgaggagac accgcccacc accagcagcg 1320
actctgagga ggaacaagaa gatgaggaag aaatcgatgt tgtttctgtg gaaaagaggc 1380
aggctcctgg caaaaggtca gagtctggat caccttctgc tggaggccac agcaaacctc 1440
ctcacagccc actggtcctc aagaggtgcc acgtctccac acatcagcac aactacgcag 1500
cgcctccctc cactcggaag gactatcctg ctgccaagag ggtcaagttg gacagtgtca 1560
gagtcctgag acagatcagc aacaaccgaa aatgcaccag ccccaggtcc tcggacaccg 1620
aggagaatgt caagaggcga acacacaacg tcttggagcg ccagaggagg aacgagctaa 1680
aacggagctt ttttgccctg cgtgaccaga tcccggagtt ggaaaacaat gaaaaggccc 1740
ccaaggtagt tatccttaaa aaagccacag catacatcct gtccgtccaa gcagaggagc 1800
aaaagctcat ttctgaagag gacttgttgc ggaaacgacg agaacagttg aaacacaaac 1860
ttgaacagct acggaactct tgtgcgtaag gaaaagtaag gaaaacgatt ccttctaaca 1920
gaaatgtcct gagcaatcac ctatgaactt gtttcaaatg catgatcaaa tgcaacctca 1980
caaccttggc tgagtcttga gactgaaaga tttagccata atgtaaactg cctcaaattg 2040
gactttgggc ataaaagaac tttttatgc ttaccatctt tttttttct ttaacagatt 2100 tgtatttaag aattgttttt aaaaaatttt aagatttaca caatgtttct ctgtaaatat 2160
tgccattaaa tgtaaataac tttaataaaa cgtttatagc agttacacag aatttcaatc 2220
ctagtatata gtacctagta ttataggtac tataaaccct aatttttttt atttaagtac 2280
attttgcttt ttaaagttga tttttttcta ttgtttttag aaaaaataaa ataactggca 2340
aatatatcat tgagccaaaa aaaaaaaaaa aaaaaaa 2377

<210> SEQ ID NO 12
<211> LENGTH: 454
<212> TYPE: PRT
<213> ORGANISM: Homo sapiens

<400> SEQUENCE: 12

Met Asp Phe Phe Arg Val Val Glu Asn Gln Gln Pro Pro Ala Thr Met
1 5 10 15

Pro Leu Asn Val Ser Phe Thr Asn Arg Asn Tyr Asp Leu Asp Tyr Asp
20 25 30

Ser Val Gln Pro Tyr Phe Tyr Cys Asp Glu Glu Glu Asn Phe Tyr Gln
35 40 45

Gln Gln Gln Gln Ser Glu Leu Gln Pro Pro Ala Pro Ser Glu Asp Ile
50 55 60

Trp Lys Lys Phe Glu Leu Leu Pro Thr Pro Pro Leu Ser Pro Ser Arg
65 70 75 80

Arg Ser Gly Leu Cys Ser Pro Ser Tyr Val Ala Val Thr Pro Phe Ser
85 90 95

Leu Arg Gly Asp Asn Asp Gly Gly Gly Gly Ser Phe Ser Thr Ala Asp
100 105 110

Gln Leu Glu Met Val Thr Glu Leu Leu Gly Gly Asp Met Val Asn Gln
115 120 125

Ser Phe Ile Cys Asp Pro Asp Asp Glu Thr Phe Ile Lys Asn Ile Ile
130 135 140

Ile Gln Asp Cys Met Trp Ser Gly Phe Ser Ala Ala Ala Lys Leu Val
145 150 155 160

-continued

```
Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
        435                 440                 445

Leu Arg Asn Ser Cys Ala
    450


<210> SEQ ID NO 13
<211> LENGTH: 2930
<212> TYPE: DNA
<213> ORGANISM: Homo sapiens

<400> SEQUENCE: 13

agcagacgag ggcttgtgcg agaggggggcc gggcggctgc agggaaggcg gagtccaagg      60

ggaaaacgaa actgagaacc agctctcccg aagccgcggg tctccggccg gcggcggcgg     120

cggcggcggc ggcggcgcag tttgctcata ctttgtgact tgcggtcaca gtggcattca     180

gctccacact tggtagaacc acaggcacga caagcataga aacatcctaa acaatcttca     240

tcgaggcatc gaggtccatc ccaataaaaa tcaggagacc ctggctatca tagaccttag     300

tcttcgctgg tatcactcgt ctgtctgaac cagcggttgc atttttttaa gccttctttt     360

ttctctttta ccagtttctg gagcaaattc agtttgcctt cctggatttg taaattgtaa     420
```

-continued

```
tgacctcaaa actttagcag ttcttccatc tgactcaggt ttgcttctct ggcggtcttc    480
agaatcaaca tccacacttc cgtgattatc tgcgtgcatt ttggacaaag cttccaacca    540
ggatacggga agaagaaatg gctggtgatc tttcagcagg tttcttcatg gaggaactta    600
atacataccg tcagaagcag ggagtagtac ttaaatatca agaactgcct aattcaggac    660
ctccacatga taggaggttt acatttcaag ttataataga tggaagagaa tttccagaag    720
gtgaaggtag atcaaagaag gaagcaaaaa atgccgcagc caaattagct gttgagatac    780
ttaataagga aaagaaggca gttagtcctt tattattgac aacaacgaat tcttcagaag    840
gattatccat ggggaattac ataggcctta tcaatagaat tgcccagaag aaaagactaa    900
ctgtaaatta tgaacagtgt gcatcggggg tgcatgggcc agaaggattt cattataaat    960
gcaaaatggg acagaaagaa tatagtattg gtacaggttc tactaaacag gaagcaaaac   1020
aattggccgc taaacttgca tatcttcaga tattatcaga agaaacctca gtgaaatctg   1080
actacctgtc ctctggttct tttgctacta cgtgtgagtc ccaaagcaac tctttagtga   1140
ccagcacact cgcttctgaa tcatcatctg aaggtgactt ctcagcagat acatcagaga   1200
taaattctaa cagtgacagt ttaaacagtt cttcgttgct tatgaatggt ctcagaaata   1260
atcaaaggaa ggcaaaaaga tctttggcac ccagatttga ccttcctgac atgaaagaaa   1320
caaagtatac tgtggacaag aggtttggca tggattttaa agaaatagaa ttaattggct   1380
caggtggatt tggccaagtt ttcaaagcaa aacacagaat tgacggaaag acttacgtta   1440
ttaaacgtgt taaatataat aacgagaagg cggagcgtga agtaaaagca ttggcaaaac   1500
ttgatcatgt aaatattgtt cactacaatg gctgttggga tggatttgat tatgatcctg   1560
agaccagtga tgattctctt gagagcagtg attatgatcc tgagaacagc aaaaatagtt   1620
caaggtcaaa gactaagtgc cttttcatcc aaatggaatt ctgtgataaa gggaccttgg   1680
aacaatggat tgaaaaaaga agaggcgaga aactagacaa agttttggct ttggaactct   1740
ttgaacaaat aacaaaaggg gtggattata tacattcaaa aaaattaatt catagagatc   1800
ttaagccaag taatatattc ttagtagata caaaacaagt aaagattgga gactttggac   1860
ttgtaacatc tctgaaaaat gatggaaagc gaacaaggag taagggaact ttgcgataca   1920
tgagcccaga acagatttct tcgcaagact atggaaagga agtggacctc tacgctttgg   1980
ggctaattct tgctgaactt cttcatgtat gtgacactgc ttttgaaaca tcaaagtttt   2040
tcacagacct acgggatggc atcatctcag atatatttga taaaaaagaa aaaactcttc   2100
tacagaaatt actctcaaag aaacctgagg atcgacctaa cacatctgaa atactaagga   2160
ccttgactgt gtggaagaaa agcccagaga aaaatgaacg acacacatgt tagagccctt   2220
ctgaaaaagt atcctgcttc tgatatgcag ttttccttaa attatctaaa atctgctagg   2280
gaatatcaat agatatttac cttttatttt aatgtttcct ttaatttttt actattttta   2340
ctaatctttc tgcagaaaca gaaaggtttt cttctttttg cttcaaaaac attcttacat   2400
tttacttttt cctggctcat ctctttattc tttttttttt tttaaagaca gagtctcgct   2460
ctgttgccca ggctggagtg caatgacaca gtcttggctc actgcaactt ctgcctcttg   2520
ggttcaagtg attctcctgc ctcagcctcc tgagtagctg gattacaggc atgtgccacc   2580
cacccaacta atttttgtgt ttttaataaa gacagggttt caccatgttg gccaggctgg   2640
tctcaaactc ctgacctcaa gtaatccacc tgcctcggcc tcccaaagtg ctgggattac   2700
agggatgagc caccgcgccc agcctcatct ctttgttcta aagatggaaa aaccaccccc   2760
aaattttctt tttatactat taatgaatca atcaattcat atctatttat taaatttcta   2820
```

```
ccgcttttag gccaaaaaaa tgtaagatcg ttctctgcct cacatagctt acaagccagc   2880

tggagaaata tggtactcat taaaaaaaaa aaaaaaagtg atgtacaacc              2930


<210> SEQ ID NO 14
<211> LENGTH: 551
<212> TYPE: PRT
<213> ORGANISM: Homo sapiens

<400> SEQUENCE: 14

Met Ala Gly Asp Leu Ser Ala Gly Phe Phe Met Glu Glu Leu Asn Thr
1               5                   10                  15

Tyr Arg Gln Lys Gln Gly Val Val Leu Lys Tyr Gln Glu Leu Pro Asn
            20                  25                  30

Ser Gly Pro Pro His Asp Arg Arg Phe Thr Phe Gln Val Ile Ile Asp
        35                  40                  45

Gly Arg Glu Phe Pro Glu Gly Glu Gly Arg Ser Lys Lys Glu Ala Lys
    50                  55                  60

Asn Ala Ala Ala Lys Leu Ala Val Glu Ile Leu Asn Lys Glu Lys Lys
65                  70                  75                  80

Ala Val Ser Pro Leu Leu Leu Thr Thr Thr Asn Ser Ser Glu Gly Leu
                85                  90                  95

Ser Met Gly Asn Tyr Ile Gly Leu Ile Asn Arg Ile Ala Gln Lys Lys
            100                 105                 110

Arg Leu Thr Val Asn Tyr Glu Gln Cys Ala Ser Gly Val His Gly Pro
        115                 120                 125

Glu Gly Phe His Tyr Lys Cys Lys Met Gly Gln Lys Glu Tyr Ser Ile
    130                 135                 140

Gly Thr Gly Ser Thr Lys Gln Glu Ala Lys Gln Leu Ala Ala Lys Leu
145                 150                 155                 160

Ala Tyr Leu Gln Ile Leu Ser Glu Glu Thr Ser Val Lys Ser Asp Tyr
                165                 170                 175

Leu Ser Ser Gly Ser Phe Ala Thr Thr Cys Glu Ser Gln Ser Asn Ser
            180                 185                 190

Leu Val Thr Ser Thr Leu Ala Ser Glu Ser Ser Ser Glu Gly Asp Phe
        195                 200                 205

Ser Ala Asp Thr Ser Glu Ile Asn Ser Asn Ser Asp Ser Leu Asn Ser
    210                 215                 220

Ser Ser Leu Leu Met Asn Gly Leu Arg Asn Asn Gln Arg Lys Ala Lys
225                 230                 235                 240

Arg Ser Leu Ala Pro Arg Phe Asp Leu Pro Asp Met Lys Glu Thr Lys
                245                 250                 255

Tyr Thr Val Asp Lys Arg Phe Gly Met Asp Phe Lys Glu Ile Glu Leu
            260                 265                 270

Ile Gly Ser Gly Gly Phe Gly Gln Val Phe Lys Ala Lys His Arg Ile
        275                 280                 285

Asp Gly Lys Thr Tyr Val Ile Lys Arg Val Lys Tyr Asn Asn Glu Lys
    290                 295                 300

Ala Glu Arg Glu Val Lys Ala Leu Ala Lys Leu Asp His Val Asn Ile
305                 310                 315                 320

Val His Tyr Asn Gly Cys Trp Asp Gly Phe Asp Tyr Asp Pro Glu Thr
                325                 330                 335

Ser Asp Asp Ser Leu Glu Ser Ser Asp Tyr Asp Pro Glu Asn Ser Lys
            340                 345                 350
```

-continued

```
Asn Ser Ser Arg Ser Lys Thr Lys Cys Leu Phe Ile Gln Met Glu Phe
        355                 360                 365

Cys Asp Lys Gly Thr Leu Glu Gln Trp Ile Glu Lys Arg Arg Gly Glu
    370                 375                 380

Lys Leu Asp Lys Val Leu Ala Leu Glu Leu Phe Glu Gln Ile Thr Lys
385                 390                 395                 400

Gly Val Asp Tyr Ile His Ser Lys Lys Leu Ile His Arg Asp Leu Lys
                405                 410                 415

Pro Ser Asn Ile Phe Leu Val Asp Thr Lys Gln Val Lys Ile Gly Asp
            420                 425                 430

Phe Gly Leu Val Thr Ser Leu Lys Asn Asp Gly Lys Arg Thr Arg Ser
        435                 440                 445

Lys Gly Thr Leu Arg Tyr Met Ser Pro Glu Gln Ile Ser Ser Gln Asp
    450                 455                 460

Tyr Gly Lys Glu Val Asp Leu Tyr Ala Leu Gly Leu Ile Leu Ala Glu
465                 470                 475                 480

Leu Leu His Val Cys Asp Thr Ala Phe Glu Thr Ser Lys Phe Phe Thr
                485                 490                 495

Asp Leu Arg Asp Gly Ile Ile Ser Asp Ile Phe Asp Lys Lys Glu Lys
            500                 505                 510

Thr Leu Leu Gln Lys Leu Leu Ser Lys Lys Pro Glu Asp Arg Pro Asn
        515                 520                 525

Thr Ser Glu Ile Leu Arg Thr Leu Thr Val Trp Lys Lys Ser Pro Glu
    530                 535                 540

Lys Asn Glu Arg His Thr Cys
545                 550
```

<210> SEQ ID NO 15
<211> LENGTH: 1758
<212> TYPE: DNA
<213> ORGANISM: Homo sapiens

<400> SEQUENCE: 15

```
atggcgccgt ccacgccgct cttgacagtc cgaggatcag aaggactgta catggtgaat      60

ggaccaccac attttacaga aagcacagtg tttccaaggg aatctgggaa gaattgcaaa     120

gtctgtatct ttagtaagga tgggaccttg tttgcctggg gcaatggaga aaaagtaaat     180

attatcagtg tcactaacaa gggactactg cactccttcg acctcctgaa ggcagtttgc     240

cttgaattct cacccaaaaa tactgtcctg gcaacgtggc agccttacac tacttctaaa     300

gatggcacag ctgggatacc caacctacaa ctttatgatg tgaaaactgg gacatgtttg     360

aaatctttca tccagaaaaa aatgcaaaat tggtgtccat cctggtcaga agatgaaact     420

ctttgtgccc gcaatgttaa caatgaagtt cacttctttg aaaacaacaa ttttaacaca     480

attgcaaata aattgcattt gcaaaaaatt aatgattttg tattatcacc tggaccccaa     540

ccatacaagg tggctgtcta tgttccagga agtaaaggtg caccttcatt tgttagatta     600

tatcagtacc ccaactttgc tggacctcat gcagctttag ctaataaaag tttctttaag     660

gcagataaag ttacaatgct gtggaataaa aaagctactg ctgtgttggt aatagctagc     720

acagatgttg acaagacagg agcttcctac tatggagaac aaactctaca ctacattgca     780

acaaatggag aaagtgctgt agtgcaatta ccaaaaaatg gccccattta tgatgtagtt     840

tggaattcta gttctactga gttttgtgct gtatatggtt ttatgcctgc caaagcgaca     900

attttcaact tgaaatgtga tcctgtattt gactttggaa ctggtcctcg taatgcagcc     960
```

```
tactatagcc ctcatggaca tatattagta ttagctggat ttggaaatct gaggggacaa   1020

atggaagtgt gggatgtgaa aaactacaaa cttatttcta aaccggtggc ttctgattct   1080

acatattttg cttggtgccc ggatggtgag catattttaa cagctacatg tgctcccagg   1140

ttacgggtta ataatggata caaaatttgg cattatactg gctctatctt gcacaagtat   1200

gatgtgccat caaatgcaga attatggcag gtttcttggc agccattttt ggatggaata   1260

tttccagcaa aaacaataac ttaccaagca gttccaagtg aagtacccaa tgaggaacct   1320

aaagttgcaa cagcttatag acccccagct ttaagaaata aaccaatcac caattccaaa   1380

ttgcatgaag aggaaccacc tcagaatatg aaaccacaat caggaaacga taagccatta   1440

tcaaaaacag ctcttaaaaa tcaaaggaag catgaagcta agaaagctgc aaagcaggaa   1500

gcaagaagtg acaagagtcc agatttggca cctactcctg ccccacagag cacaccacga   1560

aacactgtct ctcagtcaat ttctggggac cctgagatag acaaaaaaat caagaaccta   1620

aagaagaaac tgaaagcaat cgaacaactg aaagaacaag cagcaactgg aaaacagcta   1680

gaaaaaaatc agttggagaa aattcagaaa gaaacagccc ttctccagga gctggaagat   1740

ttggaattgg gtatttaa                                                 1758
```

<210> SEQ ID NO 16
<211> LENGTH: 585
<212> TYPE: PRT
<213> ORGANISM: Homo sapiens

<400> SEQUENCE: 16

```
Met Ala Pro Ser Thr Pro Leu Leu Thr Val Arg Gly Ser Glu Gly Leu
1               5                   10                  15

Tyr Met Val Asn Gly Pro Pro His Phe Thr Glu Ser Thr Val Phe Pro
            20                  25                  30

Arg Glu Ser Gly Lys Asn Cys Lys Val Cys Ile Phe Ser Lys Asp Gly
        35                  40                  45

Thr Leu Phe Ala Trp Gly Asn Gly Glu Lys Val Asn Ile Ile Ser Val
    50                  55                  60

Thr Asn Lys Gly Leu Leu His Ser Phe Asp Leu Leu Lys Ala Val Cys
65                  70                  75                  80

Leu Glu Phe Ser Pro Lys Asn Thr Val Leu Ala Thr Trp Gln Pro Tyr
                85                  90                  95

Thr Thr Ser Lys Asp Gly Thr Ala Gly Ile Pro Asn Leu Gln Leu Tyr
            100                 105                 110

Asp Val Lys Thr Gly Thr Cys Leu Lys Ser Phe Ile Gln Lys Lys Met
        115                 120                 125

Gln Asn Trp Cys Pro Ser Trp Ser Glu Asp Glu Thr Leu Cys Ala Arg
    130                 135                 140

Asn Val Asn Asn Glu Val His Phe Phe Glu Asn Asn Asn Phe Asn Thr
145                 150                 155                 160

Ile Ala Asn Lys Leu His Leu Gln Lys Ile Asn Asp Phe Val Leu Ser
                165                 170                 175

Pro Gly Pro Gln Pro Tyr Lys Val Ala Val Tyr Val Pro Gly Ser Lys
            180                 185                 190

Gly Ala Pro Ser Phe Val Arg Leu Tyr Gln Tyr Pro Asn Phe Ala Gly
        195                 200                 205

Pro His Ala Ala Leu Ala Asn Lys Ser Phe Phe Lys Ala Asp Lys Val
    210                 215                 220

Thr Met Leu Trp Asn Lys Lys Ala Thr Ala Val Leu Val Ile Ala Ser
```

-continued

```
225                 230                 235                 240

Thr Asp Val Asp Lys Thr Gly Ala Ser Tyr Tyr Gly Glu Gln Thr Leu
                245                 250                 255

His Tyr Ile Ala Thr Asn Gly Glu Ser Ala Val Val Gln Leu Pro Lys
            260                 265                 270

Asn Gly Pro Ile Tyr Asp Val Val Trp Asn Ser Ser Ser Thr Glu Phe
        275                 280                 285

Cys Ala Val Tyr Gly Phe Met Pro Ala Lys Ala Thr Ile Phe Asn Leu
    290                 295                 300

Lys Cys Asp Pro Val Phe Asp Phe Gly Thr Gly Pro Arg Asn Ala Ala
305                 310                 315                 320

Tyr Tyr Ser Pro His Gly His Ile Leu Val Leu Ala Gly Phe Gly Asn
                325                 330                 335

Leu Arg Gly Gln Met Glu Val Trp Asp Val Lys Asn Tyr Lys Leu Ile
            340                 345                 350

Ser Lys Pro Val Ala Ser Asp Ser Thr Tyr Phe Ala Trp Cys Pro Asp
        355                 360                 365

Gly Glu His Ile Leu Thr Ala Thr Cys Ala Pro Arg Leu Arg Val Asn
    370                 375                 380

Asn Gly Tyr Lys Ile Trp His Tyr Thr Gly Ser Ile Leu His Lys Tyr
385                 390                 395                 400

Asp Val Pro Ser Asn Ala Glu Leu Trp Gln Val Ser Trp Gln Pro Phe
                405                 410                 415

Leu Asp Gly Ile Phe Pro Ala Lys Thr Ile Thr Tyr Gln Ala Val Pro
            420                 425                 430

Ser Glu Val Pro Asn Glu Glu Pro Lys Val Ala Thr Ala Tyr Arg Pro
        435                 440                 445

Pro Ala Leu Arg Asn Lys Pro Ile Thr Asn Ser Lys Leu His Glu Glu
    450                 455                 460

Glu Pro Pro Gln Asn Met Lys Pro Gln Ser Gly Asn Asp Lys Pro Leu
465                 470                 475                 480

Ser Lys Thr Ala Leu Lys Asn Gln Arg Lys His Glu Ala Lys Lys Ala
                485                 490                 495

Ala Lys Gln Glu Ala Arg Ser Asp Lys Ser Pro Asp Leu Ala Pro Thr
            500                 505                 510

Pro Ala Pro Gln Ser Thr Pro Arg Asn Thr Val Ser Gln Ser Ile Ser
        515                 520                 525

Gly Asp Pro Glu Ile Asp Lys Lys Ile Lys Asn Leu Lys Lys Lys Leu
    530                 535                 540

Lys Ala Ile Glu Gln Leu Lys Glu Gln Ala Ala Thr Gly Lys Gln Leu
545                 550                 555                 560

Glu Lys Asn Gln Leu Glu Lys Ile Gln Lys Glu Thr Ala Leu Leu Gln
                565                 570                 575

Glu Leu Glu Asp Leu Glu Leu Gly Ile
            580                 585


<210> SEQ ID NO 17
<211> LENGTH: 1203
<212> TYPE: DNA
<213> ORGANISM: Homo sapiens

<400> SEQUENCE: 17

atgatggatc tcagaaatac cccagccaaa tctctggaca agttcattga agactatctc      60

ttgccagaca cgtgtttccg catgcaaatc aaccatgcca ttgacatcat ctgtgggttc     120
```

```
ctgaaggaaa ggtgcttccg aggtagctcc taccctgtgt gtgtgtccaa ggtggtaaag    180

ggtggctcct caggcaaggg caccaccctc agaggccgat ctgacgctga cctggttgtc    240

ttcctcagtc ctctcaccac ttttcaggat cagttaaatc gccggggaga gttcatccag    300

gaaattagga gacagctgga agcctgtcaa agagagagag cattttccgt gaagtttgag    360

gtccaggctc cacgctgggg caaccccctgt gcgctcagct tcgtactgag ttcgctccag    420

ctcggggagg gggtggagtt cgatgtgctg cctgcctttg atgccctggg tcagttgact    480

ggcggctata aacctaaccc ccaaatctat gtcaagctca tcgaggagtg caccgacctg    540

cagaaagagg gcgagttctc cacctgcttc acagaactac agagagactt cctgaagcag    600

cgccccacca agctcaagag cctcatccgc ctagtcaagc actggtacca aaattgtaag    660

aagaagcttg ggaagctgcc acctcagtat gccctggagc tcctgacggt ctatgcttgg    720

gagcgaggga gcatgaaaac acatttcaac acagcccagg gatttcggac ggtcttggaa    780

ttagtcataa actaccagca actctgcatc tactggacaa agtattatga ctttaaaaac    840

cccattattg aaaagtacct gagaaggcag ctcacgaaac ccaggcctgt gatcctggac    900

ccggcggacc ctacaggaaa cttgggtggt ggagacccaa agggttggag gcagctggca    960

caagaggctg aggcctggct gaattaccca tgctttaaga attgggatgg gtccccagtg   1020

agctcctgga ttctgctggc tgaaagcaac agtgcagacg atgagaccga cgatcccagg   1080

aggtatcaga aatatggtta cattggaaca catgagtacc ctcatttctc tcatagaccc   1140

agcacactcc aggcagcatc caccccacag gcagaagagg actggacctg caccatcctc   1200

tga                                                                1203
```

<210> SEQ ID NO 18
<211> LENGTH: 400
<212> TYPE: PRT
<213> ORGANISM: Homo sapiens

<400> SEQUENCE: 18

```
Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Asn His
            20                  25                  30

Ala Ile Asp Ile Ile Cys Gly Phe Leu Lys Glu Arg Cys Phe Arg Gly
        35                  40                  45

Ser Ser Tyr Pro Val Cys Val Ser Lys Val Val Lys Gly Gly Ser Ser
    50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110

Arg Ala Phe Ser Val Lys Phe Glu Val Gln Ala Pro Arg Trp Gly Asn
        115                 120                 125

Pro Arg Ala Leu Ser Phe Val Leu Ser Ser Leu Gln Leu Gly Glu Gly
    130                 135                 140

Val Glu Phe Asp Val Leu Pro Ala Phe Asp Ala Leu Gly Gln Leu Thr
145                 150                 155                 160

Gly Gly Tyr Lys Pro Asn Pro Gln Ile Tyr Val Lys Leu Ile Glu Glu
                165                 170                 175
```

```
Cys Thr Asp Leu Gln Lys Glu Gly Glu Phe Ser Thr Cys Phe Thr Glu
            180                 185                 190

Leu Gln Arg Asp Phe Leu Lys Gln Arg Pro Thr Lys Leu Lys Ser Leu
        195                 200                 205

Ile Arg Leu Val Lys His Trp Tyr Gln Asn Cys Lys Lys Lys Leu Gly
    210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
            260                 265                 270

Thr Lys Tyr Tyr Asp Phe Lys Asn Pro Ile Ile Glu Lys Tyr Leu Arg
        275                 280                 285

Arg Gln Leu Thr Lys Pro Arg Pro Val Ile Leu Asp Pro Ala Asp Pro
    290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Pro Cys Phe Lys Asn Trp Asp
                325                 330                 335

Gly Ser Pro Val Ser Ser Trp Ile Leu Leu Ala Glu Ser Asn Ser Ala
            340                 345                 350

Asp Asp Glu Thr Asp Asp Pro Arg Arg Tyr Gln Lys Tyr Gly Tyr Ile
        355                 360                 365

Gly Thr His Glu Tyr Pro His Phe Ser His Arg Pro Ser Thr Leu Gln
    370                 375                 380

Ala Ala Ser Thr Pro Gln Ala Glu Glu Asp Trp Thr Cys Thr Ile Leu
385                 390                 395                 400
```

<210> SEQ ID NO 19
<211> LENGTH: 2160
<212> TYPE: DNA
<213> ORGANISM: Homo sapiens

<400> SEQUENCE: 19

```
atgggaaatg gggagtccca gctgtcctcg gtgcctgctc agaagctggg ttggtttatc      60

caggaatacc tgaagcccta cgaagaatgt cagacactga tcgacgagat ggtgaacacc     120

atctgtgacg tcctgcagga acccgaacag ttccccctgg tgcagggagt ggccataggt     180

ggctcctatg gacggaaaac agtcttaaga ggcaactccg atggtaccct tgtcctcttc     240

ttcagtgact taaaacaatt ccaggatcag aagagaagcc aacgtgacat cctcgataaa     300

actggggata agctgaagtt ctgtctgttc acgaagtggt tgaaaaacaa tttcgagatc     360

cagaagtccc ttgatgggtt caccatccag gtgttcacaa aaaatcagag aatctctttc     420

gaggtgctgg ccgccttcaa cgctctgagc ttaaatgata atcccagccc ctggatctat     480

cgagagctca aaagatcctt ggataagaca aatgccagtc ctggtgagtt tgcagtctgc     540

ttcactgaac tccagcagaa gtttttgac aaccgtcctg gaaaactaaa ggatttgatc      600

ctcttgataa agcactggca tcaacagtgc cagaaaaaaa tcaaggattt accctcgctg     660

tctccgtatg ccctggagct gcttacggtg tatgcctggg aacaggggtg cagaaaagac     720

aactttgaca ttgctgaagg cgtcagaacc gtactggagc tgatcaaatg ccaggagaag     780

ctgtgtatct attggatggt caactacaac tttgaagatg agaccatcag gaacatcctg     840
```

-continued

```
ctgcaccagc tccaatcagc gaggccagta atcttggatc cagttgaccc aaccaataat    900

gtgagtggag ataaaatatg ctggcaatgg ctgaaaaaag aagctcaaac ctggttgact    960

tctcccaacc tggataatga gttacctgca ccatcttgga atgttctgcc tgcaccactc   1020

ttcacgaccc caggccacct tctggataag ttcatcaagg agtttctcca gcccaacaaa   1080

tgcttcctag agcagattga cagtgctgtt aacatcatcc gtacattcct taaagaaaac   1140

tgcttccgac aatcaacagc caagatccag attgtccggg gaggatcaac cgccaaaggc   1200

acagctctga agactggctc tgatgccgat ctcgtcgtgt tccataactc acttaaaagc   1260

tacacctccc aaaaaaacga gcggcacaaa atcgtcaagg aaatccatga acagctgaaa   1320

gccttttgga gggagaagga ggaggagctt gaagtcagct ttgagcctcc caagtggaag   1380

gctcccaggg tgctgagctt ctctctgaaa tccaaagtcc tcaacgaaag tgtcagcttt   1440

gatgtgcttc ctgcctttaa tgcactgggt cagctgagtt ctggctccac acccagcccc   1500

gaggtttatg cagggctcat tgatctgtat aaatcctcgg acctcccggg aggagagttt   1560

tctacctgtt tcacagtcct gcagcgaaac ttcattcgct cccggcccac caaactaaag   1620

gatttaattc gcctggtgaa gcactggtac aaagagtgtg aaaggaaact gaagccaaag   1680

gggtctttgc ccccaaagta tgccttggag ctgctcacca tctatgcctg ggagcagggg   1740

agtggagtgc cggattttga cactgcagaa ggtttccgga cagtcctgga gctggtcaca   1800

caatatcagc agctctgcat cttctggaag gtcaattaca actttgaaga tgagaccgtg   1860

aggaagtttc tactgagcca gttgcagaaa accaggcctg tgatcttgga cccagccgaa   1920

cccacaggtg acgtgggtgg aggggaccgt tggtgttggc atcttctggc aaaagaagca   1980

aaggaatggt tatcctctcc ctgcttcaag gatgggactg gaaacccaat accaccttgg   2040

aaagtgccga caatgcagac accaggaagt tgtggagcta ggatccatcc tattgtcaat   2100

gagatgttct catccagaag ccatagaatc ctgaataata attctaaaag aaacttctag   2160


<210> SEQ ID NO 20
<211> LENGTH: 719
<212> TYPE: PRT
<213> ORGANISM: Homo sapiens

<400> SEQUENCE: 20

Met Gly Asn Gly Glu Ser Gln Leu Ser Ser Val Pro Ala Gln Lys Leu
1               5                   10                  15

Gly Trp Phe Ile Gln Glu Tyr Leu Lys Pro Tyr Glu Glu Cys Gln Thr
            20                  25                  30

Leu Ile Asp Glu Met Val Asn Thr Ile Cys Asp Val Leu Gln Glu Pro
        35                  40                  45

Glu Gln Phe Pro Leu Val Gln Gly Val Ala Ile Gly Gly Ser Tyr Gly
    50                  55                  60

Arg Lys Thr Val Leu Arg Gly Asn Ser Asp Gly Thr Leu Val Leu Phe
65                  70                  75                  80

Phe Ser Asp Leu Lys Gln Phe Gln Asp Gln Lys Arg Ser Gln Arg Asp
                85                  90                  95

Ile Leu Asp Lys Thr Gly Asp Lys Leu Lys Phe Cys Leu Phe Thr Lys
            100                 105                 110

Trp Leu Lys Asn Asn Phe Glu Ile Gln Lys Ser Leu Asp Gly Phe Thr
        115                 120                 125

Ile Gln Val Phe Thr Lys Asn Gln Arg Ile Ser Phe Glu Val Leu Ala
    130                 135                 140
```

-continued

```
Ala Phe Asn Ala Leu Ser Leu Asn Asp Asn Pro Ser Pro Trp Ile Tyr
145                 150                 155                 160

Arg Glu Leu Lys Arg Ser Leu Asp Lys Thr Asn Ala Ser Pro Gly Glu
                165                 170                 175

Phe Ala Val Cys Phe Thr Glu Leu Gln Gln Lys Phe Phe Asp Asn Arg
            180                 185                 190

Pro Gly Lys Leu Lys Asp Leu Ile Leu Leu Ile Lys His Trp His Gln
        195                 200                 205

Gln Cys Gln Lys Lys Ile Lys Asp Leu Pro Ser Leu Ser Pro Tyr Ala
    210                 215                 220

Leu Glu Leu Leu Thr Val Tyr Ala Trp Glu Gln Gly Cys Arg Lys Asp
225                 230                 235                 240

Asn Phe Asp Ile Ala Glu Gly Val Arg Thr Val Leu Glu Leu Ile Lys
                245                 250                 255

Cys Gln Glu Lys Leu Cys Ile Tyr Trp Met Val Asn Tyr Asn Phe Glu
            260                 265                 270

Asp Glu Thr Ile Arg Asn Ile Leu Leu His Gln Leu Gln Ser Ala Arg
        275                 280                 285

Pro Val Ile Leu Asp Pro Val Asp Pro Thr Asn Asn Val Ser Gly Asp
    290                 295                 300

Lys Ile Cys Trp Gln Trp Leu Lys Lys Glu Ala Gln Thr Trp Leu Thr
305                 310                 315                 320

Ser Pro Asn Leu Asp Asn Glu Leu Pro Ala Pro Ser Trp Asn Val Leu
                325                 330                 335

Pro Ala Pro Leu Phe Thr Thr Pro Gly His Leu Leu Asp Lys Phe Ile
            340                 345                 350

Lys Glu Phe Leu Gln Pro Asn Lys Cys Phe Leu Glu Gln Ile Asp Ser
        355                 360                 365

Ala Val Asn Ile Ile Arg Thr Phe Leu Lys Glu Asn Cys Phe Arg Gln
    370                 375                 380

Ser Thr Ala Lys Ile Gln Ile Val Arg Gly Gly Ser Thr Ala Lys Gly
385                 390                 395                 400

Thr Ala Leu Lys Thr Gly Ser Asp Ala Asp Leu Val Val Phe His Asn
                405                 410                 415

Ser Leu Lys Ser Tyr Thr Ser Gln Lys Asn Glu Arg His Lys Ile Val
            420                 425                 430

Lys Glu Ile His Glu Gln Leu Lys Ala Phe Trp Arg Glu Lys Glu Glu
        435                 440                 445

Glu Leu Glu Val Ser Phe Glu Pro Pro Lys Trp Lys Ala Pro Arg Val
    450                 455                 460

Leu Ser Phe Ser Leu Lys Ser Lys Val Leu Asn Glu Ser Val Ser Phe
465                 470                 475                 480

Asp Val Leu Pro Ala Phe Asn Ala Leu Gly Gln Leu Ser Ser Gly Ser
                485                 490                 495

Thr Pro Ser Pro Glu Val Tyr Ala Gly Leu Ile Asp Leu Tyr Lys Ser
            500                 505                 510

Ser Asp Leu Pro Gly Gly Glu Phe Ser Thr Cys Phe Thr Val Leu Gln
        515                 520                 525

Arg Asn Phe Ile Arg Ser Arg Pro Thr Lys Leu Lys Asp Leu Ile Arg
    530                 535                 540

Leu Val Lys His Trp Tyr Lys Glu Cys Glu Arg Lys Leu Lys Pro Lys
545                 550                 555                 560

Gly Ser Leu Pro Pro Lys Tyr Ala Leu Glu Leu Leu Thr Ile Tyr Ala
```

```
                565                 570                 575

Trp Glu Gln Gly Ser Gly Val Pro Asp Phe Asp Thr Ala Glu Gly Phe
            580                 585                 590

Arg Thr Val Leu Glu Leu Val Thr Gln Tyr Gln Gln Leu Cys Ile Phe
        595                 600                 605

Trp Lys Val Asn Tyr Asn Phe Glu Asp Glu Thr Val Arg Lys Phe Leu
    610                 615                 620

Leu Ser Gln Leu Gln Lys Thr Arg Pro Val Ile Leu Asp Pro Ala Glu
625                 630                 635                 640

Pro Thr Gly Asp Val Gly Gly Gly Asp Arg Trp Cys Trp His Leu Leu
                645                 650                 655

Ala Lys Glu Ala Lys Glu Trp Leu Ser Ser Pro Cys Phe Lys Asp Gly
            660                 665                 670

Thr Gly Asn Pro Ile Pro Pro Trp Lys Val Pro Thr Met Gln Thr Pro
        675                 680                 685

Gly Ser Cys Gly Ala Arg Ile His Pro Ile Val Asn Glu Met Phe Ser
    690                 695                 700

Ser Arg Ser His Arg Ile Leu Asn Asn Asn Ser Lys Arg Asn Phe
705                 710                 715


<210> SEQ ID NO 21
<211> LENGTH: 2226
<212> TYPE: DNA
<213> ORGANISM: Homo sapiens

<400> SEQUENCE: 21

atggagagca gggatcataa caacccccag gagggaccca cgtcctccag cggtagaagg     60

gctgcagtgg aagacaatca cttgctgatt aaagctgttc aaaacgaaga tgttgacctg    120

gtccagcaat tgctggaagg tggagccaat gttaatttcc aggaagagga agggggctgg    180

acacctctgc ataacgcagt acaaatgagc agggaggaca ttgtggaact tctgcttcgt    240

catggtgctg accctgttct gaggaagaag aatggggcca cgccttttat cctcgcagcg    300

attgcgggga gcgtgaagct gctgaaactt ttcctttcta aaggagcaga tgtcaatgag    360

tgtgattttt atggcttcac agccttcatg gaagccgctg tgtatggtaa ggtcaaagcc    420

ctaaaattcc tttataagag aggagcaaat gtgaatttga ggcgaaagac aaaggaggat    480

caagagcggc tgaggaaagg aggggccaca gctctcatgg acgctgctga aaaaggacac    540

gtagaggtct tgaagattct ccttgatgag atgggggcag atgtaaacgc ctgtgacaat    600

atgggcagaa atgccttgat ccatgctctc ctgagctctg acgatagtga tgtggaggct    660

attacgcatc tgctgctgga ccatggggct gatgtcaatg tgaggggaga aagagggaag    720

actcccctga tcctggcagt ggagaagaag cacttgggtt tggtgcagag gcttctggag    780

caagagcaca tagagattaa tgacacagac agtgatggca aaacagcact gctgcttgct    840

gttgaactca aactgaagaa aatcgccgag ttgctgtgca aacgtggagc cagtacagat    900

tgtggggatc ttgttatgac agcgaggcgg aattatgacc attcccttgt gaaggttctt    960

ctctctcatg gagccaaaga agattttcac cctcctgctg aagactggaa gcctcagagc   1020

tcacactggg ggcagccct gaaggatctc cacagaatat accgccctat gattggcaaa   1080

ctcaagttct ttattgatga aaaatacaaa attgctgata cttcagaagg aggcatctac   1140

ctggggttct atgagaagca agaagtagct gtgaagacgt tctgtgaggg cagcccacgt   1200

gcacagcggg aagtctcttg tctgcaaagc agccgagaga acagtcactt ggtgacattc   1260
```

```
tatgggagtg agagccacag gggccacttg tttgtgtgtg tcaccctctg tgagcagact   1320

ctggaagcgt gtttggatgt gcacagaggg gaagatgtgg aaaatgagga agatgaattt   1380

gcccgaaatg tcctgtcatc tatatttaag gctgttcaag aactacactt gtcctgtgga   1440

tacacccacc aggatctgca accacaaaac atcttaatag attctaagaa agctgctcac   1500

ctggcagatt ttgataagag catcaagtgg gctggagatc cacaggaagt caagagagat   1560

ctagaggacc ttggacggct ggtcctctat gtggtaaaga agggaagcat ctcatttgag   1620

gatctgaaag ctcaaagtaa tgaagaggtg gttcaacttt ctccagatga ggaaactaag   1680

gacctcattc atcgtctctt ccatcctggg gaacatgtga gggactgtct gagtgacctg   1740

ctgggtcatc ccttcttttg gacttgggag agccgctata ggacgcttcg gaatgtggga   1800

aatgaatccg acatcaaaac acgaaaatct gaaagtgaga tcctcagact actgcaacct   1860

gggccttctg aacattccaa aagttttgac aagtggacga ctaagattaa tgaatgtgtt   1920

atgaaaaaaa tgaataagtt ttatgaaaaa agaggcaatt tctaccagaa cactgtgggt   1980

gatctgctaa agttcatccg gaatttggga gaacacattg atgaagaaaa gcataaaaag   2040

atgaaattaa aaattggaga cccttccctg tattttcaga agacatttcc agatctggtg   2100

atctatgtct acacaaaact acagaacaca gaatatagaa agcatttccc ccaaacccac   2160

agtccaaaca agcctcagtg tgatggagct ggtggggcca gtgggttggc cagccctggg   2220

tgctga                                                              2226


<210> SEQ ID NO 22
<211> LENGTH: 741
<212> TYPE: PRT
<213> ORGANISM: Homo sapiens

<400> SEQUENCE: 22

Met Glu Ser Arg Asp His Asn Asn Pro Gln Glu Gly Pro Thr Ser Ser
1               5                   10                  15

Ser Gly Arg Arg Ala Ala Val Glu Asp Asn His Leu Leu Ile Lys Ala
            20                  25                  30

Val Gln Asn Glu Asp Val Asp Leu Val Gln Gln Leu Leu Glu Gly Gly
        35                  40                  45

Ala Asn Val Asn Phe Gln Glu Glu Glu Gly Gly Trp Thr Pro Leu His
    50                  55                  60

Asn Ala Val Gln Met Ser Arg Glu Asp Ile Val Glu Leu Leu Leu Arg
65                  70                  75                  80

His Gly Ala Asp Pro Val Leu Arg Lys Lys Asn Gly Ala Thr Pro Phe
                85                  90                  95

Ile Leu Ala Ala Ile Ala Gly Ser Val Lys Leu Leu Lys Leu Phe Leu
            100                 105                 110

Ser Lys Gly Ala Asp Val Asn Glu Cys Asp Phe Tyr Gly Phe Thr Ala
        115                 120                 125

Phe Met Glu Ala Ala Val Tyr Gly Lys Val Lys Ala Leu Lys Phe Leu
    130                 135                 140

Tyr Lys Arg Gly Ala Asn Val Asn Leu Arg Arg Lys Thr Lys Glu Asp
145                 150                 155                 160

Gln Glu Arg Leu Arg Lys Gly Gly Ala Thr Ala Leu Met Asp Ala Ala
                165                 170                 175

Glu Lys Gly His Val Glu Val Leu Lys Ile Leu Leu Asp Glu Met Gly
            180                 185                 190

Ala Asp Val Asn Ala Cys Asp Asn Met Gly Arg Asn Ala Leu Ile His
```

-continued

```
        195                 200                 205

Ala Leu Leu Ser Ser Asp Asp Ser Asp Val Glu Ala Ile Thr His Leu
    210                 215                 220

Leu Leu Asp His Gly Ala Asp Val Asn Val Arg Gly Glu Arg Gly Lys
225                 230                 235                 240

Thr Pro Leu Ile Leu Ala Val Glu Lys Lys His Leu Gly Leu Val Gln
                245                 250                 255

Arg Leu Leu Glu Gln Glu His Ile Glu Ile Asn Asp Thr Asp Ser Asp
            260                 265                 270

Gly Lys Thr Ala Leu Leu Leu Ala Val Glu Leu Lys Leu Lys Lys Ile
        275                 280                 285

Ala Glu Leu Leu Cys Lys Arg Gly Ala Ser Thr Asp Cys Gly Asp Leu
    290                 295                 300

Val Met Thr Ala Arg Arg Asn Tyr Asp His Ser Leu Val Lys Val Leu
305                 310                 315                 320

Leu Ser His Gly Ala Lys Glu Asp Phe His Pro Pro Ala Glu Asp Trp
                325                 330                 335

Lys Pro Gln Ser Ser His Trp Gly Ala Ala Leu Lys Asp Leu His Arg
            340                 345                 350

Ile Tyr Arg Pro Met Ile Gly Lys Leu Lys Phe Phe Ile Asp Glu Lys
        355                 360                 365

Tyr Lys Ile Ala Asp Thr Ser Glu Gly Gly Ile Tyr Leu Gly Phe Tyr
    370                 375                 380

Glu Lys Gln Glu Val Ala Val Lys Thr Phe Cys Glu Gly Ser Pro Arg
385                 390                 395                 400

Ala Gln Arg Glu Val Ser Cys Leu Gln Ser Ser Arg Glu Asn Ser His
                405                 410                 415

Leu Val Thr Phe Tyr Gly Ser Glu Ser His Arg Gly His Leu Phe Val
            420                 425                 430

Cys Val Thr Leu Cys Glu Gln Thr Leu Glu Ala Cys Leu Asp Val His
        435                 440                 445

Arg Gly Glu Asp Val Glu Asn Glu Glu Asp Glu Phe Ala Arg Asn Val
    450                 455                 460

Leu Ser Ser Ile Phe Lys Ala Val Gln Glu Leu His Leu Ser Cys Gly
465                 470                 475                 480

Tyr Thr His Gln Asp Leu Gln Pro Gln Asn Ile Leu Ile Asp Ser Lys
                485                 490                 495

Lys Ala Ala His Leu Ala Asp Phe Asp Lys Ser Ile Lys Trp Ala Gly
            500                 505                 510

Asp Pro Gln Glu Val Lys Arg Asp Leu Glu Asp Leu Gly Arg Leu Val
        515                 520                 525

Leu Tyr Val Val Lys Lys Gly Ser Ile Ser Phe Glu Asp Leu Lys Ala
    530                 535                 540

Gln Ser Asn Glu Glu Val Val Gln Leu Ser Pro Asp Glu Glu Thr Lys
545                 550                 555                 560

Asp Leu Ile His Arg Leu Phe His Pro Gly Glu His Val Arg Asp Cys
                565                 570                 575

Leu Ser Asp Leu Leu Gly His Pro Phe Phe Trp Thr Trp Glu Ser Arg
            580                 585                 590

Tyr Arg Thr Leu Arg Asn Val Gly Asn Glu Ser Asp Ile Lys Thr Arg
        595                 600                 605

Lys Ser Glu Ser Glu Ile Leu Arg Leu Leu Gln Pro Gly Pro Ser Glu
    610                 615                 620
```

His Ser Lys Ser Phe Asp Lys Trp Thr Thr Lys Ile Asn Glu Cys Val
625 630 635 640

Met Lys Lys Met Asn Lys Phe Tyr Glu Lys Arg Gly Asn Phe Tyr Gln
645 650 655

Asn Thr Val Gly Asp Leu Leu Lys Phe Ile Arg Asn Leu Gly Glu His
660 665 670

Ile Asp Glu Glu Lys His Lys Lys Met Lys Leu Lys Ile Gly Asp Pro
675 680 685

Ser Leu Tyr Phe Gln Lys Thr Phe Pro Asp Leu Val Ile Tyr Val Tyr
690 695 700

Thr Lys Leu Gln Asn Thr Glu Tyr Arg Lys His Phe Pro Gln Thr His
705 710 715 720

Ser Pro Asn Lys Pro Gln Cys Asp Gly Ala Gly Gly Ala Ser Gly Leu
725 730 735

Ala Ser Pro Gly Cys
740

<210> SEQ ID NO 23
<211> LENGTH: 1056
<212> TYPE: DNA
<213> ORGANISM: Vaccinia virus

<400> SEQUENCE: 23
atgacgatga aaatgatggt acatatatat ttcgtatcat tattgttatt gctattccac 60
agttacgcca tagacatcga aaatgaaatc acagaattct tcaataaaat gagagatact 120
ctaccagcta aagactctaa atggttgaat ccagcatgta tgttcggagg cacaatgaat 180
gatatagccg ctctaggaga gccattcagc gcaaagtgtc ctcctattga agacagtctt 240
ttatcgcaca gatataaaga ctatgtggtt aaatgggaaa ggctagaaaa aaatagacgg 300
cgacaggttt ctaataaacg tgttaaacat ggtgatttat ggatagccaa ctatacatct 360
aaattcagta accgtaggta tttgtgcacc gtaactacaa agaatggtga ctgtgttcag 420
ggtatagtta gatctcatat tagaaaacct ccttcatgca ttccaaaaac atatgaacta 480
ggtactcatg ataagtatgg catagactta tactgtggaa ttctttacgc aaaacattat 540
aataatataa cttggtataa agataataag gaaattaata tcgacgacat taagtattca 600
caaacgggaa aggaattaat tattcataat ccagagttag aagatagcgg aagatacgac 660
tgttacgttc attacgacga cgttagaatc aagaatgata tcgtagtatc aagatgtaaa 720
atacttacgg ttataccgtc acaagaccac aggtttaaac taatactaga tccaaaaatc 780
aacgtaacga taggagaacc tgccaatata acatgcactg ctgtgtcaac gtcattattg 840
attgacgatg tactgattga atgggaaaat ccatccggat ggcttatagg attcgatttt 900
gatgtatact ctgttttaac tagtagaggc ggtattaccg aggcgacctt gtactttgaa 960
aatgttactg aagaatatat aggtaataca tataaatgtc gtggacacaa ctattatttt 1020
gaaaaaaccc ttacaactac agtagtattg gagtaa 1056

<210> SEQ ID NO 24
<211> LENGTH: 351
<212> TYPE: PRT
<213> ORGANISM: Vaccinia virus

<400> SEQUENCE: 24

Met Thr Met Lys Met Met Val His Ile Tyr Phe Val Ser Leu Leu Leu
1 5 10 15

```
Leu Leu Phe His Ser Tyr Ala Ile Asp Ile Glu Asn Glu Ile Thr Glu
            20                  25                  30

Phe Phe Asn Lys Met Arg Asp Thr Leu Pro Ala Lys Asp Ser Lys Trp
        35                  40                  45

Leu Asn Pro Ala Cys Met Phe Gly Gly Thr Met Asn Asp Ile Ala Ala
    50                  55                  60

Leu Gly Glu Pro Phe Ser Ala Lys Cys Pro Pro Ile Glu Asp Ser Leu
65                  70                  75                  80

Leu Ser His Arg Tyr Lys Asp Tyr Val Val Lys Trp Glu Arg Leu Glu
                85                  90                  95

Lys Asn Arg Arg Arg Gln Val Ser Asn Lys Arg Val Lys His Gly Asp
            100                 105                 110

Leu Trp Ile Ala Asn Tyr Thr Ser Lys Phe Ser Asn Arg Arg Tyr Leu
        115                 120                 125

Cys Thr Val Thr Thr Lys Asn Gly Asp Cys Val Gln Gly Ile Val Arg
    130                 135                 140

Ser His Ile Arg Lys Pro Pro Ser Cys Ile Pro Lys Thr Tyr Glu Leu
145                 150                 155                 160

Gly Thr His Asp Lys Tyr Gly Ile Asp Leu Tyr Cys Gly Ile Leu Tyr
                165                 170                 175

Ala Lys His Tyr Asn Asn Ile Thr Trp Tyr Lys Asp Asn Lys Glu Ile
            180                 185                 190

Asn Ile Asp Asp Ile Lys Tyr Ser Gln Thr Gly Lys Glu Leu Ile Ile
        195                 200                 205

His Asn Pro Glu Leu Glu Asp Ser Gly Arg Tyr Asp Cys Tyr Val His
    210                 215                 220

Tyr Asp Asp Val Arg Ile Lys Asn Asp Ile Val Val Ser Arg Cys Lys
225                 230                 235                 240

Ile Leu Thr Val Ile Pro Ser Gln Asp His Arg Phe Lys Leu Ile Leu
                245                 250                 255

Asp Pro Lys Ile Asn Val Thr Ile Gly Glu Pro Ala Asn Ile Thr Cys
            260                 265                 270

Thr Ala Val Ser Thr Ser Leu Leu Ile Asp Asp Val Leu Ile Glu Trp
        275                 280                 285

Glu Asn Pro Ser Gly Trp Leu Ile Gly Phe Asp Phe Asp Val Tyr Ser
    290                 295                 300

Val Leu Thr Ser Arg Gly Gly Ile Thr Glu Ala Thr Leu Tyr Phe Glu
305                 310                 315                 320

Asn Val Thr Glu Glu Tyr Ile Gly Asn Thr Tyr Lys Cys Arg Gly His
                325                 330                 335

Asn Tyr Tyr Phe Glu Lys Thr Leu Thr Thr Thr Val Val Leu Glu
            340                 345                 350


<210> SEQ ID NO 25
<211> LENGTH: 573
<212> TYPE: DNA
<213> ORGANISM: Vaccinia virus

<400> SEQUENCE: 25

atgtctaaaa tctatatcga cgagcgttct aacgcagaga ttgtgtgtga ggctattaaa      60

accattggaa tcgaaggagc tactgctgca caactaacta gacaacttaa tatggagaag     120

cgagaagtta ataaagctct gtacgatctt caacgtagtg ctatggtgta cagctccgac     180

gatattcctc ctcgttggtt tatgacaacg gaggcggata agccggatgc tgatgctatg     240
```

```
gctgacgtca taatagatga tgtatcccgc gaaaaatcaa tgagagagga tcataagtct    300

tttgatgatg ttattccggc taaaaaaatt attgattgga aaggtgctaa ccctgtcacc    360

gttattaatg agtactgcca aattactagg agagattggt cttttcgtat tgaatcagtg    420

gggcctagta actctcctac attttatgcc tgtgtagaca tcgacggaag agtattcgat    480

aaggcagatg gaaaatctaa acgagatgct aaaaataatg cagctaaatt ggcagtagat    540

aaacttcttg gttacgtcat cattagattc tga                                 573
```

<210> SEQ ID NO 26
<211> LENGTH: 190
<212> TYPE: PRT
<213> ORGANISM: Vaccinia virus

<400> SEQUENCE: 26

```
Met Ser Lys Ile Tyr Ile Asp Glu Arg Ser Asn Ala Glu Ile Val Cys
1               5                   10                  15

Glu Ala Ile Lys Thr Ile Gly Ile Glu Gly Ala Thr Ala Ala Gln Leu
            20                  25                  30

Thr Arg Gln Leu Asn Met Glu Lys Arg Glu Val Asn Lys Ala Leu Tyr
        35                  40                  45

Asp Leu Gln Arg Ser Ala Met Val Tyr Ser Ser Asp Asp Ile Pro Pro
    50                  55                  60

Arg Trp Phe Met Thr Thr Glu Ala Asp Lys Pro Asp Ala Asp Ala Met
65                  70                  75                  80

Ala Asp Val Ile Ile Asp Asp Val Ser Arg Glu Lys Ser Met Arg Glu
                85                  90                  95

Asp His Lys Ser Phe Asp Asp Val Ile Pro Ala Lys Lys Ile Ile Asp
            100                 105                 110

Trp Lys Gly Ala Asn Pro Val Thr Val Ile Asn Glu Tyr Cys Gln Ile
        115                 120                 125

Thr Arg Arg Asp Trp Ser Phe Arg Ile Glu Ser Val Gly Pro Ser Asn
    130                 135                 140

Ser Pro Thr Phe Tyr Ala Cys Val Asp Ile Asp Gly Arg Val Phe Asp
145                 150                 155                 160

Lys Ala Asp Gly Lys Ser Lys Arg Asp Ala Lys Asn Asn Ala Ala Lys
                165                 170                 175

Leu Ala Val Asp Lys Leu Leu Gly Tyr Val Ile Ile Arg Phe
            180                 185                 190
```

<210> SEQ ID NO 27
<211> LENGTH: 267
<212> TYPE: DNA
<213> ORGANISM: Vaccinia virus

<400> SEQUENCE: 27

```
atgcttgcat tttgttattc gttgcccaat gcgggtgatg taataaaggg cagagtatac     60

gagaaggatt atgctctata tatttatctt tttgactatc ctcactttga agctatcttg    120

gcagagagtg ttaagatgca tatggataga tatgttgaat atagggataa actggtaggg    180

aaaactgtaa aagttaaagt gattagagtt gattatacaa aaggatatat agatgtcaat    240

tacaaaagga tgtgtagaca tcaataa                                        267
```

<210> SEQ ID NO 28
<211> LENGTH: 88
<212> TYPE: PRT

-continued

<213> ORGANISM: Vaccinia virus

<400> SEQUENCE: 28

```
Met Leu Ala Phe Cys Tyr Ser Leu Pro Asn Ala Gly Asp Val Ile Lys
1               5                   10                  15

Gly Arg Val Tyr Glu Lys Asp Tyr Ala Leu Tyr Ile Tyr Leu Phe Asp
            20                  25                  30

Tyr Pro His Phe Glu Ala Ile Leu Ala Glu Ser Val Lys Met His Met
        35                  40                  45

Asp Arg Tyr Val Glu Tyr Arg Asp Lys Leu Val Gly Lys Thr Val Lys
    50                  55                  60

Val Lys Val Ile Arg Val Asp Tyr Thr Lys Gly Tyr Ile Asp Val Asn
65                  70                  75                  80

Tyr Lys Arg Met Cys Arg His Gln
                85
```

<210> SEQ ID NO 29
<211> LENGTH: 685
<212> TYPE: PRT
<213> ORGANISM: Hepatitis C virus

<400> SEQUENCE: 29

```
Ala Pro Ile Thr Ala Tyr Ala Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Ile Val Ser Thr Ala Thr Gln Thr Phe Leu Ala Thr Cys Ile
        35                  40                  45

Asn Gly Val Cys Trp Thr Val Tyr His Gly Ala Gly Thr Arg Thr Ile
    50                  55                  60

Ala Ser Pro Lys Gly Pro Val Ile Gln Met Tyr Thr Asn Val Asp Gln
65                  70                  75                  80

Asp Leu Val Gly Trp Pro Ala Pro Gln Gly Ser Arg Ser Leu Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
        115                 120                 125

Pro Arg Pro Ile Ser Tyr Leu Lys Gly Ser Ser Gly Gly Pro Leu Leu
    130                 135                 140

Cys Pro Ala Gly His Ala Val Gly Leu Phe Arg Ala Ala Val Cys Thr
145                 150                 155                 160

Arg Gly Val Ala Lys Ala Val Asp Phe Ile Pro Val Glu Asn Leu Glu
                165                 170                 175

Thr Thr Met Arg Ser Pro Val Phe Thr Asp Asn Ser Ser Pro Pro Ala
            180                 185                 190

Val Pro Gln Ser Phe Gln Val Ala His Leu His Ala Pro Thr Gly Ser
        195                 200                 205

Gly Lys Ser Thr Lys Val Pro Ala Ala Tyr Ala Ala Gln Gly Tyr Lys
    210                 215                 220

Val Leu Val Leu Asn Pro Ser Val Ala Ala Thr Leu Gly Phe Gly Ala
225                 230                 235                 240

Tyr Met Ser Lys Ala His Gly Val Asp Pro Asn Ile Arg Thr Gly Val
                245                 250                 255

Arg Thr Ile Thr Thr Gly Ser Pro Ile Thr Tyr Ser Thr Tyr Gly Lys
```

-continued

```
            260                 265                 270

Phe Leu Ala Asp Gly Gly Cys Ser Gly Gly Ala Tyr Asp Ile Ile Ile
        275                 280                 285

Cys Asp Glu Cys His Ser Thr Asp Ala Thr Ser Ile Leu Gly Ile Gly
    290                 295                 300

Thr Val Leu Asp Gln Ala Glu Thr Ala Gly Ala Arg Leu Val Val Leu
305                 310                 315                 320

Ala Thr Ala Thr Pro Pro Gly Ser Val Thr Val Ser His Pro Asn Ile
                325                 330                 335

Glu Glu Val Ala Leu Ser Thr Thr Gly Glu Ile Pro Phe Tyr Gly Lys
            340                 345                 350

Ala Ile Pro Leu Glu Val Ile Lys Gly Gly Arg His Leu Ile Phe Cys
        355                 360                 365

His Ser Lys Lys Lys Cys Asp Glu Leu Ala Ala Lys Leu Val Ala Leu
    370                 375                 380

Gly Ile Asn Ala Val Ala Tyr Tyr Arg Gly Leu Asp Val Ser Val Ile
385                 390                 395                 400

Pro Thr Ser Gly Asp Val Val Val Val Ser Thr Asp Ala Leu Met Thr
                405                 410                 415

Gly Phe Thr Gly Asp Phe Asp Ser Val Ile Asp Cys Asn Thr Cys Val
            420                 425                 430

Thr Gln Thr Val Asp Phe Ser Leu Asp Pro Thr Phe Thr Ile Glu Thr
        435                 440                 445

Thr Thr Leu Pro Gln Asp Ala Val Ser Arg Thr Gln Arg Arg Gly Arg
    450                 455                 460

Thr Gly Arg Gly Lys Pro Gly Ile Tyr Arg Phe Val Ala Pro Gly Glu
465                 470                 475                 480

Arg Pro Ser Gly Met Phe Asp Ser Ser Val Leu Cys Glu Cys Tyr Asp
                485                 490                 495

Ala Gly Cys Ala Trp Tyr Glu Leu Thr Pro Ala Glu Thr Thr Val Arg
            500                 505                 510

Leu Arg Ala Tyr Met Asn Thr Pro Gly Leu Pro Val Cys Gln Asp His
        515                 520                 525

Leu Glu Phe Trp Glu Gly Val Phe Thr Gly Leu Thr His Ile Asp Ala
    530                 535                 540

His Phe Leu Ser Gln Thr Lys Gln Ser Gly Glu Asn Phe Pro Tyr Leu
545                 550                 555                 560

Val Ala Tyr Gln Ala Thr Val Cys Ala Arg Ala Gln Ala Pro Pro Pro
                565                 570                 575

Ser Trp Asp Gln Met Trp Lys Cys Leu Ile Arg Leu Lys Pro Thr Leu
            580                 585                 590

His Gly Pro Thr Pro Leu Leu Tyr Arg Leu Gly Ala Val Gln Asn Glu
        595                 600                 605

Val Thr Leu Thr His Pro Ile Thr Lys Tyr Ile Met Thr Cys Met Ser
    610                 615                 620

Ala Asp Leu Glu Val Val Thr Ser Thr Trp Val Leu Val Gly Gly Val
625                 630                 635                 640

Leu Ala Ala Leu Ala Ala Tyr Cys Leu Ser Thr Gly Cys Val Val Ile
                645                 650                 655

Val Gly Arg Ile Val Leu Ser Gly Lys Pro Ala Ile Ile Pro Asp Arg
            660                 665                 670

Glu Val Leu Tyr Gln Glu Phe Asp Glu Met Glu Glu Cys
        675                 680                 685
```

```
<210> SEQ ID NO 30
<211> LENGTH: 263
<212> TYPE: PRT
<213> ORGANISM: Herpes simplex virus

<400> SEQUENCE: 30

Met Ala Arg Arg Arg Arg His Arg Gly Pro Arg Arg Pro Arg Pro Pro
1               5                   10                  15

Gly Pro Thr Gly Ala Val Pro Thr Ala Gln Ser Gln Val Thr Ser Thr
            20                  25                  30

Pro Asn Ser Glu Pro Ala Val Arg Ser Ala Pro Ala Ala Ala Pro Pro
        35                  40                  45

Pro Pro Pro Ala Ser Gly Pro Pro Pro Ser Cys Ser Leu Leu Leu Arg
    50                  55                  60

Gln Trp Leu His Val Pro Glu Ser Ala Ser Asp Asp Asp Asp Asp Asp
65                  70                  75                  80

Asp Trp Pro Asp Ser Pro Pro Pro Glu Pro Ala Pro Glu Ala Arg Pro
                85                  90                  95

Thr Ala Ala Ala Pro Arg Pro Arg Ser Pro Pro Pro Gly Ala Gly Pro
            100                 105                 110

Gly Gly Gly Ala Asn Pro Ser His Pro Pro Ser Arg Pro Phe Arg Leu
        115                 120                 125

Pro Pro Arg Leu Ala Leu Arg Leu Arg Val Thr Ala Glu His Leu Ala
    130                 135                 140

Arg Leu Arg Leu Arg Arg Ala Gly Gly Glu Gly Ala Pro Glu Pro Pro
145                 150                 155                 160

Ala Thr Pro Ala Thr Pro Ala Thr Pro Ala Thr Pro Ala Thr Pro Ala
                165                 170                 175

Thr Pro Ala Thr Pro Ala Thr Pro Ala Thr Pro Ala Thr Pro Ala Arg
            180                 185                 190

Val Arg Phe Ser Pro His Val Arg Val Arg His Leu Val Val Trp Ala
        195                 200                 205

Ser Ala Ala Arg Leu Ala Arg Arg Gly Ser Trp Ala Arg Glu Arg Ala
    210                 215                 220

Asp Arg Ala Arg Phe Arg Arg Arg Val Ala Glu Ala Glu Ala Val Ile
225                 230                 235                 240

Gly Pro Cys Leu Gly Pro Glu Ala Arg Ala Arg Ala Leu Ala Arg Gly
                245                 250                 255

Ala Gly Pro Ala Asn Ser Val
            260
```

METHOD FOR CELLULAR RNA EXPRESSION

RELATED APPLICATIONS

This application is a continuation of International Application No. PCT/EP2013/003362, which designated the United States and was filed on Nov. 7, 2013, published in English, which claims priority to International Application No. PCT/EP2013/002234, which designated the United States and was filed on Jul. 29, 2013, published in English and International Application No. PCT/EP2012/004673, which designated the United States and was filed on Nov. 9, 2012, published in English.

The entire teachings of the above applications are incorporated herein by reference.

TECHNICAL FIELD OF THE INVENTION

The present invention relates to expressing RNA in cells and, in particular, enhancing viability of cells in which RNA is to be expressed. The cells are preferably transfected with the RNA such as by repetitive transfection. Specifically, the present invention provides methods for expressing RNA in cells comprising the steps of preventing engagement of IFN receptor by extracellular IFN and inhibiting intracellular IFN signalling in the cells. Preventing engagement of IFN receptor by extracellular IFN and inhibiting intracellular IFN signalling in the cells allows stable expression of RNA in the cells, in particular, if cells are transfected repetitively with RNA. Alternatively or additionally, preventing engagement of IFN receptor by extracellular IFN and inhibiting intracellular IFN signalling enhances survival of the cells, in particular, if cells are transfected repetitively with RNA. Thus, preventing engagement of IFN receptor by extracellular IFN and inhibiting intracellular IFN signalling in the cells allows repetitive transfer of RNA into the cells.

BACKGROUND OF THE INVENTION

The advantages of using RNA as a kind of reversible gene therapy include transient expression and a non-transforming character. RNA does not need to enter the nucleus in order to be expressed and moreover cannot integrate into the host genome, thereby eliminating the risk of oncogenesis. Transfection rates attainable with RNA are relatively high, for many cell types even >90%, and therefore, there is no need for selection of transfected cells. Furthermore, the amounts of protein achieved correspond to those in physiological expression.

RNA has been described for as being useful in de-differentiating somatic cells into stem-like cells without generating embryos or fetuses. De-differentiation of somatic cells to cells having stem cell characteristics, in particular pluripotency, can be effected by introducing RNA encoding factors inducing the de-differentiation of somatic cells into the somatic cells (also termed reprogramming transcription factors (rTF)) and culturing the somatic cells allowing the cells to de-differentiate. After being de-differentiated, the cells could be induced to re-differentiate into the same or a different somatic cell type such as neuronal, hematopoietic, muscle, epithelial, and other cell types. Thus, such stem-like cells have medical applications for treatment of degenerative diseases by “cell therapy” and may be utilized in novel therapeutic strategies in the treatment of cardiac, neurological, endocrinological, vascular, retinal, dermatological, muscular-skeletal disorders, and other diseases.

Furthermore, the use of RNA provides an attractive alternative to circumvent the potential risks of DNA based vaccines. As with DNA, transfer of RNA into cells can also induce both the cellular and humoral immune responses in vivo. In particular, two different strategies have been pursued for immunotherapy with in vitro transcribed RNA (IVT-RNA), which have both been successfully tested in various animal models. Either the RNA is directly injected into the patient by different immunization routes or cells are transfected with IVT-RNA using conventional transfection methods in vitro and then the transfected cells are administered to the patient. RNA may, for example, be translated and the expressed protein presented on the MHC molecules on the surface of the cells to elicit an immune response.

It has been attempted to stabilize IVT-RNA by various modifications in order to achieve higher and prolonged expression of transferred IVT-RNA. However, despite the success of RNA transfection-based strategies to express peptides and proteins in cells, there remain issues related to RNA stability, sustained expression of the encoded peptide or protein and cytotoxicity of the RNA. For example, it is known that exogenous single-stranded RNA activates defense mechanisms in mammalian cells. Furthermore, reprogramming of somatic cells into induced pluripotent stem cells (iPS) requires the continuous expression of reprogramming transcription factors (rTF) and thus, the delivery has to be performed repetitively to assure constant expression of the rTF. However, as demonstrated herein, repetitive RNA-based gene transfer is accompanied with an induction of the IFN-response which hinders the continuous expression of rTF when delivered as mRNA and therefore successful RNA-based reprogramming.

SUMMARY OF THE INVENTION

The invention relates to a method for expressing RNA in a cell comprising the steps of (i) preventing engagement of IFN receptor by extracellular IFN and (ii) inhibiting intracellular IFN signalling.

In one embodiment, the RNA is or has been introduced into the cell such as by electroporation or lipofection. In one embodiment, the RNA is or has been introduced into the cell repetitively.

In one embodiment, the RNA is in vitro transcribed RNA.

In one embodiment, preventing engagement of IFN receptor by extracellular IFN inhibits autocrine and/or paracrine IFN functions. In one embodiment, preventing engagement of IFN receptor by extracellular IFN comprises providing a binding agent for extracellular IFN such as a viral binding agent for extracellular IFN. In one embodiment, the viral binding agent for extracellular IFN is a viral interferon receptor. In one embodiment, the viral binding agent for extracellular IFN is vaccinia virus B18R. In one embodiment, the viral binding agent for extracellular IFN is provided to the cell in the form of a nucleic acid encoding the binding agent, wherein the nucleic acid is preferably RNA which preferably is or has been introduced into the cell together with the RNA which is to be expressed in the cell.

In one embodiment, the intracellular IFN signalling if not inhibited according to the invention results in inhibition of translation and/or RNA degradation. In one embodiment, inhibiting intracellular IFN signalling comprises inhibiting one or more IFN-inducible antivirally active effector proteins. In one embodiment, the IFN-inducible antivirally active effector protein is selected from the group consisting of RNA-dependent protein kinase (PKR), 2',5'-oligoadenylate synthetase (OAS) and RNaseL.

In one embodiment, inhibiting intracellular IFN signalling comprises inhibiting the PKR-dependent pathway and/or the OAS-dependent pathway.

In one embodiment, inhibiting the PKR-dependent pathway comprises inhibiting eIF2-alpha phosphorylation. In one embodiment, inhibiting eIF2-alpha phosphorylation comprises inhibiting PKR and/or providing a pseudosubstrate mimicking eIF2-alpha. In one embodiment, the pseudosubstrate mimicking eIF2-alpha is a viral pseudosubstrate mimicking eIF2-alpha. In one embodiment, the viral pseudosubstrate mimicking eIF2-alpha is vaccinia virus K3. In one embodiment, the viral pseudosubstrate mimicking eIF2-alpha is provided to the cell in the form of a nucleic acid encoding the viral pseudosubstrate, wherein the nucleic acid is preferably RNA which preferably is or has been introduced into the cell together with the RNA which is to be expressed in the cell.

In one embodiment, inhibiting PKR comprises treating the cell with at least one PKR inhibitor. In one embodiment, the PKR inhibitor inhibits RNA-induced PKR autophosphorylation. In one embodiment, the PKR inhibitor is an ATP-binding site directed inhibitor of PKR. In one embodiment, the PKR inhibitor is an imidazolo-oxindole compound. In one embodiment, the PKR inhibitor is 6,8-dihydro-8-(1H-imidazol-5-ylmethylene)-7H-pyrrolo[2,3-g]benzothiazol-7-one and/or 2-aminopurine. In one embodiment, the PKR inhibitor is a viral inhibitor of PKR. In one embodiment, the viral inhibitor of PKR is vaccinia virus E3. In one embodiment, the viral inhibitor of PKR is provided to the cell in the form of a nucleic acid encoding the inhibitor, wherein the nucleic acid is preferably RNA which preferably is or has been introduced into the cell together with the RNA which is to be expressed in the cell. In one embodiment, inhibiting PKR comprises silencing expression of the PKR gene.

In one embodiment, inhibiting the OAS-dependent pathway comprises inhibiting activation of RNaseL. In one embodiment, inhibiting the OAS-dependent pathway comprises inhibiting OAS.

In one embodiment, inhibiting OAS comprises treating the cell with at least one OAS inhibitor. In one embodiment, the OAS inhibitor is a viral inhibitor of OAS. In one embodiment, the viral inhibitor of OAS is vaccinia virus E3. In one embodiment, the viral inhibitor of OAS is provided to the cell in the form of a nucleic acid encoding the inhibitor, wherein the nucleic acid is preferably RNA which preferably is or has been introduced into the cell together with the RNA which is to be expressed in the cell.

In one embodiment, the RNA expressed in the cell is not modified by pseudouridine and/or 5-methylcytidine.

In one embodiment, the steps of (i) preventing engagement of IFN receptor by extracellular IFN and (ii) inhibiting intracellular IFN signalling result in an enhancement of stability and/or an enhancement of expression of the RNA in the cell compared to the situation where engagement of IFN receptor by extracellular IFN is not prevented and/or intracellular IFN signalling is not inhibited. In one embodiment, the enhancement of expression of the RNA in the cell preferably comprises an increase in the level of expression and/or an increase in the duration of expression of the RNA in the cell.

In one embodiment, the steps of (i) preventing engagement of IFN receptor by extracellular IFN and (ii) inhibiting intracellular IFN signalling result in an enhancement of cell viability compared to the situation where engagement of IFN receptor by extracellular IFN is not prevented and/or intracellular IFN signalling is not inhibited.

In one embodiment, the steps of (i) preventing engagement of IFN receptor by extracellular IFN and (ii) inhibiting intracellular IFN signalling comprise treating the cell with (i) vaccinia virus B18R and (ii) vaccinia virus E3 or vaccinia virus K3, or both. In one embodiment, the vaccinia virus B18R, vaccinia virus E3 and/or vaccinia virus K3 are provided to the cell in the form of nucleic acid encoding the vaccinia virus B18R, vaccinia virus E3 and/or vaccinia virus K3, either on the same or on two or more different nucleic acid molecules, wherein the nucleic acid is preferably RNA which preferably is or has been introduced into the cell together with the RNA which is to be expressed in the cell.

In one embodiment, the cell is a cell having a barrier function. In one embodiment, the cell is a fibroblast, a keratinocyte, an epithelial cell, or an endothelial cell, wherein the endothelial cell preferably is an endothelial cell of the heart, an endothelial cell of the lung, or an umbilical vein endothelial cell. Preferably, the cell is a human cell.

The invention also relates to the use of (i) means which are suitable for preventing engagement of IFN receptor by extracellular IFN and (ii) means which are suitable for inhibiting intracellular IFN signalling, such as the means described herein, for treating a cell in which RNA is to be expressed. Various embodiments of this method and the means useful therein are described above.

The invention also relates to a method for providing cells having stem cell characteristics comprising the steps of (i) providing a cell population comprising somatic cells, (ii) preventing engagement of IFN receptor of the somatic cells by extracellular IFN, (iii) inhibiting intracellular IFN signalling in the somatic cells, (iv) introducing RNA capable of expressing one or more factors allowing the reprogramming of the somatic cells to cells having stem cell characteristics into the somatic cells, and (v) allowing the development of cells having stem cell characteristics.

In one embodiment, the method further comprises introducing into the somatic cells miRNA enhancing reprogramming of the somatic cells to cells having stem cell characteristics.

In one embodiment, the one or more factors comprise OCT4 and SOX2. The one or more factors may further comprise KLF4 and/or c-MYC and/or NANOG and/or LIN28. In one embodiment, the one or more factors comprise OCT4, SOX2, KLF4 and c-MYC and may further comprise LIN28 and optionally NANOG. In one embodiment, the one or more factors comprise OCT4, SOX2, NANOG and LIN28.

In one embodiment, the method further comprises the step of culturing the somatic cells in the presence of at least one histone deacetylase inhibitor, wherein the at least one histone deacetylase inhibitor preferably comprises valproic acid, sodium butyrate, trichostatin A and/or scriptaid.

In one embodiment, step (v) comprises culturing the somatic cells under embryonic stem cell culture conditions.

In one embodiment, the stem cell characteristics comprise an embryonic stem cell morphology.

In one embodiment, the cells having stem cell characteristics have normal karyotypes, express telomerase activity, express cell surface markers that are characteristic for embryonic stem cells and/or express genes that are characteristic for embryonic stem cells.

In one embodiment, the cells having stem cell characteristics exhibit a pluripotent state. In one embodiment, the cells having stem cell characteristics have the developmental potential to differentiate into advanced derivatives of all three primary germ layers.

In one embodiment, the somatic cells are fibroblasts such as lung fibroblasts, foreskin fibroblasts or dermal fibroblasts. Preferably, the somatic cells are human cells.

In one embodiment, the RNA is introduced into the somatic cells by electroporation or lipofection. In one embodiment, the RNA is introduced into the somatic cells repetitively.

In one embodiment, the RNA is in vitro transcribed RNA.

In one embodiment, preventing engagement of IFN receptor by extracellular IFN inhibits autocrine and/or paracrine IFN functions. In one embodiment, preventing engagement of IFN receptor by extracellular IFN comprises providing a binding agent for extracellular IFN such as a viral binding agent for extracellular IFN. In one embodiment, the viral binding agent for extracellular IFN is a viral interferon receptor. In one embodiment, the viral binding agent for extracellular IFN is vaccinia virus B18R. In one embodiment, the viral binding agent for extracellular IFN is provided to the somatic cells in the form of a nucleic acid encoding the binding agent, wherein the nucleic acid is preferably RNA which preferably is or has been introduced into the somatic cells together with the RNA capable of expressing one or more factors allowing the reprogramming of the somatic cells to cells having stem cell characteristics.

In one embodiment, the intracellular IFN signalling if not inhibited according to the invention results in inhibition of translation and/or RNA degradation. In one embodiment, inhibiting intracellular IFN signalling comprises inhibiting one or more IFN-inducible antivirally active effector proteins. In one embodiment, the IFN-inducible antivirally active effector protein is selected from the group consisting of RNA-dependent protein kinase (PKR), 2',5'-oligoadenylate synthetase (OAS) and RNaseL.

In one embodiment, inhibiting intracellular IFN signalling comprises inhibiting the PKR-dependent pathway and/or the OAS-dependent pathway.

In one embodiment, inhibiting the PKR-dependent pathway comprises inhibiting eIF2-alpha phosphorylation. In one embodiment, inhibiting eIF2-alpha phosphorylation comprises inhibiting PKR and/or providing a pseudosubstrate mimicking eIF2-alpha. In one embodiment, the pseudosubstrate mimicking eIF2-alpha is a viral pseudosubstrate mimicking eIF2-alpha. In one embodiment, the viral pseudosubstrate mimicking eIF2-alpha is vaccinia virus K3. In one embodiment, the viral pseudosubstrate mimicking eIF2-alpha is provided to the somatic cells in the form of a nucleic acid encoding the viral pseudosubstrate, wherein the nucleic acid is preferably RNA which preferably is or has been introduced into the somatic cells together with the RNA capable of expressing one or more factors allowing the reprogramming of the somatic cells to cells having stem cell characteristics.

In one embodiment, inhibiting PKR comprises treating the cell with at least one PKR inhibitor. In one embodiment, the PKR inhibitor inhibits RNA-induced PKR autophosphorylation. In one embodiment, the PKR inhibitor is an ATP-binding site directed inhibitor of PKR. In one embodiment, the PKR inhibitor is an imidazolo-oxindole compound.

In one embodiment, the PKR inhibitor is 6,8-dihydro-8-(1H-imidazol-5-ylmethylene)-7H-pyrrolo[2,3-g]benzothiazol-7-one and/or 2-aminopurine. In one embodiment, the PKR inhibitor is a viral inhibitor of PKR. In one embodiment, the viral inhibitor of PKR is vaccinia virus E3. In one embodiment, the viral inhibitor of PKR is provided to the somatic cells in the form of a nucleic acid encoding the inhibitor, wherein the nucleic acid is preferably RNA which preferably is or has been introduced into the somatic cells together with the RNA capable of expressing one or more factors allowing the reprogramming of the somatic cells to cells having stem cell characteristics. In one embodiment, inhibiting PKR comprises silencing expression of the PKR gene.

In one embodiment, inhibiting the OAS-dependent pathway comprises inhibiting activation of RNaseL. In one embodiment, inhibiting the OAS-dependent pathway comprises inhibiting OAS.

In one embodiment, inhibiting OAS comprises treating the somatic cells with at least one OAS inhibitor. In one embodiment, the OAS inhibitor is a viral inhibitor of OAS. In one embodiment, the viral inhibitor of OAS is vaccinia virus E3. In one embodiment, the viral inhibitor of OAS is provided to the somatic cells in the form of a nucleic acid encoding the inhibitor, wherein the nucleic acid is preferably RNA which preferably is or has been introduced into the somatic cells together with the RNA capable of expressing one or more factors allowing the reprogramming of the somatic cells to cells having stem cell characteristics.

In one embodiment, the RNA capable of expressing one or more factors allowing the reprogramming of the somatic cells to cells having stem cell characteristics is not modified by pseudouridine and/or 5-methylcytidine.

In one embodiment, the steps of (i) preventing engagement of IFN receptor by extracellular IFN and (ii) inhibiting intracellular IFN signalling result in an enhancement of stability and/or an enhancement of expression of the RNA capable of expressing one or more factors allowing the reprogramming of the somatic cells to cells having stem cell characteristics in the somatic cells compared to the situation where engagement of IFN receptor by extracellular IFN is not prevented and/or intracellular IFN signalling is not inhibited. In one embodiment, the enhancement of expression of the RNA in the somatic cells preferably comprises an increase in the level of expression and/or an increase in the duration of expression of the RNA in the somatic cells.

In one embodiment, the steps of (i) preventing engagement of IFN receptor by extracellular IFN and (ii) inhibiting intracellular IFN signalling result in an enhancement of cell viability compared to the situation where engagement of IFN receptor by extracellular IFN is not prevented and/or intracellular IFN signalling is not inhibited.

In one embodiment, the steps of (i) preventing engagement of IFN receptor by extracellular IFN and (ii) inhibiting intracellular IFN signalling comprise treating the somatic cells with (i) vaccinia virus B18R and (ii) vaccinia virus E3 or vaccinia virus K3, or both. In one embodiment, the vaccinia virus B18R, vaccinia virus E3 and/or vaccinia virus K3 are provided to the somatic cells in the form of nucleic acid encoding the vaccinia virus B18R, vaccinia virus E3 and/or vaccinia virus K3, either on the same or on two or more different nucleic acid molecules, wherein the nucleic acid is preferably RNA which preferably is introduced or has been introduced into the somatic cells together with the RNA capable of expressing one or more factors allowing the reprogramming of the somatic cells to cells having stem cell characteristics.

The invention also relates to a method for providing differentiated cell types comprising the steps of (i) providing cells having stem cell characteristics using the method for providing cells having stem cell characteristics according to the invention, and (ii) culturing the cells having stem cell characteristics under conditions that induce or direct partial or complete differentiation to a differentiated cell type.

The invention also relates to a composition comprising (i) an agent useful for preventing engagement of IFN receptor by extracellular IFN and (ii) an agent useful for inhibiting intracellular IFN signalling. Furthermore, the invention also relates to a kit comprising the composition of the invention. Various embodiments of the composition or kit of the invention are described above for the methods of the invention. In one embodiment, the composition or kit of the invention is useful in the methods of the invention.

In one embodiment, the composition or kit of the invention comprises RNA to be introduced into a cell for expression, e.g. RNA capable of expressing one or more factors allowing the reprogramming of somatic cells to cells having stem cell characteristics as described above.

In one embodiment, an agent useful for preventing engagement of IFN receptor by extracellular IFN inhibits autocrine and/or paracrine IFN functions. In one embodiment, an agent useful for preventing engagement of IFN receptor by extracellular IFN comprises a binding agent for extracellular IFN such as a viral binding agent for extracellular IFN. In one embodiment, the viral binding agent for extracellular IFN is a viral interferon receptor. In one embodiment, the viral binding agent for extracellular IFN is vaccinia virus B18R. In one embodiment, the viral binding agent for extracellular IFN is present in the form of a nucleic acid encoding the binding agent, wherein the nucleic acid is preferably RNA.

In one embodiment, an agent useful for inhibiting intracellular IFN signalling comprises an agent inhibiting one or more IFN-inducible antivirally active effector proteins. In one embodiment, the IFN-inducible antivirally active effector protein is selected from the group consisting of RNA-dependent protein kinase (PKR), 2',5'-oligoadenylate synthetase (OAS) and RNaseL.

In one embodiment, an agent useful for inhibiting intracellular IFN signalling comprises an agent useful for inhibiting the PKR-dependent pathway and/or the OAS-dependent pathway.

In one embodiment, an agent useful for inhibiting the PKR-dependent pathway comprises an agent useful for inhibiting eIF2-alpha phosphorylation. In one embodiment, an agent useful for inhibiting eIF2-alpha phosphorylation comprises an agent useful for inhibiting PKR and/or a pseudosubstrate mimicking eIF2-alpha. In one embodiment, the pseudosubstrate mimicking eIF2-alpha is a viral pseudosubstrate mimicking eIF2-alpha. In one embodiment, the viral pseudosubstrate mimicking eIF2-alpha is vaccinia virus K3. In one embodiment, the viral pseudosubstrate mimicking eIF2-alpha is present in the form of a nucleic acid encoding the viral pseudosubstrate, wherein the nucleic acid is preferably RNA.

In one embodiment, an agent useful for inhibiting PKR comprises at least one PKR inhibitor. In one embodiment, the PKR inhibitor inhibits RNA-induced PKR autophosphorylation. In one embodiment, the PKR inhibitor is an ATP-binding site directed inhibitor of PKR. In one embodiment, the PKR inhibitor is an imidazolo-oxindole compound. In one embodiment, the PKR inhibitor is 6,8-dihydro-8-(1H-imidazol-5-ylmethylene)-7H-pyrrolo[2,3-g]benzothiazol-7-one and/or 2-aminopurine. In one embodiment, the PKR inhibitor is a viral inhibitor of PKR. In one embodiment, the viral inhibitor of PKR is vaccinia virus E3. In one embodiment, the viral inhibitor of PKR is present in the form of a nucleic acid encoding the inhibitor, wherein the nucleic acid is preferably RNA. In one embodiment, an agent useful for inhibiting PKR comprises an agent useful for silencing expression of the PKR gene.

In one embodiment, an agent useful for inhibiting the OAS-dependent pathway comprises an agent useful for inhibiting activation of RNaseL. In one embodiment, an agent useful for inhibiting the OAS-dependent pathway comprises an agent useful for inhibiting OAS.

In one embodiment, an agent useful for inhibiting OAS comprises at least one OAS inhibitor. In one embodiment, the OAS inhibitor is a viral inhibitor of OAS. In one embodiment, the viral inhibitor of OAS is vaccinia virus E3. In one embodiment, the viral inhibitor of OAS is present in the form of a nucleic acid encoding the inhibitor, wherein the nucleic acid is preferably RNA.

In one embodiment, an agent useful for preventing engagement of IFN receptor by extracellular IFN and an agent useful for inhibiting intracellular IFN signalling comprise (i) vaccinia virus B18R and (ii) vaccinia virus E3 or vaccinia virus K3, or both. In one embodiment, the vaccinia virus B18R, vaccinia virus E3 and/or vaccinia virus K3 are present in the form of nucleic acid encoding the vaccinia virus B18R, vaccinia virus E3 and/or vaccinia virus K3, either on the same or on two or more different nucleic acid molecules, wherein the nucleic acid is preferably RNA.

Figure 1:
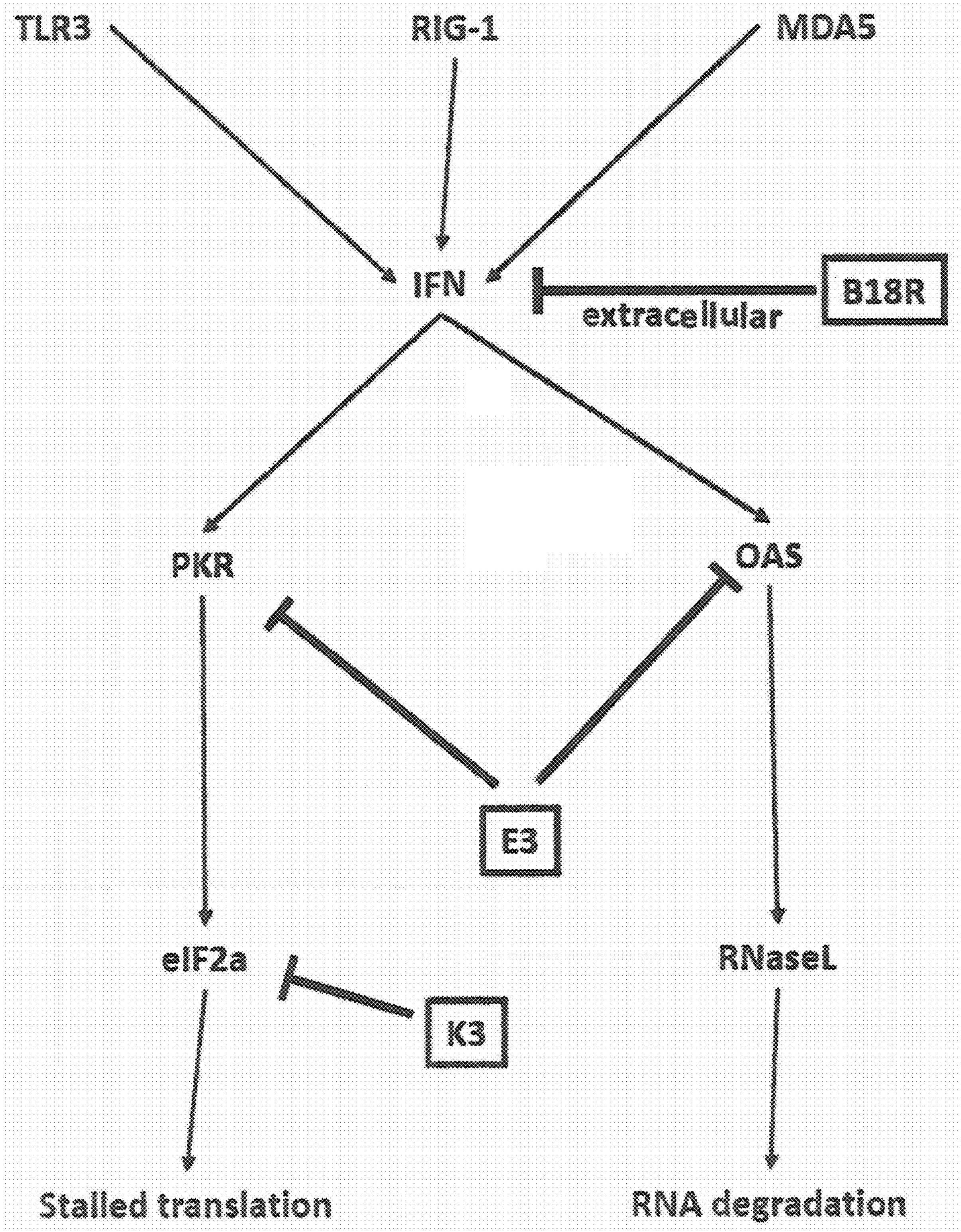
FIG. 1: Viral Escape Mechanism

Viruses have evolved many escape mechanism that are mediated by viral proteins or viral nucleic acids. RNA that codes for these viral escape proteins can easily be co-transfered with RNA coding for rTF. Antagonistic protein E3 (Vaccinia virus) acts on PKR & OAS, K3 (Vaccinia virus) acts on eIF2a and B18R (Vaccinia virus) acts on IFN. Whereas E3 and K3 are acting intracellular, B18R protein coded by IVT-RNA is secreted from the cell where it binds extracellular type I IFNs and prevents engagement of IFN receptors.

FIG. 2A-2E: Repetitive Transfer of IVT-RNA (Reprogramming-TF)

(A) CCD1079Sk fibroblasts were electroporated as indicated in the side panel either with 15 μg or 5 μg of each in vitro transcribed (IVT)-RNA encoding the transcription factors OCT4 (O), SOX2 (S), KLF4 (K) and cMYC (M) and cultivated in human embryonic stem (ES) cell medium. Electroporations were performed in 4 mm gap cuvettes using optimized parameters for CCD1079Sk fibroblasts. At the indicated time points, 10% of the cells were removed from the cultures prior to subsequent electroporation, total RNA was isolated and mRNA-expression of the human ES-marker genes OCT4 (endogenous), TERT, GDF3 and DPPA4 was quantified by qRT-PCR. (B) CCD1079Sk fibroblasts were electroporated as indicated in the side panel with 15 μg of each IVT-RNA encoding the transcription factors OSKM and cultivated in human ES cell medium. Electroporations were performed in 4 mm gap cuvettes using optimized parameters for CCD1079Sk fibroblasts. At the indicated time points remaining cells were counted and survival rate in relation to the starting cells was calculated. (C) CCD1079Sk fibroblasts were electroporated with 1 μg IVT RNA encoding for firefly luciferase (Luc) and 5 μg IVT RNA encoding for green fluorescent protein (GFP). Electroporations were performed in 2 mm gap cuvettes using optimized parameters for CCD1079Sk fibroblasts. 24 h post electroporation, cells were pelleted, total RNA was isolated and mRNA-expression of Interferon (IFN)-a and -b was quantified by qRT-PCR. (D) CCD1079Sk fibroblasts were electroporated with 33.4 μg IVT RNA encoding reprogramming mixture (29.5 μg rTF (OSKM NANOG (N) LIN28 (L) (1:1:1:1:1:1)), 1.3 μg SV40 largeT antigen (lgT), 1.3 μg HTLV E6 and 1.25 μg GFP). Electroporations were performed in 4 mm gap cuvettes using optimized parameters for CCD1079Sk fibroblasts. 48 h post electroporation, cells were pelleted, total RNA was isolated and mRNA-expression of the IFN-response genes OAS1, OAS2, MX1, IFITM1 and IRF9 was quantified by qRT-PCR. (E) CCD1079Sk fibroblasts were electroporated once with the indicated amounts of IVT-RNA encoding the reporter genes Luc, GFP or the Protein Kinase R (PKR) wild type. Electroporations were performed in 4 mm gap cuvettes using optimized parameters for CCD1079Sk fibroblasts. Cells were lysed 24 h post electroporation and expression and phosphorylation status of the PKR target eukaryotic initiation factor 2a (eIF2a) was monitored by Western Blotting using specific antibodies.

Figure 3A:
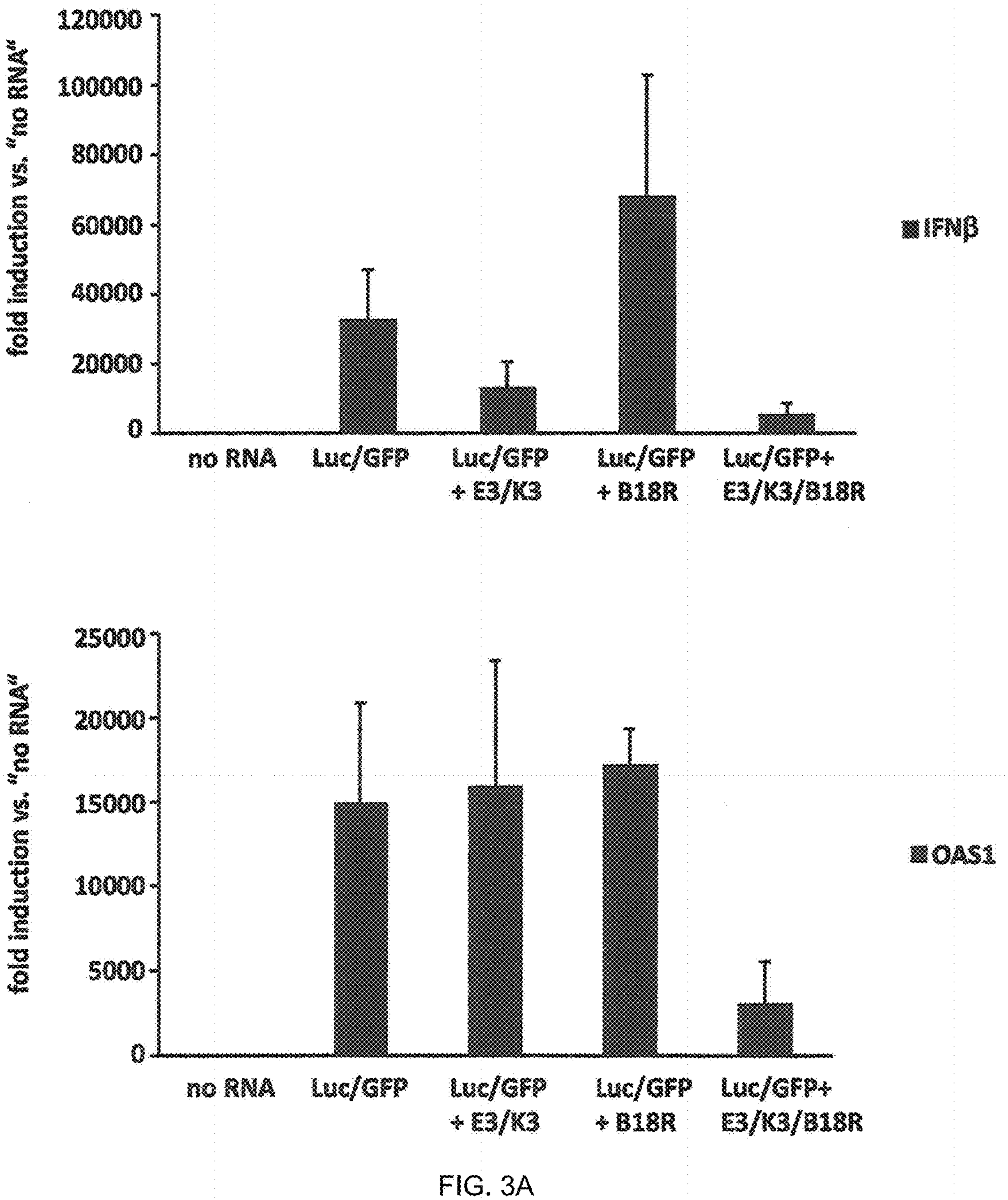
Figure 3B:
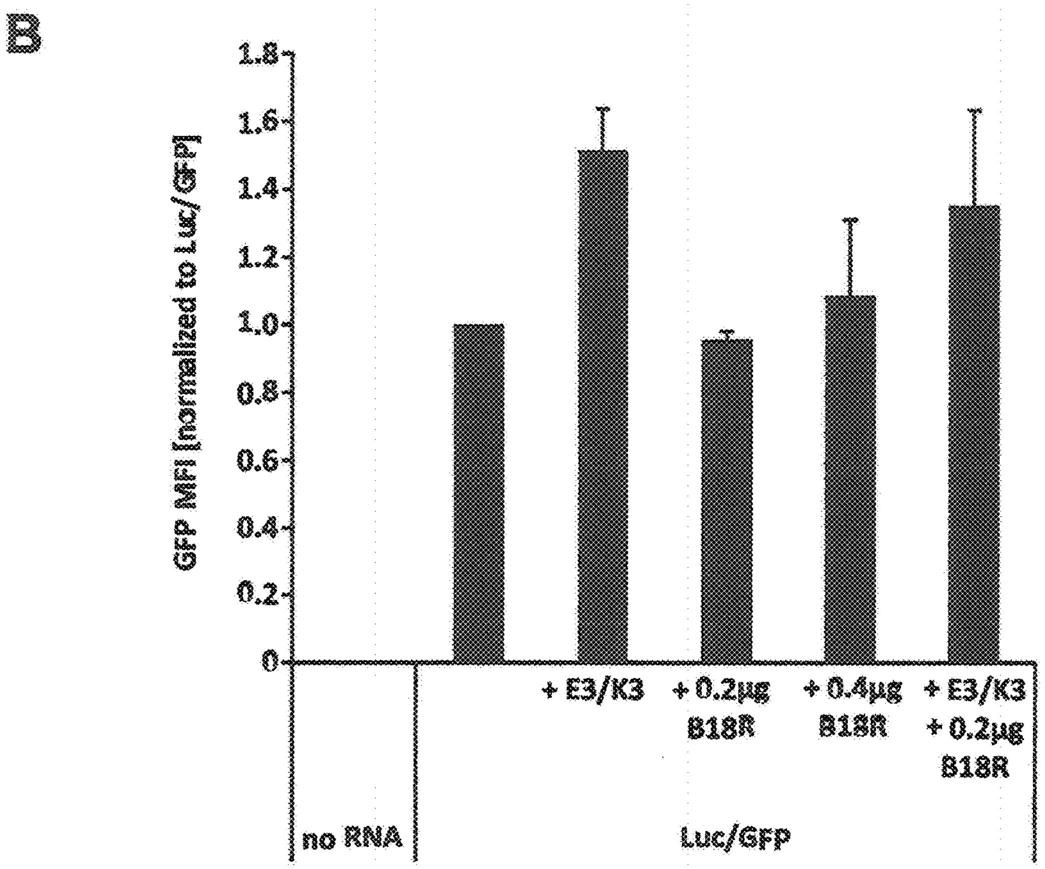
Figure 3C:
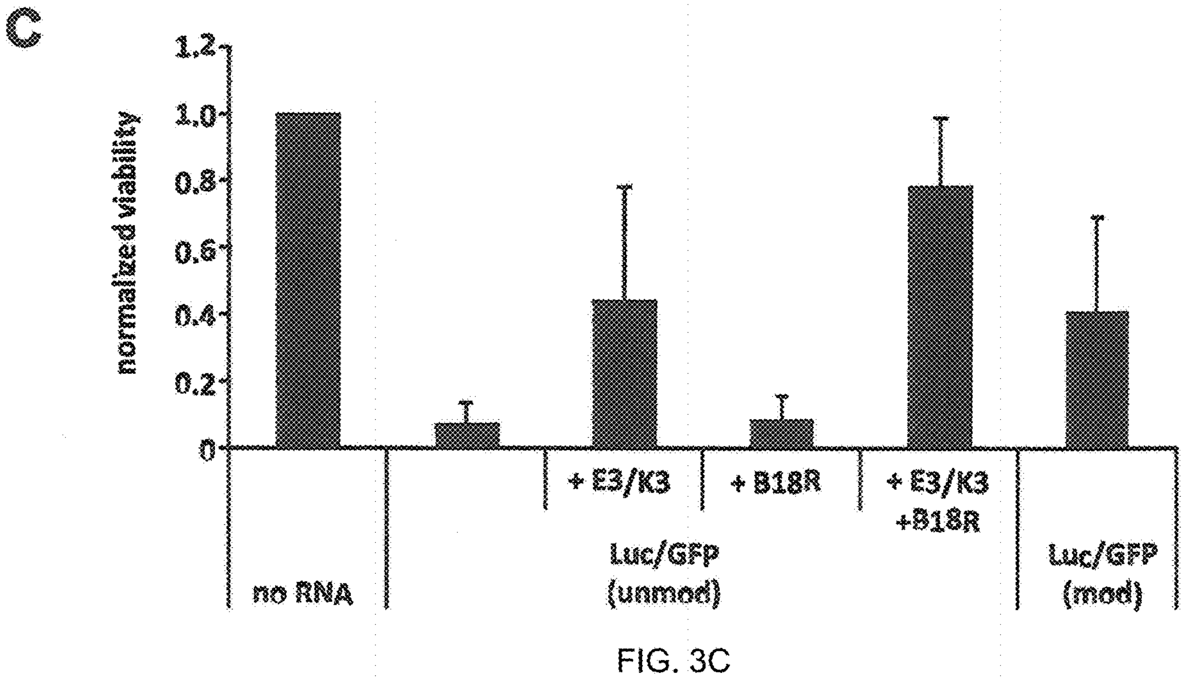

FIG. 3A-3C: Use of E3, K3 and B18R in RNA-Based Gene Transfer (AB) CCD1079Sk fibroblasts were plated into 6 wells (100,000 cells/well) and lipofected the next day using 6 μl RNAiMAX (Invitrogen) and 1.4 μg IVT. The IVT-RNA mixtures was thereby composed of 0.8 μg GFP with 0.2 μg of each B18R, E3 or K3 (as indicated). IVT-RNA encoding for Luc was used to sum up the mixtures to 1.4 μg. Lipofections were performed according to the manufacturers instructions and cells were harvested 48 h post transfection. 20% of the cells were used for analysis of GFP expression by FACS (B), whereas the rest of the cells were pelleted, total RNA was isolated and mRNA-expression of IFNb and OAS1 was quantified by qRT-PCR (A). (C) CCD1079Sk fibroblasts were plated into 6 wells (100.000 cells/well) and lipofected the next four consecutive days using 6 μl RNAiMAX (Invitrogen) and 1.4 μg IVT. The IVT-RNA mixture was thereby composed of 0.8 μg GFP with 0.2 μg of each B18R, E3 or K3 (as indicated). IVT-RNA encoding for Luc was used to sum up the mixture to 1.4 μg total IVT-RNA. As a control, 1.4 μg modified (mod.) IVT-RNA encoding for Luc (0.6 μg) and GFP (0.8 μg) was used. These RNAs were composed of 100% pseudouridine (psi) and 100% 5-methylcytidine (5mC) instead of uridine and cytidine which display less immunstimulatory characteristics. Lipofections were performed according to the manufacturers instructions. 24 h after the last lipofection, cell viability was assayed using the Cell Proliferation Kit II (Roche) and normalized to the mock transfected cells.

Figure 4A:
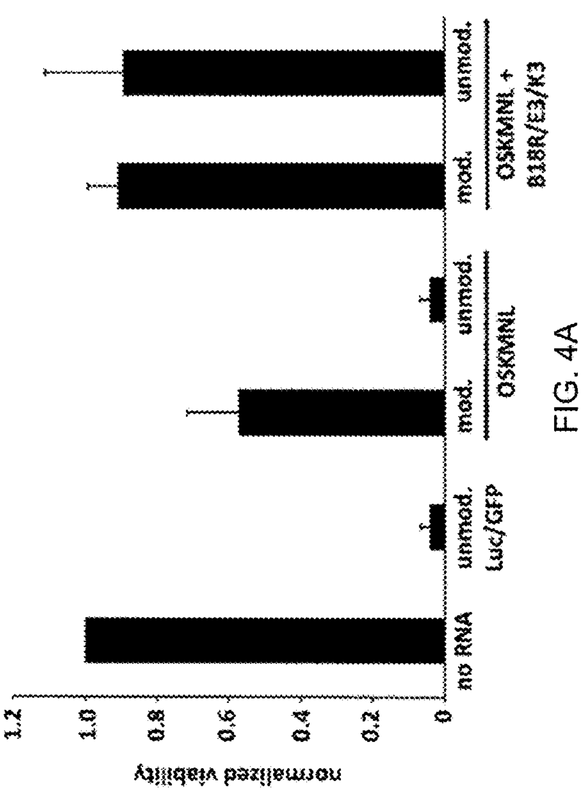
Figure 4B:
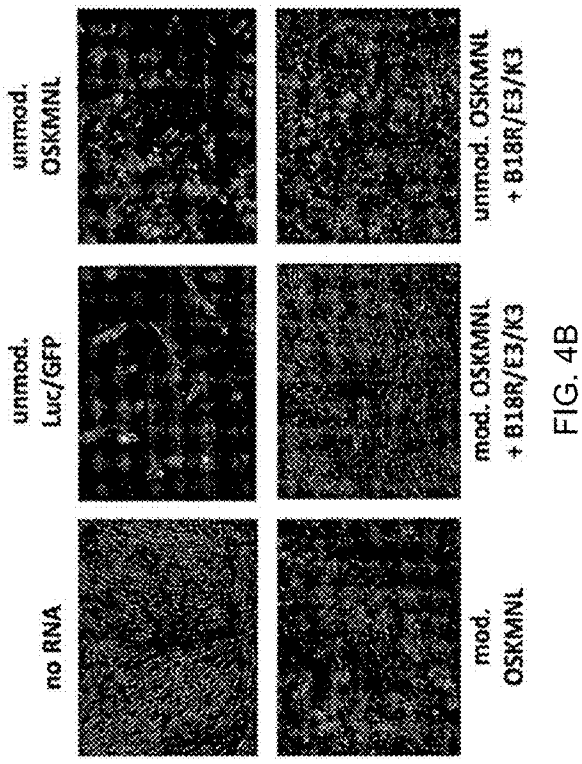
Figure 4C:
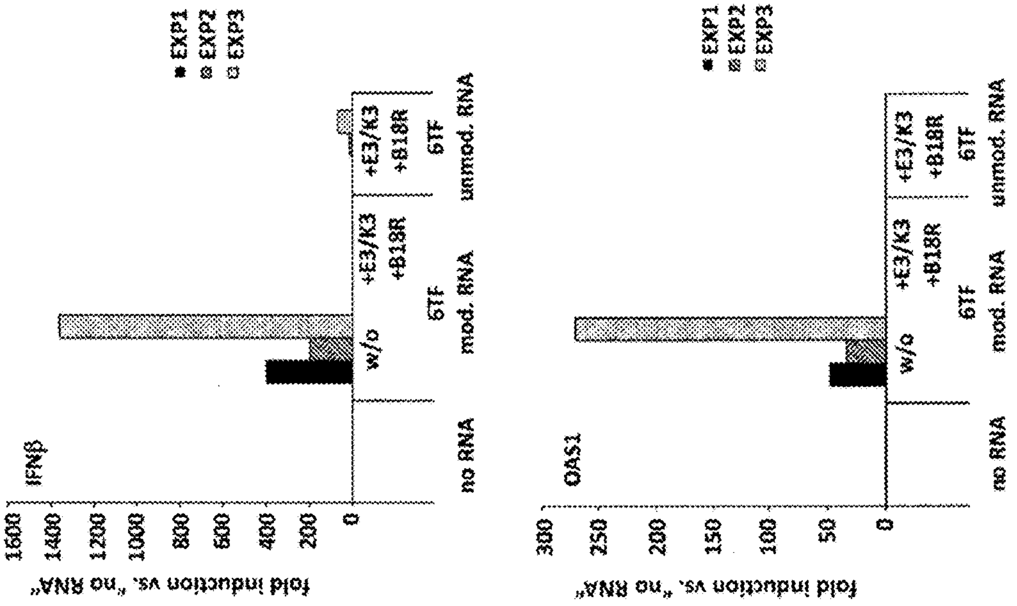

FIG. 4A-4C: Use of E3, K3 and B18R in RNA-Based Gene Transfer for Reprogramming CCD1079Sk fibroblasts were plated into 6 wells (80,000 cells/well) and lipofected the next four consecutive days using 6 μg RNAiMAX (Invitrogen) and 1.4 μg IVT. The IVT-RNA mixtures were thereby composed of 0.8 μg unmodified GFP or 0.8 μg OSKMNL (1:1:1:1:1:1) either unmodified or modified and either with 0.2 μg of each B18R, E3 and K3 unmodified or modified. If necessary IVT-RNA encoding for Luc was used to sum up the mixture to 1.4 μg total IVT-RNA. Modified RNAs were composed of 100% psi and 100% 5mC instead of uridine and cytidine which display less immunstimulatory characteristics. Lipofections were performed according to the manufacturers instructions. 24 h after the last lipofection, cell viability was assayed using the Cell Proliferation Kit II (Roche) with normalization to mock transfected cells (A) and by microscopy (B). After that, cells were pelleted, total RNA was isolated and mRNA-expression of IFNb and OAS1 was quantified by qRT-PCR (C).

Figure 5:
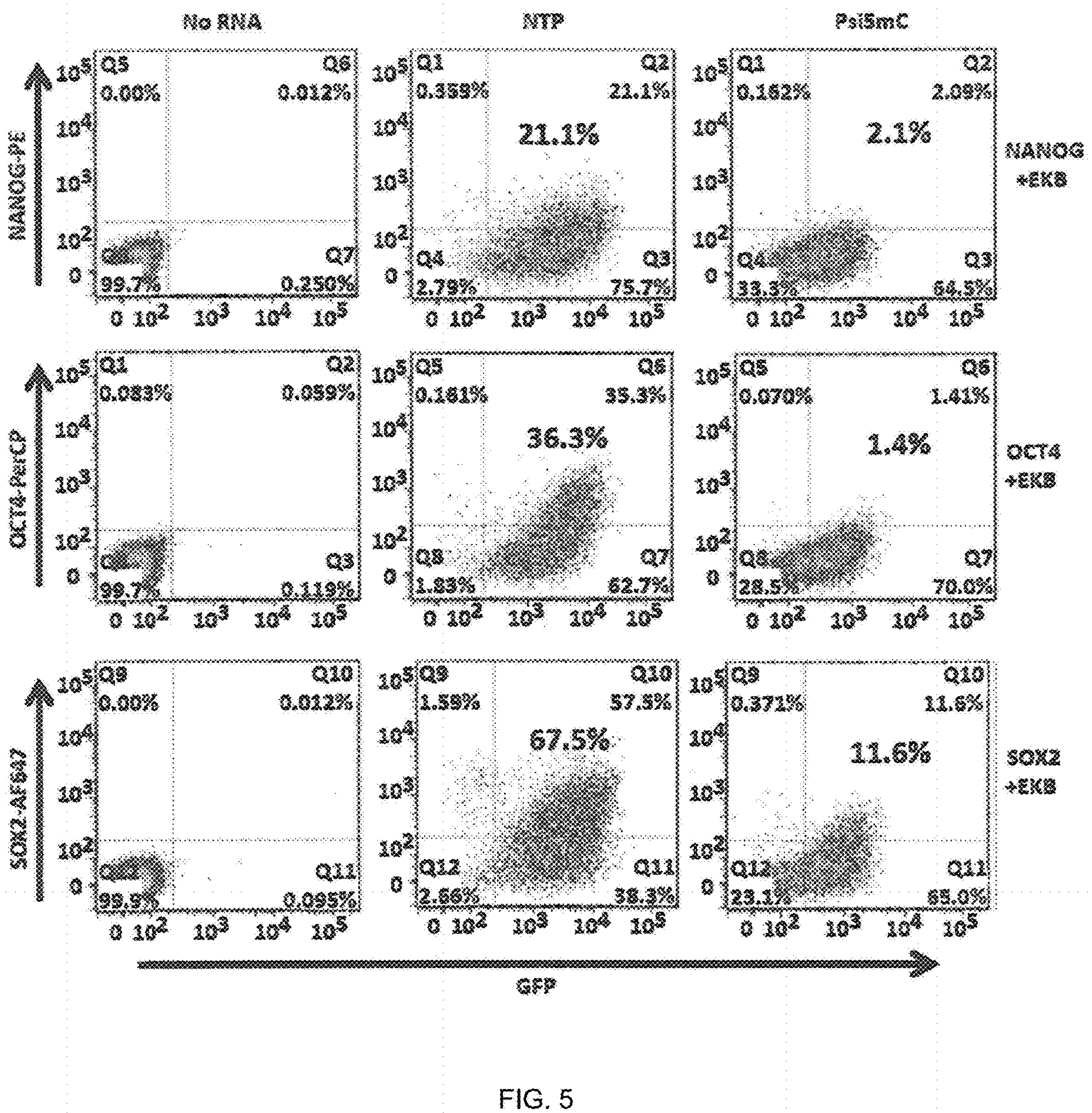

FIG. 5: Translation of rTF After Repetitive Lipofection in the Presence of E3, K3 and B18R CCD1079Sk fibroblasts were plated into 6 wells (100,000 cells/well) and lipofected the next three consecutive days using 6 μl RNAiMAX (Invitrogen) and 1.4 μg IVT. The IVT-RNA mixtures was thereby composed of 0.2 μg GFP with 0.6 μg OCT4 or SOX2 or NANOG either unmodified or modified and 0.2 μg of each B18R, E3 and K3 (EKB) either unmodified or modified. Modified RNAs were composed of 100% psi and 100% 5mC instead of uridine and cytidine which display less immunstimulatory characteristics. Lipofections were performed according to the manufacturers instructions. 24 h after the last lipofection, intracellular expression of OSN was monitored by FACS analysis using the human pluripotent stem cell transcription factor analysis kit (BD 560589).

FIG. 6A-6D: Reprogramming of HFF Using rTF and MicroRNA in the Presence of EKB HFF fibroblasts (System Bioscience) were plated into 6 wells (100,000 cells/well) and lipofected 5 times a week (Monday to Friday) for two weeks using 6 μl RNAiMAX (Invitrogen) and 1.4 μg IVT-RNA (A). The IVT-RNA mixtures were thereby composed of 0.8 μg unmodified GFP or 0.8 μg OSKMNL (1:1:1:1:1:1) either unmodified or modified with either 0.2 μg of each B18R, E3 and K3 (EKB) either unmodified or modified and 0.4 μg of a miRNA mixture composed of miRNAs 302a-d and 367 [0.4 μM each]. Modified RNAs were composed of 100% psi and 100% 5mC instead of uridine and cytidine which display less immunstimulatory characteristics. Lipofections in stem cell media (Nutristem media, Stemgent) were performed according to the manufacturers instructions. On day 6 and day 13, cells were pelleted, total RNA was isolated and mRNA-expression of the human ES-marker TERT, DPPA4, GDF3, LIN28 (endogenous) and REX1 was quantified by qRT-PCR (B). Colony growth was observed by microscopy (C) and for further analysis, colonies were stained for the ES surface marker TRA-1-60 using the StainAlive TRA-1-60 antibody (Stemgent) following the manufacturers instructions (D).

FIG. 7A-7D: Reprogramming of HFF Using rTF and MicroRNA in the Presence of EKB (Splitting 1:8)

HFF fibroblasts (System Bioscience) were plated into 6 wells (100,000 cells/well) and lipofected 5 times a week (Monday to Friday) for two weeks using 6 μl RNAiMAX (Invitrogen) and 1.4 μg IVT-RNA (A). The IVT-RNA mixtures were thereby composed of 0.8 μg OSKMNL (1:1:1:1:1:1) either unmodified or modified with either 0.2 μg of each B18R, E3 and K3 (EKB) unmodified or modified and 0.4 μg of a miRNA mixture composed of miRNAs 302a-d and 367 [0.4 μM each]. Modified RNAs were composed of 100% psi and 100% 5mC instead of uridine and cytidine which display less immunstimulatory characteristics. Lipofections in stem cell media (Nutristem media, Stemgent) were performed according to the manufacturers instructions. On day 5 and day 12, cells were pelleted, total RNA was isolated and mRNA-expression of the human ES-marker TERT, DPPA4, GDF3, LIN28 (endogenous) and REX1 was quantified by qRT-PCR (B). Colony growth was observed by microscopy and for further analysis, colonies were stained for the ES surface marker TRA-1-60 using the StainAlive TRA-1-60 antibody (Stemgent) (C) or for the activity of alkaline phosphatase (Vector Red staining kit) following the manufacturers instructions (D).

Figure 8A:
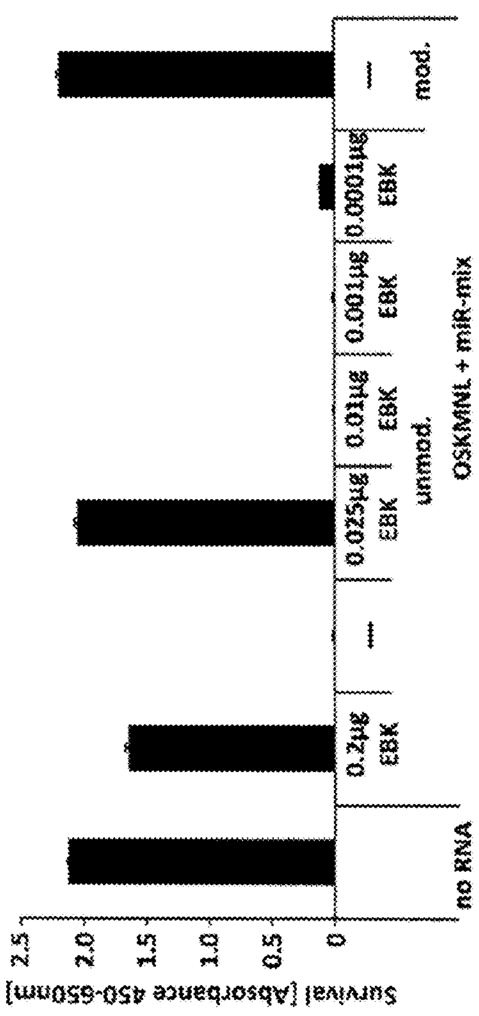
Figure 8B:
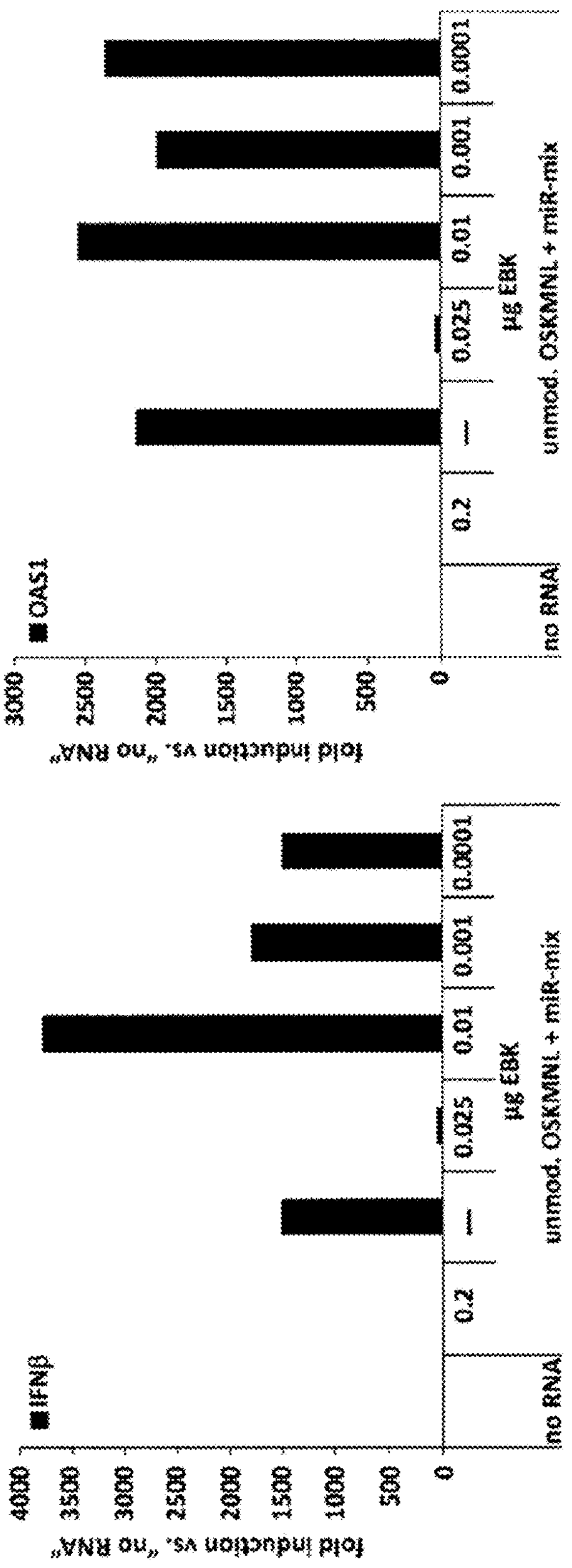

FIG. 8A-8B: Titration of EKB

HFF fibroblasts (System Bioscience) were plated into 6 wells (100,000 cells/well) and lipofected the next four consecutive days using 6 μl RNAiMAX (Invitrogen) and 1.4 μg IVT. The IVT-RNA mixtures were thereby composed of 0.8 μg unmodified OSKMNL (1:1:1:1:1:1) with variable amounts of unmodfied B18R, E3 and K3 as indicated.

IVT-RNA encoding for Luc was used to sum up the mixture to 1.4 μg total IVT-RNA. According to the reprogramming experiments 0.4 μg of a miRNA mixture composed of miRNAs 302a-d and 367 [0.4 μM each] was added to the samples. As a control, 1.4 μg modified (mod.) IVT-RNA encoding for Luc (0.6 μg) and OSKMNL (0.8 μg; 1:1:1:1: 1:1) was used. These RNAs were composed of 100% psi and 5mC instead of uridine and cytidine which display less immunstimulatory characteristics. Lipofections were performed according to the manufacturers instructions. 24 h after the last lipofection, cell viability was assayed using the Cell Proliferation Kit II (Roche) (A). After that, cells were pelleted, total RNA was isolated and mRNA-expression of IFNb and OAS1 was quantified by qRT-PCR (B).

Figure 9A:
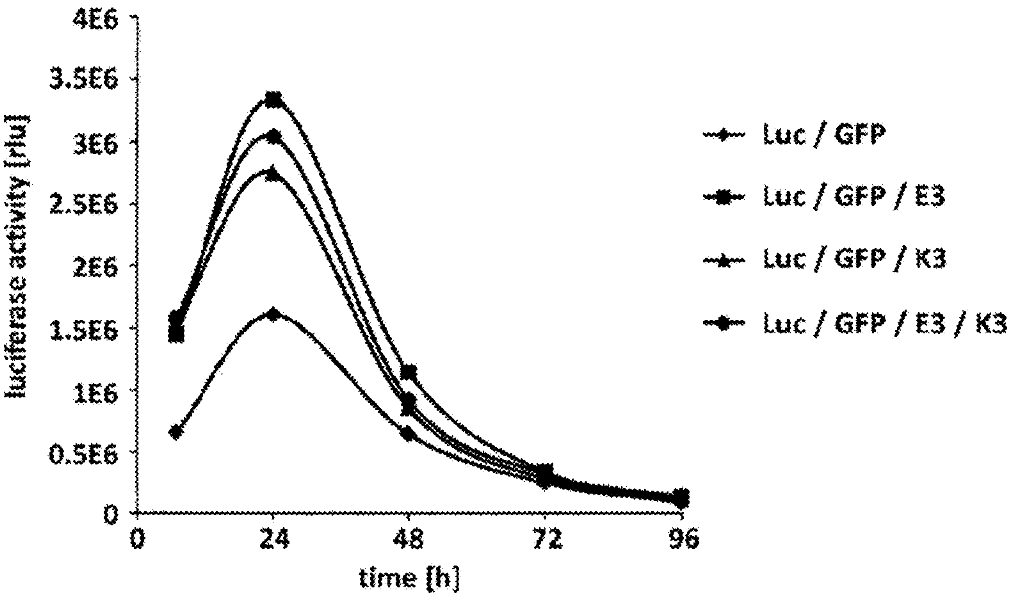
Figure 9B:
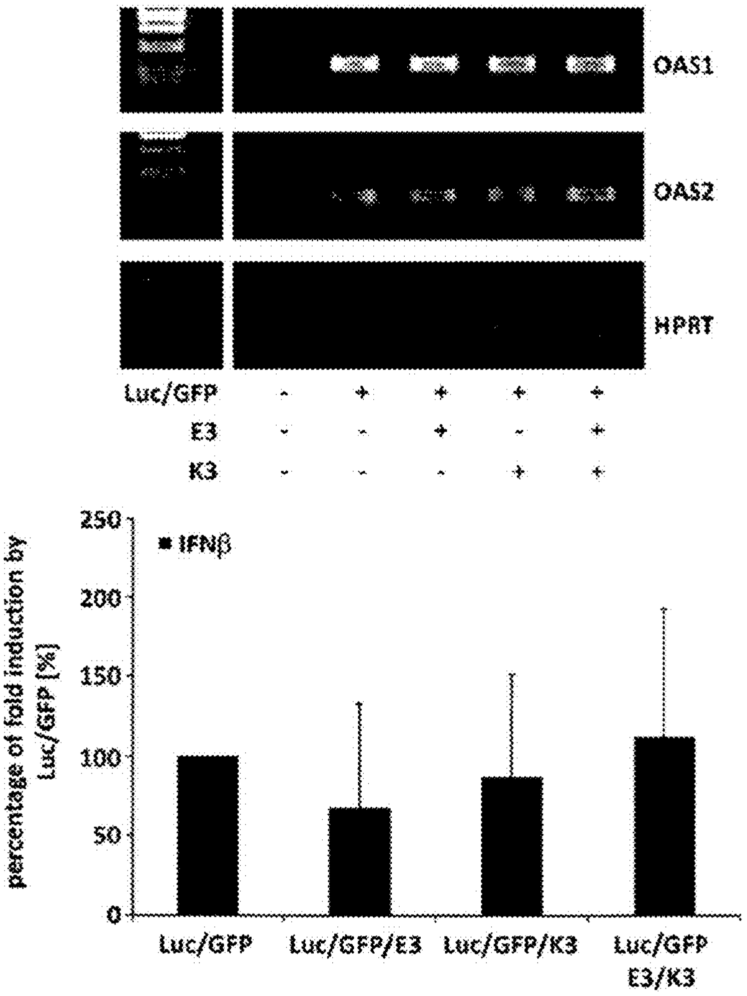

FIG. 9A-9B: Effect E3 and K3 Alone

CCD1079SK fibroblasts were electroporated with IVT RNA encoding Luc (1 μg), GFP (5 μg) and 3 μg of E3 or K3 or both as indicated. Electroporations were performed in 2 mm gap cuvettes using optimized parameters for CCD1079Sk fibroblasts. (A) 10000 cells/well were plated in duplicates into 96-well-plates. Luciferase activity was measured at the indicated time points after electroporation using the Bright Glo Luciferase Assay System (Promega). Mean values of the duplicates are given. (B) 300000 cells/well were plated into 6-well-plates and 24 h post electroporation, cells were pelleted, total RNA was isolated and mRNA-expression of OAS1 and IFN-b was analyzed by RT-PCR and in case of IFN-b quantified using the Quanti Tect SYBR Green PCR Kit.

Figure 10:
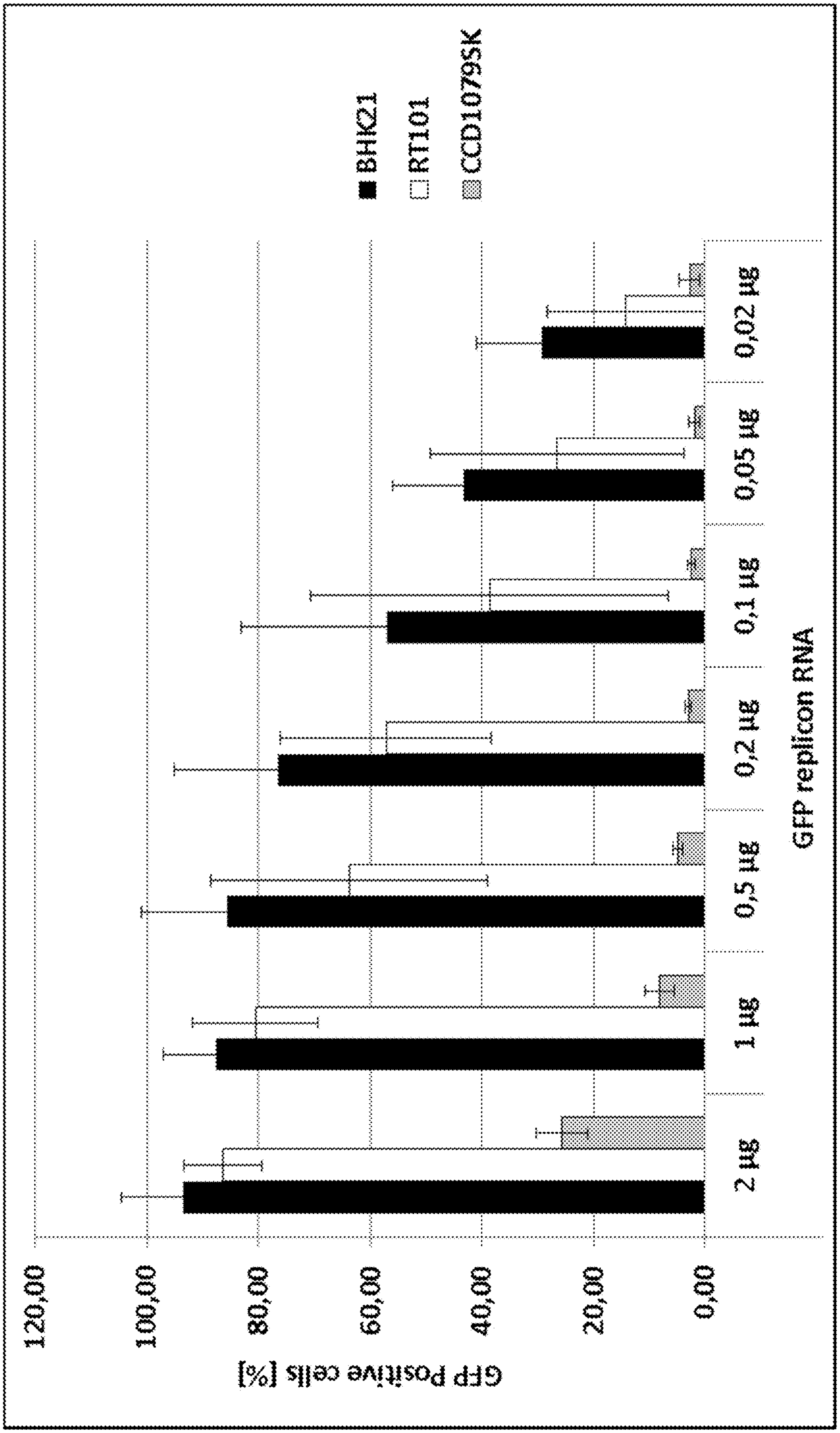

FIG. 10: Efficiency of Replicon Expression Displays a Great Variability in Different Cell Types Baby hamster kidney cells (BHK21), mouse epidermal RT101 cells and human foreskin fibroblasts (CCD1079SK) were lipofected with a serial dilution of replicon RNA encoding GFP as indicated (see example 9.2 for details). Shown is the percentage of GFP positive cells, which depends on the amount of replicon RNA.

Figure 11:
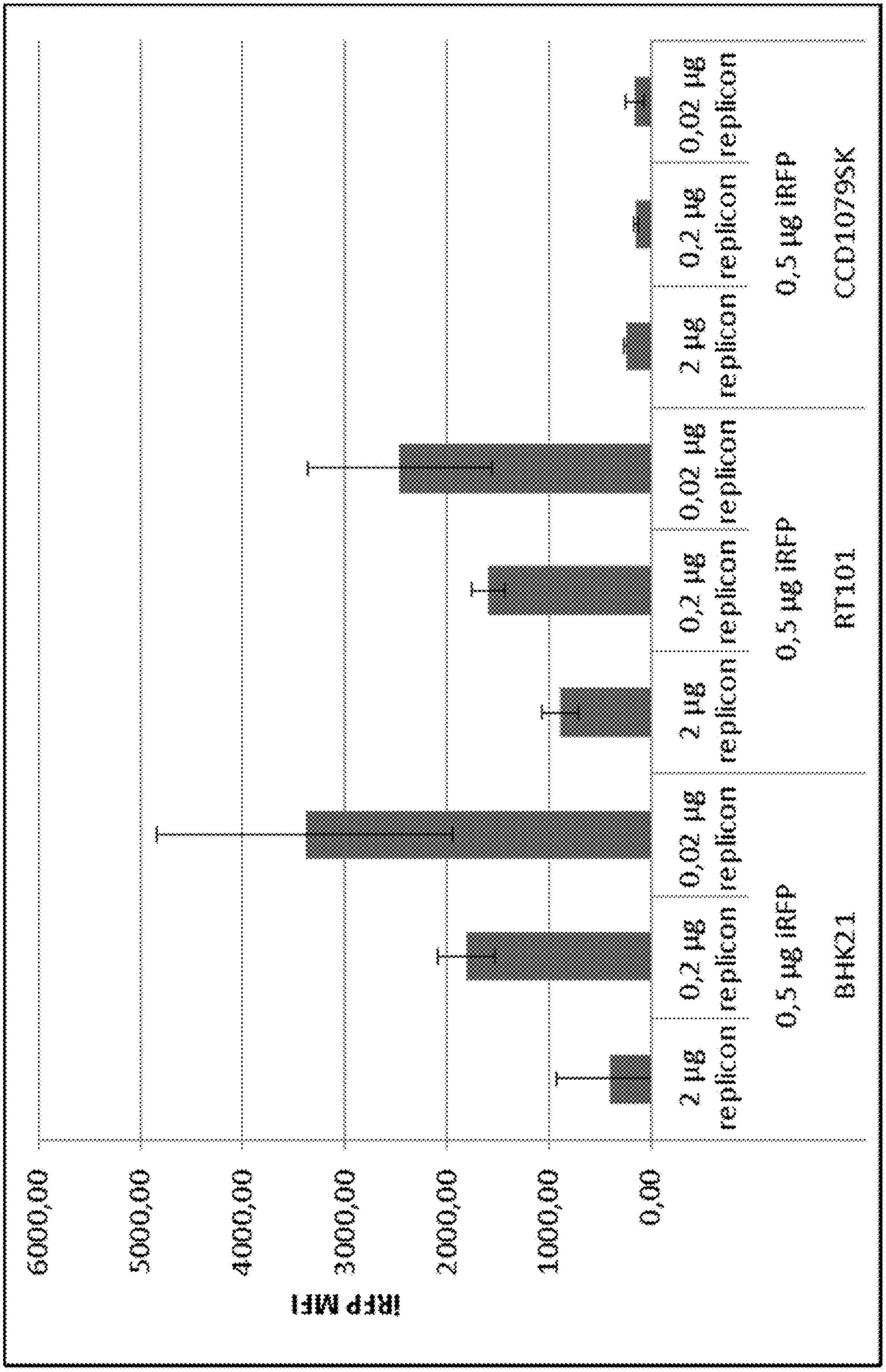

FIG. 11: The Expression of IVT RNA that is Cotransfected with Replicon RNA is Inhibited to Different Extend in Cells that Are Permissive or Non-Permissive for Replicons Baby hamster kidney cells (BHK21), mouse epidermal RT101 cells and human foreskin fibroblasts (CCD1079SK) were lipofected with a serial dilution of replicon RNA encoding GFP (see example 9.3 for details). To monitor successful transfection, IVT RNA encoding infrared fluorescent protein (iRFP) was cotransfected. Shown is the mean fluorescent intensity (MFI) of iRFP in the different cell samples which illustrates the efficiency of translation in the cells. In permissive cells (BHK21 and RT101), the inhibition of IVT RNA expression correlates to the amount of cotransfected replicon RNA. In non-permissive cells (CCD1079SK), the inhibition is independent from the amount of replicon RNA. Even very low amounts of replicon RNA efficiently block IVT RNA expression, which presumably relates to stronger protein kinase R (PKR) activation and IFN-response in these cells.

Figure 12A:
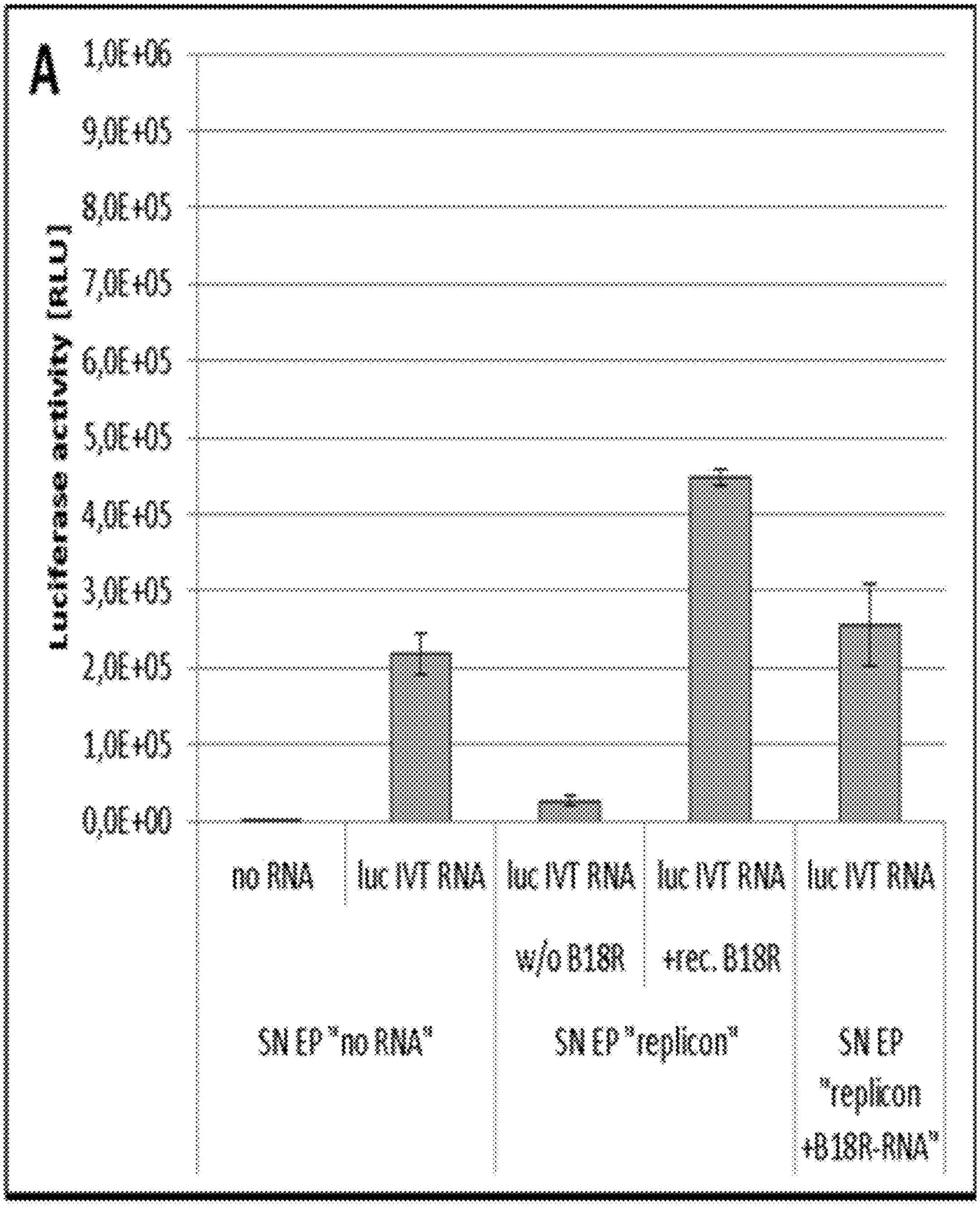
Figure 12B:
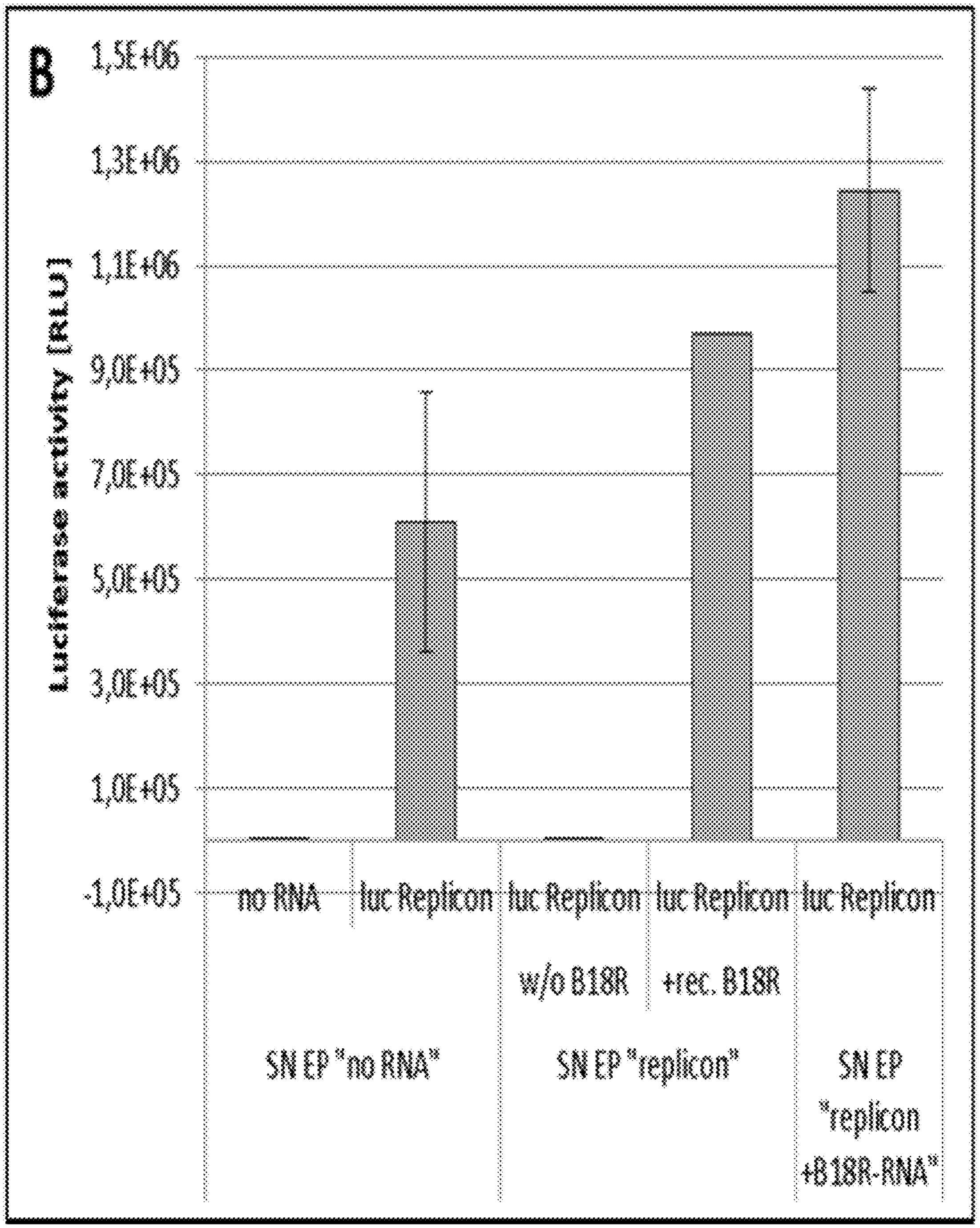

FIG. 12A-12B: Replicon Expression is Efficiently Blocked in Cells Exposed to IFN. Recombinant B18R Releases this Block Human fibroblasts were exposed to supernatants from electroporated human fibroblasts and then lipofected with a luciferase encoding replicon (see example 9.4 for details). To generate the supernatants, cells were electroporated without RNA (SN EP "no RNA"), replicon RNA (SN EP "replicon") or replicon RNA plus B18R encoding IVT RNA (EP SN "replicon +B18R RNA"). Shown is the luciferase activity after lipofection.

Figure 13A:
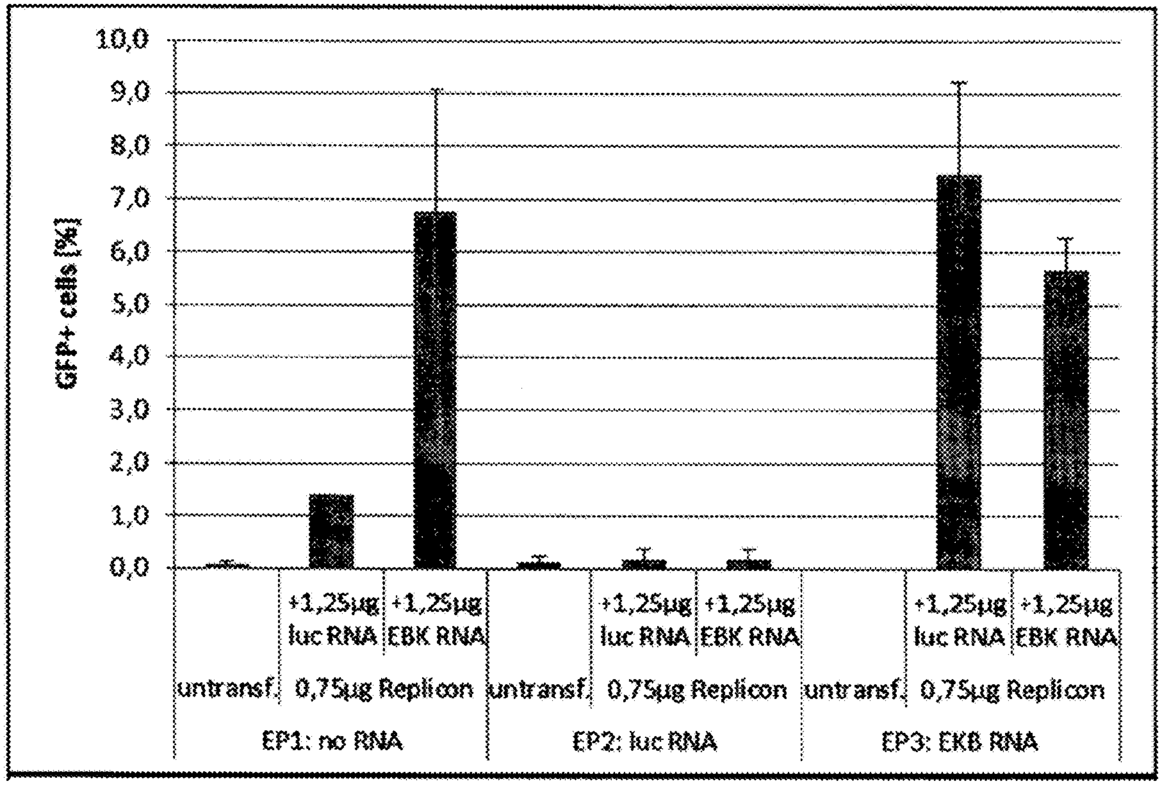
Figure 13B:
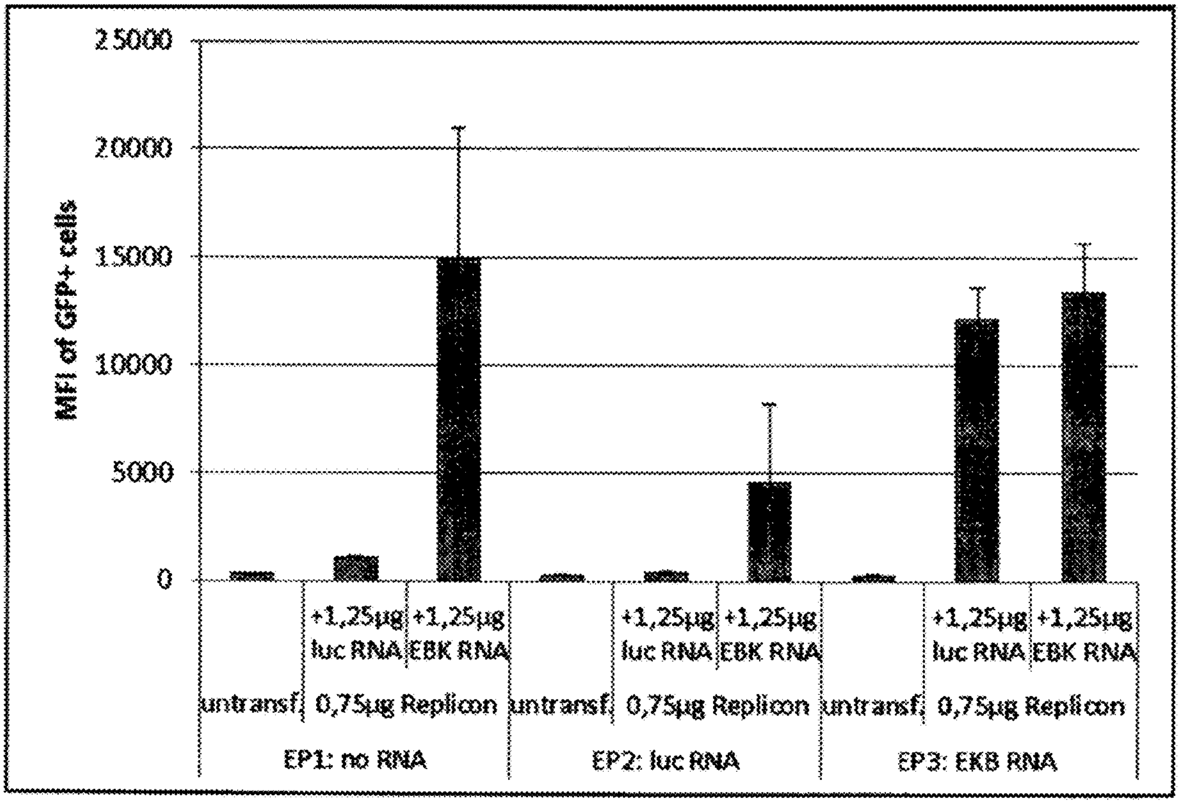
Figure 14B:
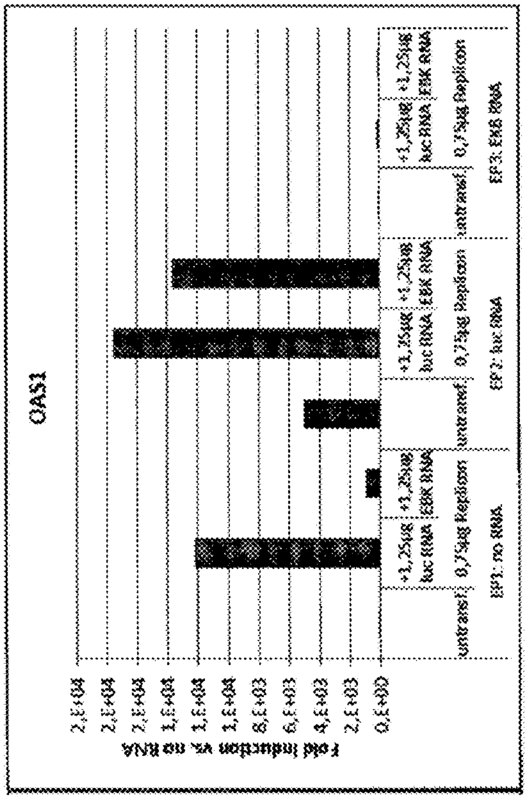
Figure 14D:
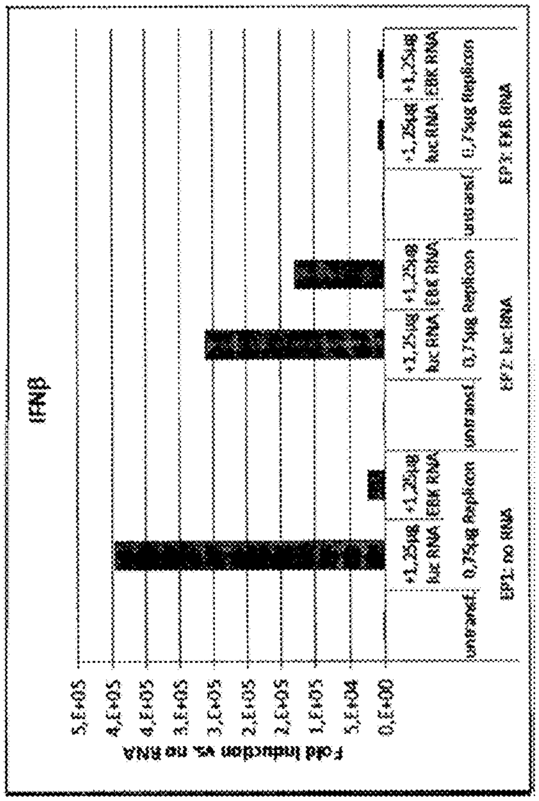
Figure 14A:
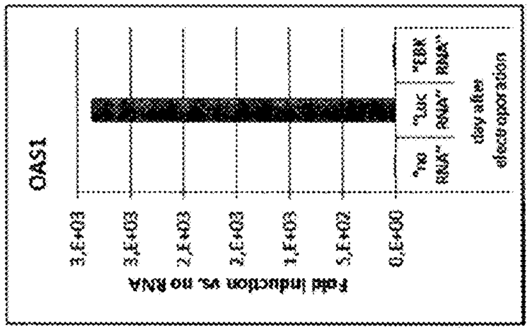
Figure 14C:
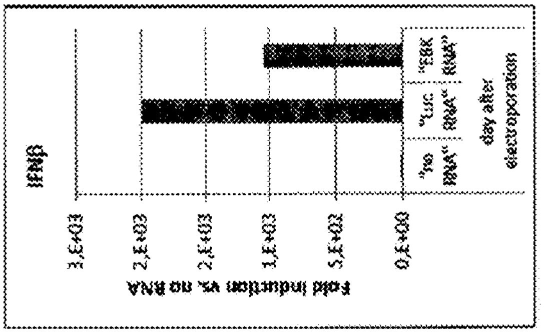

FIG. 13A-13B: RNA Electroporation Blocks Subsequent Replicon Lipofection Human fibroblasts were electroporated (EP) either without RNA (EP1: no RNA), luciferase encoding IVT RNA (EP2: luc RNA) or IVT RNA encoding E3, K3 and B18R (EP3: EKB RNA). The next day, the cells were lipofeccted with a GFP encoding replicon together with either luciferase encoding IVT RNA or EKB encoding IVT RNA (see example 9.5 for details). Electroporation with luciferase encoding IVT RNA blocks subsequent replicon expression. This block cannot be released by colipofection of EBK RNA. Electroporation of RNA that encodes EKB does not inhibit replicon expression.

FIG. 14A-14D: VacV Proteins Encoded on IVT RNA Prevent IFN Response to RNA, But have Limited Action on an Established IFN Response Same experiment as in FIG. 13. Shown are IFN-beta and OAS1 transcript amounts measured by qPCR one day after electroporation (A, C) and one day after lipofection (B,D). Overall, OAS1 is upregulated in samples that blocked replicon expression (compared to FIG. 13).

Figure 15A:
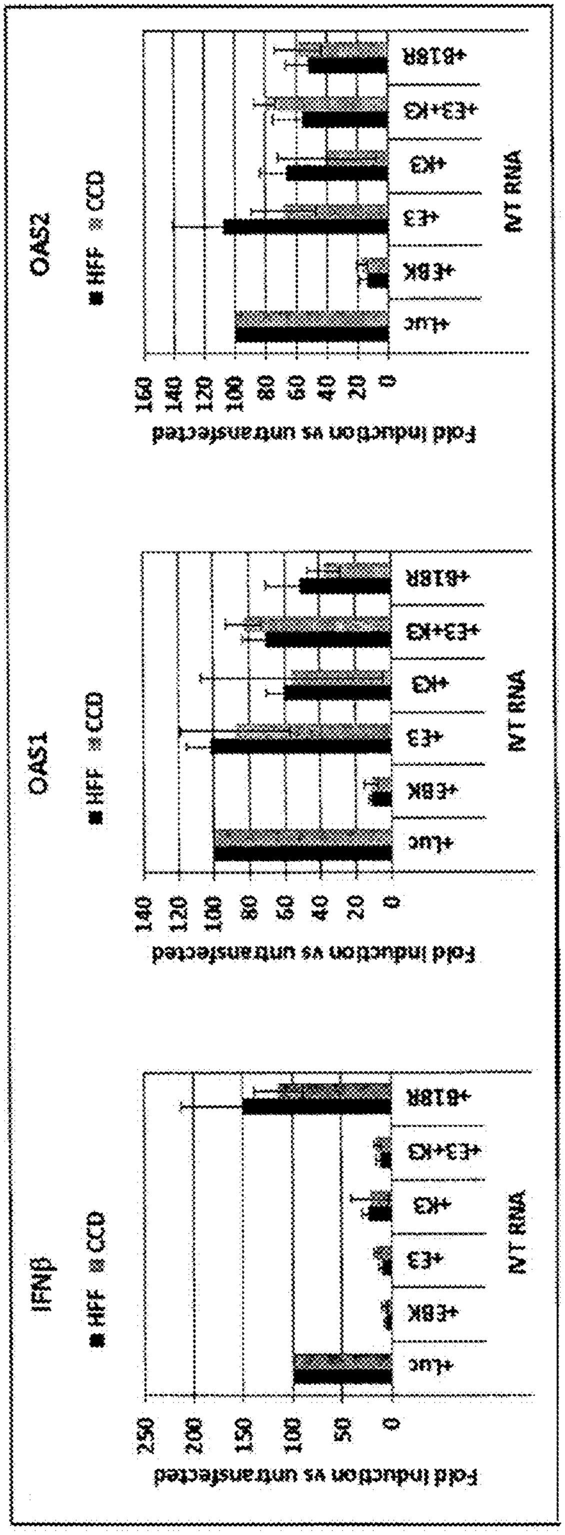
Figure 15B:
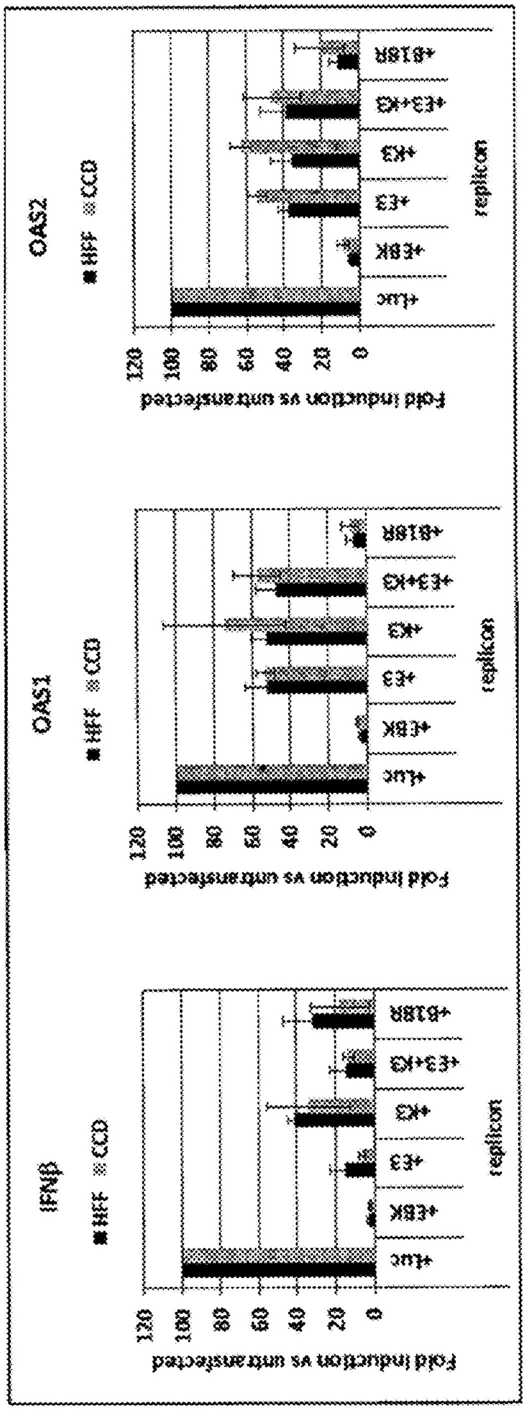

FIG. 15A-15B: IFN-Response to IVT RNA is Reduced By VacV Proteins, But Only the Combination of VacV Proteins E3L, K3L and B18R Abrogates IFN Response Human fibroblasts were cotransfected with either IVT RNA encoding GFP plus IVT RNA encoding Vaccinia virus proteins (A) or replicon RN encoding GFP plus IVT RNA encoding Vaccinia virus proteins (B) in the indicated combinations (see table 2 and example 9.7 for details). Shown are IFN-beta, OAS1 and OAS2 transcript amounts measured by qPCR one day after electroporation normalized to transcript amounts of cells transfected without VacV proteins.

Figure 16A:
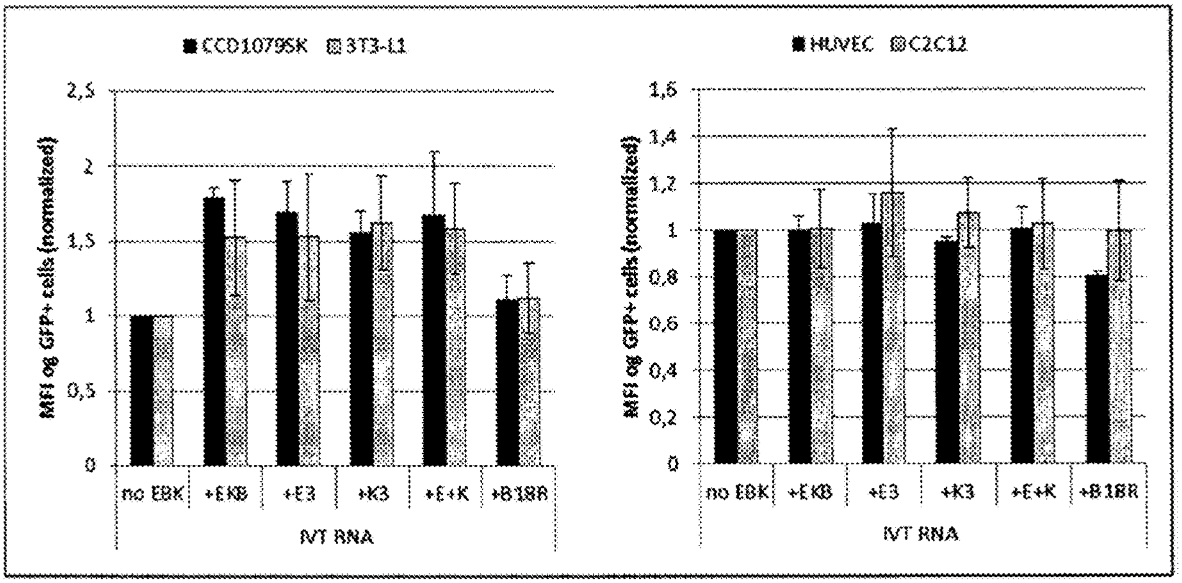
Figure 16B:
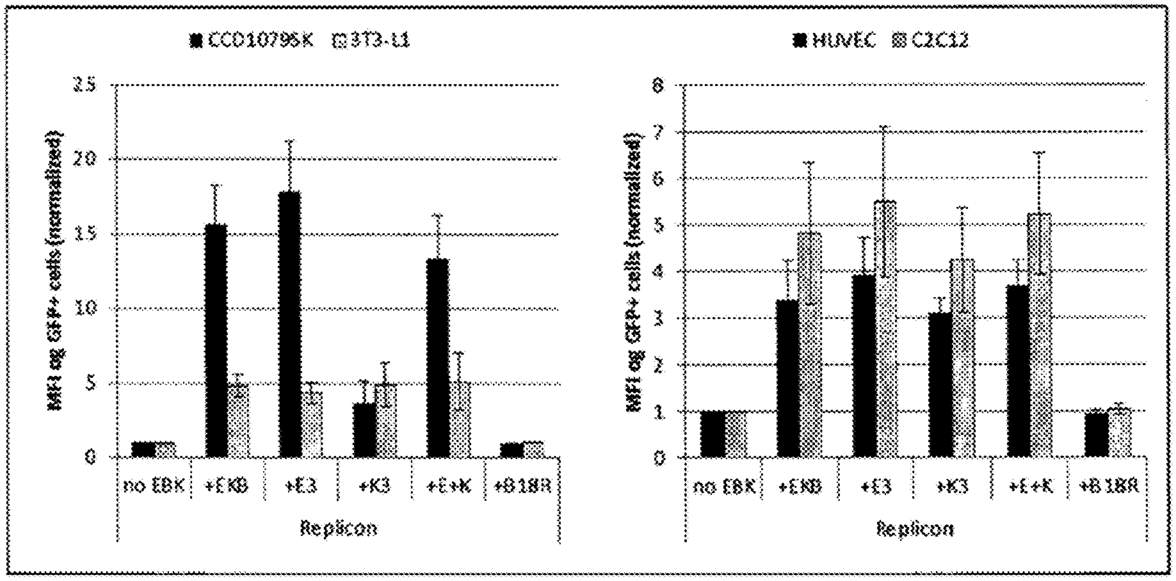

FIG. 16A-16B: Coelectroporation of VacV Proteins Increases IVT RNA and Replicon Expression in Different Mouse and Human Cell Types Human fibroblasts (CCD1079SK), mouse fibroblasts (3T3-L1), human umbelical vein endothelial cells (HUVEC) and mouse myoblasts (C2C12) were coelectroporated with IVT RNA encoding VacV proteins and either with GFP encoding IVT RNA (A) or replicon RNA (B) (see table 2 and example 9.8 for details). Shown are fold changes of GFP mean fluorescence normalized to the MFI of samples without VacV proteins. In human cells, the boost of replicon expression was about 3-fold stronger than in mouse fibroblasts. E3 had greater effects in human fibroblasts thanK3.

Figure 17A:
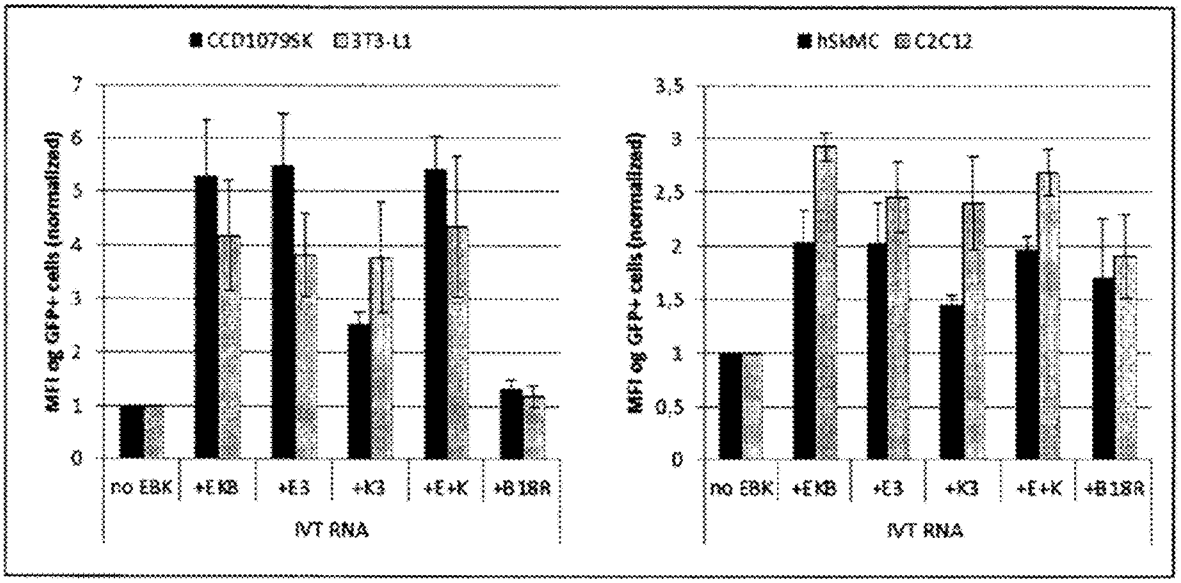
Figure 17B:
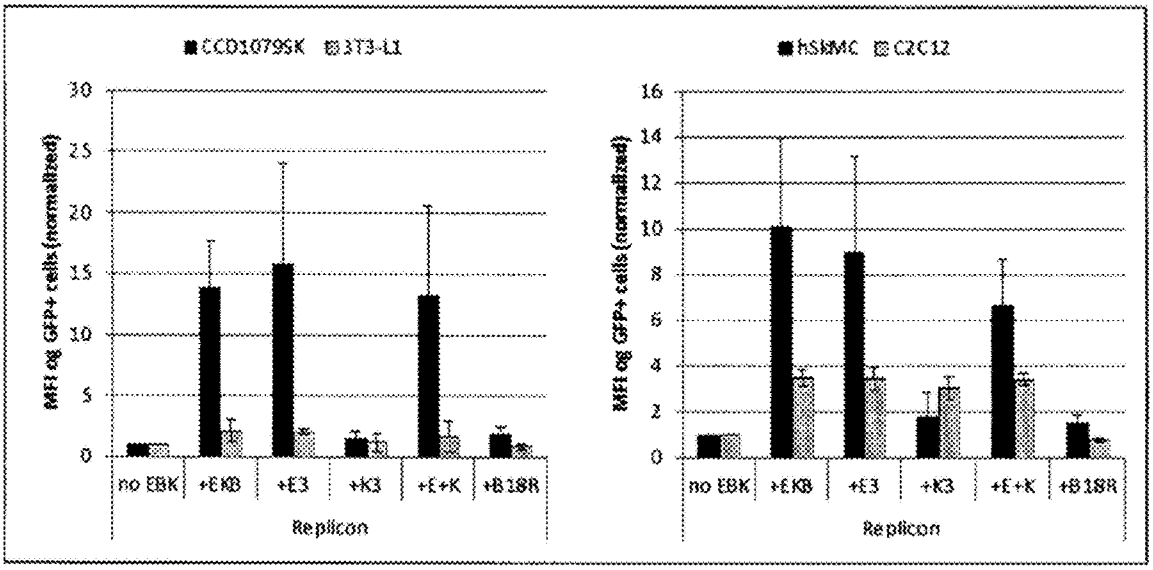

FIG. 17A-17B: Colipofection of VacV Proteins Increases IVT RNA and Replicon Expression in Mouse and Human Fibroiblasts and Myoblasts.

The results from FIG. 16 were confirmed by lipofection (see table 3 and example 9.9 for details regarding lipofected RNA mixtures). Shown are fold changes of GFP mean fluorescence normalized to the MFI of samples without VacV proteins. VacV proteins are more effective in human fibroblasts and myoblast, than in their mouse counterparts. E3L was the major player in human cells.

Figure 18:
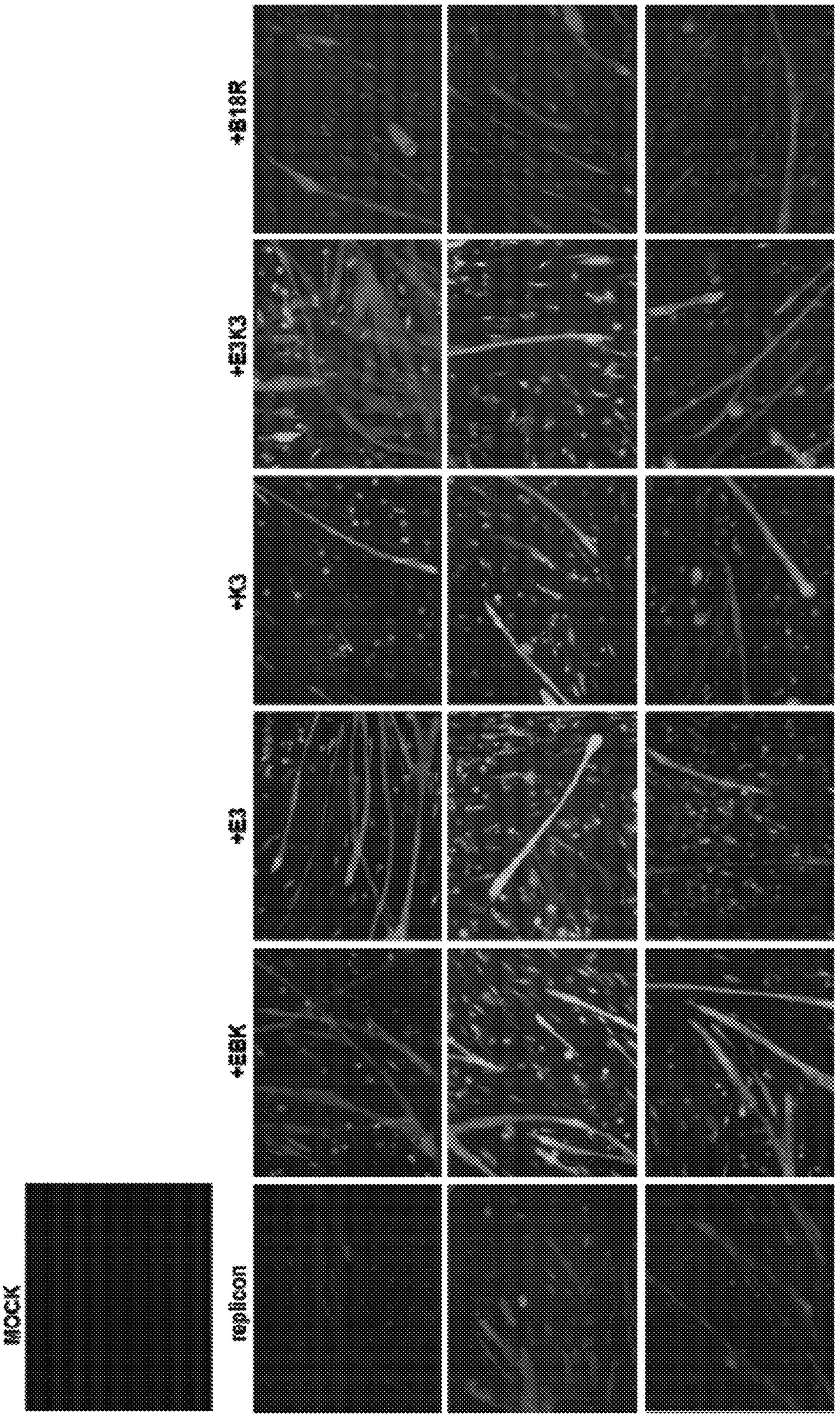

FIG. 18: VacV Proteins Increase Expression in Mature Mouse Myotubes, with Exception of B18R Similar experiment as in FIG. 17. After differentiation of C2C12 cells to myotubes, the same RNA mixtures as before (table 3) were colipofected. Pictures of GFP fluorescence were taken one day after lipofecton. The brightness of GFP signals indicate GFP expression in the myotubes.

Figure 19:
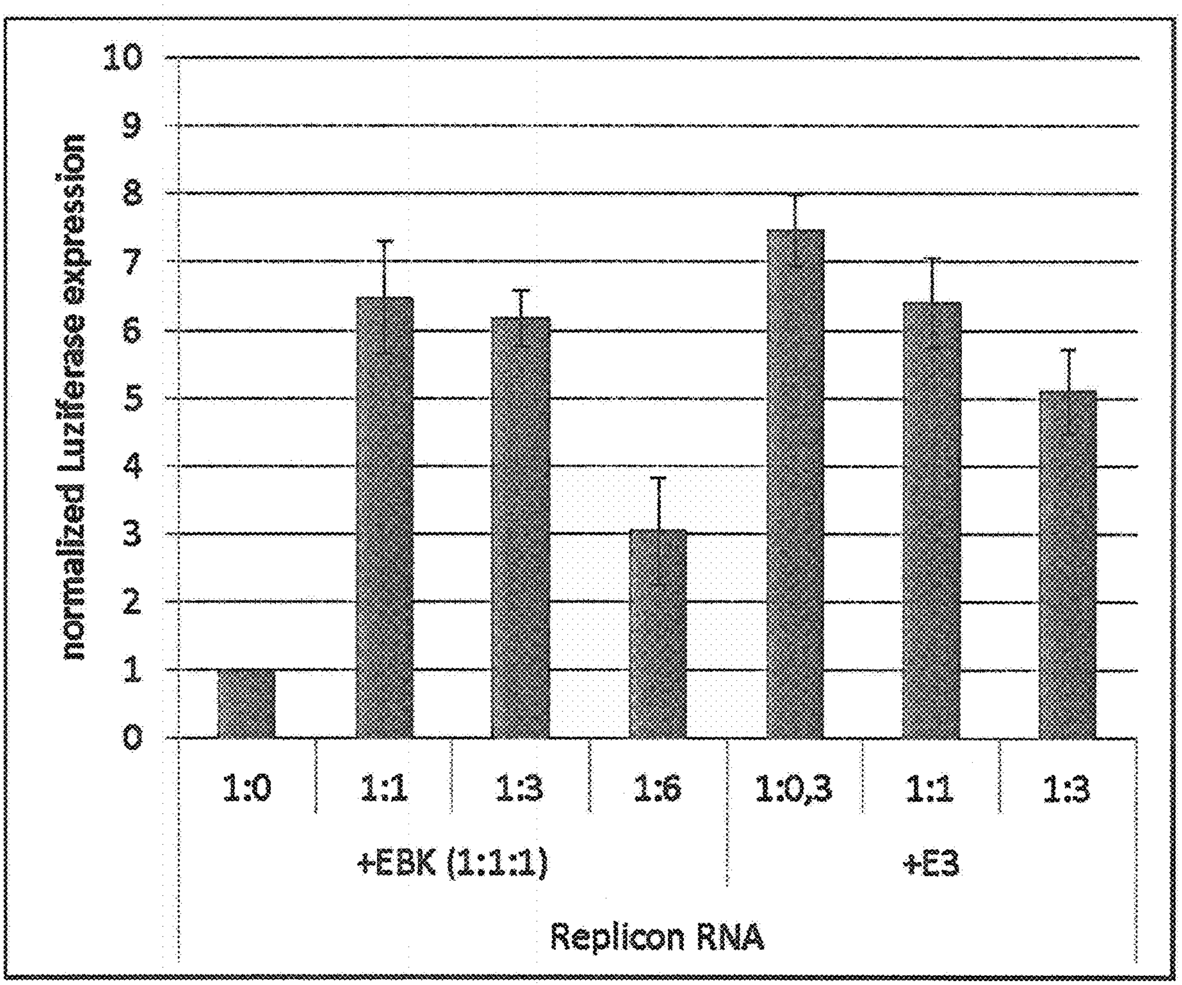

FIG. 19: A 1:1 (w:w) Ratio of Replicon RNA and EBK RNA is Sufficient to Achieve Maximal Replicon Expression An increasing amount of EBK RNA or E3 RNA was coelectroporated with a luciferase encoding replicon into mouse myoblasts (C2C12)(see example 9.11 for details).

Shown are fold changes of luciferase activity normalized to samples without VacV proteins. An excess does not further increase the expression.

Figure 20:
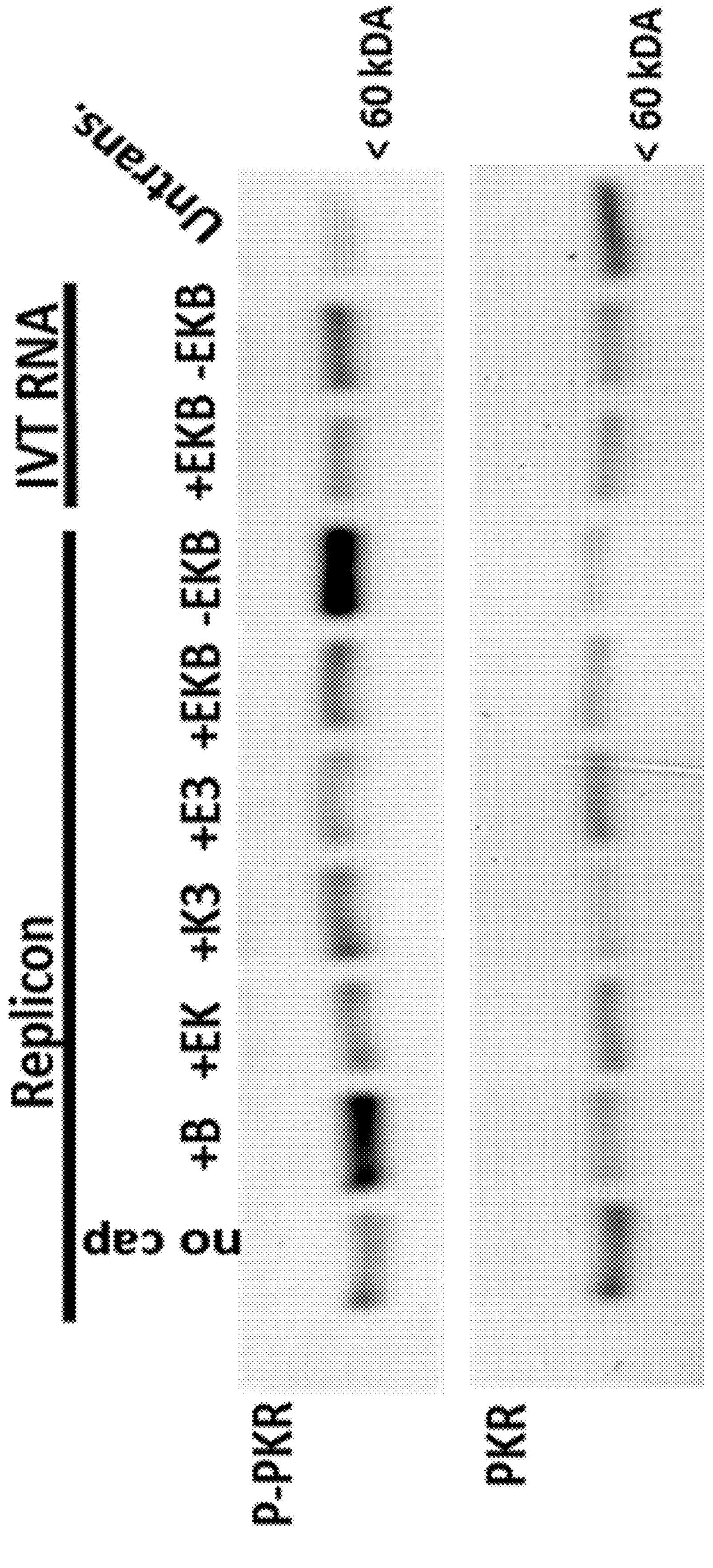

FIG. 20: VacV protein E3L and K3L Both Inhibit Replicon Induced PKR Autophosphorylation. B18R Has No Effect Human CCD1079SK fibroblasts were coelectroporated with replicon RNA coding GFP, together with IVT RNA encoding iRFP and the indicated VacV protein. Mock electroporated cells (untrans.) and uncapped replicon RNA (no cap) served as negative controls (see example 9.12 for details). Shown are the autophosphorylation of PKR with a phospho-PKR specific antibody (P-PKR) and total PKR expression using a PKR antibody (PKR).

Figure 21B:
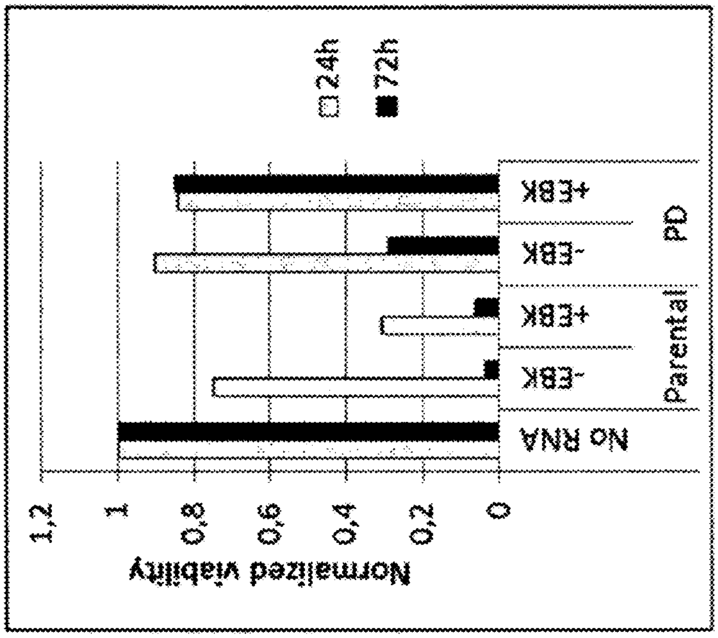
Figure 21A:
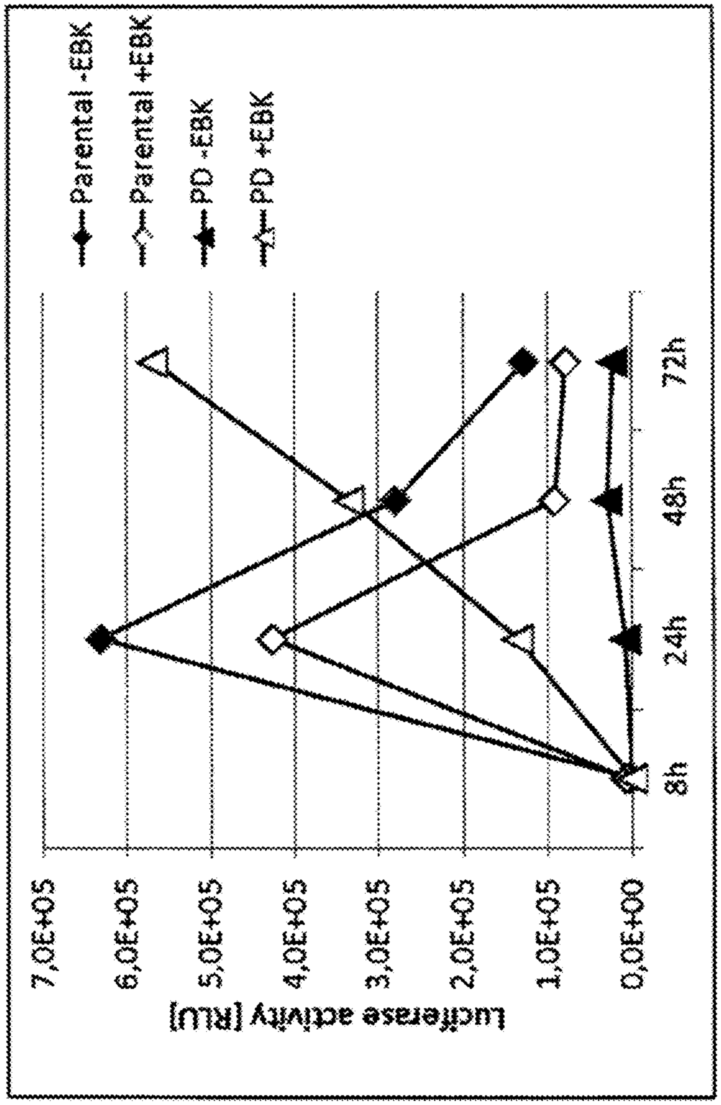

FIG. 21A-21B: VacV Proteins Enable Efficient Replication of Non-Cytotoxic Mutant Replicons and Inhibit Residual Cytotoxicity of these Vectors Parental and non-cytotoxic PD replicons encoding luciferase were electroporated into human fibroblasts alongside with IVT NA encoding E3, B18R and K3 (EBK) or not (see example 9.13 for details). Sown are luciferase expression over time (A) and viability of the cells normalized to untransfected samples (B).

Figure 22:
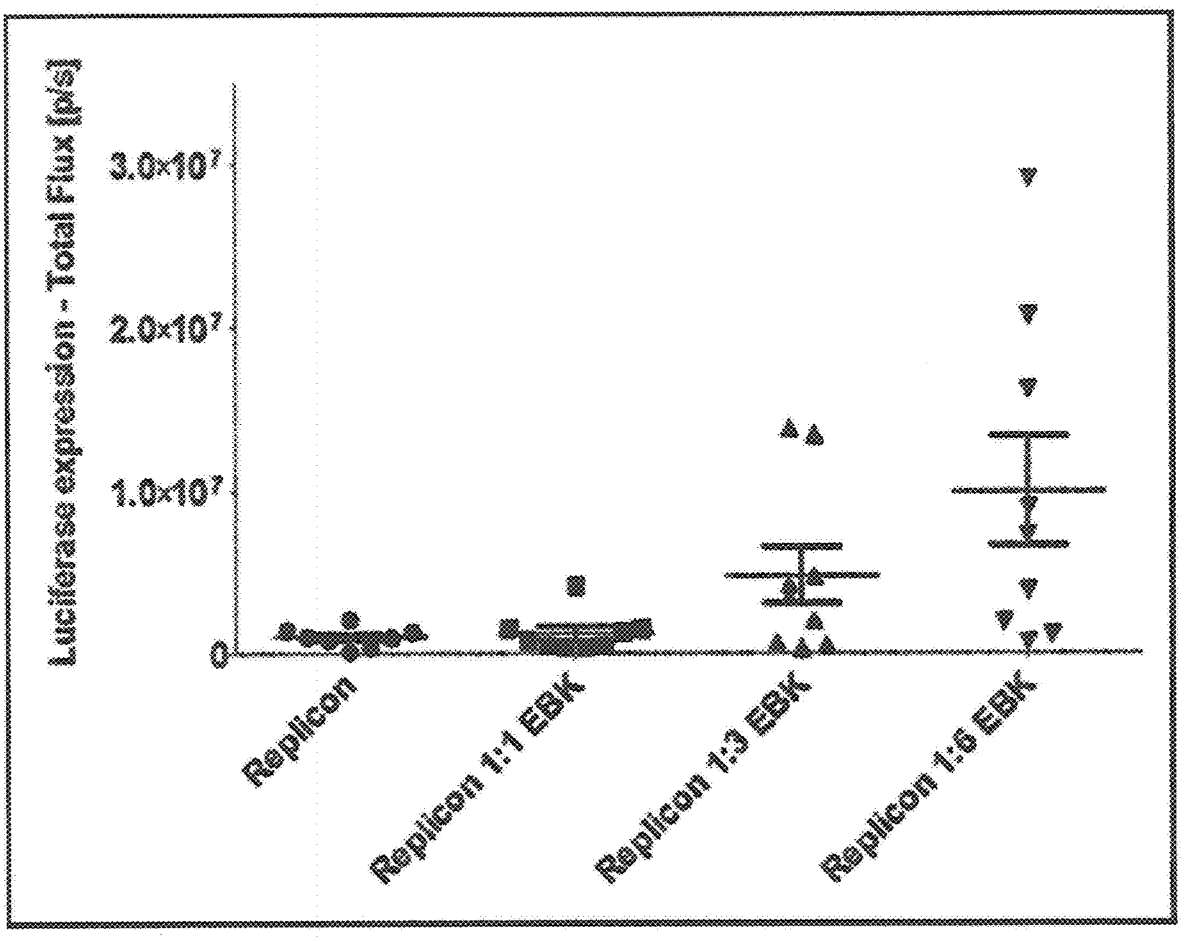

FIG. 22: VacV Proteins Enhanced the Expression of Naked Replicon in the Muscle of Mice. The Best Ratio In Vivo is a 6-Fold Excess of EBK Encoding IVT RNA 2 μg Replicon RNA encoding luciferase were coinjected with IVT RNA coding E3, K3 and B18R (EBK) in different w/w ratios as indicated (1- to 6-fold as much EKB as replicon RNA) into the tibialis anterior of Balb/C mice (see example 9.14 for details). Shown is the in vivo luciferase signal.

Figure 23:
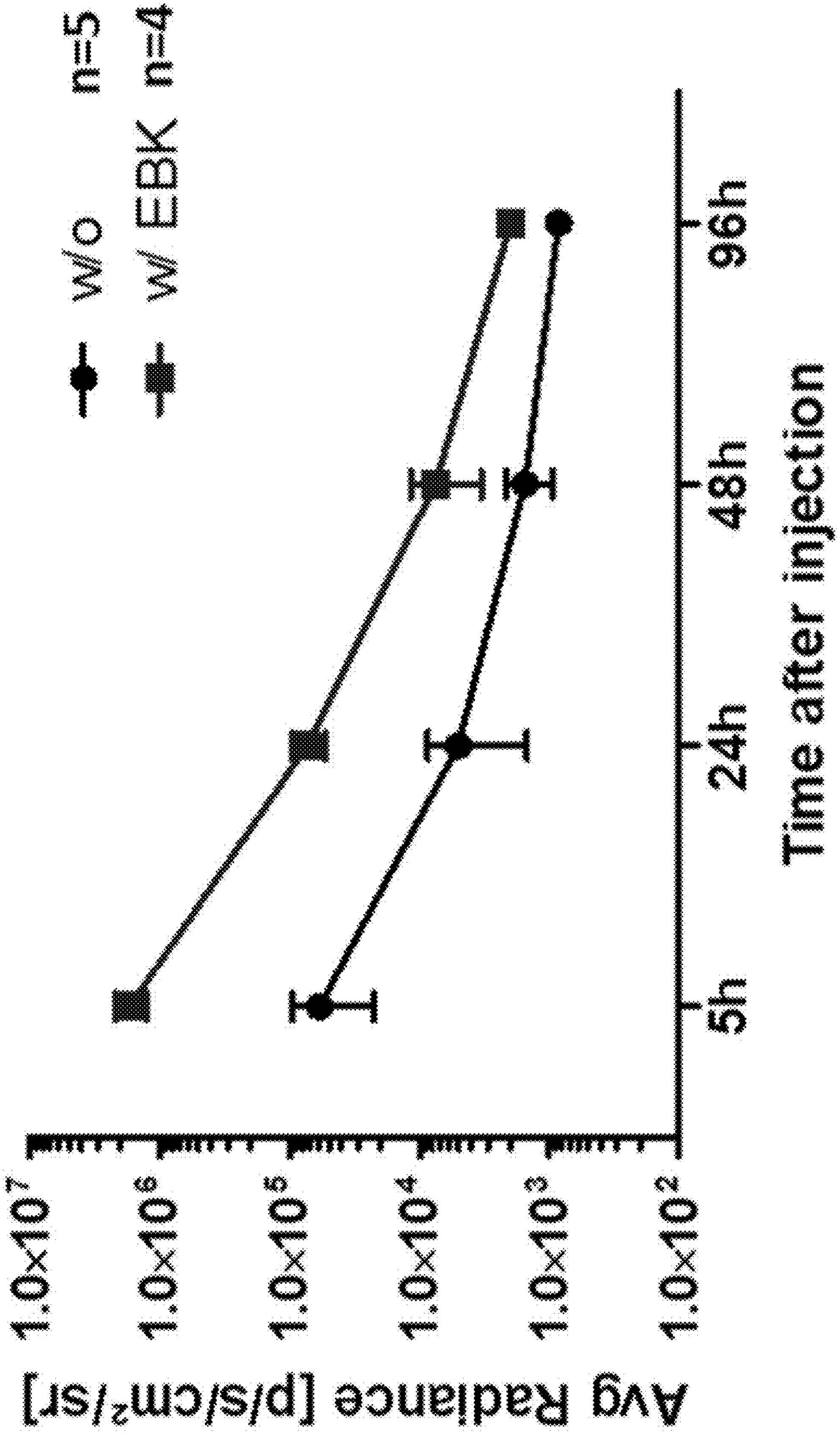

FIG. 23: VacV Proteins Enhanced IVT RNA Expression in the Spleen of Mice Upon i.v. Liposomal Delivery 10 μg IVT RNA encoding luciferase was copackaged with 30 μg GFP RNA or 30 μg EBK RNA into liposomes that target the spleen. Luciferase expression was monitored over 4 days.

Figure 24A:
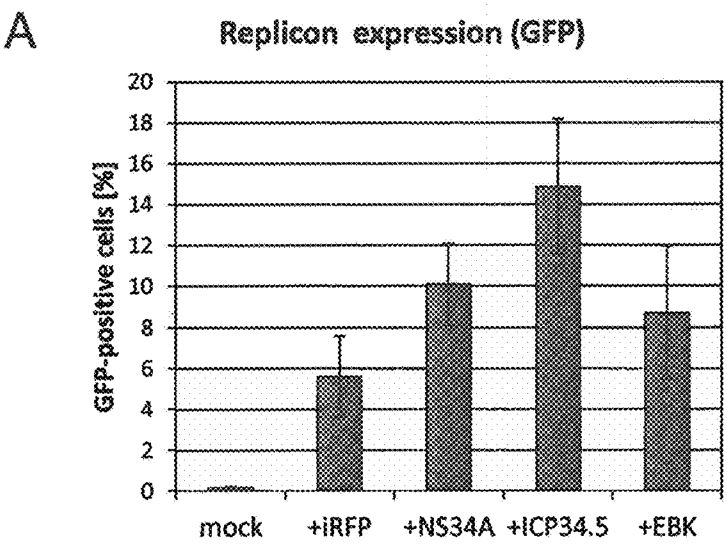
Figure 24B:
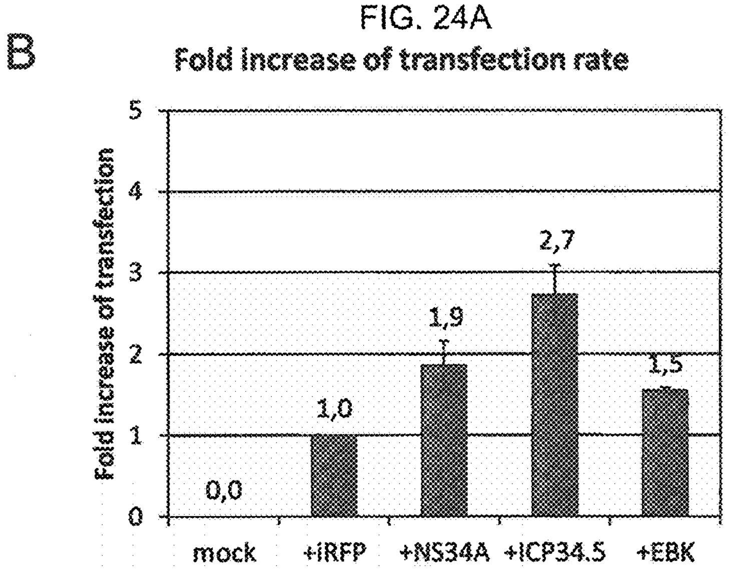
Figure 24C:
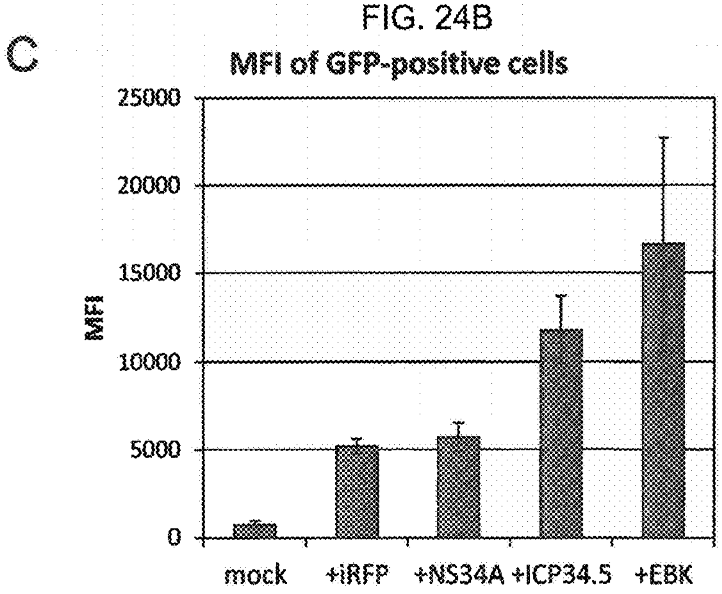

FIG. 24A-24C: NS34A and ICP34.5 Enhance Replicon Expression

Human fibroblasts were cotransfected with 1.5 μg replicon RNA encoding a luciferase-GFP fusion and 1 μg mRNA encoding interferon inhibitors, or iRFP as a control. The next day, transgene expression was measured by FACS. (A) Percentage of transfected cells determined by GFP expression. NS34A increases transfection rates to the same extend as EBK, while ICP34.5 was more potently increasing transfection rates. (B) Same data as in A, expressed as fold increased transfection rates compared to the sample without inhibitors. (C) Change of GFP translation, expressed as mean fluorescence intensity (MFI). NS34A does not increase translation, while ICP34.4 does.

Figure 25A:
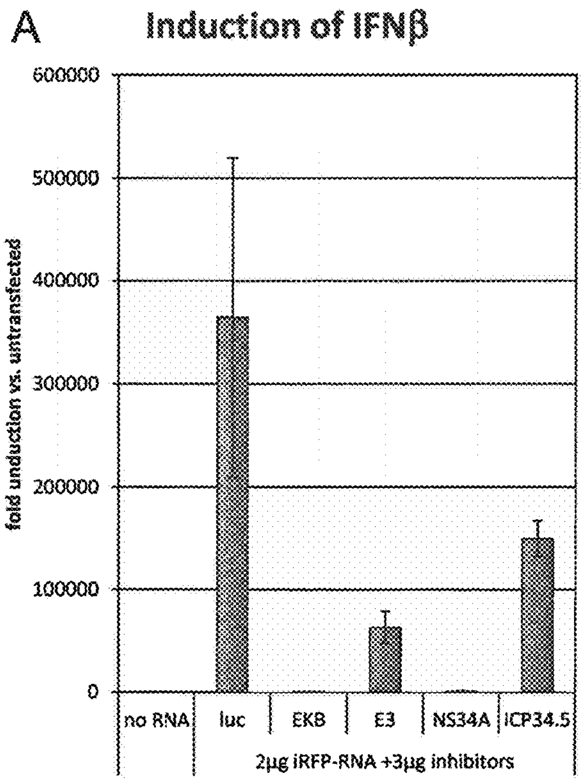
Figure 25B:
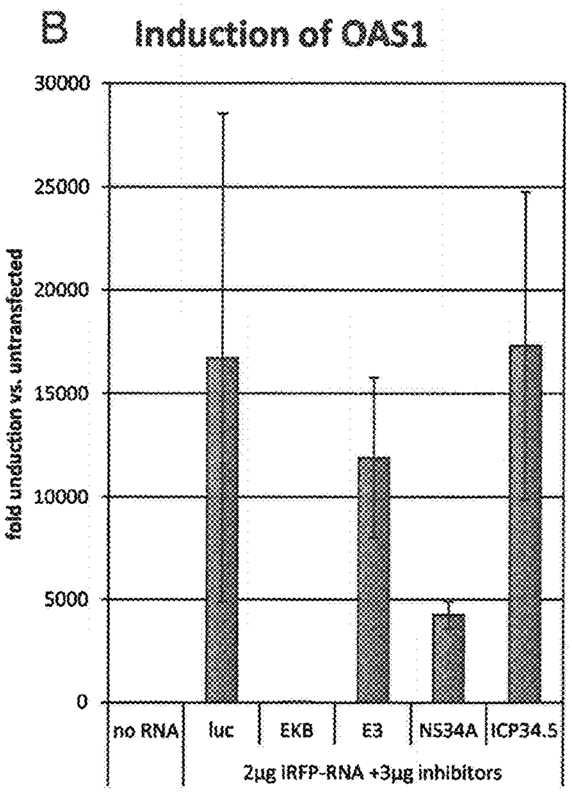
Figure 25C:
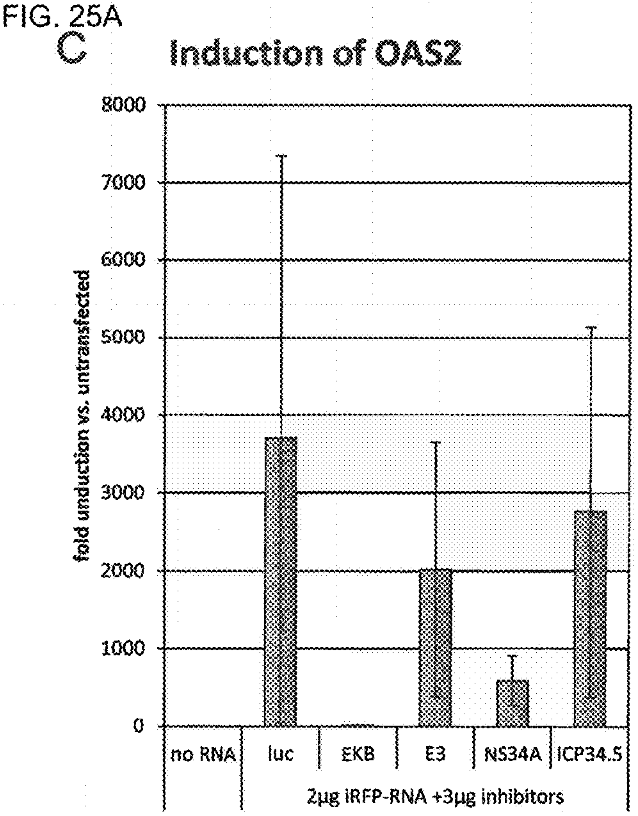
Figure 26A:
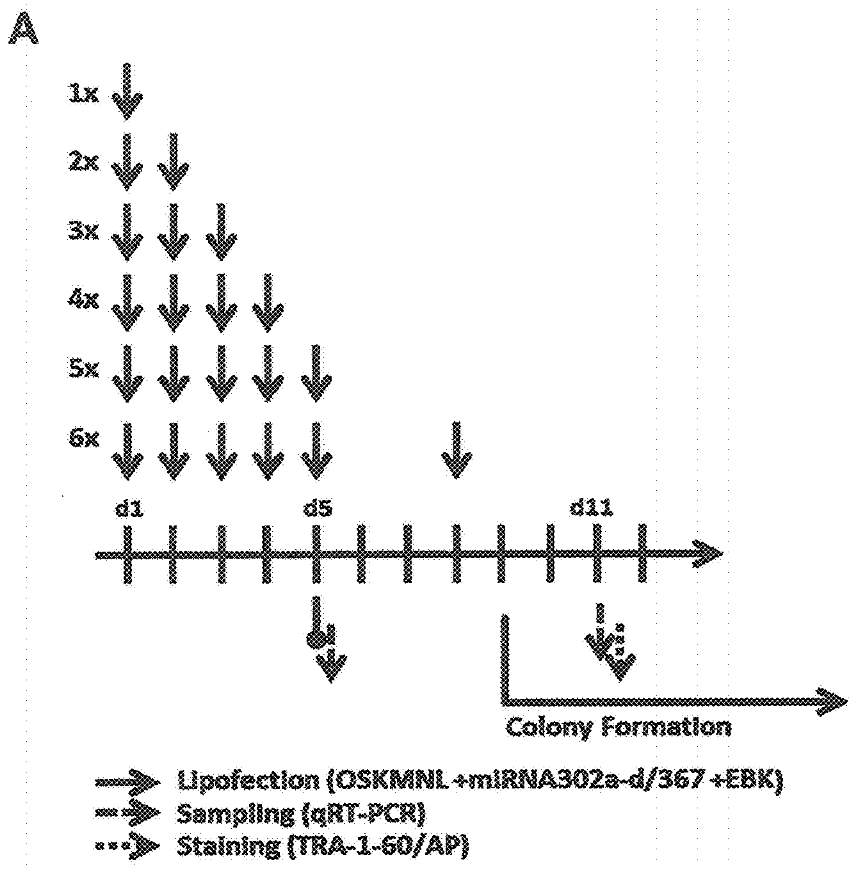
Figure 26B:
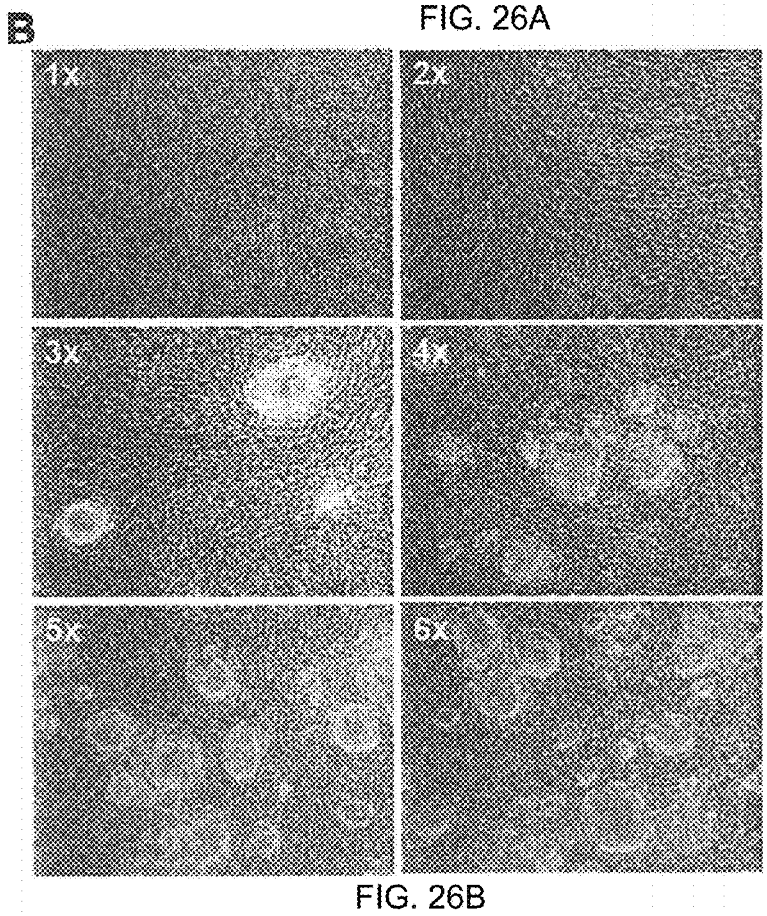
Figure 26C:
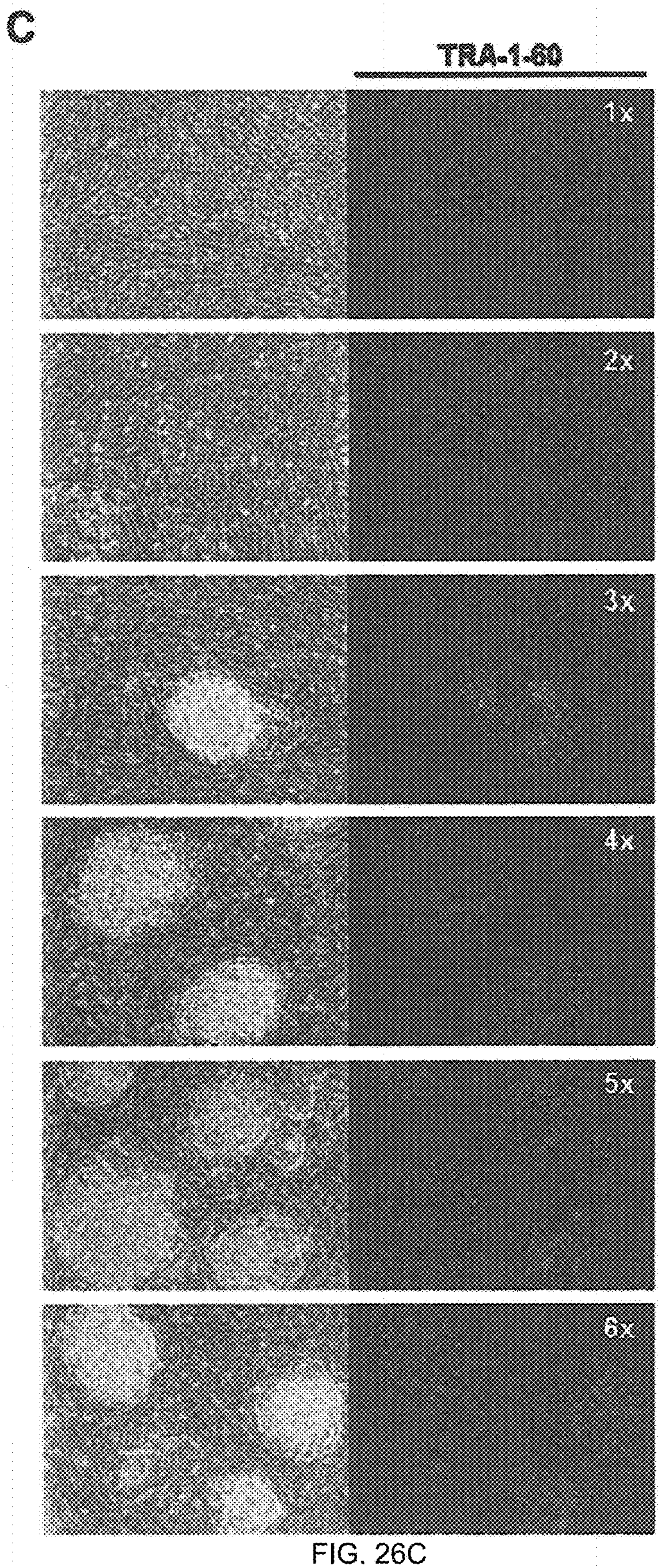
Figure 26D:
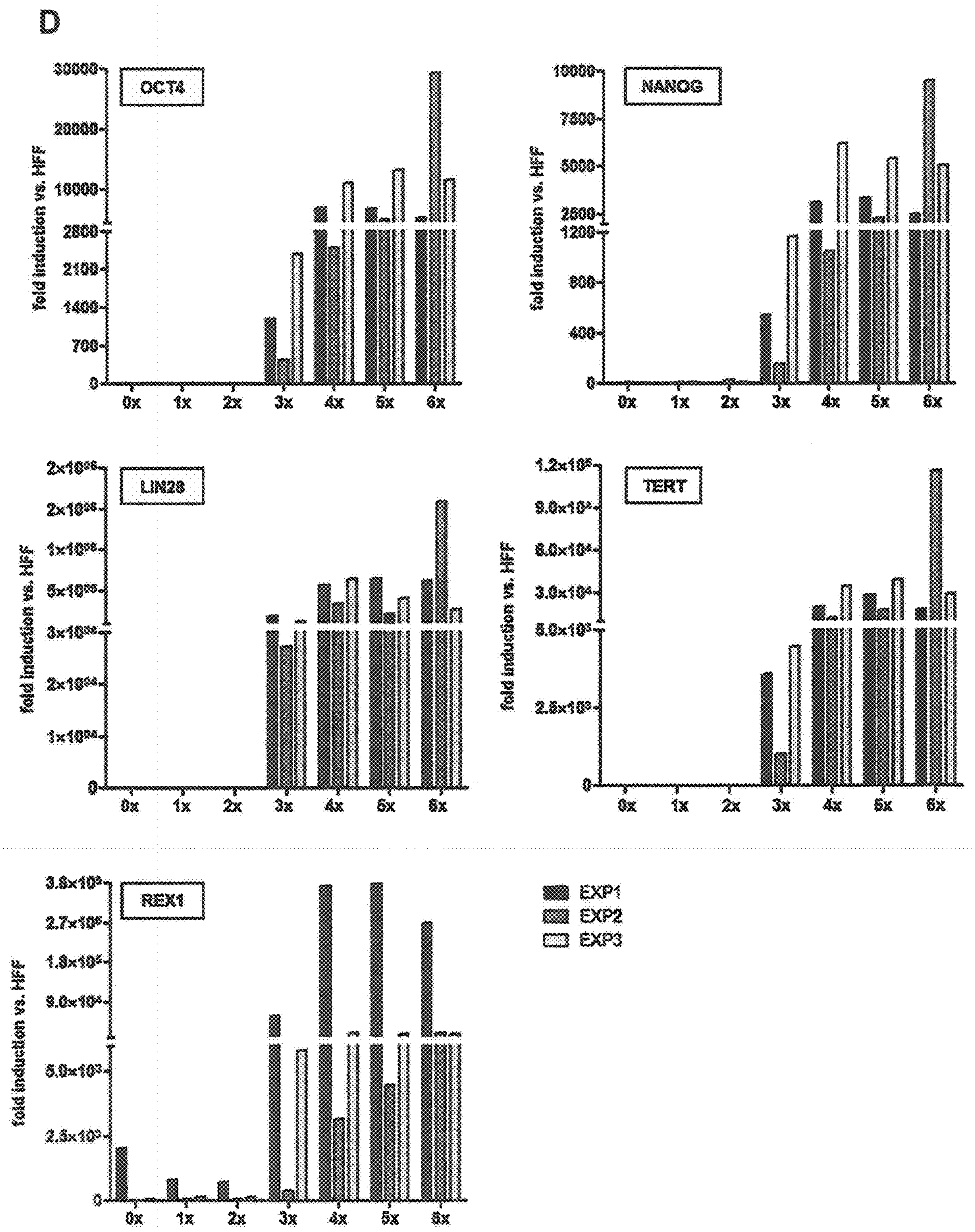

FIG. 25A-25C: NS34A inhibits and ICP34.5 reduces IFN response to synthetic mRNA Human fibroblasts were transfected with 5 μg synthetic mRNA mixtures to induce or prevent IFN reponse. All mixtures contained 2 μg synthetic mRNA encoding infrared fluorescent protein (iRFP) and 3 μg of either IFN inhibitors (as indicated) or luciferase as a control. The next day, cells were harvested an lysed to extract RNA for qRT-PCR. The induction of IFNβ and OAS1/2 were normalized to the base line expression in untransfected cells. (A) Transcriptional induction of IFNβ. Vaccinia virus proteins EKB abrogated IFNβ and E3 reduced IFN0 induction as we have observed before. NS34A also abrogated IFNβ induction similar to EBK, and ICP34.5 reduced IFNβ induction similar to E3. (B, C) Transcriptional induction of IFnβ target genes OAS1/2. EBK blocked OAS1/2 induction, while E3 alone could only partially prevent OAS1/2 upregulation. Similar to E3, ICP34.5 cannot prevent OAS1/2 induction, but NS34A greatly reduced the induction of both markers.

FIG. 26A-26D: Minimal Lipofection Required for Generation of Ribo-iPS

HFF fibroblasts (System Bioscience) were plated into 6 wells (100,000 cells/well) and lipofected 1 to 6 times as depictured in the scheme using 6 μl RNAiMAX (Invitrogen) and 1.4 μg IVT-RNA (A). The IVT-RNA mixtures were thereby composed of 0.8 μg unmodified OSKMNL (1:1:1:1:1:1) with 0.2 μg of each B18R, E3 and K3 (EKB) and 0.4 μg of a miRNA mixture composed of miRNAs 302a-d and 367 [0.4 μM each]. Lipofections in stem cell media (Nutristem media, Stemgent) were performed according to the manufacturer's instructions. From day 9 on, colony formation was observed and representative pictures were taken on d11 by microscopy (B). For further analysis, colonies were stained for the ES surface marker TRA-1-60 using the StainAlive TRA-1-60 antibody (Stemgent) (C) and cells were pelleted afterwards, total RNA isolated and mRNA-expression of the human ES-marker OCT4 (endogenous), NANOG (endogenous), LIN28 (endogenous), TERT and REX1 was quantified by qRT-PCR (D). (B) It became obvious that 3 daily transfections were required to get a few colonies, but 4 daily transfections were sufficient for robust induction of colony formation. The colonies became visible from d9 on and were fully grown on d11 where they could be stained positive for TRA-1-60 (C). Analysis of the expression levels of several pluripotency markers revealed that consistent with colony formation, induction of ES-marker genes can be achieved with 3 or more lipofections. Nevertheless, robust induction of ES-marker expression was achieved with 4 or more lipofections. It should be mentioned that the expression of ES-marker genes was not further enhanced by more than four lipofections (D).

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in a preferred embodiment RNA comprises a poly(A)-tail consisting of 120 nucleotides and in another preferred embodiment the RNA molecule comprises a 5'-cap analog, then in a preferred embodiment, the RNA comprises the poly(A)-tail consisting of 120 nucleotides and the 5'-cap analog.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, and recombinant DNA techniques which are explained in the literature in the field (cf., e.g., *Molecular Cloning: A Laboratory Manual,* 2$^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Terms such as "preventing", "reducing" or "inhibiting" relate to the ability to cause an overall decrease, preferably of 5% or greater, 10% or greater, 20% or greater, more preferably of 50% or greater, and most preferably of 75% or greater, in the level. This also includes a complete or essentially complete decrease, i.e. a decrease to zero or essentially to zero.

Terms such as "increasing", "enhancing", or "prolonging" preferably relate to an increase, enhancement, or prolongation by about at least 10%, preferably at least 20%, preferably at least 30%, preferably at least 40%, preferably at least 50%, preferably at least 80%, preferably at least 100%, preferably at least 200% and in particular at least 300%. These terms may also relate to an increase, enhancement, or prolongation from zero or a non-measurable or non-detectable level to a level of more than zero or a level which is measurable or detectable.

The term "recombinant" in the context of the present invention means "made through genetic engineering". Preferably, a "recombinant entity" such as a recombinant protein in the context of the present invention is not occurring naturally, and preferably is a result of a combination of entities such as amino acid or nucleic acid sequences which are not combined in nature. For example, a recombinant protein in the context of the present invention may contain several amino acid sequences derived from different proteins fused together, e.g., by peptide bonds.

The term "naturally occurring" as used herein refers to the fact that an object can be found in nature. For example, a protein or nucleic acid that is present in an organism (including viruses) and can be isolated from a source in nature and which has not been intentionally modified by man in the laboratory is naturally occurring.

A nucleic acid is according to the invention preferably deoxyribonucleic acid (DNA) or ribonucleic acid (RNA), more preferably RNA, most preferably in vitro transcribed RNA (IVT RNA). Nucleic acids include according to the invention genomic DNA, cDNA, mRNA, recombinantly produced and chemically synthesized molecules. According to the invention, a nucleic acid may be present as a single-stranded or double-stranded and linear or covalently circularly closed molecule. A nucleic acid can, according to the invention, be isolated. The term "isolated nucleic acid" means, according to the invention, that the nucleic acid (i) was amplified in vitro, for example via polymerase chain reaction (PCR), (ii) was produced recombinantly by cloning, (iii) was purified, for example, by cleavage and separation by gel electrophoresis, or (iv) was synthesized, for example, by chemical synthesis. A nucleic can be employed for introduction into, i.e. transfection of, cells, in particular, in the form of RNA which can be prepared by in vitro transcription from a DNA template. The RNA can moreover be modified before application by stabilizing sequences, capping, and polyadenylation.

As a nucleic acid, in particular RNA, for expression of more than one peptide or protein, either of a nucleic acid type in which the different peptides or proteins are present in different nucleic acid molecules or a nucleic acid type in which the peptides or proteins are present in the same nucleic acid molecule can be used.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a β-D-ribofuranosyl group. The term "RNA" comprises double-stranded RNA, single-stranded RNA, isolated RNA such as partially or completely purified RNA, essentially pure RNA, synthetic RNA, and recombinantly generated RNA such as modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA. In one embodiment of the invention, RNA is not chemically modified. In one embodiment of the invention, RNA only comprises standard nucleotides, such as naturally occurring nucleotides.

According to the present invention, the term "RNA" includes and preferably relates to "mRNA". The term "mRNA" means "messenger-RNA" and relates to a "transcript" which is generated by using a DNA template and encodes a peptide or protein. Typically, an mRNA comprises a 5'-UTR, a protein coding region, and a 3'-UTR. mRNA only possesses limited half-life in cells and in vitro. In the context of the present invention, mRNA may be generated by in vitro transcription from a DNA template. The in vitro transcription methodology is known to the skilled person. For example, there is a variety of in vitro transcription kits commercially available.

In one embodiment of the present invention, RNA, in particular RNA which is to be expressed in a cell, is self-replicating RNA, such as single stranded self-replicating RNA. In one embodiment, the self-replicating RNA is single stranded RNA of positive sense. In one embodiment, the self-replicating RNA is viral RNA or RNA derived from viral RNA. In one embodiment, the self-replicating RNA is alphaviral genomic RNA or is derived from alphaviral genomic RNA. In one embodiment, the self-replicating RNA is a viral gene expression vector. In one embodiment, the virus is Semliki forest virus. In one embodiment, the self-replicating RNA contains one or more transgenes which in one embodiment, if the RNA is viral RNA, may partially or completely replace viral sequences such as viral sequences encoding structural proteins. In one embodiment, the self-replicating RNA is introduced into a cell in the form of in vitro transcribed RNA.

According to the invention, the stability and translation efficiency of RNA may be modified as required. For example, RNA may be stabilized and its translation increased by one or more modifications having a stabilizing effects and/or increasing translation efficiency of RNA. Such modifications are described, for example, in PCT/EP2006/009448 incorporated herein by reference. In order to increase expression of the RNA used according to the present invention, it may be modified within the coding region, i.e. the sequence encoding the expressed peptide or protein, preferably without altering the sequence of the expressed peptide or protein, so as to increase the GC-content to increase mRNA stability and to perform a codon optimization and, thus, enhance translation in cells.

The term "modification" in the context of the RNA used in the present invention includes any modification of an RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA and/or enhance translation of RNA if attached thereto, preferably in vivo and/or in a cell.

Preferably, the 5' end of the RNA includes a Cap structure having the following general formula:

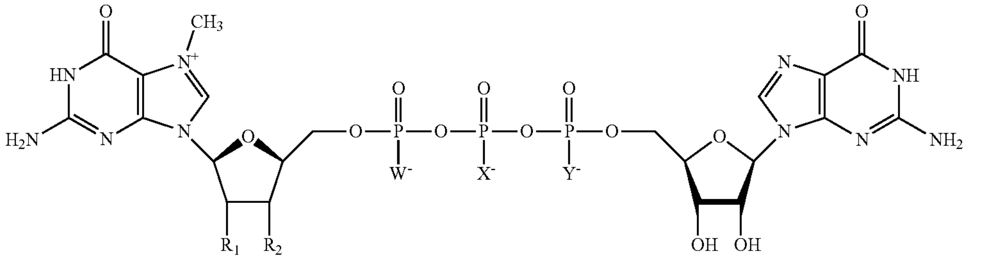

wherein $R_1$ and $R_2$ are independently hydroxy or methoxy and $W^-$, $X^-$ and $Y^-$ are independently oxygen, sulfur, selenium, or $BH_3$. In a preferred embodiment, $R_1$ and $R_2$ are hydroxy and $W^-$, $X^-$ and $Y^-$ are oxygen. In a further preferred embodiment, one of $R_1$ and $R_2$, preferably $R_1$ is hydroxy and the other is methoxy and $W^-$, $X^-$ and r are oxygen. In a further preferred embodiment, $R_1$ and $R_2$ are hydroxy and one of $W^-$, $X^-$ and $Y^-$, preferably $X^-$ is sulfur, selenium, or $BH_3$, preferably sulfur, while the other are oxygen. In a further preferred embodiment, one of $R_1$ and $R_2$, preferably $R_2$ is hydroxy and the other is methoxy and one of $W^-$, $X^-$ and $Y^-$, preferably $X^-$ is sulfur, selenium, or $BH_3$, preferably sulfur while the other are oxygen.

In the above formula, the nucleotide on the right hand side is connected to the RNA chain through its 3' group.

Those Cap structures wherein at least one of $W^-$, $X^-$ and $Y^-$ is sulfur, i.e. which have a phosphorothioate moiety, exist in different diastereoisomeric forms all of which are encompassed herein. Furthermore, the present invention encompasses all tautomers and stereoisomers of the above formula.

For example, the Cap structure having the above structure wherein $R_1$ is methoxy, $R_2$ is hydroxy, $X^-$ is sulfur and $W^-$ and $Y^-$ are oxygen exists in two diastereoisomeric forms (Rp and Sp). These can be resolved by reverse phase HPLC and are named D1 and D2 according to their elution order from the reverse phase HPLC column. According to the invention, the D1 isomer of $m_2^{7,2'-O}$GppspG is particularly preferred.

Providing an RNA with a 5'-cap or 5'-cap analog may be achieved by in vitro transcription of a DNA template in presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the exchange of the existing 3'-UTR with or the insertion of one or more, preferably two copies of a 3'-UTR derived from a globin gene, such as alpha2-globin, alpha1-globin, beta-globin, preferably beta-globin, more preferably human beta-globin.

RNA having an unmasked poly-A sequence is translated more efficiently than RNA having a masked poly-A sequence. The term "poly(A) tail" or "poly-A sequence" relates to a sequence of adenyl (A) residues which typically is located on the 3'-end of a RNA molecule and "unmasked poly-A sequence" means that the poly-A sequence at the 3' end of an RNA molecule ends with an A of the poly-A sequence and is not followed by nucleotides other than A located at the 3' end, i.e. downstream, of the poly-A sequence. Furthermore, a long poly-A sequence of about 120 base pairs results in an optimal transcript stability and translation efficiency of RNA.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. To further increase stability and/or expression of the RNA used according to the invention, the poly-A sequence can be unmasked.

In addition, incorporation of a 3'-non translated region (UTR) into the 3'-non translated region of an RNA molecule can result in an enhancement in translation efficiency. A synergistic effect may be achieved by incorporating two or more of such 3'-non translated regions. The 3'-non translated regions may be autologous or heterologous to the RNA into which they are introduced. In one particular embodiment the 3'-non translated region is derived from the human β-globin gene.

A combination of the above described modifications, i.e. incorporation of a poly-A sequence, unmasking of a poly-A sequence and incorporation of one or more 3'-non translated regions, has a synergistic influence on the stability of RNA and increase in translation efficiency.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

Of course, if according to the present invention it is desired to decrease stability and/or translation efficiency of RNA, it is possible to modify RNA so as to interfere with the function of elements as described above increasing the stability and/or translation efficiency of RNA.

The term "expression" is used according to the invention in its most general meaning and comprises the production of RNA and/or peptides or proteins, e.g. by transcription and/or translation. With respect to RNA, the term "expression" or "translation" relates in particular to the production of peptides or proteins. It also comprises partial expression of nucleic acids. Moreover, expression can be transient or stable.

According to the invention, terms such as "RNA expression", "expressing RNA", or "expression of RNA" relate to the production of peptide or protein encoded by the RNA. Preferably, such terms relate to the translation of RNA so as to express, i.e. produce peptide or protein encoded by the RNA.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, the RNA used in the present invention preferably is in vitro transcribed RNA (IVT-RNA) and may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription according to the invention is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

The cDNA containing vector template may comprise vectors carrying different cDNA inserts which following transcription results in a population of different RNA molecules optionally capable of expressing different peptides or proteins or may comprise vectors carrying only one species of cDNA insert which following transcription only results in a population of one RNA species capable of expressing only one peptide or protein. Thus, it is possible to produce RNA capable of expressing a single peptide or protein only or to produce compositions of different RNAs such as RNA libraries and whole-cell RNA capable of expressing more than one peptide or protein, e.g. a composition of peptides or proteins. The present invention envisions the introduction of all such RNA into cells.

The term "translation" according to the invention relates to the process in the ribosomes of a cell by which a strand of messenger RNA directs the assembly of a sequence of amino acids to make a peptide or protein.

Expression control sequences or regulatory sequences, which according to the invention may be linked functionally with a nucleic acid, can be homologous or heterologous with respect to the nucleic acid. A coding sequence and a regulatory sequence are linked together "functionally" if they are bound together covalently, so that the transcription or translation of the coding sequence is under the control or under the influence of the regulatory sequence. If the coding sequence is to be translated into a functional protein, with functional linkage of a regulatory sequence with the coding sequence, induction of the regulatory sequence leads to a transcription of the coding sequence, without causing a reading frame shift in the coding sequence or inability of the coding sequence to be translated into the desired protein or peptide.

The term "expression control sequence" or "regulatory sequence" comprises, according to the invention, promoters, ribosome-binding sequences and other control elements, which control the transcription of a nucleic acid or the translation of the derived RNA. In certain embodiments of the invention, the regulatory sequences can be controlled. The precise structure of regulatory sequences can vary depending on the species or depending on the cell type, but generally comprises 5'-untranscribed and 5'- and 3'-untranslated sequences, which are involved in the initiation of transcription or translation, such as TATA-box, capping-sequence, CAAT-sequence and the like. In particular, 5'-untranscribed regulatory sequences comprise a promoter region that includes a promoter sequence for transcriptional control of the functionally bound gene. Regulatory sequences can also comprise enhancer sequences or upstream activator sequences.

Terms such as "enhancement of expression", "enhanced expression" or "increased expression" mean in the context of the present invention that the amount of peptide or protein expressed by a given number of RNA molecules is higher than the amount of peptide or protein expressed by the same number of RNA molecules, wherein expression of the RNA molecules is performed under the same conditions except the condition which results in the enhanced or increased expression of the RNA, such as preventing engagement of IFN receptor by extracellular IFN and inhibiting intracellular IFN signalling in a cell versus not preventing engagement of IFN receptor by extracellular IFN and not inhibiting intracellular IFN signalling in a cell. In this context, "same conditions" refer to a situation wherein the same RNA sequences encoding the same peptide or protein are introduced by the same means into the same cells, the cells are cultured under the same conditions (except the condition which results in the enhanced or increased expression) and the amount of peptide or protein is measured by the same means. The amount of peptide or protein may be given in moles, or by weight, e.g. in grams, or by mass or by polypeptide activity, e.g. if the peptide or protein is an enzyme it may be given as catalytic activity or if the peptide or protein is an antibody or antigen or a receptor it may be given as binding affinity. In one embodiment, terms such as "enhancement of expression", "enhanced expression" or "increased expression" mean in the context of the present invention that the amount of peptide or protein expressed by a given number of RNA molecules and within a given period of time is higher than the amount of peptide or protein expressed by the same number of RNA molecules and within the same period of time. For example, the maximum value of peptide or protein expressed by a given number of RNA molecules at a particular time point may be higher than the maximum value of peptide or protein expressed by the same number of RNA molecules. In other embodiments, the maximum value of peptide or protein expressed by a given number of RNA molecules does not need to be higher than the maximum value of peptide or protein expressed by the same number of RNA molecules, however, the average amount of peptide or protein expressed by the given number of RNA molecules within a given period of time may be higher than the average amount of peptide or protein expressed by the same number of RNA molecules. The latter cases are referred to herein as "higher level of expression" or "increased level of expression" and relate to higher maximum values of expression and/or higher average values of expression. Alternatively or additionally, terms such as "enhancement of expression", "enhanced expression" or "increased expression" mean in the context of the present invention also that the time in which peptide or protein is expressed by RNA molecules may be longer than the time in which the peptide or protein is expressed by the same RNA molecules. Thus, in one embodiment, terms such as "enhancement of expression", "enhanced expression" or "increased expression" mean in the context of the present invention also that the amount of peptide or protein expressed by a given number of RNA molecules is higher than the amount of peptide or protein expressed by the same number of RNA molecules since the period of time in which the RNA is stably present and expressed is longer than the period of time in which the same number of RNA molecules is stably present and expressed. These cases are referred to herein also as "increased duration of expression". Preferably, such longer time periods refer to expression for at least 48 h, preferably for at least 72 h, more preferably for at least 96 h, in particular for at least 120 h or even longer following introduction of RNA or following the first introduction (e.g. in case of repeated transfections) of RNA into a cell.

The level of expression and/or duration of expression of RNA may be determined by measuring the amount, such as the total amount expressed and/or the amount expressed in a given time period, and/or the time of expression of the peptide or protein encoded by the RNA, for example, by using an ELISA procedure, an immunohistochemistry procedure, a quantitative image analysis procedure, a Western Blot, mass spectrometry, a quantitative immunohistochemistry procedure, or an enzymatic assay.

In particular embodiments, the RNA according to the invention comprises a population of different RNA molecules, e.g. a mixture of different RNA molecules optionally encoding different peptides and/or protein, whole-cell RNA, an RNA library, or a portion of thereof, e.g. a library of RNA molecules expressed in a particular cell type, such as undifferentiated cells, in particular stem cells such as embryonic stem cells, or a fraction of the library of RNA molecules such as RNA with enriched expression in undifferentiated cells, in particular stem cells such as embryonic stem cells relative to differentiated cells. Thus, according to the invention, the term "RNA" may include a mixture of RNA molecules, whole-cell RNA or a fraction thereof, which may be obtained by a process comprising the isolation of RNA from cells and/or by recombinant means, in particular by in vitro transcription.

Preferably, according to the invention, the RNA to be expressed in a cell is introduced into said cell, either in vitro or in vivo, preferably in vitro. RNA may be introduced into a cell either prior to, after and/or simultaneously with preventing engagement of IFN receptor by extracellular IFN and/or inhibiting intracellular IFN signalling in the cell. Preferably, engagement of IFN receptor by extracellular IFN is prevented and intracellular IFN signalling is inhibited as long as expression of the RNA in the cell is desired. In one embodiment of the methods according to the invention, the RNA that is to be introduced into a cell is obtained by in vitro transcription of an appropriate DNA template.

The RNA used according to the present invention may have a known composition (in this embodiment it is preferably known which peptides or proteins are being expressed by the RNA) or the composition of the RNA may be partially or entirely unknown. Alternatively, the RNA used according to the present invention may have a known function or the function of the RNA may be partially or entirely unknown.

According to the invention, the terms “RNA capable of expressing” and “RNA encoding” are used interchangeably herein and with respect to a particular peptide or protein mean that the RNA, if present in the appropriate environment, preferably within a cell, can be expressed to produce said peptide or protein. Preferably, RNA according to the invention is able to interact with the cellular translation machinery to provide the peptide or protein it is capable of expressing.

According to the invention, RNA may be introduced into cells either in vitro or in vivo, preferably in vitro. The cells into which the RNA has been introduced in vitro may, preferably following expression of the RNA in vitro by the methods of the invention, be administered to a patient.

Terms such as “transferring”, “introducing” or “transfecting” are used interchangeably herein and relate to the introduction of nucleic acids, in particular exogenous or heterologous nucleic acids, in particular RNA, into a cell. Said terms also include the repetitive introduction of nucleic acids, in particular RNA, into a cell, wherein repetitive mean more than once, e.g. two times or more, three times or more, four times or more, five times or more, six times or more, seven times or more, eight times or more. The time interval between said repetitive introductions of nucleic acids may be 3 days or less, 2 days or less, 24 h ours or less or even lower. Those aspects of the present invention relating to the provision of cells having stem cell characteristics may involve the repetitive introduction into cells of nucleic acids, in particular RNA, for at least 3 consecutive days, at least 4 consecutive days, at least 5 consecutive days, or at least 6 consecutive days. The nucleic acids may comprise RNA capable of expressing one or more factors allowing the reprogramming of somatic cells to cells having stem cell characteristics. However, the nucleic acids may also comprise nucleic acids, in particular RNA, encoding one or more proteins or peptides preventing engagement of IFN receptor by extracellular IFN, such as proteins or peptides disclosed herein, and/or nucleic acids, in particular RNA, encoding one or more proteins or peptides inhibiting intracellular IFN signalling, such as proteins or peptides disclosed herein. Thus, the nucleic acids may also comprise, for example, nucleic acids, in particular RNA, encoding B18R and one or both of E3 and K3. Furthermore, the nucleic acids may comprise miRNA enhancing reprogramming of somatic cells to cells having stem cell characteristics. Preferably, repetitive introduction into cells of nucleic acids, in particular RNA, is not performed for more than 10 consecutive days, 8 consecutive days or 6 consecutive days. Preferably, repetitive introduction into cells of nucleic acids, in particular RNA, is performed for 3, 4, 5 or 6 consecutive days. Preferably, nucleic acids, in particular RNA, are introduced into cells once, twice or three times per day, preferably once per day.

According to the present invention, a cell can be an isolated cell or it can form part of an organ, a tissue and/or an organism. According to the present invention, any technique which is suitable to introduce RNA into cells may be used. Preferably, the RNA is introduced into cells by standard techniques. Such techniques comprise transfection of nucleic acid calcium phosphate precipitates, transfection of nucleic acids which are associated with DEAE, the transfection or infection with viruses which carry the nucleic acids of interest, electroporation, lipofection, and microinjection. According to the present invention, the administration of a nucleic acid is either achieved as naked nucleic acid or in combination with an administration reagent. Preferably, administration of nucleic acids is in the form of naked nucleic acids. Preferably, the RNA is administered in combination with stabilizing substances such as RNase inhibitors. The present invention also envisions the repeated introduction of nucleic acids into cells to allow sustained expression for extended time periods.

Cells can be transfected, for example, using commercially available liposome-based transfection kits such as LIPOFECTAMINE™ (Invitrogen) and can be transfected with any carriers with which RNA can be associated, e.g. by forming complexes with the RNA or forming vesicles in which the RNA is enclosed or encapsulated, resulting in increased stability of the RNA compared to naked RNA. Carriers useful according to the invention include, for example, lipid-containing carriers such as cationic lipids, liposomes, in particular cationic liposomes, and micelles. Cationic lipids may form complexes with negatively charged nucleic acids. Any cationic lipid may be used according to the invention.

Preferably, the introduction of RNA which encodes a peptide or protein into a cell results in expression of said peptide or protein in the cell. In particular embodiments, the targeting of the nucleic acids to particular cells is preferred. In such embodiments, a carrier which is applied for the administration of the nucleic acid to a cell (for example, a retrovirus or a liposome), exhibits a targeting molecule. For example, a molecule such as an antibody which is specific for a surface membrane protein on the target cell or a ligand for a receptor on the target cell may be incorporated into the nucleic acid carrier or may be bound thereto. In case the nucleic acid is administered by liposomes, proteins which bind to a surface membrane protein which is associated with endocytosis may be incorporated into the liposome formulation in order to enable targeting and/or uptake. Such proteins encompass capsid proteins of fragments thereof which are specific for a particular cell type, antibodies against proteins which are internalized, proteins which target an intracellular location etc.

Electroporation or electropermeabilization relates to a significant increase in the electrical conductivity and permeability of the cell plasma membrane caused by an externally applied electrical field. It is usually used in molecular biology as a way of introducing some substance into a cell. Electroporation is usually done with electroporators, appliances which create an electro-magnetic field in the cell solution. The cell suspension is pipetted into a glass or plastic cuvette which has two aluminum electrodes on its sides. For electroporation, tyically a cell suspension of around 50 microliters is used. Prior to electroporation it is mixed with the nucleic acid to be transfected. The mixture is pipetted into the cuvette, the voltage and capacitance is set and the cuvette inserted into the electroporator. Preferably, liquid medium is added immediately after electroporation (in the cuvette or in an eppendorf tube), and the tube is incubated at the cells' optimal temperature for an hour or more to allow recovery of the cells and optionally expression of antibiotic resistance.

According to the invention it is preferred that a nucleic acid such as RNA encoding a peptide or protein once taken up by or introduced into a cell which cell may be present in vitro or in a subject results in expression of said peptide or protein. The cell may express the encoded peptide or protein intracellularly (e.g. in the cytoplasm and/or in the nucleus), may secrete the encoded peptide or protein, or may express it on the surface. If a peptide or protein (e.g. B18R) is to prevent engagement of IFN receptor by extracellular IFN, secretion of the peptide or protein is preferred. If a peptide or protein (e.g. E3, K3) is to inhibit intracellular IFN signalling, intracellular expression of the peptide or protein is preferred.

If according to the invention RNA capable of expressing certain factors for reprogramming of somatic cells is introduced into somatic cells, it is preferred that this introduction of RNA results in expression of said factors for a time period to complete the reprogramming process and in the development of cells having stem cell characteristics. Preferably, introduction of RNA capable of expression certain factors as disclosed herein into somatic cells results in expression of said factors for an extended period of time, preferably for at least 10 days, preferably for at least 11 days and more preferably for at least 12 days. To achieve such long term expression, RNA is preferably periodically (i.e. repetitively) introduced into the cells more than one time, preferably using electroporation. Preferably, RNA is introduced into the cells at least twice, more preferably at least 3 times, more preferably at least 4 times, even more preferably at least 5 times up to preferably 6 times, more preferably up to 7 times or even up to 8, 9 or 10 times, preferably over a time period of at least 10 days, preferably for at least 11 days and more preferably for at least 12 days to ensure expression of one or more factors for an extended period of time. Preferably, the time periods elapsing between the repeated introductions of the RNA are from 24 h ours to 120 h ours, preferably 48 hours to 96 h ours. In one embodiment, time periods elapsing between the repeated introductions of the RNA are not longer than 72 h ours, preferably not longer than 48 h ours or 36 h ours. In one embodiment, prior to the next electroporation, cells are allowed to recover from the previous electroporation. In this embodiment, the time periods elapsing between the repeated introductions of the RNA are at least 72 h ours, preferably at least 96 h ours, more preferably at least 120 h ours. In any case, the conditions should be selected so that the factors are expressed in the cells in amounts and for periods of time which support the reprogramming process.

Preferably at least 1 μg, preferably at least 1.25 μg, more preferably at least 1.5 μg and preferably up to 20 μg, more preferably up to 15 μg, more preferably up to 10 μg, more preferably up to 5 μg, preferably 1 to 10 μg, even more preferably 1 to 5 μg, or 1 to 2.5 μg of RNA for each peptide, protein or factor is used per electroporation.

Preferably, if a loss of viability of cells occurs by repeated electroporations, previously not electroporated cells are added as carrier cells. Preferably, previously not electroporated cells are added prior to, during or after one or more of the $4^{th}$ and subsequent, preferably, the $5^{th}$ and subsequent electroporations such as prior to, during or after the $4^{th}$ and $6^{th}$ electroporation. Preferably, previously not electroporated cells are added prior to, during or after the $4^{th}$ or $5^{th}$ and each subsequent electroporation. Preferably, the previously not electroporated cells are the same cells as those into which RNA is introduced.

Terms such as "enhancement of cell viability", "enhanced cell viability" or "increased cell viability" mean in the context of the present invention that the amount of viable or living cells under certain conditions is higher than the amount of viable or living cells under other conditions, wherein cultivation is performed under the same conditions except the condition which results in the enhanced or increased cell viability, such as preventing engagement of IFN receptor by extracellular IFN and inhibiting intracellular IFN signalling in a cell versus not preventing engagement of IFN receptor by extracellular IFN and not inhibiting intracellular IFN signalling in a cell. In this context, "same conditions" refer to a situation wherein the same cells are used, the cells are cultured under the same conditions (except the condition which results in the enhanced or increased cell viability) and the cell viability is measured by the same means. "Same conditions" also encompasses the introduction or repetitive introduction of RNA into cells.

Double-stranded RNA (dsRNA) produced during viral infection activates several cellular antiviral responses. Double-stranded RNA (dsRNA) not only constitutes the genetic material of dsRNA viruses but is also produced in infected cells by positive-strand RNA viruses and some DNA viruses. Among the best characterized cellular antiviral responses is the shutoff of protein synthesis mediated by the RNA-dependent protein kinase (PKR) and the oligoadenylate synthetase (OAS)/RNase L systems. Toll-like receptor 3 ($TLR_3$) and the RNA helicases RIG-I and MDAS serve as sensors for dsRNA; cf. FIG. 1. Upon activation, they induce signaling cascades culminating in the expression of type I interferons (IFNs). Induction of type I IFNs is controlled predominantly at the transcription level by a family of transcription factors termed the interferon regulatory factors (IRFs).

Interferons are important cytokines characterized by antiviral, antiproliferative and immunomodulatory activities. Interferons are proteins that alter and regulate the transcription of genes within a cell by binding to interferon receptors on the regulated cell's surface, thereby preventing viral replication within the cells. According to the invention, the phrase "engagement of IFN receptor by extracellular IFN" relates to the binding of IFNs, in particular type I IFNs, to interferon receptors on the cell surface.

The interferons can be grouped into two types. IFN-gamma is the sole type II interferon; all others are type I interferons. Type I and type II interferons differ in gene structure (type II interferon genes have three exons; type I, one), chromosome location (in humans, type II is located on chromosome-12; the type I interferon genes are linked and on chromosome-9), and the types of tissues where they are produced (type I interferons are synthesized ubiquitously, type II by lymphocytes). Type I interferons competitively inhibit each others binding to cellular receptors, while type II interferon has a distinct receptor. According to the invention, the term "interferon" or "IFN" preferably relates to type I interferons, in particular IFN-alpha and IFN-beta.

Human IFN-alpha's are encoded by a multigene family consisting of about 20 genes; each gene encodes a single subtype of the human IFN-alpha. Human IFN-alpha polypeptides are produced by a number of human cell lines and human leukocyte cells after exposure to viruses or double-stranded RNA, or in transformed leukocyte cell lines (e.g., lymphoblastoid lines). IFN-alpha's interact with cell-surface receptors and induce the expression, primarily at the transcriptional level, of a broad but specific set of cellular genes.

Human IFN-beta is a regulatory polypeptide with a molecular weight of 22 kDa consisting of 166 amino acid residues. It can be produced by most cells in the body, in particular fibroblasts, in response to viral infection or exposure to other biologics. It binds to a multimeric cell surface receptor, and productive receptor binding results in a cascade of intracellular events leading to the expression of IFN-beta inducible genes which, in turn, produces effects which can be classified as antiviral, antiproliferative, or immunomodulatory.

IFNs induce the expression of a plethora of antiviral genes, which can interfere with the viral replication cycle.

According to the invention, the term "antivirally active effector protein" relates to a group of proteins encoded by IFN-stimulated genes (ISGs) the transcription of which is signaled by type I IFNs. These proteins target distinct viral components and distinct stages of the viral life cycle, aiming to eliminate invading viruses. "Antivirally active effector proteins" are involved in different effector pathways individually blocking viral transcription, degrading viral RNA, inhibiting translation, and modifying protein function to control all steps of viral replication. Such proteins include 2',5'-oligoadenylate synthetase (OAS), in particular 2',5'-oligoadenylate synthetase 1 (OAS1), RNA-dependent protein kinase R (PKR), and RNaseL. Both PKR and OAS are directly activated by dsRNA. Hence, dsRNA induces the expression of these antivirally active effector proteins and is also necessary for their activation.

PKR is constitutively expressed, and induced by type I IFNs. Upon binding to dsRNA, PKR dimerizes and undergoes autophosphorylation to gain full catalytic activity. Once activated, PKR phosphorylates the eukaryotic translation initiation factor eIF2-alpha. In its phosphorylated state, eIF2-alpha forms a stable complex with the nucleotide exchange factor eIF2-beta, which is then no longer recycled for initiation of protein translation by GDP/GTP exchange. Consequently, PKR activation leads to a global block to protein synthesis in the infected cell, which can hamper the production of virus progeny. In this way, PKR in combination with eIF2-alpha constitutes an antiviral pathway (PKR-dependent pathway).

The term "RNA-dependent protein kinase" (protein kinase RNA-activated; PKR) relates to a RNA-binding protein which is an interferon-induced serine/threonine protein kinase initially identified in viral response by virtue of its binding to and activation by the extensive secondary structure formed by viral RNA sequences. Human PKR is 68 kDa with an about 20 kDa N-terminal dsRNA-binding domain and a C-terminal protein kinase domain. In vitro PKR is activated by binding to RNA molecules with extensive duplex secondary structure. In vivo the enzyme is believed to be activated by viral double-stranded RNA (dsRNA) or viral replicative intermediates comprising dsRNA. Binding to double-stranded RNA to PKR causes a conformational change in the enzyme that alters the ATP-binding site in the kinase domain and leads to autophosphorylation at multiple serine and threonine residues throughout the PKR sequence. RNA-stimulated autophosphorylation increases cellular sensitivity to apoptotic and pro-inflammatory stimuli through a number of putative pathways, including phosphorylation of its known substrate eukaryotic initiation factor 2 (eIF2-alpha).

The term "PKR" preferably relates to human PKR, and, in particular, to a protein comprising the amino acid sequence according to SEQ ID NO: 14 of the sequence listing or a variant of said amino acid sequence. In one embodiment, the term "PKR" relates to a protein comprising an amino acid sequence encoded by the nucleic acid sequence according to SEQ ID NO: 13. The term "PKR" includes any variants, in particular mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. One skilled in the art would understand that the cDNA sequence of PKR as described above would be equivalent to PKR mRNA, and can be used for the generation of inhibitory nucleic acids against PKR.

Protein kinase activity including protein kinase autophosphorylation can be measured by a variety of techniques known to the skilled person. One method involves separation of unreacted ATP from the phosphorylated kinase substrate by e.g. precipitating phosphoprotein onto cellulose strips by trichloroacetic acid followed by washing, or adsorption of phosphoprotein onto phosphocellulose strips. For example, dephosphoPKR can be activated by incubation with poly[I:C] and autophosphorylation can be allowed to proceed in the presence of [γ-32P]ATP. The ability of compounds to block this RNA-induced PKR autophosphorylation can be tested. Another method involves detection and quantification of phospho-PKR in relation to the total amount of PKR in the same lysate of cells by Western blotting with antibodies specific for phospho-PKR or full length PKR. Another method involves detection and quantification of the phosphorylated substrate of PKR, e.g. phospho-eIF2-alpha in relation to the total amount of eIF2-alpha in the same lysate of cells by Western blotting with antibodies specific for phospho-eIF2-alpha or full length eIF2-alpha.

The term "eIF2-alpha" preferably relates to human eIF2-alpha, and, in particular, to a protein comprising the amino acid sequence according to SEQ ID NO: 16 of the sequence listing or a variant of said amino acid sequence. In one embodiment, the term "eIF2-alpha" relates to a protein comprising an amino acid sequence encoded by the nucleic acid sequence according to SEQ ID NO: 15. The term "eIF2-alpha" includes any variants, in particular mutants, splice variants, conformations, isoforms, allelic variants, species variants and species homologs, in particular those which are naturally present.

OAS is expressed at low constitutive levels and is induced by type I IFNs. The protein accumulates in the cell cytoplasm as inactive monomers. Upon activation by viral dsRNA the enzyme oligomerizes to (in the instance of OAS1) form a tetramer that is able to condense ATP molecules via unusual 2',5'-phosphodiester linkages and synthesizes 2',5'-oligoadenlylates that, in turn, activate the constitutively expressed inactive RNaseL. Binding of 2',5'-oligoadenlylates to RNaseL triggers dimerization of enzyme monomers, via their kinase-like domains, which then cleaves cellular (and viral) RNAs. As a result, synthesis of viral proteins is inhibited, and viral RNA genomes are directly destroyed. In this way, OAS in combination with RNaseL constitutes an antiviral RNA decay pathway (OAS-RNaseL antiviral pathway or OAS-dependent pathway).

The four OAS genes identified in humans, termed OAS1, OAS2, OAS3 and OASL (OAS-like), have been mapped to chromosome 12 (chromosome 5 in mice). OAS1 h as two spliced forms in humans (eight in mice) that produce two, 40 and 46 kDa, proteins that differ at their C-termini by 18 and 54 amino acids, respectively. OAS2 produces four alternatively spliced transcripts that encode two proteins of 69 and 71 kDa. OAS3 encodes a single transcript that produces a 100 kDa protein. These proteins have considerable homology to each other, with OAS1, OAS2 and OAS3 encoding one, two and three, respectively, "OAS" domains. The most distinctive of the OAS proteins is OASL. Two OASL transcripts are expressed producing two proteins of 30 and 59 kDa. The higher molecular weight OASL contains a putative nucleolar localization signal at its C-terminus that, probably, accounts for its unique (from the other OAS isoforms) distribution in the cell. The OASL protein also has an OAS domain, however, mutations at key residues disable the catalytic function of this human protein. Interestingly, one of the two mouse homologues retains its 2',5'-polymerase activity. In addition to the OAS domain, OASL has a unique 160 amino acid C-terminus that encodes a ubiquitin-like domain that is homologous to ISG15. Accordingly, OASL becomes conjugated (ISGylation) to cellular proteins following the treatment of cells with type I IFNs. There appears to be differential expression and induction of each form of the human OAS proteins. Also, each of the three functional OAS proteins has unique biological functions. A tripeptide motif (CFK) within the OAS domains of OAS1 and OAS2 mediate oligomerization, so the catalytically active form of these enzymes is a tetramer and dimer, for OAS1 and OAS2, respectively. This tripeptide motif is not conserved in the OAS domains of OAS3 and OASL and therefore these proteins function as monomers. The polymerization of OAS monomers influences their processivity, with OAS3 synthesizing dimeric molecules of 2',5'-linked oligomers, whereas OAS1 and OAS2 are capable of synthesizing trimeric and tetrameric oligomers. The dimeric 2',5'-linked oligomers are not efficient activators of RNaseL and, consequently, are thought to regulate alternative processes, with one report suggesting a role in gene expression by regulating DNA topoisomerase I. According to the invention the term "2',5'-oligoadenylate synthetase" or "OAS" preferably relates to molecules which are activators of RNaseL and preferably to OAS1 and OAS2.

The term "OAS" preferably relates to human OAS, and, in particular, to a protein comprising the amino acid sequence according to SEQ ID NO: 18 or 20 of the sequence listing or a variant of said amino acid sequence. In one embodiment, the term "OAS" relates to a protein comprising an amino acid sequence encoded by the nucleic acid sequence according to SEQ ID NO: 17 or 19. The term "OAS" includes any variants, in particular mutants, splice variants, conformations, isoforms, allelic variants, species variants and species homologs, in particular those which are naturally present.

The 2',5'-dependent RNaseL is expressed as an 80 kDa protein with two kinase-like domains (PUG and STYKc) and eight ankyrin repeats. The enzyme is constitutively expressed as an inactive monomer. Autoinhibition of the enzyme is relieved upon binding of 2',5'-oligomers (generated by OAS proteins) to the ankyrin repeats, and subsequent homodimerization. The active dimeric enzyme then degrades ssRNA.

The term "RNaseL" preferably relates to human RNaseL, and, in particular, to a protein comprising the amino acid sequence according to SEQ ID NO: 22 of the sequence listing or a variant of said amino acid sequence. In one embodiment, the term "RNaseL" relates to a protein comprising an amino acid sequence encoded by the nucleic acid sequence according to SEQ ID NO: 21. The term "RNaseL" includes any variants, in particular mutants, splice variants, conformations, isoforms, allelic variants, species variants and species homologs, in particular those which are naturally present.

According to the invention, the term "preventing engagement of IFN receptor by extracellular IFN" relates to an inhibition, i.e. blocking, or reduction, of the interaction of IFNs, in particular type I IFNs, with their specific receptors thus, inhibiting or reducing IFN function. Engagement of IFN receptor by extracellular IFN may be prevented, for example, by the provision of a binding agent for extracellular IFN. Those aspects of the present invention which involve one or more proteins or peptides in preventing engagement of IFN receptor by extracellular IFN, such as proteins or peptides disclosed herein, e.g. one or more binding agents for extracellular IFN, may involve the provision of nucleic acids, in particular RNA, encoding these one or more proteins or peptides to cells, e.g. by introducing the nucleic acids into cells.

For example, the B18R protein is a vaccinia virus-encoded type I interferon receptor with specificity for mouse, human, rabbit, pig, rat, and cow type I interferons which has potent neutralizing activity. The B18R protein encoded by the B18R gene of the Western Reserve vaccinia virus strain. The 60-65 kD glycoprotein is related to the interleukin-1 receptors and is a member of the immunoglobulin superfamily, unlike other type I IFN-receptors, which belong to the class II cytokine receptor family. The B18R protein has a high affinity (KD, 174 pM) for human IFN alpha. Among viral host response modifiers, the B18R protein is unique in that it exists as a soluble extracellular, as well as a cell surface protein, enabling blockage of both autocrine and paracrine IFN functions. The B18R protein has been shown to inhibit the antiviral potency of IFN-alpha1, IFN-alpha2, IFN-alpha-8/1/8, and IFN-omega on human cells. The soluble B18R protein is highly potent for neutralizing type I interferons, which include IFN-alpha, beta, delta, kappa.

The term "B18R" preferably relates to a protein comprising the amino acid sequence according to SEQ ID NO: 24 of the sequence listing or a variant of said amino acid sequence. In one embodiment, the term "B18R" relates to a protein comprising an amino acid sequence encoded by the nucleic acid sequence according to SEQ ID NO: 23. The term "B18R" includes any variants, in particular mutants, splice variants, conformations, isoforms, allelic variants, species variants and species homologs, in particular those which are naturally present.

Engagement of IFN receptor by extracellular IFN may further be prevented, for example, by reducing the level of IFN, in particular extracellular IFN. In one embodiment, engagement of IFN receptor by extracellular IFN is prevented by interfering with IFN gene expression. For example, Hepatitis C virus serine protease NS3/4A protein complex is able to interfere with and reduce IFN promoter activity and is a specific inhibitor of IFN gene expression. The term "NS3/4A" preferably relates to a protein comprising the amino acid sequence according to SEQ ID NO: 29 of the sequence listing or a variant of said amino acid sequence. The term "NS3/4A" includes any variants, in particular mutants, splice variants, conformations, isoforms, allelic variants, species variants and species homologs, in particular those which are naturally present.

According to the invention, the term "intracellular IFN signalling" relates to the intracellular signaling events and effector functions, in particular antiviral functions, activated by IFNs interacting with their specific receptors and includes the functions of proteins that are induced by IFN, in particular antivirally active effector proteins. In particular, the term "intracellular IFN signalling" includes the signal propagation through and effector functions, in particular antiviral functions, exerted by proteins which are part of the PKR-dependent pathway, in particular PKR and eIF2-alpha, and/or the OAS-dependent pathway, in particular OAS and RNaseL.

The term "inhibiting intracellular IFN signalling" relates to an inhibition or reduction of intracellular IFN signalling and may be achieved by inhibiting expression, activity or activation of proteins which are involved in intracellular IFN signaling, in particular proteins which are part of the PKR-dependent pathway and/or the OAS-dependent pathway. For example, many viruses have evolved mechanisms for counteracting the PKR and OAS/RNase L pathways. These mechanisms may be used according to the invention for inhibiting intracellular IFN signaling. Those aspects of the present invention which involve one or more proteins or peptides in inhibiting intracellular IFN signalling, such as proteins or peptides disclosed herein, e.g. one or more proteins or peptides inhibiting the PKR-dependent pathway and/or the OAS-dependent pathway, may involve the provision of nucleic acids, in particular RNA, encoding these one or more proteins or peptides to cells, e.g. by introducing the nucleic acids into cells.

According to the invention, the PKR-dependent pathway may be inhibited by an agent inhibiting or reducing the activity or activation of PKR or by an agent dephosphorylating eIF2-alpha or preventing its phosphorylation, thereby terminating the PKR-induced signal. For example, intracellular IFN signalling may be inhibited according to the invention by utilizing any of the viral defense mechanisms against the PKR signaling cascade. In this respect, the invention may involve the use of decoy dsRNA (e.g. adenovirus VAI RNA; Epstein-Barr virus EBER; HIV TAR), compounds effecting PKR degradation (e.g. poliovirus $2A^{pro}$), compounds inhibiting activation of PKR, e.g. through hiding viral dsRNA (e.g. vaccinia virus E3/E3L; reovirus sigma3; influenza virus NS1, herpes simplex virus type 1 (HSV-1) US11), compounds blocking dimerization (e.g. influenza virus $p58^{IPK}$; Hepatitis C virus NSSA), pseudosubstrates (e.g. vaccinia virus K3/K3L; HIV Tat) or dephosphorylation of substrate (e.g. herpes simplex virus ICP34.5). Vaccinia virus E3 is a 25 kDa dsRNA-binding protein (encoded by gene E3L) that binds and sequesters dsRNA to prevent the activation of PKR and OAS. E3 can bind directly to PKR and inhibits its activity, resulting in reduced phosphorylation of eIF2-alpha. Vaccinia virus gene K3L encodes a 10.5 kDa homolog of the eIF2-alpha subunit that acts as a non-phosphorylable pseudosubstrate of PKR and competitively inhibits phosphorylation of eIF2-alpha. Vaccinia virus C7/C7L inhibits phosphorylation of eIF2-alpha. The ICP34.5 protein from HSV-1 functions as a regulatory subunit of the cellular PP1 phosphatase, directing it to dephosphorylate eIF2-alpha, thereby terminating the PKR-induced signal. The murine cytomegalovirus (MCMV) proteins m142 and m143 have been characterized as dsRNA binding proteins that inhibit PKR activation, phosphorylation of the translation initiation factor eIF2, and a subsequent protein synthesis shutoff.

A decoy RNA is pseudosubstrate RNA that has similar structure to the RNA substrate of an enzyme, in order to make the enzyme bind to the pseudosubstrate rather than to the real substrate, thus blocking the activity of the enzyme.

The term "E3" preferably relates to a protein comprising the amino acid sequence according to SEQ ID NO: 26 of the sequence listing or a variant of said amino acid sequence. In one embodiment, the term "E3" relates to a protein comprising an amino acid sequence encoded by the nucleic acid sequence according to SEQ ID NO: 25. The term "E3" includes any variants, in particular mutants, splice variants, conformations, isoforms, allelic variants, species variants and species homologs, in particular those which are naturally present.

The term "K3" preferably relates to a protein comprising the amino acid sequence according to SEQ ID NO: 28 of the sequence listing or a variant of said amino acid sequence. In one embodiment, the term "K3" relates to a protein comprising an amino acid sequence encoded by the nucleic acid sequence according to SEQ ID NO: 27. The term "K3" includes any variants, in particular mutants, splice variants, conformations, isoforms, allelic variants, species variants and species homologs, in particular those which are naturally present.

The term "ICP34.5" preferably relates to a protein comprising the amino acid sequence according to SEQ ID NO: 30 of the sequence listing or a variant of said amino acid sequence. The term "ICP34.5" includes any variants, in particular mutants, splice variants, conformations, isoforms, allelic variants, species variants and species homologs, in particular those which are naturally present.

According to the present invention, the term "reducing the activity of RNA-dependent protein kinase (PKR)" relates to measures that result in a lower degree of homodimerization of PKR, in a lower degree of autophosphorylation of PKR and/or in a lower degree of phosphorylation of targets which are kinase substrates of PKR such as eIF2-alpha compared to the normal situation, in particular the normal situation in a cell, wherein the activity of PKR is not reduced/has not been reduced by man. Preferably, said term includes all measures that result in a lower degree of autophosphorylation of PKR and/or in a lower degree of phosphorylation of targets which are kinase substrates of PKR.

In one embodiment, reducing the activity of RNA-dependent protein kinase (PKR) in a cell comprises treating the cell with an inhibitor of expression and/or activity of PKR. According to the invention, the phrase "inhibit expression and/or activity" includes a complete or essentially complete inhibition of expression and/or activity and a reduction in expression and/or activity.

In one embodiment, said PKR inhibitor is directed at the PKR protein and preferably is specific for PKR. PKR can be inhibited in various ways, e.g. through inhibiting PKR autophosphorylation and/or dimerization, providing a PKR pseudo-activator, or providing a PKR pseudo-substrate. The PKR inhibitor may be an agent which is involved in a viral defense mechanism as discussed above. For example, vaccinia virus E3L encodes a dsRNA binding protein that inhibits PKR in virus-infected cells, presumably by sequestering dsRNA activators. K3, also encoded by vaccinia virus, functions as a pseudosubstrate inhibitor by binding to PKR. Thus, providing vaccinia virus E3L may result in inhibition of PKR. Providing adenovirus VAI RNA, HIV Tat or Epstein-Barr virus $EBER_1$ RNA may result in PKR pseudo-activation. Thus, for example, all viral factors, i.e. virally derived inhibitors, blocking PKR activity such as those described herein may be used for reducing the activity of PKR.

In one embodiment, the PKR inhibitor is a chemical inhibitor. Preferably, the PKR inhibitor is an inhibitor of RNA-induced PKR autophosphorylation. Preferably, the PKR inhibitor is an ATP-binding site directed inhibitor of PKR.

In one embodiment, the PKR inhibitor is 6,8-dihydro-8-(1H-imidazol-5-ylmethylene)-7H-pyrrolo[2,3-g]benzothiazol-7-one. In one embodiment, the PKR inhibitor has the following formula:

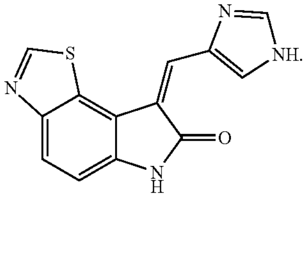 [SMILES: O=C1Nc2ccc3ncsc3c2/C1=C/c1c[nH]cn1]

In one embodiment, the PKR inhibitor is 2-aminopurine. In one embodiment, the PKR inhibitor has the following formula:

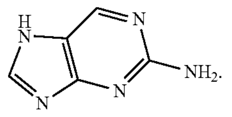

Preferably, an inhibitor as disclosed above is used in a concentration of at least 0.5 μM or higher, at least 1 μM or higher or at least 2 μM or higher and preferably in a concentration up to 5 up to 4 up to 3 μM or up to 2 μM.

In a further embodiment, the inhibitor of activity of PKR is an antibody that specifically binds to PKR. Binding of the antibody to PKR can interfere with the function of PKR, e.g. by inhibiting binding activity or catalytic activity.

In one embodiment, it is envisioned to reduce the activity of PKR in a cell by treating the cell with one or more virally derived inhibitors such as vaccinia virus E3 and/or K3 as well as treating the cell with one or more chemical PKR inhibitors such as 6,8-dihydro-8-(1H-imidazol-5-ylmethylene)-7H-pyrrolo[2,3-g]benzothiazol-7-one and/or 2-aminopurine.

According to the invention, the OAS-dependent pathway may be inhibited by an agent inhibiting or reducing the activity or activation of OAS and/or RNaseL. For example, vaccinia virus E3 is a 25 kDa dsRNA-binding protein (encoded by gene E3L) that binds and sequesters dsRNA to prevent the activation of OAS.

According to the present invention, the terms "reducing the activity of OAS" preferably relates to measures that result in a lower degree of production of 2',5'-oligoadenylates and thus, activation of RNaseL.

In one embodiment, reducing the activity of OAS and/or RNaseL in a cell comprises treating the cell with an inhibitor of expression and/or activity of OAS and/or RNaseL. According to the invention, the phrase "inhibit expression and/or activity" includes a complete or essentially complete inhibition of expression and/or activity and a reduction in expression and/or activity.

In one embodiment, inhibition of expression of PKR, OAS or RNaseL, in the following referred to as "target protein", may take place by inhibiting the production of or reducing the level of transcript, i.e. mRNA, coding for the target protein, e.g. by inhibiting transcription or inducing degradation of transcript, and/or by inhibiting the production of the target protein, e.g. by inhibiting translation of transcript coding for the target protein. In one embodiment, said inhibitor is specific for a nucleic acid encoding the target protein. In a particular embodiment, the inhibitor of expression of the target protein is an inhibitory nucleic acid (e.g., antisense molecule, ribozyme, iRNA, siRNA or a DNA encoding the same) selectively hybridizing to and being specific for nucleic acid encoding the target protein, thereby inhibiting (e.g., reducing) transcription and/or translation thereof.

Inhibitory nucleic acids of this invention include oligonucleotides having sequences in the antisense orientation relative to the target nucleic acids. Suitable inhibitory oligonucleotides typically vary in length from five to several hundred nucleotides, more typically about 20-70 nucleotides in length or shorter, even more typically about 10-30 nucleotides in length. These inhibitory oligonucleotides may be applied, either in vitro or in vivo, as free (naked) nucleic acids or in protected forms, e.g., encapsulated in liposomes. The use of liposomal or other protected forms may be advantageous as it may enhance in vivo stability and thus facilitate delivery to target sites.

Also, the target nucleic acid may be used to design ribozymes that target the cleavage of the corresponding mRNAs in cells. Similarly, these ribozymes may be administered in free (naked) form or by the use of delivery systems that enhance stability and/or targeting, e.g., liposomes.

Also, the target nucleic acid may be used to design siRNAs that can inhibit (e.g., reduce) expression of the nucleic acid. The siRNAs may be administered in free (naked) form or by the use of delivery systems that enhance stability and/or targeting, e.g., liposomes. They may also be administered in the form of their precursors or encoding DNAs.

siRNA preferably comprises a sense RNA strand and an antisense RNA strand, wherein the sense and antisense RNA strands form an RNA duplex, and wherein the sense RNA strand comprises a nucleotide sequence substantially identical to a target sequence of about 19 to about 25 contiguous nucleotides in a target nucleic acid, preferably mRNA coding for PKR.

It is to be understood that according to the invention instead of the peptides or proteins mentioned above for (i) preventing engagement of IFN receptor by extracellular IFN and (ii) inhibiting intracellular IFN signalling, nucleic acids encoding the peptides or proteins can be provided. The phrase "provided in the form of a nucleic acid" as used herein is to account for this possibility. For example, cells may be transfected with nucleic acid, in particular RNA, encoding the peptides or proteins and the nucleic acid may be expressed in the cells so as to produce the peptides or proteins.

In one embodiment, cells are treated to (i) prevent engagement of IFN receptor by extracellular IFN and/or (ii) inhibit intracellular IFN signalling prior to, simultaneously with and/or following introduction of RNA encoding the peptide or protein to be expressed, e.g. one or more factors allowing the reprogramming of the somatic cells to cells having stem cell characteristics, or the first introduction (e.g. in case of repeated transfections) of RNA. In one embodiment, cells are treated to (i) prevent engagement of IFN receptor by extracellular IFN and/or (ii) inhibit intracellular IFN signalling following, preferably immediately following introduction of RNA or the first introduction (e.g. in case of repeated transfections) of RNA.

In one embodiment, cells are treated to (i) prevent engagement of IFN receptor by extracellular IFN and/or (ii) inhibit intracellular IFN signalling for at least 24 h, at least 48 h, at least 72 h, at least 96 h, at least 120 h or even longer. Most preferably, cells are treated to (i) prevent engagement of IFN receptor by extracellular IFN and/or (ii) inhibit intracellular IFN signalling for the entire period of time in which expression of RNA is desired, such as permanently, optionally with repeated transfection of RNA.

According to the invention, it is envisioned to (i) prevent engagement of IFN receptor by extracellular IFN and (ii) inhibit intracellular IFN signalling in a cell in vitro or in vivo, preferably in vitro. Thus, according to the present invention, the cell can be an isolated cell or it can form part of an organ, a tissue and/or an organism.

"Antisense molecules" or "antisense nucleic acids" may be used for regulating, in particular reducing, expression of a nucleic acid. The term "antisense molecule" or "antisense nucleic acid" refers according to the invention to an oligonucleotide which is an oligoribonucleotide, oligodeoxyribonucleotide, modified oligoribonucleotide or modified oligodeoxyribonucleotide and which hybridizes under physiological conditions to DNA comprising a particular gene or to mRNA of said gene, thereby inhibiting transcription of said gene and/or translation of said mRNA. According to the invention, an "antisense molecule" also comprises a construct which contains a nucleic acid or a part thereof in reverse orientation with respect to its natural promoter. An antisense transcript of a nucleic acid or of a part thereof may form a duplex with naturally occurring mRNA and thus prevent accumulation of or translation of the mRNA. Another possibility is the use of ribozymes for inactivating a nucleic acid.

In preferred embodiments, the antisense oligonucleotide hybridizes with an N-terminal or 5' upstream site such as a translation initiation site, transcription initiation site or promoter site. In further embodiments, the antisense oligonucleotide hybridizes with a 3'-untranslated region or mRNA splicing site.

By "small interfering RNA" or "siRNA" as used herein is meant an RNA molecule, preferably greater than 10 nucleotides in length, more preferably greater than 15 nucleotides in length, and most preferably 18, 19, 20, 21, 22, 23, 24, 25, 26, 27, 28, 29, or 30 nucleotides in length that is used to identify a target gene or mRNA to be degraded. A range of 19-25 nucleotides is the most preferred size for siRNAs.

One or both strands of the siRNA can also comprise a 3'-overhang. As used herein, a "3'-overhang" refers to at least one unpaired nucleotide extending from the 3'-end of an RNA strand. Thus in one embodiment, the siRNA comprises at least one 3'-overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length. In the embodiment in which both strands of the siRNA molecule comprise a 3'-overhang, the length of the overhangs can be the same or different for each strand. In a most preferred embodiment, the 3'-overhang is present on both strands of the siRNA, and is 2 nucleotides in length. For example, each strand of the siRNA of the invention can comprise 3'-overhangs of dideoxythymidylic acid ("TT") or diuridylic acid ("uu").

In order to enhance the stability of the siRNA, the 3'-overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3'-overhangs with 2'-deoxythymidine, is tolerated and does not affect the efficiency of RNAi degradation. In particular, the absence of a 2'-hydroxyl in the 2'-deoxythymidine significantly enhances the nuclease resistance of the 3'-overhang in tissue culture medium.

The sense and antisense strands of the siRNA can comprise two complementary, single-stranded RNA molecules or can comprise a single molecule in which two complementary portions are base-paired and are covalently linked by a single-stranded "hairpin" area. That is, the sense region and antisense region can be covalently connected via a linker molecule. The linker molecule can be a polynucleotide or non-nucleotide linker. Without wishing to be bound by any theory, it is believed that the hairpin area of the latter type of siRNA molecule is cleaved intracellularly by the "Dicer" protein (or its equivalent) to form a siRNA of two individual base-paired RNA molecules.

As used herein, "target mRNA" refers to an RNA molecule that is a target for downregulation.

siRNA can be expressed from pol III expression vectors without a change in targeting site, as expression of RNAs from pol III promoters is only believed to be efficient when the first transcribed nucleotide is a purine.

siRNA according to the invention can be targeted to any stretch of approximately 19-25 contiguous nucleotides in any of the target mRNA sequences (the "target sequence"). Techniques for selecting target sequences for siRNA are given, for example, in Tuschl T. et al., "The siRNA User Guide", revised Oct. 11, 2002, the entire disclosure of which is herein incorporated by reference. "The siRNA User Guide" is available on the world wide web at a website maintained by Dr. Thomas Tuschl, Laboratory of RNA Molecular Biology, Rockefeller University, New York, USA, and can be found by accessing the website of the Rockefeller University and searching with the keyword "siRNA". Thus, the sense strand of the present siRNA comprises a nucleotide sequence substantially identical to any contiguous stretch of about 19 to about 25 nucleotides in the target mRNA.

Generally, a target sequence on the target mRNA can be selected from a given cDNA sequence corresponding to the target mRNA, preferably beginning 50 to 100 nt downstream (i.e., in the 3'-direction) from the start codon. The target sequence can, however, be located in the 5'- or 3'-untranslated regions, or in the region nearby the start codon.

siRNA can be obtained using a number of techniques known to those of skill in the art. For example, siRNA can be chemically synthesized or recombinantly produced using methods known in the art, such as the Drosophila in vitro system described in U.S. published application 2002/0086356 of Tuschl et al., the entire disclosure of which is herein incorporated by reference.

Preferably, siRNA is chemically synthesized using appropriately protected ribonucleoside phosphoramidites and a conventional DNA/RNA synthesizer. siRNA can be synthesized as two separate, complementary RNA molecules, or as a single RNA molecule with two complementary regions.

Alternatively, siRNA can also be expressed from recombinant circular or linear DNA plasmids using any suitable promoter. Suitable promoters for expressing siRNA of the invention from a plasmid include, for example, the U6 or H1 RNA pol III promoter sequences and the cytomegalovirus promoter.

Selection of other suitable promoters is within the skill in the art. The recombinant plasmids of the invention can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly. The use of recombinant plasmids to deliver siRNA to cells in vivo is within the skill in the art. siRNA can be expressed from a recombinant plasmid either as two separate, complementary RNA molecules, or as a single RNA molecule with two complementary regions.

Selection of plasmids suitable for expressing siRNA, methods for inserting nucleic acid sequences for expressing the siRNA into the plasmid, and methods of delivering the recombinant plasmid to the cells of interest are within the skill in the art.

The term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transformed or transfected with an exogenous nucleic acid.

The term "cell" includes according to the invention prokaryotic cells (e.g., *E. coli*) or eukaryotic cells. Mammalian cells are particularly preferred, such as cells from humans, mice, hamsters, pigs, goats, and primates. In one embodiment, the cell is a somatic cell as described herein. In one embodiment, the cell is a cell having a barrier function. Preferably, the cell is a fibroblast such as a fibroblast described herein, a keratinocyte, an epithelial cell, or an endothelial cell such as an endothelial cell of the heart, an endothelial cell of the lung, or an umbilical vein endothelial cell. Preferably, the cell is a human cell.

A fibroblast is a type of cell that synthesizes the extracellular matrix and collagen and plays a critical role in wound healing. The main function of fibroblasts is to maintain the structural integrity of connective tissues by continuously secreting precursors of the extracellular matrix. Fibroblasts are the most common cells of connective tissue in animals. Fibroblasts are morphologically heterogeneous with diverse appearances depending on their location and activity.

Keratinocytes are the predominant cell type in the epidermis, the outermost layer of the human skin. The primary function of keratinocytes is the formation of the keratin layer that protects the skin and the underlying tissue from environmental damage such as heat, UV radiation and water loss.

Epithelium is a tissue composed of cells that line the cavities and surfaces of structures throughout the body. Many glands are also formed from epithelial tissue. It lies on top of connective tissue, and the two layers are separated by a basement membrane. In humans, epithelium is classified as a primary body tissue, the other ones being connective tissue, muscle tissue and nervous tissue. Functions of epithelial cells include secretion, selective absorption, protection, transcellular transport and detection of sensation.

The endothelium is the thin layer of cells that lines the interior surface of blood vessels, forming an interface between circulating blood in the lumen and the rest of the vessel wall. These cells are called endothelial cells. Endothelial cells line the entire circulatory system, from the heart to the smallest capillary. Endothelial tissue is a specialized type of epithelium tissue.

According to the present invention, the term "peptide" comprises oligo- and polypeptides and refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

The present invention also includes "variants" of the peptides, proteins, or amino acid sequences described herein.

For the purposes of the present invention, "variants" of an amino acid sequence comprise amino acid insertion variants, amino acid addition variants, amino acid deletion variants and/or amino acid substitution variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids or nucleotides that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

Homologous amino acid sequences exhibit according to the invention at least 40%, in particular at least 50%, at least 60%, at least 70%, at least 80%, at least 90% and preferably at least 95%, at least 98 or at least 99% identity of the amino acid residues.

The amino acid sequence variants described herein may readily be prepared by the skilled person, for example, by recombinant DNA manipulation. The manipulation of DNA sequences for preparing peptides or proteins having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

The invention includes derivatives of the peptides or proteins described herein which are comprised by the terms "peptide" and "protein". According to the invention, "derivatives" of proteins and peptides are modified forms of proteins and peptides. Such modifications include any chemical modification and comprise single or multiple substitutions, deletions and/or additions of any molecules associated with the protein or peptide, such as carbohydrates, lipids and/or proteins or peptides. In one embodiment, "derivatives" of proteins or peptides include those modified analogs resulting from glycosylation, acetylation, phosphorylation, amidation, palmitoylation, myristoylation, isoprenylation, lipidation, alkylation, derivatization, introduction of protective/blocking groups, proteolytic cleavage or binding to an antibody or to another cellular ligand. The term "derivative" also extends to all functional chemical equivalents of said proteins and peptides. Preferably, a modified peptide has increased stability and/or increased immunogenicity.

According to the invention, a variant of a peptide or protein preferably has a functional property of the peptide or protein from which it has been derived. Such functional properties are described herein for OCT4, SOX2, NANOG, LIN28, KLF4 and c-MYC, respectively. Preferably, a variant of a peptide or protein has the same property in reprogramming an animal differentiated cell as the peptide or protein from which it has been derived. Preferably, the variant induces or enhances reprogramming of an animal differentiated cell.

In one embodiment, the peptide or protein encoded by the RNA is a factor allowing the reprogramming of somatic cells to cells having stem cell characteristics. In one embodiment, the peptide or protein comprises one or more antigens and/or one or more antigen peptides. Preferably, said RNA is capable of expressing said peptide or protein, in particular if introduced into a cell.

A "stem cell" is a cell with the ability to self-renew, to remain undifferentiated, and to become differentiated. A stem cell can divide without limit, for at least the lifetime of the animal in which it naturally resides. A stem cell is not terminally differentiated; it is not at the end stage of a differentiation pathway. When a stem cell divides, each daughter cell can either remain a stem cell or embark on a course that leads toward terminal differentiation.

Totipotent stem cells are cells having totipotential differentiation properties and being capable of developing into a complete organism. This property is possessed by cells up to the 8-cell stage after fertilization of the oocyte by the sperm. When these cells are isolated and transplanted into the uterus, they can develop into a complete organism.

Pluripotent stem cells are cells capable of developing into various cells and tissues derived from the ectodermal, mesodermal and endodermal layers. Pluripotent stem cells which are derived from the inner cell mass located inside of blastocysts, generated 4-5 days after fertilization are called "embryonic stem cells" and can differentiate into various other tissue cells but cannot form new living organisms.

Multipotent stem cells are stem cells differentiating normally into only cell types specific to their tissue and organ of origin. Multipotent stem cells are involved not only in the growth and development of various tissues and organs during the fetal, neonatal and adult periods but also in the maintenance of adult tissue homeostasis and the function of inducing regeneration upon tissue damage. Tissue-specific multipotent cells are collectively called "adult stem cells".

An "embryonic stem cell" or "ESC" is a stem cell that is present in or isolated from an embryo. It can be pluripotent, having the capacity to differentiate into each and every cell present in the organism, or multipotent, with the ability to differentiate into more than one cell type.

As used herein, "embryo" refers to an animal in the early stages of it development. These stages are characterized by implantation and gastrulation, where the three germ layers are defined and established and by differentiation of the germs layers into the respective organs and organ systems. The three germ layers are the endoderm, ectoderm and mesoderm.

A "blastocyst" is an embryo at an early stage of development in which the fertilized ovum has undergone cleavage, and a spherical layer of cells surrounding a fluid-filled cavity is forming, or has formed. This spherical layer of cells is the trophectoderm. Inside the trophectoderm is a cluster of cells termed the inner cell mass (ICM). The trophectoderm is the precursor of the placenta, and the ICM is the precursor of the embryo.

An adult stem cell, also called a somatic stem cell, is a stem cell found in an adult. An adult stem cell is found in a differentiated tissue, can renew itself, and can differentiate, with some limitations, to yield specialized cell types of its tissue of origin. Examples include mesenchymal stem cells, hematopoietic stem cells, and neural stem cells.

A "differentiated cell" is a mature cell that has undergone progressive developmental changes to a more specialized form or function. Cell differentiation is the process a cell undergoes as it matures to an overtly specialized cell type. Differentiated cells have distinct characteristics, perform specific functions, and are less likely to divide than their less differentiated counterparts.

An "undifferentiated" cell, for example, an immature, embryonic, or primitive cell, typically has a nonspecific appearance, may perform multiple, non-specific activities, and may perform poorly, if at all, in functions typically performed by differentiated cells.

"Somatic cell" refers to any and all differentiated cells and does not include stem cells, germ cells, or gametes. Preferably, "somatic cell" as used herein refers to a terminally differentiated cell.

As used herein, "committed" refers to cells which are considered to be permanently committed to a specific function. Committed cells are also referred to as "terminally differentiated cells".

As used herein, "differentiation" refers to the adaptation of cells for a particular form or function. In cells, differentiation leads to a more committed cell.

As used herein, "de-differentiation" refers to loss of specialization in form or function. In cells, de-differentiation leads to a less committed cell.

As used herein "reprogramming" refers to the resetting of the genetic program of a cell. A reprogrammed cell preferably exhibits pluripotency.

The terms "de-differentiated" and "reprogrammed" or similar terms are used interchangeably herein to denote somatic cell-derived cells having stem cell characteristics. However, said terms are not intended to limit the subject-matter disclosed herein by mechanistic or functional considerations.

The term "RNA inducing the development of stem cell characteristics" or "RNA capable of expressing one or more factors allowing the reprogramming of the somatic cells to cells having stem cell characteristics" refers to RNA which when introduced into a somatic cell induces the cell to de-differentiate.

As used herein, "germ cell" refers to a reproductive cell such as a spermatocyte or an oocyte, or a cell that will develop into a reproductive cell.

As used herein, "pluripotent" refers to cells that can give rise to any cell type except the cells of the placenta or other supporting cells of the uterus.

Terms such as "cell having stem cell characteristics", "cell having stem cell properties" or "stem like cell" are used herein to designate cells which, although they are derived from differentiated somatic non-stem cells, exhibit one or more features typical for stem cells, in particular embryonic stem cells. Such features include an embryonic stem cell morphology such as compact colonies, high nucleus to cytoplasm ratio and prominent nucleoli, normal karyotypes, expression of telomerase activity, expression of cell surface markers that are characteristic for embryonic stem cells, and/or expression of genes that are characteristic for embryonic stem cells. The cell surface markers that are characteristic for embryonic stem cells are, for example, selected from the group consisting of stage-specific embryonic antigen-3 (SSEA-3), SSEA-4, tumor-related antigen-1-60 (TRA-1-60), TRA-1-81, and TRA-2-49/6E. The genes that are characteristic for embryonic stem cells are selected, for example, from the group consisting of endogenous OCT4, endogenous NANOG, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, and telomerase reverse transcriptase (TERT). In one embodiment, the one or more features typical for stem cells include pluripotency.

In one embodiment of the method of the invention, the stem cell characteristics comprise an embryonic stem cell morphology, wherein said embryonic stem cell morphology preferably comprises morphological ciriteria selected from the group consisting of compact colonies, high nucleus to cytoplasm ratio and prominent nucleoli. In certain embodiments, the cells having stem cell characteristics have normal karyotypes, express telomerase activity, express cell surface markers that are characteristic for embryonic stem cells and/or express genes that are characteristic for embryonic stem cells. The cell surface markers that are characteristic for embryonic stem cells may be selected from the group consisting of stage-specific embryonic antigen-3 (SSEA-3), SSEA-4, tumor-related antigen-1-60 (TRA-1-60), TRA-1-81, and TRA-2-49/6E and the genes that are characteristic for embryonic stem cells may be selected from the group consisting of endogenous OCT4, endogenous NANOG, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, and telomerase reverse transcriptase (TERT).

Preferably, the cells having stem cell characteristics are de-differentiated and/or reprogrammed somatic cells. Preferably, the cells having stem cell characteristics exhibit the essential characteristics of embryonic stem cells such as a pluripotent state. Preferably, the cells having stem cell characteristics have the developmental potential to differentiate into advanced derivatives of all three primary germ layers. In one embodiment, the primary germ layer is endoderm and the advanced derivative is gut-like epithelial tissue. In a further embodiment, the primary germ layer is mesoderm and the advanced derivative is striated muscle and/or cartilage. In an even further embodiment, the primary germ layer is ectoderm and the advanced derivative is neural tissue and/or epidermal tissue. In one preferred embodiment, the cells having stem cell characteristics have the developmental potential to differentiate into neuronal cells and/or cardiac cells.

In one embodiment, the somatic cells are embryonic stem cell derived somatic cells with a mesenchymal phenotype. In a preferred embodiment, the somatic cells are fibroblasts such as fetal fibroblasts or postnatal fibroblasts or keratinocytes, preferably hair follicle derived keratinocytes. In further embodiments, the fibroblasts are lung fibroblasts, foreskin fibroblasts or dermal fibroblasts. In particular embodiments, the fibroblasts are fibroblasts as deposited at the American Type Culture Collection (ATCC) under Catalog No. CCL-186, as deposited at the American Type Culture Collection (ATCC) under Catalog No. CRL-2097 or as deposited at the American Type Culture Collection (ATCC) under Catalog No. CRL-2522, or as distributed by System Biosciences under the catalog no. PC501A-HFF. In one embodiment, the fibroblasts are adult human dermal fibroblasts. Preferably, the somatic cells are human cells. According to the present invention, the somatic cells may be genetically modified.

The term "factor" according to the invention when used in conjunction with the expression thereof by RNA includes proteins and peptides as well as derivatives and variants thereof. For example, the term "factor" comprises OCT4, SOX2, NANOG, LIN28, KLF4 and c-MYC.

The factors can be of any animal species; e.g., mammals and rodents. Examples of mammals include but are not limited to human and non-human primates. Primates include but are not limited to humans, chimpanzees, baboons, cynomolgus monkeys, and any other New or Old World monkeys. Rodents include but are not limited to mouse, rat, guinea pig, hamster and gerbil.

According to the present invention, one or more factors capable of allowing the reprogramming of somatic cells to cells having stem cell characteristics comprise an assembly of factors selected from the group consisting of (i) OCT4 and SOX2, (ii) OCT4, SOX2, and one or both of NANOG and LIN28, (iii) OCT4, SOX2 and one or both of KLF4 and c-MYC. In one embodiment, said one or more factors capable of being expressed by the RNA comprise OCT4, SOX2, NANOG and LIN28 or OCT4, SOX2, KLF4 and c-MYC. Preferably, the RNA is introduced into said animal differentiated somatic cell by electroporation or microinjection. Preferably, the method of the invention further comprises allowing the development of cells having stem cell characteristics, e.g. by culturing the somatic cell under embryonic stem cell culture conditions, preferably conditions suitable for maintaining pluripotent stem cells in an undifferentiated state.

OCT4 is a transcription factor of the eukaryotic POU transcription factors and an indicator of pluripotency of embryonic stem cells. It is a maternally expressed Octomer binding protein. It has been observed to be present in oocytes, the inner cell mass of blastocytes and also in the primordial germ cell. The gene POU5F1 encodes the OCT4 protein. Synonyms to the gene name include OCT3, OCT4, OTF3 and MGC22487. The presence of OCT4 at specific concentrations is necessary for embryonic stem cells to remain undifferentiated.

Preferably, "OCT4 protein" or simply "OCT4" relates to human OCT4 and preferably comprises an amino acid sequence encoded by the nucleic acid according to SEQ ID NO: 1, preferably the amino acid sequence according to SEQ ID NO: 2. One skilled in the art would understand that the cDNA sequence of OCT4 as described above would be equivalent to OCT4 mRNA, and can be used for the generation of RNA capable of expressing OCT4.

Sox2 is a member of the Sox (SRY-related HMG box) gene family that encode transcription factors with a single HMG DNA-binding domain. SOX2 h as been found to control neural progenitor cells by inhibiting their ability to differentiate. The repression of the factor results in delamination from the ventricular zone, which is followed by an exit from the cell cycle. These cells also begin to lose their progenitor character through the loss of progenitor and early neuronal differentiation markers.

Preferably, "SOX2 protein" or simply "SOX2" relates to human SOX2 and preferably comprises an amino acid sequence encoded by the nucleic acid according to SEQ ID NO: 3, preferably the amino acid sequence according to SEQ ID NO: 4. One skilled in the art would understand that the cDNA sequence of SOX2 as described above would be equivalent to SOX2 mRNA, and can be used for the generation of RNA capable of expressing SOX2.

NANOG is a NK-2 type homeodomain gene, and has been proposed to play a key role in maintaining stem cell pluripotency presumably by regulating the expression of genes critical to embryonic stem cell renewal and differentiation. NANOG behaves as a transcription activator with two unusually strong activation domains embedded in its C terminus. Reduction of NANOG expression induces differentiation of embryonic stem cells.

Preferably, "NANOG protein" or simply "NANOG" relates to human NANOG and preferably comprises an amino acid sequence encoded by the nucleic acid according to SEQ ID NO: 5, preferably the amino acid sequence according to SEQ ID NO: 6. One skilled in the art would understand that the cDNA sequence of NANOG as described above would be equivalent to NANOG mRNA, and can be used for the generation of RNA capable of expressing NANOG.

LIN28 is a conserved cytoplasmic protein with an unusual pairing of RNA-binding motifs: a cold shock domain and a pair of retroviral-type CCHC zinc fingers. In mammals, it is abundant in diverse types of undifferentiated cells. In pluripotent mammalian cells, LIN28 is observed in RNase-sensitive complexes with Poly(A)-Binding Protein, and in polysomal fractions of sucrose gradients, suggesting it is associated with translating mRNAs.

Preferably, "LIN28 protein" or simply "LIN28" relates to human LIN28 and preferably comprises an amino acid sequence encoded by the nucleic acid according to SEQ ID NO: 7, preferably the amino acid sequence according to SEQ ID NO: 8. One skilled in the art would understand that the cDNA sequence of LIN28 as described above would be equivalent to LIN28 mRNA, and can be used for the generation of RNA capable of expressing LIN28.

Krueppel-like factor (KLF4) is a zinc-finger transcription factor, which is strongly expressed in postmitotic epithelial cells of different tissues, e.g. the colon, the stomach and the skin. KLF4 is essential for the terminal differentiation of these cells and involved in the cell cycle regulation.

Preferably, "KLF4 protein" or simply "KLF4" relates to human KLF4 and preferably comprises an amino acid sequence encoded by the nucleic acid according to SEQ ID NO: 9, preferably the amino acid sequence according to SEQ ID NO: 10. One skilled in the art would understand that the cDNA sequence of KLF4 as described above would be equivalent to KLF4 mRNA, and can be used for the generation of RNA capable of expressing KLF4.

MYC (cMYC) is a protooncogene, which is overexpressed in a wide range of human cancers. When it is specifically-mutated, or overexpressed, it increases cell proliferation and functions as an oncogene. MYC gene encodes for a transcription factor that regulates expression of 15% of all genes through binding on Enhancer Box sequences (E-boxes) and recruiting histone acetyltransferases (HATs). MYC belongs to MYC family of transcription factors, which also includes N-MYC and L-MYC genes. MYC-family transcription factors contain the bHLH/LZ (basic Helix-Loop-Helix Leucine Zipper) domain.

Preferably, "cMYC protein" or simply "cMYC" relates to human cMYC and preferably comprises an amino acid sequence encoded by the nucleic acid according to SEQ ID NO: 11, preferably the amino acid sequence according to SEQ ID NO: 12. One skilled in the art would understand that the cDNA sequence of cMYC as described above would be equivalent to cMYC mRNA, and can be used for the generation of RNA capable of expressing cMYC.

A reference herein to specific factors such as OCT4, SOX2, NANOG, LIN28, KLF4 or c-MYC or to specific sequences thereof is to be understood so as to also include all variants of these specific factors or the specific sequences thereof as described herein. In particular, it is to be understood so as to also include all splice variants, posttranslationally modified variants, conformations, isoforms and species homologs of these specific factors/sequences which are naturally expressed by cells.

The term "miRNA" (microRNA) relates to 21-23-nucleotide-long noncoding RNAs found in eukaryotic cells that, by inducing degradation and/or preventing translation of target mRNAs, modulate a plethora of cell functions, including those related to ESC self-renewal/differentiation and cell cycle progression. miRNAs are post-transcriptional regulators that bind to complementary sequences on target messenger RNA transcripts (mRNAs), usually resulting in translational repression or target degradation and gene silencing. It has been found that miRNAs in the right combination are capable of inducing direct cellular reprogramming of somatic cells to cells having stem cell characteristics in vitro. For example, it has been observed that miRNA cluster 302-367 enhances somatic cell reprogramming.

Preferably, the step of allowing the development of cells having stem cell characteristics used in the methods for providing cells having stem cell characteristics described herein comprises culturing the somatic cells under embryonic stem cell culture conditions, preferbly conditions suitable for maintaining pluripotent stem cells in an undifferentiated state.

Preferably, to allow the development of cells having stem cell characteristics, cells are cultivated in the presence of one or more DNA methyltransferase inhibitors and/or one or more histone deacetylase inhibitors. Preferred compounds are selected from the group consisting of 5'-azacytidine (5'-azaC), suberoylanilide hydroxamic acid (SAHA), dexamethasone, trichostatin A (TSA), sodium butyrate (NaBu), Scriptaid and valproic acid (VPA). Preferably, cells are cultivated in the presence of valproic acid (VPA), preferably in a concentration of between 0.5 and 10 mM, more preferably between 1 and 5 mM, most preferably in a concentration of about 2 mM.

The methods of the present invention can be used to effect de-differentiation of any type of somatic cell. Cells that may be used include cells that can be de-differentiated or reprogrammed by the methods of the present invention, in particular cells that are fully or partially differentiated, more preferably terminally differentiated. Preferably, the somatic cell is a diploid cell derived from pre-embryonic, embryonic, fetal, and post-natal multi-cellular organisms. Examples of cells that may be used include but are not limited to fibroblasts, such as fetal and neonatal fibroblasts or adult fibroblasts, keratinocytes, in particular primary keratinocytes, more preferably keratinocytes derived from hair, adipose cells, epithelial cells, epidermal cells, chondrocytes, cumulus cells, neural cells, glial cells, astrocytes, cardiac cells, esophageal cells, muscle cells, melanocytes, hematopoietic cells, osteocytes, macrophages, monocytes, and mononuclear cells.

The cells with which the methods of the invention can be used can be of any animal species; e.g., mammals and rodents. Examples of mammalian cells that can be de-differentiated and re-differentiated by the present invention include but are not limited to human and non-human primate cells. Primate cells with which the invention may be performed include but are not limited to cells of humans, chimpanzees, baboons, cynomolgus monkeys, and any other New or Old World monkeys. Rodent cells with which the invention may be performed include but are not limited to mouse, rat, guinea pig, hamster and gerbil cells.

De-differentiated cells prepared according to the present invention are expected to display many of the same requirements as pluripotent stem cells and can be expanded and maintained under conditions used for embryonic stem cells, e.g. ES cell medium or any medium that supports growth of the embryonic cells. Embryonic stem cells retain their pluripotency in vitro when maintained on inactivated fetal fibroblasts such as irradiated mouse embryonic fibroblasts or human fibroblasts (e.g., human foreskin fibroblasts, human skin fibroblasts, human endometrial fibroblasts, human oviductal fibroblasts) in culture. In one embodiment, the human feeder cells may be autologous feeder cells derived from the same culture of reprogrammed cells by direct differentiation.

Furthermore, human embryonic stem cells can successfully be propagated on Matrigel in a medium conditioned by mouse fetal fibroblasts. Human stem cells can be grown in culture for extended period of time and remain undifferentiated under specific culture conditions.

In certain embodiments, the cell culture conditions may include contacting the cells with factors that can inhibit differentiation or otherwise potentiate de-differentiation of cells, e.g., prevent the differentiation of cells into non-ES cells, trophectoderm or other cell types.

De-differentiated cells prepared according to the present invention can be evaluated by methods including monitoring changes in the cells' phenotype and characterizing their gene and protein expression. Gene expression can be determined by RT-PCR, and translation products can be determined by immunocytochemistry and Western blotting. In particular, de-differentiated cells can be characterized to determine the pattern of gene expression and whether the reprogrammed cells display a pattern of gene expression similar to the expression pattern expected of undifferentiated, pluripotent control cells such as embryonic stem cells using techniques well known in the art including transcriptomics.

The expression of the following genes of de-differentiated cells can be assessed in this respect: OCT4, NANOG, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, telomerase reverse transcriptase (TERT), embryonic antigen-3 (SSEA-3), SSEA-4, tumor-related antigen-1-60 (TRA-1-60), TRA-1-81, and TRA-2-49/6E.

The undifferentiated or embryonic stem cells to which the reprogrammed cells may be compared may be from the same species as the differentiated somatic cells. Alternatively, the undifferentiated or embryonic stem cells to which the reprogrammed cells may be compared may be from a different species as the differentiated somatic cells.

In some embodiments, a similarity in gene expression pattern exists between a reprogrammed cell and an undifferentiated cell, e.g., embryonic stem cell, if certain genes specifically expressed in an undifferentiated cell are also expressed in the reprogrammed cell. For example, certain genes, e.g., telomerase, that are typically undetectable in differentiated somatic cells may be used to monitor the extent of reprogramming. Likewise, for certain genes, the absence of expression may be used to assess the extent of reprogramming.

Self-renewing capacity, marked by induction of telomerase activity, is another characteristic of stem cells that can be monitored in de-differentiated cells.

Karyotypic analysis may be performed by means of chromosome spreads from mitotic cells, spectral karyotyping, assays of telomere length, total genomic hybridization, or other techniques well known in the art.

Using the present invention, RNA encoding appropriate factors is incorporated into one or more somatic cells, e.g. by electroporation. After incorporation, cells are preferably cultured using conditions that support maintenance of de-differentiated cells (i.e. stem cell culture conditions). The de-differentiated cells can then be expanded and induced to re-differentiate into different type of somatic cells that are needed for cell therapy. De-differentiated cells obtained according to the present invention can be induced to differentiate into one or more desired somatic cell types in vitro or in vivo.

Preferably, the de-differentiated cells obtained according to the present invention may give rise to cells from any of three embryonic germ layers, i.e., endoderm, mesoderm, and ectoderm. For example, the de-differentiated cells may differentiate into skeletal muscle, skeleton, dermis of skin, connective tissue, urogenital system, heart, blood (lymph cells), and spleen (mesoderm); stomach, colon, liver, pancreas, urinary bladder; lining of urethra, epithelial parts of trachea, lungs, pharynx, thyroid, parathyroid, intestine (endoderm); or central nervous system, retina and lens, cranial and sensory, ganglia and nerves, pigment cells, head connective tissue, epidermis, hair, mammary glands (ectoderm). The de-differentiated cells obtained according to the present invention can be re-differentiated in vitro or in vivo using techniques known in the art.

In one embodiment of the present invention, the reprogrammed cells resulting from the methods of this invention are used to produce differentiated progeny. Thus, in one aspect, the present invention provides a method for producing differentiated cells, comprising: (i) obtaining reprogrammed cells using the methods of this invention; and (ii) inducing differentiation of the reprogrammed cells to produce differentiated cells. Step (ii) can be performed in vivo or in vitro. Furthermore, differentiation can be induced through the presence of appropriate differentiation factors which can either be added or are present in situ, e.g. in a body, organ or tissue into which the reprogrammed cells have been introduced. The differentiated cells can be used to derive cells, tissues and/or organs which are advantageously used in the area of cell, tissue, and/or organ transplantation. If desired, genetic modifications can be introduced, for example, into somatic cells prior to reprogramming. The differentiated cells of the present invention preferably do not possess the pluripotency of an embryonic stem cell, or an embryonic germ cell, and are, in essence, tissue-specific partially or fully differentiated cells.

One advantage of the methods of the present invention is that the reprogrammed cells obtained by the present invention can be differentiated without prior selection or purification or establishment of a cell line. Accordingly in certain embodiments, a heterogeneous population of cells comprising reprogrammed cells are differentiated into a desired cell type. In one embodiment, a mixture of cells obtained from the methods of the present invention is exposed to one or more differentiation factors and cultured in vitro.

Methods of differentiating reprogrammed cells obtained by the methods disclosed herein may comprise a step of permeabilization of the reprogrammed cell. For example, cells generated by the reprogramming techniques described herein, or alternatively a heterogeneous mixture of cells comprising reprogrammed cells, may be permeabilized before exposure to one or more differentiation factors or cell extract or other preparation comprising differentiation factors.

For example, differentiated cells may be obtained by culturing undifferentiated reprogrammed cells in the presence of at least one differentiation factor and selecting differentiated cells from the culture. Selection of differentiated cells may be based on phenotype, such as the expression of certain cell markers present on differentiated cells, or by functional assays (e.g., the ability to perform one or more functions of a particular differentiated cell type).

In another embodiment, the cells reprogrammed according to the present invention are genetically modified through the addition, deletion, or modification of their DNA sequence(s).

The reprogrammed or de-differentiated cells prepared according to the present invention or cells derived from the reprogrammed or de-differentiated cells are useful in research and in therapy. Reprogrammed pluripotent cells may be differentiated into any of the cells in the body including, without limitation, skin, cartilage, bone skeletal muscle, cardiac muscle, renal, hepatic, blood and blood forming, vascular precursor and vascular endothelial, pancreatic beta, neurons, glia, retinal, neuronal, intestinal, lung, and liver cells.

The reprogrammed cells are useful for regenerative/reparative therapy and may be transplanted into a patient in need thereof. In one embodiment, the cells are autologous with the patient.

The reprogrammed cells provided in accordance with the present invention may be used, for example, in therapeutic strategies in the treatment of cardiac, neurological, endocrinological, vascular, retinal, dermatological, muscular-skeletal disorders, and other diseases.

For example, and not intended as a limitation, the reprogrammed cells of the present invention can be used to replenish cells in animals whose natural cells have been depleted due to age or ablation therapy such as cancer radiotherapy and chemotherapy. In another non-limiting example, the reprogrammed cells of the present invention are useful in organ regeneration and tissue repair. In one embodiment of the present invention, reprogrammed cells can be used to reinvigorate damaged muscle tissue including dystrophic muscles and muscles damaged by ischemic events such as myocardial infarcts. In another embodiment of the present invention, the reprogrammed cells disclosed herein can be used to ameliorate scarring in animals, including humans, following a traumatic injury or surgery. In this embodiment, the reprogrammed cells of the present invention are administered systemically, such as intravenously, and migrate to the site of the freshly traumatized tissue recruited by circulating cytokines secreted by the damaged cells. In another embodiment of the present invention, the reprogrammed cells can be administered locally to a treatment site in need or repair or regeneration.

In further embodiments, the RNA used in the present invention encodes a peptide or protein which is of therapeutic value. Cells containing the RNA can, for example, be manipulated in vitro to express the RNA and thus, the peptide or protein, using the methods of the invention. The cells expressing the peptide or protein can subsequently be introduced into a patient.

In a particularly preferred embodiment, the RNA used in the present invention encodes a peptide or protein comprising an immunogen, antigen or antigen peptide. In one embodiment, the peptide or protein is processed after expression to provide said immunogen, antigen or antigen peptide. In another embodiment, the peptide or protein itself is the immunogen, antigen or antigen peptide. Cells expressing such peptide or protein comprising an immunogen, antigen or antigen peptide can be used, for example, in immunotherapy to elicit an immune response against the immunogen, antigen or antigen peptide in a patient.

An "antigen" according to the invention covers any substance that will elicit an immune response. In particular, an "antigen" relates to any substance that reacts specifically with antibodies or T-lymphocytes (T-cells). According to the present invention, the term "antigen" comprises any molecule which comprises at least one epitope. Preferably, an antigen in the context of the present invention is a molecule which, optionally after processing, induces an immune reaction, which is preferably specific for the antigen. According to the present invention, any suitable antigen may be used, which is a candidate for an immune reaction, wherein the immune reaction may be both a humoral as well as a cellular immune reaction. In the context of the embodiments of the present invention, the antigen is preferably presented by a cell, preferably by an antigen presenting cell, in the context of MHC molecules, which results in an immune reaction against the antigen. An antigen is preferably a product which corresponds to or is derived from a naturally occurring antigen. Such naturally occurring antigens may include or may be derived from allergens, viruses, bacteria, fungi, parasites and other infectious agents and pathogens or an antigen may also be a tumor antigen. According to the present invention, an antigen may correspond to a naturally occurring product, for example, a viral protein, or a part thereof.

In a preferred embodiment, the antigen is a tumor antigen, i.e., a part of a tumor cell which may be derived from the cytoplasm, the cell surface or the cell nucleus, in particular those which primarily occur intracellularly or as surface antigens of tumor cells. For example, tumor antigens include the carcinoembryonal antigen, a1-fetoprotein, isoferritin, and fetal sulphoglycoprotein, a2-H-ferroprotein and γ-fetoprotein, as well as various virus tumor antigens. According to the present invention, a tumor antigen preferably comprises any antigen which is characteristic for tumors or cancers as well as for tumor or cancer cells with respect to type and/or expression level. In another embodiment, the antigen is a virus antigen such as viral ribonucleoprotein or coat protein. In particular, the antigen should be presented by MEW molecules which results in modulation, in particular activation of cells of the immune system, preferably $CD4^+$ and $CD8^+$ lymphocytes, in particular via the modulation of the activity of a T-cell receptor.

In preferred embodiments, the antigen is a tumor antigen and the present invention involves the stimulation of an anti-tumor CTL response against tumor cells expressing such tumor antigen and preferably presenting such tumor antigen with class I MHC.

The term "immunogenicity" relates to the relative effectivity of an antigen to induce an immune reaction.

The term "pathogen" relates to pathogenic microorganisms and comprises viruses, bacteria, fungi, unicellular organisms, and parasites. Examples for pathogenic viruses are human immunodeficiency virus (HIV), cytomegalovirus (CMV), herpes virus (HSV), hepatitis A-virus (HAV), HBV, HCV, papilloma virus, and human T-lymphotrophic virus (HTLV). Unicellular organisms comprise plasmodia trypanosomes, amoeba, etc.

Examples for antigens that may be used in the present invention are p53, ART-4, BAGE, ss-catenin/m, Bcr-abL CAMEL, CAP-1, CASP-8, CDC27/m, CDK4/m, CEA, CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, h TERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Plac-1, Pm1/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT, preferably WT-1.

"A portion or fragment of an antigen" or "an antigen peptide" according to the invention preferably is an incomplete representation of an antigen and is capable of eliciting an immune response against the antigen.

In this context, the invention also makes use of peptides comprising amino acid sequences derived from antigens, also termed "antigen peptides" herein. By "antigen peptide", or "antigen peptide derived from an antigen" is meant an oligopeptide or polypeptide comprising an amino acid sequence substantially corresponding to the amino acid sequence of a fragment or peptide of an antigen. An antigen peptide may be of any length.

Preferably, the antigen peptides are capable of stimulating an immune response, preferably a cellular response against the antigen or cells characterized by expression of the antigen and preferably by presentation of the antigen. Preferably, an antigen peptide is capable of stimulating a cellular response against a cell characterized by presentation of an antigen with class I MHC and preferably is capable of stimulating an antigen-responsive CTL. Preferably, the antigen peptides according to the invention are MHC class I and/or class II presented peptides or can be processed to produce MHC class I and/or class II presented peptides. Preferably, the antigen peptides comprise an amino acid sequence substantially corresponding to the amino acid sequence of a fragment of an antigen. Preferably, said fragment of an antigen is an MHC class I and/or class II presented peptide. Preferably, an antigen peptide according to the invention comprises an amino acid sequence substantially corresponding to the amino acid sequence of such fragment and is processed to produce such fragment, i.e., an MHC class I and/or class II presented peptide derived from an antigen.

If an antigen peptide is to be presented directly, i.e., without processing, in particular without cleavage, it has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length. Preferably the sequence of an antigen peptide which is to be presented directly is derived from the amino acid sequence of an antigen, i.e., its sequence substantially corresponds and is preferably completely identical to a fragment of an antigen.

If an antigen peptide is to be presented following processing, in particular following cleavage, the peptide produced by processing has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length. Preferably, the sequence of the peptide which is to be presented following processing is derived from the amino acid sequence of an antigen, i.e., its sequence substantially corresponds and is preferably completely identical to a fragment of an antigen. Thus, an antigen peptide according to the invention in one embodiment comprises a sequence of 7-20 amino acids in length, more preferably 7-12 amino acids in length, more preferably 8-11 amino acids in length, in particular 9 or 10 amino acids in length which substantially corresponds and is preferably completely identical to a fragment of an antigen and following processing of the antigen peptide makes up the presented peptide. However, the antigen peptide may also comprise a sequence which substantially corresponds and preferably is completely identical to a fragment of an antigen which is even longer than the above stated sequence. In one embodiment, an antigen peptide may comprise the entire sequence of an antigen.

Peptides having amino acid sequences substantially corresponding to a sequence of a peptide which is presented by the class I MHC may differ at one or more residues that are not essential for TCR recognition of the peptide as presented by the class I MHC, or for peptide binding to MHC. Such substantially corresponding peptides are also capable of stimulating an antigen-responsive CTL. Peptides having amino acid sequences differing from a presented peptide at residues that do not affect TCR recognition but improve the stability of binding to MHC may improve the immunogenicity of the antigen peptide, and may be referred to herein as "optimized peptide". Using existing knowledge about which of these residues may be more likely to affect binding either to the MHC or to the TCR, a rational approach to the design of substantially corresponding peptides may be employed. Resulting peptides that are functional are contemplated as antigen peptides.

"Antigen processing" refers to the degradation of an antigen into fragments (e.g., the degradation of a protein into peptides) and the association of one or more of these fragments (e.g., via binding) with MHC molecules for presentation by "antigen presenting cells" to specific T-cells.

"Antigen presenting cells" (APC) are cells which present peptide fragments of protein antigens in association with MHC molecules on their cell surface. Some APCs may activate antigen-specific T-cells.

The term "immunotherapy" relates to a treatment involving activation of a specific immune reaction.

The term "in vivo" relates to the situation in a subject.

The terms "subject" and "individual" are used interchangeably and relate to mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term "animal" as used herein also includes humans. The term "subject" may also include a patient, i.e., an animal, preferably a human having a disease.

If according to the invention administration to a subject is desired the composition for administration is generally administered in pharmaceutically compatible amounts and in pharmaceutically compatible preparations. The term "pharmaceutically compatible" refers to a nontoxic material which does not interact with the action of the active component of the pharmaceutical composition. Preparations of this kind may usually contain salts, buffer substances, preservatives, excipients and carriers and are administered in a manner known to the skilled person.

The present invention is described in detail by the figures and examples below, which are used only for illustration purposes and are not meant to be limiting. Owing to the description and the examples, further embodiments which are likewise included in the invention are accessible to the skilled worker.

EXAMPLES

Example 1

Repetitive Transfer of IVT-RNA (Reprogramming-TF)

Reprogramming of somatic cells into induced pluripotent stem cells (iPS) requires the continuous expression of reprogramming transcription factors (rTF). To avoid the risk of genomic integration which arises when the rTF are delivered virally into the cell, rTF can be efficiently delivered as mRNA by electroporation or lipofection without accompanied modifications of the host genome. Nevertheless the delivery has to be performed repetitively to assure constant expression of the rTF.

Figure 2A:
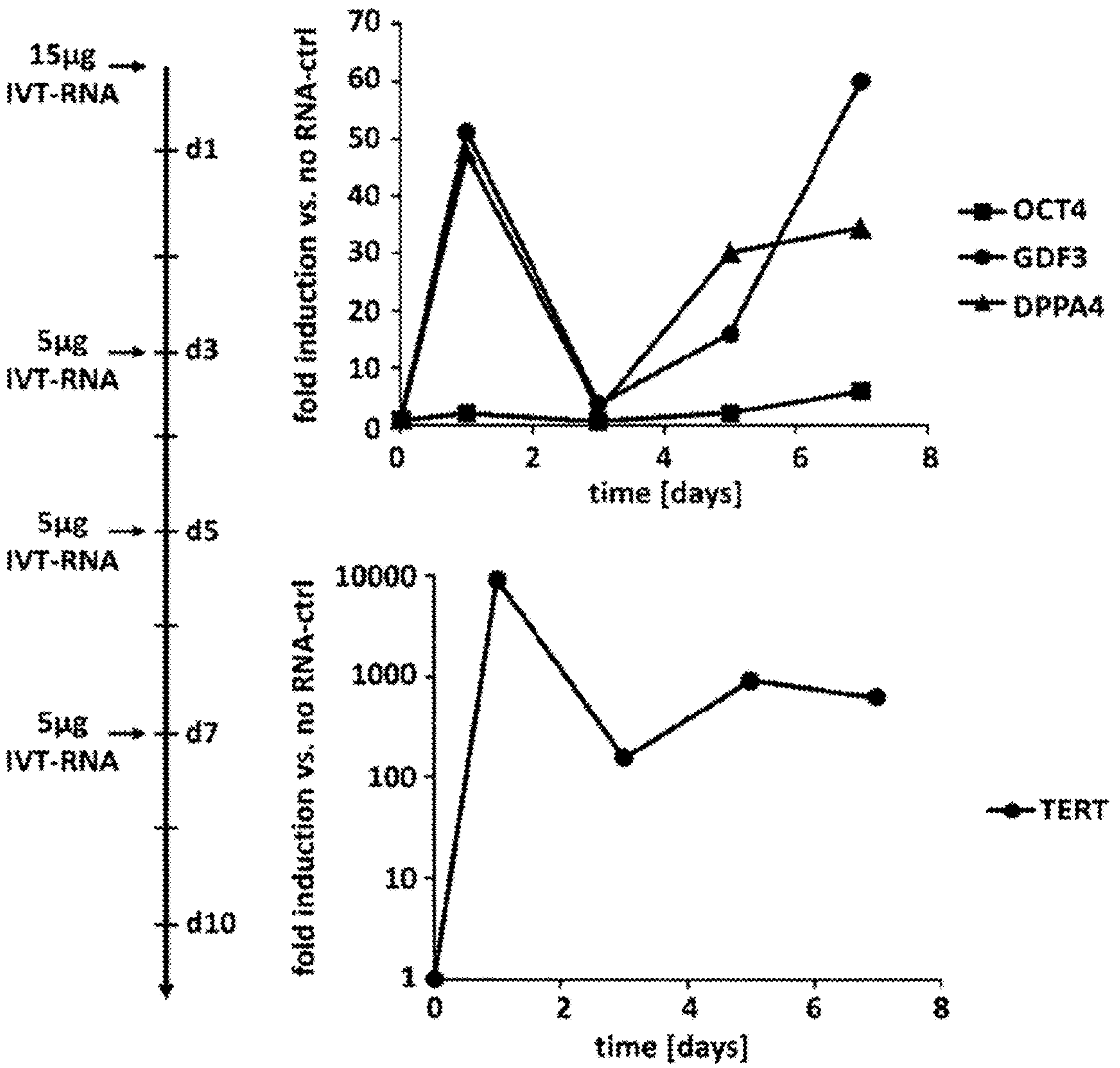

CCD1079Sk fibroblasts were electroporated as indicated in the side panel of FIG. 2A either with 15 μg or 5 μg of each in vitro transcribed (IVT)-RNA encoding the transcription factors OCT4 (O), SOX2 (S), KLF4 (K) and cMYC (M) and cultivated in human embryonic stem (ES) cell medium. Electroporations were performed in 4 mm gap cuvettes using optimized parameters for CCD1079Sk fibroblasts. At the indicated time points, 10% of the cells were removed from the cultures prior to subsequent electroporation, total RNA was isolated and mRNA-expression of the human ES-marker genes OCT4 (endogenous), TERT, GDF3 and DPPA4 was quantified by qRT-PCR. Repetitive electroporation of IVT-RNA coding for 4 rTF (OCT4, SOX2, KLF4 and cMYC) results in rapid induction of some pluripotency markers such as GFD3, DPPA4 and TERT. Other markers such as endogenous OCT4 were not or slightly induced.

Figure 2B:
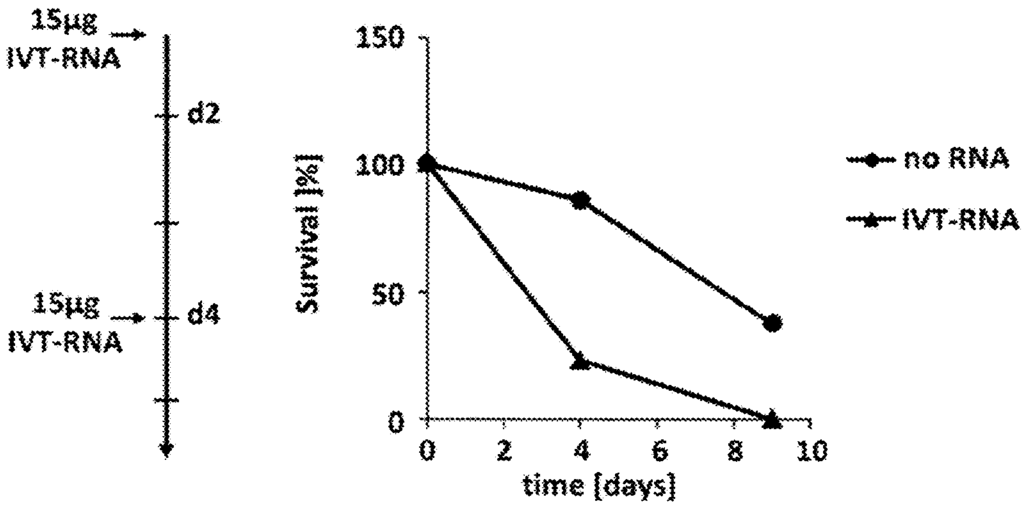
Figure 2C:
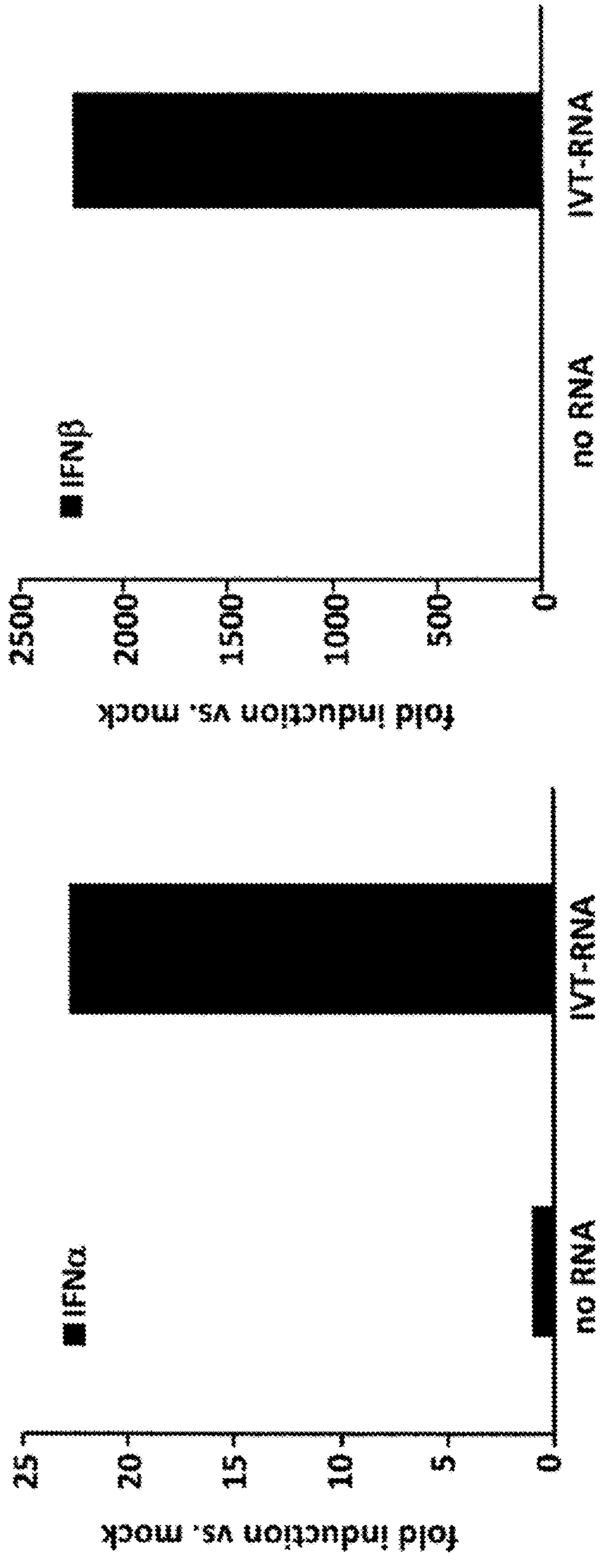
Figure 2D:
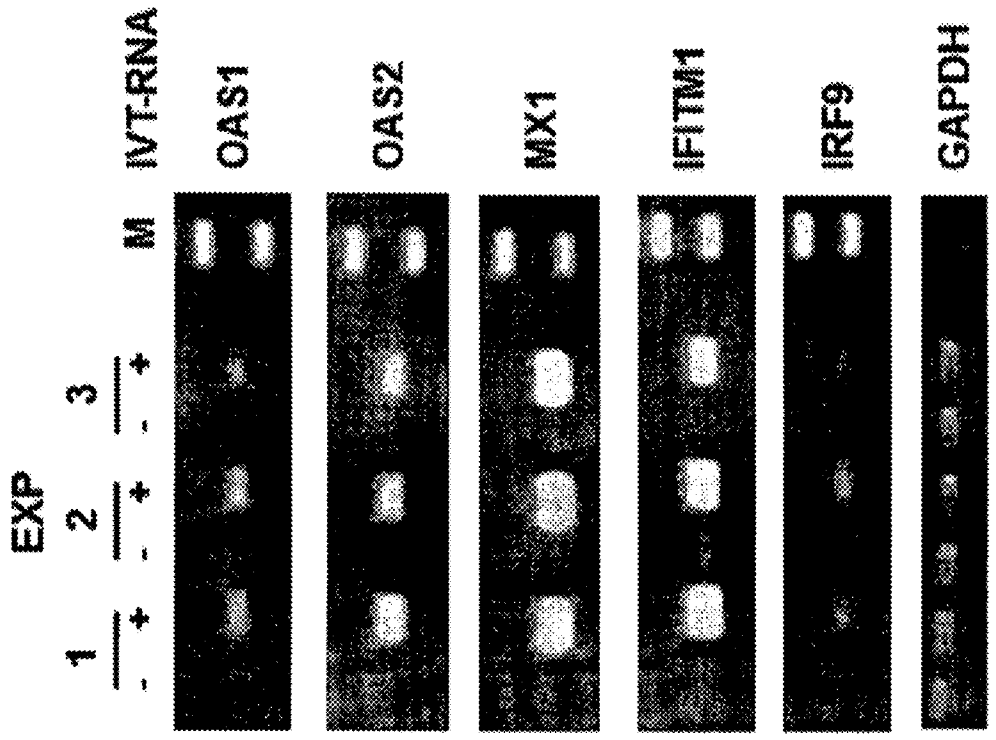

CCD1079Sk fibroblasts were electroporated as indicated in the side panel of FIG. 2B with 15 μg of each IVT-RNA encoding the transcription factors OSKM and cultivated in human ES cell medium. Electroporations were performed in 4 mm gap cuvettes using optimized parameters for CCD1079Sk fibroblasts. At the indicated time points remaining cells were counted and survival rate in relation to the starting cells was calculated. Repetitive IVT-RNA transfer is accompanied with massive cell death and successful reprogramming is therefore not achievable.

CCD1079Sk fibroblasts were electroporated with 1 μg IVT RNA encoding for firefly luciferase (Luc) and 5 μg IVT RNA encoding for green fluorescent protein (GFP). Electroporations were performed in 2 mm gap cuvettes using optimized parameters for CCD1079Sk fibroblasts. 24 h post electroporation, cells were pelleted, total RNA was isolated and mRNA-expression of Interferon (IFN)-a and -b was quantified by qRT-PCR. It was observed that electroporation of IVT-RNA is followed by an induction of IFNa and b 24 h thereafter; cf. FIG. 2C.

CCD1079Sk fibroblasts were electroporated with 33, 4 μg IVT RNA encoding reprogramming mixture (29.5 μg rTF (OSKM NANOG (N) LIN28 (L) (1:1:1:1:1:1)), 1.3 μg SV40 largeT antigen (1gT), 1.3 μg HTLV E6 and 1.25 μg GFP). Electroporations were performed in 4 mm gap cuvettes using optimized parameters for CCD1079Sk fibroblasts. 48 h post electroporation, cells were pelleted, total RNA was isolated and mRNA-expression of the IFN-response genes OAS1, OAS2, MX1, IFITM1 and IRF9 was quantified by qRT-PCR. All 5 investigated IFN-response genes are induced 48 h post electroporation of IVT-RNA; cf. FIG. 2D. The IFN-response has originally evolved as part of the host innate immune response to viral infections. Viral nucleic acids are efficiently recognized by sensor molecules which leads to antiviral activities including apoptosis, cytoskeletal remodeling, RNA degradation and a halt in protein translation. These mechanisms obviously hinder RNA-based gene transfer.

Figure 2E:
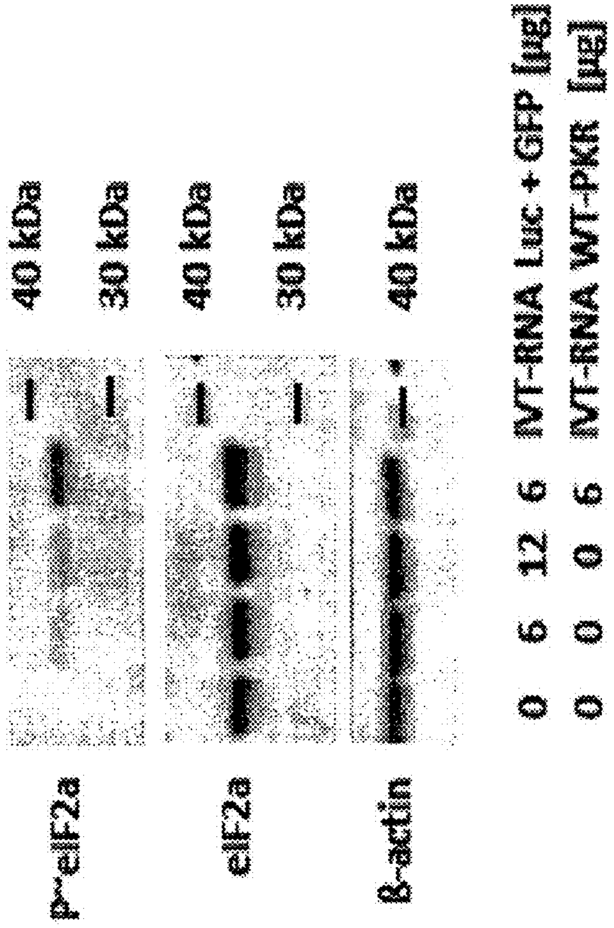

CCD1079Sk fibroblasts were electroporated once with the amounts of IVT-RNA encoding the reporter genes Luc, GFP or the Protein Kinase R (PKR) wild type indicated in FIG. 2E. Electroporations were performed in 4 mm gap cuvettes using optimized parameters for CCD1079Sk fibroblasts. Cells were lysed 24 h post electroporation and expression and phosphorylation status of the PKR target eukaryotic initiation factor 2a (eIF2a) was monitored by Western Blotting using specific antibodies. One of the major player in the IFN response is the PKR which upon activation phosphorylates its target eIF2a leading to an inhibition of translation. We could show that eIF2a is phosphorylated 24 h after electroporation of IVT-RNA identifying activation of PKR as one of the prominent obstacles in RNA-based reprogramming.

Repetitive RNA-based gene transfer is accompanied with an induction of the IFN-response which hinders the continuous expression of rTF and therefore successful RNA-based reprogramming.

Example 2

Use of E3, K3 and B18R in RNA-Based Gene Transfer

As a proof of concept unmodified IVT-RNAs coding for the viral escape proteins E3, K3 and B18R (vaccinia virus) were added to a mixture of unmodified IVT-RNA (Luciferase/GFP), lipofected into human foreskin fibroblasts (HFF) and translation of the reporter gene GFP and IFN-response to the RNA was analyzed. Furthermore the survival of the cells after repetitive lipofections was assessed by an Cell Proliferation Kit II (Roche).

CCD1079Sk fibroblasts were plated into 6 wells (100,000 cells/well) and lipofected the next day using 6 μl RNAiMAX (Invitrogen) and 1.4 μg IVT. The IVT-RNA mixtures was thereby composed of 0.8 μg GFP with 0.2 μg of each B18R, E3 or K3 (as indicated in FIG. 3A,B). IVT-RNA encoding for Luc was used to sum up the mixtures to 1.4 μg. Lipofections were performed according to the manufacturers instructions and cells were harvested 48 h post transfection. 20% of the cells were used for analysis of GFP expression by FACS (FIG. 3B), whereas the rest of the cells were pelleted, total RNA was isolated and mRNA-expression of IFNb and OAS1 was quantified by qRT-PCR (FIG. 3A). As shown in FIG. 3A, IFNb and the IFN-response gene OAS1 are clearly induced by lipofection of IVT-RNA (Luc/GFP). This induction can be reduced in the case of IFNb by E3/K3 alone, but only the combination of all 3 viral escape proteins is able to reduce significantly both IFNb and OAS1-induction by IVT-RNA 48 h post lipofection. As shown in FIG. 3B, expression of the reporter gene GFP is enhanced by addition of E3 and K3. B18R has no effect on the translation of GFP.

CCD1079Sk fibroblasts were plated into 6 wells (100.000 cells/well) and lipofected the next four consecutive days using $6_1$A RNAiMAX (Invitrogen) and 1.4 μg IVT. The IVT-RNA mixture was thereby composed of 0.8 μg GFP with 0.2 μg of each B18R, E3 or K3 (as indicated). IVT-RNA encoding for Luc was used to sum up the mixture to 1.4 μg total IVT-RNA. As a control, 1.4 μg modified (mod.) IVT-RNA encoding for Luc (0.6 μg) and GFP (0.8 μg) was used. These RNAs were composed of 100% pseudouridine (psi) and 100% 5-methylcytidine (5mC) instead of uridine and cytidine which display less immunstimulatory characteristics. Lipofections were performed according to the manufacturers instructions. 24 h after the last lipofection, cell viability was assayed using the Cell Proliferation Kit II (Roche) and normalized to the mock transfected cells. As shown in FIG. 3C, daily lipofection of unmodified IVT-RNA (Luc/GFP, 4 times) is accompanied with massive loss in cell viability.

The combination of all 3 viral escape proteins is able to overcome this obstacle and enhances survival of the cells even more than the use of modified IVT-RNA (100% psi and 5mC). It is concluded that repetitive RNA-based gene transfer is possible when the combination of E3, K3 and B18R coded by IVT-RNA is added. Proof of concept was achieved.

Example 3

Use of E3, K3 and B18R in RNA-Based Gene Transfer for Reprogramming

After reaching the proof of concept that the addition of IVT-RNA coding for E3, K3 and B18R allows repetitive RNA-based gene transfer, we investigated whether this also holds true for the transfer of a reprogramming mixture. To this aim 6 rTF (OCT4, SOX2, KLF4, cMYC, NANOG, LIN28; short: OSKMNL) were mixed in a molar ratio of 1:1:1:1:1:1 and transferred by lipofection to HFFs. Again, survival of the cells and induction of IFN-response was analyzed after 4 daily repetitive lipofections.

CCD1079Sk fibroblasts were plated into 6 wells (80,000 cells/well) and lipofected the next four consecutive days using $6_1$A RNAiMAX (Invitrogen) and 1.4 μg IVT. The IVT-RNA mixtures were thereby composed of 0.8 μg unmodified GFP or 0.8 μg OSKMNL (1:1:1:1:1:1) either unmodified or modified and either with 0.2 μg of each B18R, E3 and K3 unmodified or modified. If necessary IVT-RNA encoding for Luc was used to sum up the mixture to 1.4 μg total IVT-RNA. Modified RNAs were composed of 100% psi and 100% 5mC instead of uridine and cytidine which display less immunstimulatory characteristics. Lipofections were performed according to the manufacturers instructions. 24 h after the last lipofection, cell viability was assayed using the Cell Proliferation Kit II (Roche) with normalization to mock transfected cells (FIG. 4A) and by microscopy (FIG. 4B). After that, cells were pelleted, total RNA was isolated and mRNA-expression of IFNb and OAS1 was quantified by qRT-PCR (FIG. 4C). As expected viability of the cells transfected with unmodified IVT-RNA (Luc/GFP or OSKMNL) is lost when E3/K3/B18R (EKB) are not present. In this set of experiments the viability is comparable to mock transfected cells when EKB are present. As seen with reporter gene IVT-RNA (see FIG. 3), the survival is even higher in the presence of EKB than with modified IVT-RNA alone. The effects observed in FIG. 4A are visualized in FIG. 4B by representative pictures taken with a microscope. Since the cells transfected with unmodified IVT-RNA did not survive 4 daily repetitive lipofections in this set of experiments, IFN-response could only be analyzed in the remaining samples by qRT-PCR. As can be seen in FIG. 4C, IFN-response measured by the induction of IFNb and OAS1 is nearly diminished in samples with EKB. The reduction in IFN-response is even lesser than with the use of modified IVT-RNA.

It is concluded that repetitive RNA-based gene transfer with reprogramming rTF is possible when the combination of E3, K3 and B18R coded by IVT-RNA is added. Survival of the cells and reduction of IFN-response is even more pronounced than with modified IVT-RNA.

Example 4

Translation of rTF After Repetitive Lipofection in the Presence of E3, K3 and B18R Besides the survival of the cells and the reduction of IFN-response, it was also addressed how the rTF are translated after 3 daily lipofections in the presence of E3, K3 and B18R. Expression levels of transferred rTF OCT4, SOX2 and NANOG were analyzed by intracellular FACS-Staining.

CCD1079Sk fibroblasts were plated into 6 wells (100,000 cells/well) and lipofected the next three consecutive days using $6_{1}11$ RNAiMAX (Invitrogen) and 1.4 μg IVT. The IVT-RNA mixtures was thereby composed of 0.2 μg GFP with 0.6 μg OCT4 or SOX2 or NANOG either unmodified or modified and 0.2 μg of each B18R, E3 and K3 (EKB) either unmodified or modified. Modified RNAs were composed of 100% psi and 100% 5mC instead of uridine and cytidine which display less immunstimulatory characteristics. Lipofections were performed according to the manufacturers instructions. 24 h rs after the last lipofection, intracellular expression of OSN was monitored by FACS analysis using the human pluripotent stem cell transcription factor analysis kit (BD 560589). Expression levels of NANOG, OCT4 and SOX2 were higher in the presence of EKB when applicated unmodified; cf. FIG. 5.

It is concluded that in the presence of EKB, unmodified IVT-RNA leads to higher expressions of rTF which may result in a more efficient reprogramming.

Example 5

Reprogramming of HFF Using rTF and microRNA in the Presence of EKB

Repetitive lipofection of rTF-mixture was achieved by addition of EKB to the reprogramming mixture leading to a better survival and higher reduction of IFN-response after daily lipofections. Furthermore higher expression levels of rTF were achieved in the presence of EKB. In the next experiments these mixture was used for long time lipofections to achieve reprogramming of HFFs. To further enhance reprogramming the microRNAs of cluster 302/367 were added to the reprogramming mixture as well. These miRNAs are thought to be mainly involved in the cellular maintenance of self-renewal and pluripotency, and could lead to reprogramming when expressed by lentiviral vectors (Anokye-Danso et al., 2011).

Figure 6A:
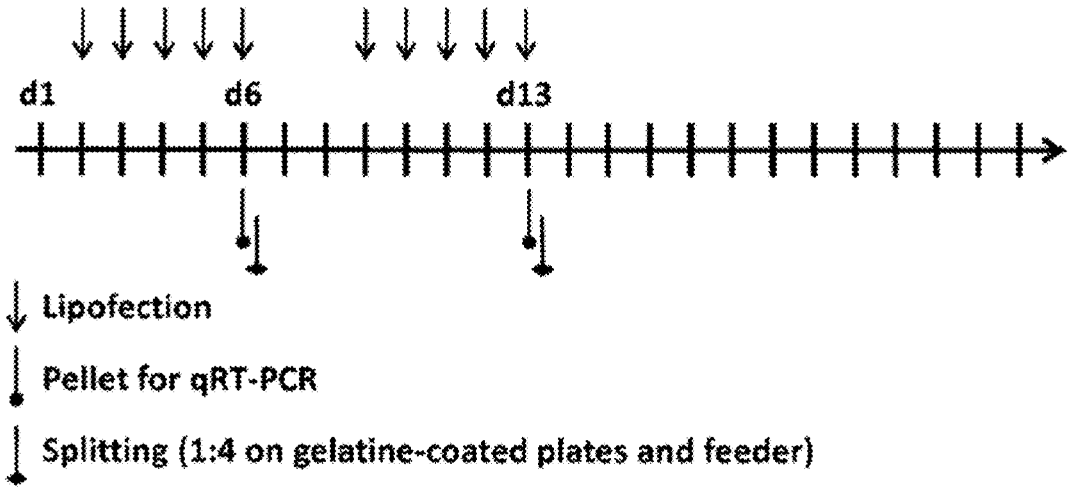

HFF fibroblasts (System Bioscience) were plated into 6 wells (100,000 cells/well) and lipofected 5 times a week (Monday to Friday) for two weeks using 6 μl RNAiMAX (Invitrogen) and 1.4 μg IVT-RNA (FIG. 6A). The IVT-RNA mixtures were thereby composed of 0.8 μg unmodified GFP or 0.8 μg OSKMNL (1:1:1:1:1:1) either unmodified or modified with either 0.2 μg of each B18R, E3 and K3 (EKB) either unmodified or modified and 0.4 μg of a miRNA mixture composed of miRNAs 302a-d and 367 [0.4 μM each]. Modified RNAs were composed of 100% psi and 100% 5mC instead of uridine and cytidine which display less immunstimulatory characteristics. Lipofections in stem cell media (Nutristem media, Stemgent) were performed according to the manufacturers instructions. On day 6 and day 13, cells were pelleted, total RNA was isolated and mRNA-expression of the human ES-marker TERT, DPPA4, GDF3, LIN28 (endogenous) and REX1 was quantified by qRT-PCR. Colony growth was observed by microscopy and for further analysis, colonies were stained for the ES surface marker TRA-1-60 using the StainAlive TRA-1-60 antibody (Stemgent) following the manufacturers instructions.

Figure 6B:
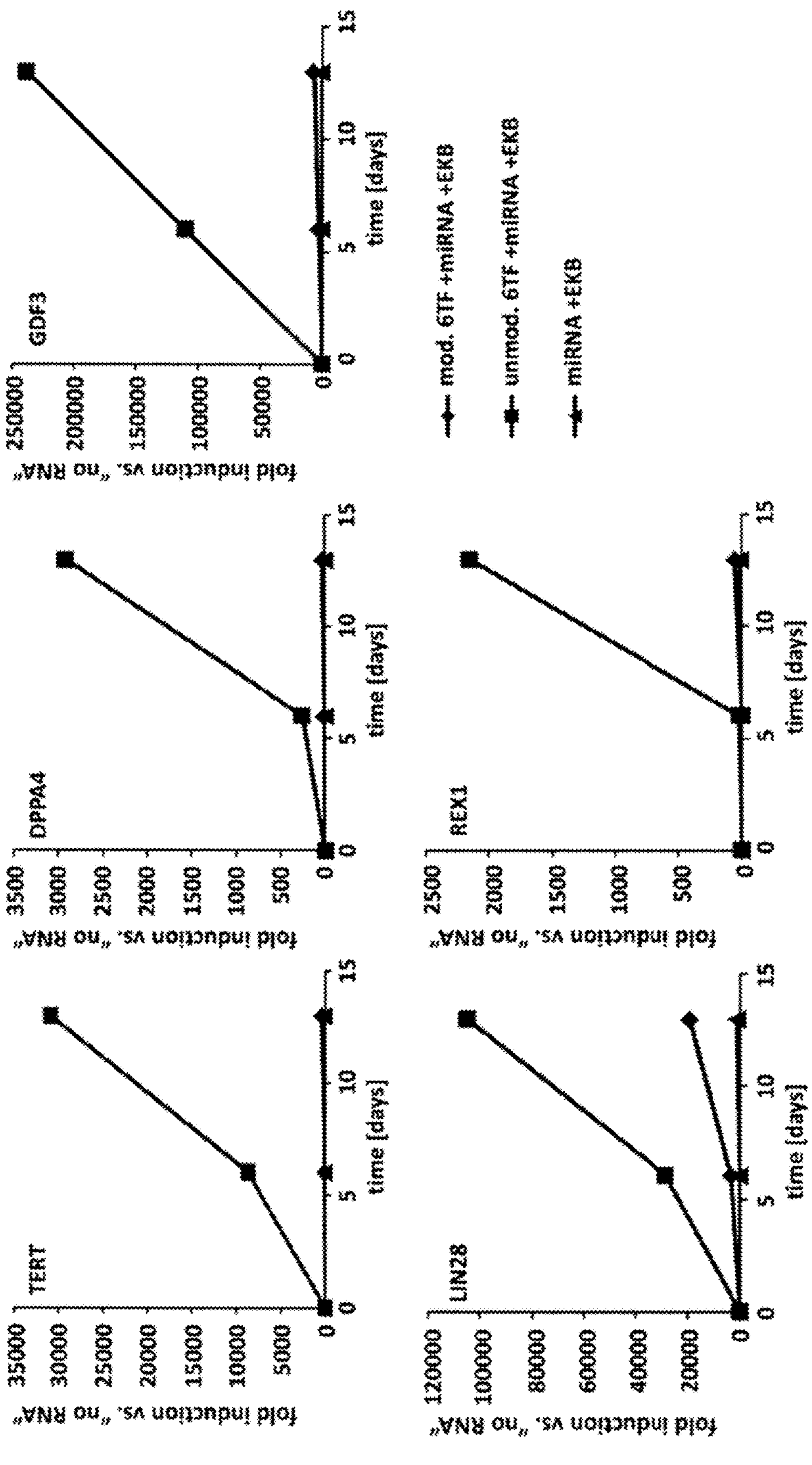
Figure 6C:
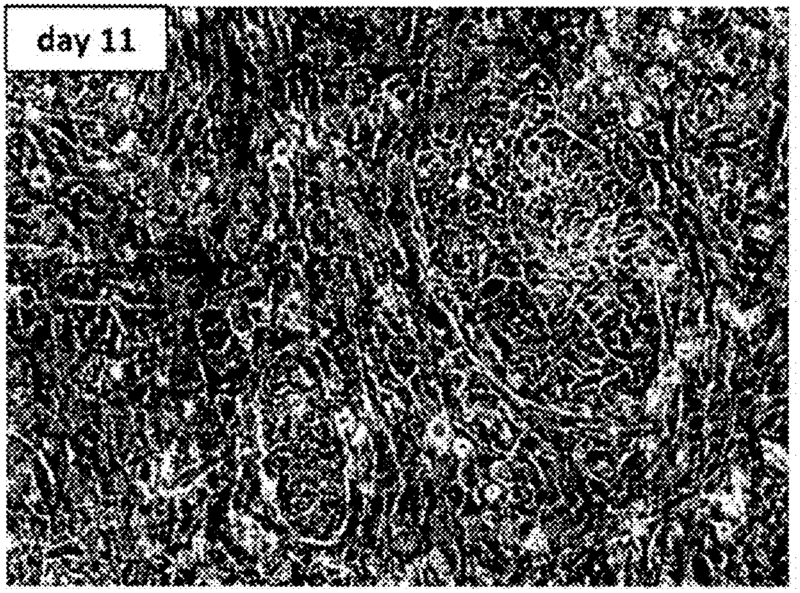
Figure 6D:
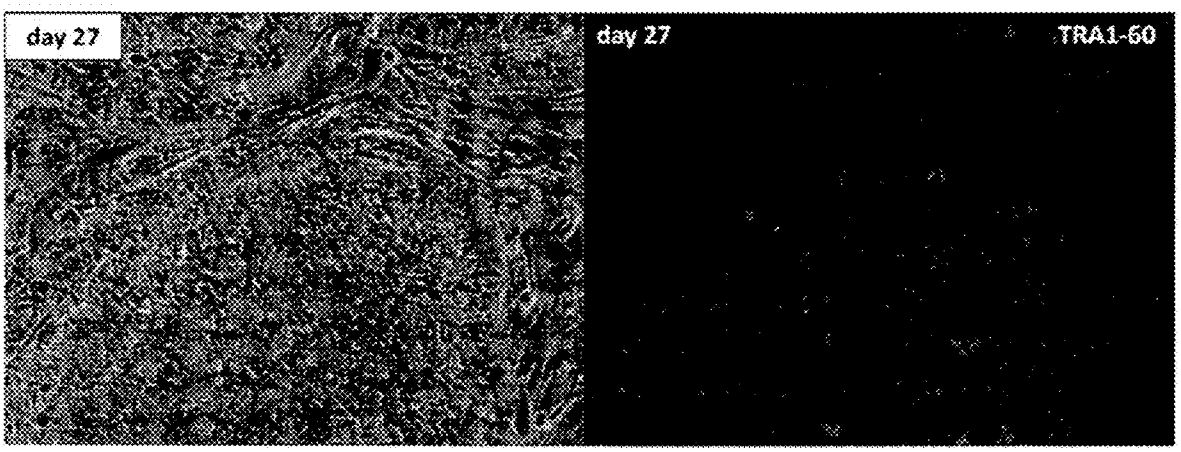

As shown in FIG. 6B, analysis of the expression levels of several pluripotency marker revealed that in the sample with unmodified OSKMNL, unmodified EKB and miRNA mixture, all analysed pluripotency marker were highly expressed compared to modified OSMNL, modified EKB and miRNA-mixture or miRNA-mixture with unmodified EKB alone. Unmodified IVT-RNA outstands thereby modification with 5mC and Psi. From d10 on colony formation was observed in the sample with unmodified OSKMNL, unmodified EKB and miRNA mixture; cf. FIG. 6C. In other samples such as miRNA alone no colony formation was observed. In the combination of modified OSKMNL with modified EKB and miRNA 1-3 colonies appeared, which was way behind the combination of unmodified OSKMNL and miRNA-mixture in the presence of EKB. As shown in FIG. 6D, the Ribo-iPS achieved by repetitive transfection with unmodified OSMNL, unmodified EKB and miRNA-mixture could be stained positive for TRA-1-60, a surface marker for human embryonic stem cells.

It is concluded that repetitive RNA-based gene transfer with rTF encoded by unmodified IVT-RNA in combination with unmodified EKB and a miRNA-mixture of mature miRNAs from the cluster 302/367 leads to a highly efficient and robust generation of Ribo-iPS cells characterized by high expression of pluripotency markers and stem cell surface marker. The use of unmodified IVT-RNA thereby outstands the use of modified IVT-RNA.

Example 6

Reprogramming of HFF Using rTF and microRNA in the Presence of EKB (Splitting 1:8)

In the first set of experiments for reprogramming with rTF coded by unmodified IVT-RNA, EKB and miRNA-mixture 302/367 cells were splitted 1:4. In the next experiments cells were splitted 1:8 to avoid a dense growing of the cells.

Figure 7A:
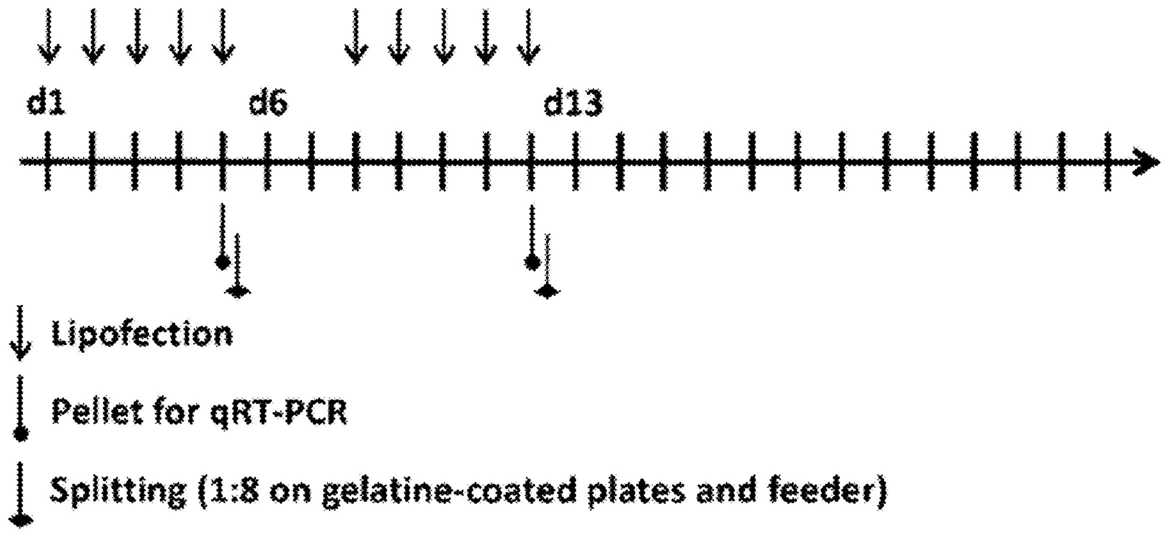

HFF fibroblasts (System Bioscience) were plated into 6 wells (100,000 cells/well) and lipofected 5 times a week (Monday to Friday) for two weeks using 6 μl RNAiMAX (Invitrogen) and 1.4 μg IVT-RNA (FIG. 7A). The IVT-RNA mixtures were thereby composed of 0.8 μg OSKMNL (1:1:1:1:1:1) either unmodified or modified with either 0.2 μg of each B18R, E3 and K3 (EKB) unmodified or modified and 0.4 μg of a miRNA mixture composed of miRNAs 302a-d and 367 [0.4 μM each]. Modified RNAs were composed of 100% psi and 100% 5mC instead of uridine and cytidine which display less immunstimulatory characteristics. Lipofections in stem cell media (Nutristem media, Stemgent) were performed according to the manufacturers instructions. On day 5 and day 12, cells were pelleted, total RNA was isolated and mRNA-expression of the human ES-marker TERT, DPPA4, GDF3, LIN28 (endogenous) and REX1 was quantified by qRT-PCR. Colony growth was observed by microscopy and for further analysis, colonies were stained for the ES surface marker TRA-1-60 using the StainAlive TRA-1-60 antibody (Stemgent) or for the activity of alkaline phosphatase (Vector Red staining kit) following the manufacturers instructions.

Figure 7B:
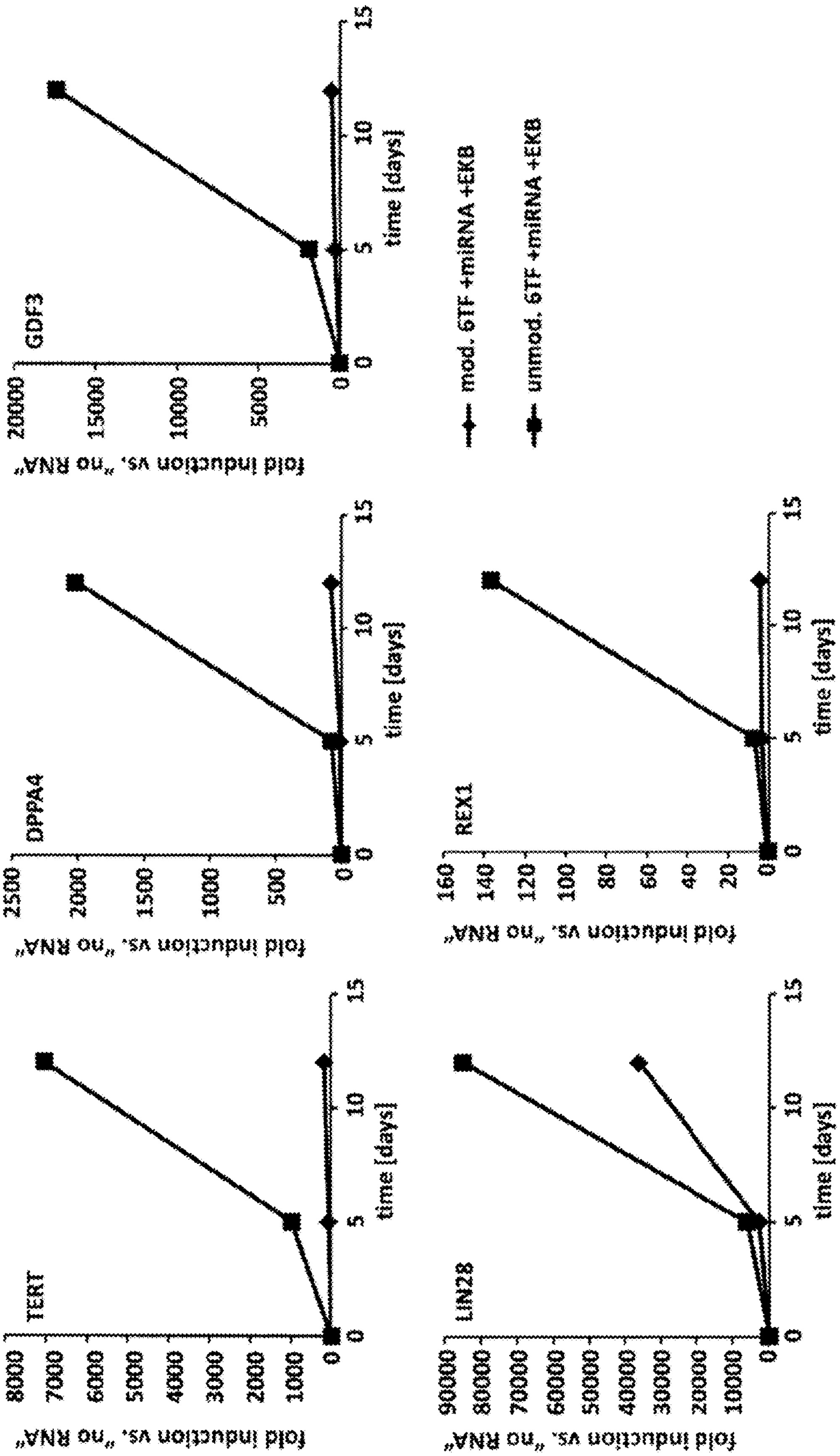
Figure 7C:
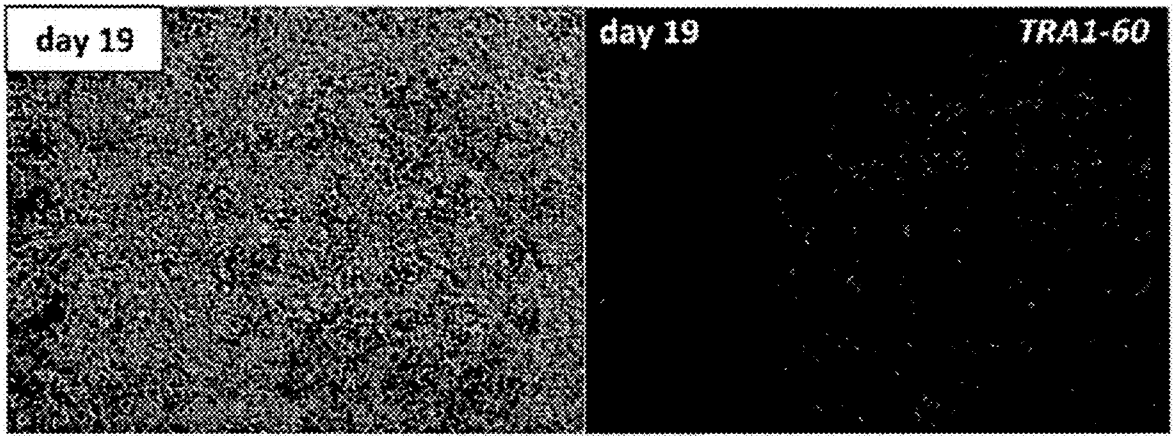
Figure 7D:
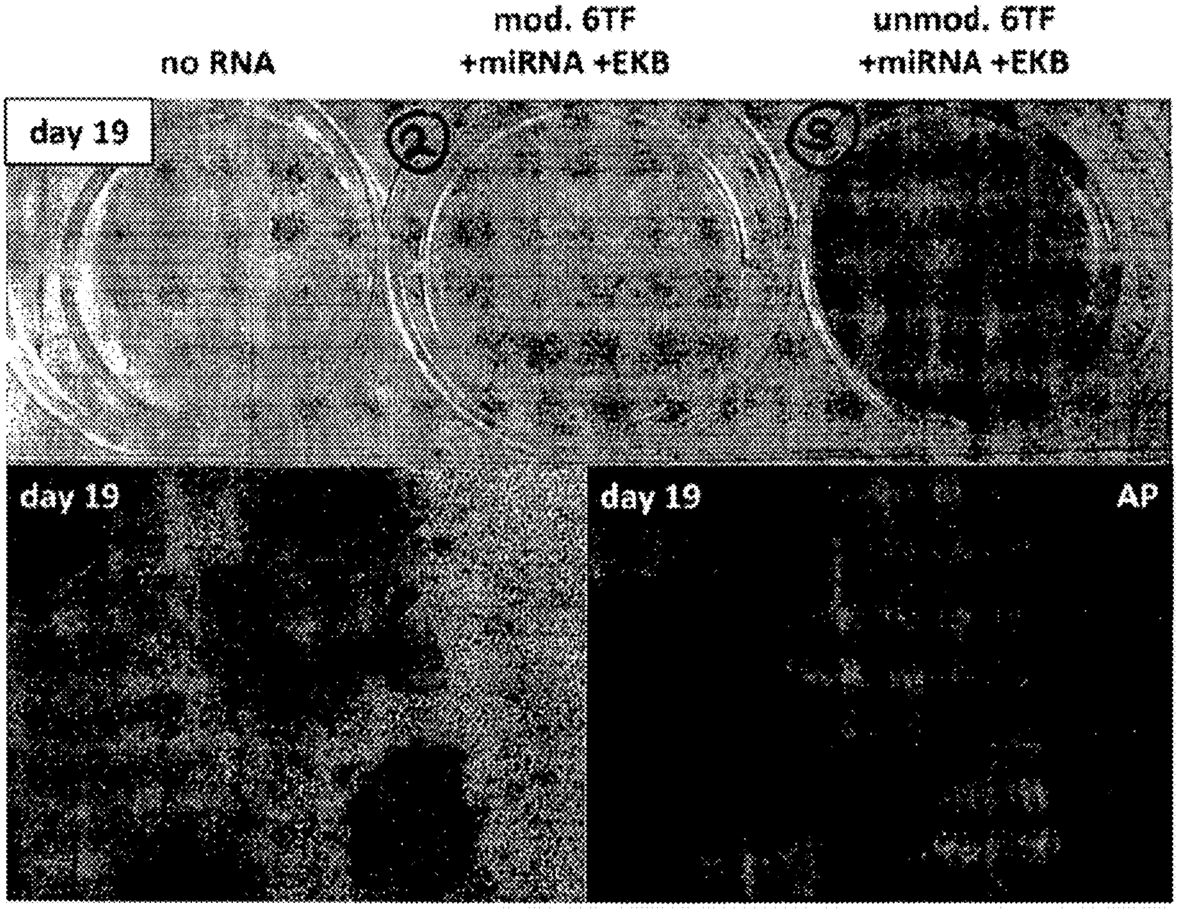

As shown in FIG. 7B, analysis of the expression levels of several pluripotency marker revealed that in the sample with unmodified OSKMNL, unmodified EKB and miRNA mixture, all analysed pluripotency marker were highly expressed compared to modified OSMNL, modified EKB and miRNA-mixture. Again, unmodified IVT-RNA outstands modification with 5mC and Psi. Also, from d10 on colony formation was observed in both samples (unmodified or modified OSKMNL). These colonies could be stained positive for TRA-1-60—a surface marker for human embryonic stem cells; cf. FIG. 7C. As shown in FIG. 7D, the colonies also displayed high activity of Alkaline Phosphatase—another stem cell marker. The obvious higher efficiency of unmodified OSKMNL compared to modified OSKMNL can clearly be seen in the upper panel of FIG. 7D.

It is concluded that repetitive RNA-based gene transfer with reprogramming rTF coded by unmodified IVT-RNA in combination with unmodified EKB and a miRNA-mixture of mature miRNAs from the cluster 302/367 leads to a highly efficient and robust generation of Ribo-iPS cells characterized by high expression of pluripotency markers and stem cell surface marker. The use of unmodified IVT-RNA thereby outstands the use of modified IVT-RNA.

Example 7

Titration of EKB

One possibility to further enhance the efficiency of reprogramming would be the addition of more rTF-IVT-RNA or other enhancing factors encoded by IVT-RNA. Since the lipofection protocol is limited to a certain amount of IVT-RNA, we investigated whether the amount of EKB can be reduced when added to the reprogramming cocktail. HFFs were therefore lipofected with the 6 rTF and miRNA combined with different amounts of EKB reaching from 0.0001 μg to 0.2 μg (amount used in reprogramming experiments) each. Survival of the cells and induction of IFN-response was analyzed after 4 daily repetitive lipofections.

HFF fibroblasts (System Bioscience) were plated into 6 wells (100,000 cells/well) and lipofected the next four consecutive days using 6 μl RNAiMAX (Invitrogen) and 1.4 μg IVT. The IVT-RNA mixtures were thereby composed of 0.8 μg unmodified OSKMNL (1:1:1:1:1:1) with variable amounts of unmodfied B18R, E3 and K3 as indicated. IVT-RNA encoding for Luc was used to sum up the mixture to 1.4 μg total IVT-RNA. According to the reprogramming experiments 0.4 μg of a miRNA mixture composed of miRNAs 302a-d and 367 [0.4 μM each] was added to the samples. As a control, 1.4 μg modified (mod.) IVT-RNA encoding for Luc (0.6 μg) and OSKMNL (0.8 μg; 1:1:1:1:1:1) was used. These RNAs were composed of 100% psi and 5mC instead of uridine and cytidine which display less immunstimulatory characteristics. Lipofections were performed according to the manufacturers instructions. 24 h after the last lipofection, cell viability was assayed using the Cell Proliferation Kit II (Roche). After that, cells were pelleted, total RNA was isolated and mRNA-expression of IFNb and OAS1 was quantified by qRT-PCR.

As shown in FIG. 8A, viability of HFFs after repetitive lipofections was sustained down to a reduction of EKB to 0.025 μg IVT-RNA of each factor. Analysis of the IFN-response by measuring the expression levels of IFNb and OAS1 revealed that again the IFN-response to IVT-RNA is clearly reduced down to an amount of 0.025 μg of EKB; cf. FIG. 8B. Nevertheless with the residual induction of IFN-response we recommend the use of 0.05 μg of EKB.

It is concluded that the amount of EKB can be reduced to 0.025-0.05 μg of each IVT-RNA.

Example 8

Effect E3 and K3 Alone

So far, only the combination of E3 and K3 was used. In this set of experiments the effect of E3 and K3 alone on translation of the reporter gene Luc and on IFN response was analyzed.

CCD1079SK fibroblasts were electroporated with IVT RNA encoding Luc (1 μg), GFP (5 μg) and 3 μg of E3 or K3 or both as indicated. Electroporations were performed in 2 mm gap cuvettes using optimized parameters for CCD1079Sk fibroblasts. 10000 cells/well were plated in duplicates into 96-well-plates. Luciferase activity was measured at the time points indicated in FIG. 9A after electroporation using the Bright Glo Luciferase Assay System (Promega). Mean values of the duplicates are given. Furthermore, 300000 cells/well were plated into 6-well-plates and 24 h post electroporation, cells were pelleted, total RNA was isolated and mRNA-expression of OAS1 and IFN-b was analyzed by RT-PCR and in case of IFN-b quantified using the Quanti Tect SYBR Green PCR Kit.

As shown in FIG. 9A, the translation of Luc was enhanced with E3 or K3 alone as much as with both of them together. As seen for lipofection of IVT-RNA, IFNb and the IFN-response gene OAS1 are clearly induced by electroporation of IVT-RNA (Luc/GFP). These inductions cannot be reduced neither by E3 or K3 nor by the combination of both 24 h post electroporation; cf. FIG. 9B.

These experiments indicate that one intracellular viral escape protein (E3 or K3) coded by IVT-RNA may be sufficient to allow repetitive RNA-based gene transfer as seen with the combination EKB.

Example 9

Use of Viral Interferon Inhibitors to Enhance Self-Replicating RNA-Expression

The genome of alphaviruses is single stranded RNA of positive sense (ssRNA(+)) that encodes two open reading frames (ORF) for large polyproteins. The ORF at the the 5'-end of the genome encodes the non-structural proteins nsP1 to nsP4 (nsP1-4), which are translated and processed to an RNA-dependent RNA-polymerase (replicase); the ORF at the 3'-end encodes the structural proteins—capsid and glycoproteins. Both ORFs are separated by the so called subgenomic promoter (SGP), which governs the transcription of the structural ORF (Strauss and Strauss, 1994, Microbiol. Rev. 58, 491-562). When exploited as gene vectors, the structural proteins behind the SGP are replaced by transgenes. In order to package such vectors into viral particles, the structural proteins must be expressed in trans from helper constructs (Smerdou and Liljestrom, 1999, J. Virol. 73, 1092-1098; Ehrengruber and Lundstrom, 2007, Proc. Natl. Acad. Sci. U.S.A 96, 7041-7046).

Alphaviruses replicate in the cytoplasm of infected cells exclusively at the RNA level (for review of the alphaviral life cycle (Jose et al., 2009, Future. Microbiol. 4, 837-856). After infection, the ssRNA(+) genome acts as mRNA for the translation of the nsP1234 poly-protein precursor which is at early stages of the viral life cycle autoproteolytically processed to the fragments nsP123 and nsP4. Fragments nsP123 and nsP4 form the (−)strand replicase complex that transcribes (−)stranded RNA from the genomic RNA template. At later stages, the nsP1234 polyprotein is completely cleaved to the single proteins (Shirako and Strauss, 1994, J. Virol. 68, 1874-1885) which assemble to the (+)strand replicase complex that synthesizes new (+)stranded genomes, as well as subgenomic transcripts that code the structural proteins or transgenes (Kim et al., 2004, Virology 323, 153-163; Vasiljeva et al., 2003, J. Biol. Chem. 278, 41636-41645). Subgenomic RNA as well as new genomic RNA is capped (Cross and Gomatos, 1981, Virology 114, 542-554; Pettersson et al., 1980, Eur. J. Biochem. 105, 435-443) and poly-adenylated (Sawicki and Gomatos, 1976, J. Virol. 20, 446-464) and thus recognized as mRNA after target cells infection. Only new genomic RNA contains a packaging signal which ensures exclusive packaging of genomic RNA into budding virions.

The beauty of alphaviral replicons for vectorology grounds on the positive orientation of the capped and poly-adenylated RNA genome. Translatable replicon RNA can easily be synthesized in vitro, whereby capping is achieved with cap-analoga added to the in vitro transcription reaction and poly-A tails are encoded as poly-T tracks on the plasmid templates (Ehrengruber and Lundstrom, 2007, Curr. Protoc. Neurosci. Chapter 4, Unit). In vitro transcribed (IVT) replicons are transfected by conventional transfection techniques and even low amounts of starting IVT replicons are multiplied rapidly. Within a few hours after transfer (Bruton and Kennedy, 1975, J. Gen. Virol. 28, 111-127), transgenes which are placed downstream of the SGP are transcribed to very high copy numbers of about 40.000 to 200.000 copies of subgenomic RNA per cell (Tuomi et al., 1975, Nucleic Acids Res. 2, 555-565), thus it is not surprising that recombinant proteins are strongly expressed.

Dependent on the specific aim, IVT replicons may be transfected directly into target cells, or packaged into alphaviral particles with helper vectors that provide structural genes in trans (Smerdou and Liljestrom, 1999, J. Virol. 73, 1092-1098; Berglund et al., 1993, Biotechnology (N. Y.) 11, 916-920). Transfer into the skin or muscles leads to high and sustained local expression, paralleled by a strong induction of humoral and cellular immune response (Johansson et al., 2012, PLoS. One. 7, e29732; Geall et al., 2012, Proc. Natl. Acad. Sci. U.S.A 109, 14604-14609). Taken together, ease of in vitro replicon production and transfer, high expression levels and immune responses by replicons are ideal for vaccination against infectious diseases or cancer (discussed recently by (Ulmer et al., 2012, Vaccine 30, 4414-4418)).

Despite these overall positive aspects, replicon based gene transfer faces limitations imposed by an effective block of translation in host cells which causes cell death. The block of translation is provoqued by two mechanisms: first, the replicase protein nsP2 actively shuts down host translation by degrading RNA-polymerase-II (Akhrymuk et al., 2012, J. Virol. 86, 7180-7191) and second, interferon (IFN) response mediates a shutdown of translation by protein kinase R (PKR) activation (Gorchakov et al., 2004, J. Virol. 78, 8455-8467). The nsP2 related cytotoxicity was overcome by selecting non-cytotoxic mutants capable of persistent replication and gene expression in cells (Casales et al., 2008, Virology 376, 242-251;

Lundstrom et al., 2003, Mol. Ther. 7, 202-209). However, most of these studies were performed in BHK21 cells that are highly permissive for replicon expression which is most likely related to defects in IFN response (Chinsangaram et al., 1999, J. Virol. 73, 9891-9898). In IFN competent cells, PKR activation and IFN response can still be expected and this would limit stable expression of non-cytotoxic vectors.

Besides inhibiting translation, IFN response is also an obstacle for alphaviral replication (Deuber and Pavlovic, 2007, J. Gen. Virol. 88, 1952-1959). Especially PKR, which is activated by dsRNA, blocks replication (Barry et al., 2009, J. Gen. Virol. 90, 1382-1391). Activated PKR phosphorylates the eukaryotic initiation factor 2alpha (eIF2alpha) which thereafter is no longer able to initiate translation of capped mRNA (Pindel and Sadler, 2011, J. Interferon Cytokine Res. 31, 59-70). Thereby cells inhibit protein expression of many viruses, and as a concequence of virus-host coevolution, many viruses in return express PKR inhibitory proteins (Garcia et al., 2006, Microbiol. Mol. Biol. Rev. 70, 1032-1060). Alphaviruses, however, achieve their life cycle without inhibiting PKR, although they strongly activate PKR. Their subgenomic transcripts are efficiently translated to structural proteins in presence of activated PKR, which is dependent on a 5'-terminal subgenomic RNA-motif called translational enhancer (TE) (Gorchakov et al., 2004, J. Virol. 78, 8455-8467). The replication of mutant viruses devoid of the TE is severely impaired, but can be rescued in trans by expression of E3L, a PKR inhibitor from Vaccinia virus (VacV) (Domingo-Gil et al., 2011, PLoS. One. 6, e16711).

Replicon vectors are usually devoid of the TE, because the TE extends into the coding region of the capsid and is therefore removed when structural proteins are replaced with transgenes. Thus, transgene expression is repressed by PKR activation. Coexpression of dominant-negative PKR may derepress expression (Gorchakov et al., 2004, J. Virol. 78, 8455-8467), similar to the above mentioned rescue of TE-deficient virus replication by E3L. On the other hand, fusion of the TE-sequences to the N-terminal part of the transgene ORF allows transgene expression, with the disadvantage that a functional TE comprises not only the subgenomic UTR, but also the N-terminal amino acids of the capsid protein (34 Aa in SFV) (Sjoberg et al., 1994, Biotechnology (N. Y.) 12, 1127-1131). As long as capsid-transgene fusions are acceptable, such a vector design can be used, otherwise the TE should precede a 2A self cleavage, realized for instance in pSFV-Helper-S of the two-helper RNA system (Smerdou and Liljestrom, 1999, J. Virol. 73, 1092-1098).

Here we demonstrate that the expression replicons devoid of TE- can be improved by inhibiting interferon (IFN) response of transfected cells. We improved replicon expression by coexpressing proteins from Vaccinia virus (VacV), namely E3L, B18R and K3L (EKB). We show for the first time that EBK can be encoded on synthetic mRNA and enhance replicon expression in trans by simple cotransfection. We found that cotransfected VacV proteins inhibited IFN response and prevents PKR-activation and thereby increased the translation of replicon encoded proteins. Expression was increased in different cell types from humans and mice, but overall, the increase was more pronounced in human than in mouse cells. We confirmed increased expression by EBK RNA in vivo upon delivery into the muscle and spleen. When we assessed the contribution of the different single proteins, we found that E3 acts as the main enhancer of expression, while B18R is indispensable to completely block IFN response.

We conclude that the cotransfer of IFN-inhibitors is a promising tool to enhance the efficacy of replicon-based vectors for therapeutic gene delivery or vaccination. Thereby the overall amount of RNA needed to treat patients can be reduced which would increase effectiveness and profitability of RNA vaccines.

9.1 Material and Methods:

Vectors and In Vitro Transcription of RNA:

Semliki forest virus replicon vectors (pSFV-gen-GFP) and the non-cytotoxic mutant vectors (pSFV4(PD)) were kindly provided by K. Lundström (Lundstrom et al., 2001, Histochem. Cell Biol. 115, 83-91; Ehrengruber et al., 1999, Proc. Natl. Acad. Sci. U.S.A 96, 7041-7046). pSFV-encoded poly-A tails were elongated from 62 adenosin residues in the original vector to 120 adenosin residues, and a SapI restriction site was placed immediately downstrom of the poly-A. This poly-A design was copied from optimized synthetic mRNA vectors and was described to enhance translation (Holtkamp et al., 2006, Blood 108, 4009-4017). We cloned the reporter genes Luciferase and green fluorescent protein (GFP) 3' to the subgenomic promoter. pST1-vectors were cloned that encode the infrared fluorescent protein (iRFP), luciferase, E3L, B18R or K3L (EBK). In vitro transcription of pSt1-vectors and purification of RNA were previously described (Holtkamp et al., 2006, Blood 108, 4009-4017; Kuhn et al., 2010, Gene Ther. 17, 961-971). pSFV-vectors were in vitro transcribed using SP6 RNA-polymerase (Megascript Kit, Ambion). Quality of purified RNA was assessed by spectrophotometry, and analysis on the 2100 BioAnalyzer (Agilent, Santa Clara, USA).

RNA Transfer:

RNA was electroporated into the different target cells at room temperature with a square-wave electroporation device (BTX ECM 830, Harvard Apparatus, Holliston, Mass., USA) using the following settings: human fibroblasts CCD1079SK (550 V/cm; 3 pulses of 12 ms); human foreskin fibroblasts (HFF; 625 V/cm, 1 pulse of 24 ms); BJ fibroblasts (550 V/cm, 3 pulses of 12 ms); RT101 (750 V/cm, 1 pulse of 12 ms); C2C12 (600 V/cm; 5 pulses of 5 ms); BHK21 (750 V/cm, 1 pulse of 16 ms); 3T3-L1 (625 V/cm; 5 pulses of 5 ms); human skeletal muscle cell (hSKMC; 700 V/cm, 1 pulse of 10 ms). For electroporation, RNA was resuspended in a finale volume of 62.5 μl/mm cuvette gap size. Intervalls between consecutive pulses were 400 ms in all settings. RNA lipofections were performed using Lipofectamine RNAiMAX following the manufacturer's instructions (Life Technologies, Darmstadt, Germany). Cells were plated at approximately 20000 cells/cm2 growth area and transfected with a total amount of 260 ng/cm2 RNA and 1 μl/cm2 RNAiMAX. Mixtures of different RNA species were prepared (listed in table 2 and table 3) in RNAse free Eppendorf tubes and kept on ice until transfections. With exception of 3T3-L1 cells, transfected cells were harvested 24 h after transfection to measure transfection efficiencies (indicated by iRFP expression) and replicon or synthetic mRNA expression (indicated by GFP) by FACS. 3T3-L1 cells were rapidly killed by replicon expression after electroporation, therefore they were harvested 8 h after electroporation, but 24 h after lipofection.

Cells:

Cells used in the study are listed in table 1.

TABLE 1

Cell lines and cell types used in the study.

| Cell line | Tissue of origin | species | comments |
|---|---|---|---|
| RT101 | epidermis | Mouse (Balb/C) | ATCC #CRL-2002, chemically transformed |
| 3T3-L1 | Embryonic fibroblasts | mouse | ATCC #CL-173 |
| C2C12 | Skeletal muscle myoblast | Mouse (C3H) | ATCC #1772, maybe differentiated to mature myotubes |
| CCD1079SK | Foreskin fibroblasts | human | ATCC #CRL-2097, reach senescence after 56 population doublings |
| BJ | Foreskin fibroblasts | human | ATCC #CRL-2522, reach senescence after 72 population doublings |
| HFF | Neonatal foreskin fibroblasts | human | System Biosciences # PC501A-1, more than 30 population doublings |
| hSkMC | muscle | human | PromoCell #C12530; differentiate into multinucleated syncytia |

TABLE 1-continued

Cell lines and cell types used in the study.

| Cell line | Tissue of origin | species | comments |
|---|---|---|---|
| BHK-21 | kidney | hamster | ATCC #CCL-10, Standard alphavirus producer cell line |
| HUVEC | Umbelical vein endothelia | human | PromoCell |

In Vivo RNA Transfer:

Replicons coding luciferase were resuspended in PBS and injected into the tibialis anterior of mice. EBK coding IVT RNA was cotransferred as indicated in figure legends. In vivo luciferase expression was measured as described (Kuhn et al., 2010, Gene Ther. 17, 961-971).

Flow Cytometry:

The expression of IVT RNA encoding iRFP or GFP was measured by flow cytometry using a FACS Canto II flow cytometer (BD Bioscience, Heidelberg, Germany) and acquired data were analyzed by the corresponding Diva software or FlowJo software (Tree Star Inc., Ashland, Oreg., USA).

Luciferase Asays:

To assess the expression of firefly luciferase, 1E4 electroporated cells were plated in 96-well white microplates (Nunc, Langenselbold, Germany). Direct lysis of the cells and luciferase detection was performed with the Bright-Glo Luciferase Assay System (Promega, Madison, Wis., USA) according to the manufacturer's instructions. Bioluminescence was measured using a microplate luminescence reader Infinite M200 (Tecan Group, Männedorf, Switzerland). Data were represented in relative luciferase units [RLU], Luciferase-negative cells were used to substract the background signal.

Western Blot:

PKR expression and phosphorylation was detected by western blot of cell lysates. Antibodies used: Phospho-PKR (ab32036, Abcam, Cambridge, UK), PKR (ab45427; Abcam, Cambridge, UK). Secondary antibody goat anti rabbit (sc-2004; Santa Cruz, Dallas, Tex., USA).

9.2 Efficiency of Replicon Expression is Cell Line Dependent

BHK21, RT101 and CCD1079Sk cells were lipofected with a serial dilution of replicon RNA coding for GFP (2 μg to 0.02 μg as indicated in FIG. 10). A fixed amount of 0.5 μg IVT RNA coding iRFP was cotransfected to monitor lipofection success. To adjust total RNA amounts to 2.5 μg in all samples, varying amounts of luciferase coding RNA were cotransfected.

While BHK21 cells and RT101 cells are highly permissive and show high replicon expression levels over a wide range of transfected replicon RNA amounts, replicon expression is severely impaired in human fibroblasts (CCD1079SK); cf. FIG. 10.

9.3 The Expression of Cotransfected IVT RNA is Impaired in Non-Permissive Cells

Same experiment as in FIG. 10, displayed in FIG. 11 are iRFP expression levels in selected samples from the serial replicon dilution.

iRFP coexpression in BHK21 and RT101 cells increases in inverse correlation to the replicon amount. In contrast, iRFP expression is impaired in CCD1079Sk cells independently of the replicon amount, which indicates strong PKR activation even by very low amounts of replicon.

9.4 Secreted IFN Blocks IVT RNA and Replicon Expression and B18R Releases this Block Human foreskin fibroblasts (HFF) were electroporated (EP) as follows: no RNA; 40 μg/ml luciferase coding repicon RNA or 40 μg/ml replicon RNA coding GFP and 40 μg/μl IVT RNA coding for the soluble Vaccinia virus (VacV) IFN-decoy receptor B18R. After electroporation, the cells were plated at 3.3E04 cells/cm$^2$ and supplemented with 120 μl/cm$^2$ Medium. The next day, supernatant (SN) of the cells were collected and transferred onto HFF cells plated in 96-well-plate the day before (5000 cells/well). The supernatant from replicon electroporated cells was additionally supplemented with 200 ng/ml recombinant B18R (rec. B18R). Cells were incubated 6 h with the supernatant. Thereafter cells were lipofected with (A) 0.25 μg IVT RNA or (B) 0.25 μg replicon RNA encoding luciferase per well formulated with 1 μl RNAiMAX per well. Medium was not changed before lipofection. The next day Luciferase expression was measured; cf. FIG. 12.

Supernatants of replicon transfected cells inhibited the expression of luciferase coding IVT RNA and replicons. Recombinant B18R as well as B18R secreted upon coelectroporation counteracts this inhibition, which proves that IFNs are the inhibitory agent in the supernatants.

9.5 The Electroporation of IVT RNA Blocks the Expression of Subsequently Transfected Replicon RNA. VacV Proteins Release the Block of Expression Human foreskin fibroblasts (CCD1079SK) were electroporated (EP) as follows: no RNA (EP1); 80 μg/ml luciferase coding IVT RNA (EP2) or 80 μg/ml IVT RNA coding for Vaccinia virus (VacV) proteins E3, K3, B18R (EBK) (EP3). After electroporation, the cells were plated at 2E05 cells per well in 6-well plates. The next day, the cells were lipofected with a total RNA amount of 2.5 μg: 0.75 μg GFP-coding replicon RNA were cotransfected either with 1.25 μg luciferase or EBK coding RNA as indicated. GFP expression was measured by FACS 24 h later; cf. FIG. 13.

Cells that were electroporated without RNA, low basal level of replicon expression was boosted by colipofected EBK. Cells that were electroporated with luciferase coding IVT RNA blocked replicon expression, and colipofected EBK could not release this block. In cells that were electroporated with IVT RNA coding EBK, replicon expression was not inhibited.

These data show that replicon expression is impaired in cells which are in an active antiviral state before replicon RNA is transfected.

9.6 VacV Proteins Encoded on IVT RNA Prevent IFN Response to RNA, But Have Limited Action on an Established IFN Response Human foreskin fibroblasts (CCD1079SK) were first electroporated and then lipofected as in FIG. 13. RNA was isolated from these cells and analyzed by qRT-PCR for IFN-reponse markers; cf. FIG. 14. Panels (A) and (C) show OAS1 and IFNβ transcript induction the day after electroporation, meaning immediately before lipofection. Panels (B) and (D) show OAS1 and IFNβ induction after electroporation and subsequent lipofection.

(A) At the timepoint of lipofection OAS1 is induced only in cells electroporated with luciferase coding RNA. (B) Colipofected EBK inhibits replicon-induced OAS1 upregulation in previously not electroporated cells (first group of 3 columns). However, EBK colipofection does not revert the OAS1 induction by the previous electroporation of IVT RNA coding luciferase (second group of 3 columns). Cells that were electroporated with replicon and EBK are resistant towards IFN reponse induction by lipofection. Overall, the upregulation of OAS1 transcripts correlates nicely to block of replicon expression. (C) IFNβ transcripts are upregulated in both RNA-electroporated samples, although B18R reduced the level of induction. (D) Cells that were not lipofected lost IFNβ transcripts from the electroporation (column 4). IFN naïve cells that were electroporated without RNA upregulate IFNβ transcripts when lipofected with RNA, unless the RNA encodes EBK. EBK Lipofection does not revert IFNβ transcripts induction of previous electroporation (column 6). In contrast, EBK electroporation prevents the upregulation of IFNβ by lipofection, most likely thanks to secreted B18R.

9.7 VacV Proteins Reduce IFN Response to IVT RNA and Replicons in Human Cells

Human foreskin fibroblasts (HFF) and CCD1079SK fibroblasts (CCD) were transfected with (A) 0.75 μg IVT RNA or (B) 0.75 μg replicon RNA encoding GFP, together with 0.5 μg IVT RNA encoding iRFP. 1.25 μg IVT RNA coding VacV proteins was cotransfected as indicated (see table 2), mixtures of VacV-proteins were in 1:1 ratios. Luciferase coding IVT RNA (Luc) served as positive control for IFN-response induction and used to normalize the data; cf. FIG. 15.

IFNβ induction in response to IVT RNA was inhibited by the combination EKB as well as E3L and K3L, but not by B18R alone. IFNβ in response to replicon RNA was inhibited by all VacV proteins, however the combination of all three was best. OAS1 and OAS2 induction in response to IVT RNA as well as replicon RNA was abrogated by by EKB. B18R alone inhibited OAS1/2 induction in response to replicon RNA, but not IVT RNA. K3L and E3L were less effective.

B18R is indispensable to completely abrogate IFN response. Only the combination of EBK effectively blocked all IFN-response genes.

9.8 VacV Proteins Enhance the Expression of IVT RNA and Replicon RNA Electroporated in Mouse and Human Cell Lines.

Mouse 3T3-L1 fibroblasts, human CCD1079SK fibroblasts, mouse C2C12 myoblasts and human primary HUVEC cells were electroporated with (A) IVT RNA or (B) replicon RNA coding GFP, together with IVT RNA encoding VacV proteins as indicated. iRFP encoding IVT RNA was cotransfected to all samples to monitor electroporation success (refer to table 2 for details of transfection mixtures); cf. FIG. 16.

TABLE 2

IVT RNA mixes used for electroporations in examples 9.7, 9.8 and 9.12. RNA mixes were adjusted to equal final volumes with RNAse free water.

| Sample No. | iRFP [μg] | E3L [μg] | K3L [μg] | B18R [μg] | eGFP [μg] | GFP replicon [μg] |
|---|---|---|---|---|---|---|
| 1 | 2.5 | | | | 2.5 | — |
| 2 | 2.5 | 0.67 | 0.67 | 0.67 | 2.5 | — |
| 3 | 2.5 | 2 | | | 2.5 | — |
| 4 | 2.5 | | 2 | | 2.5 | — |
| 5 | 2.5 | 1 | 1 | | 2.5 | — |
| 6 | 2.5 | | | 2 | 2.5 | — |
| 7 | 2.5 | | | | — | 2.5 |
| 8 | 2.5 | 0.67 | 0.67 | 0.67 | — | 2.5 |
| 9 | 2.5 | 2 | | | — | 2.5 |
| 10 | 2.5 | | 2 | | — | 2.5 |
| 11 | 2.5 | 1 | 1 | | — | 2.5 |
| 12 | 2.5 | | | 2 | — | 2.5 |

(A) We found a moderate increase of IVT RNA based GFP expression in mouse and human fibroblasts with EKB or E3 and/or K3, while there was no effect in mouse muscle cells and human HUVEC.

(B) Replicon expression was increased to a higher degree than IVT RNA in all 4 tested cells. Cotransfer of VacV proteins results in a boost of replicon expression especially in human fibroblasts, where we found about 3-fold stronger increase than in mouse fibroblasts. E3 was the major player in human fibroblasts, K3 increases the expression less strongly.

9.9 VacV Proteins Enhance the Expression of IVT RNA and Replicon RNA Lipofected Into Mouse and Human Cells.

Mouse (3T3-L1) and human (CCD1079SK) fibroblasts, and mouse (C2C12) and human (hS1cMC) myoblasts were lipofected with (A) IVT RNA or (B) replicon RNA coding GFP, together with IVT RNA encoding VacV protein as indicated (refer to table 3 for details). iRFP encoding IVT RNA was cotransfected to all samples to monitor lipofection success (refer to table 3 for details of transfection mixtures); cf. FIG. 17.

TABLE 3

IVT RNA mixes used for transfections with liposomes (RNAiMAX) in examples 9.9 and 9.10. In order to maintain the optimal RNA to RNAiMAX ratio luciferase coding RNA was used to equalize total RNA amounts.

| Sample No. | iRFP [μg] | E3L [μg] | K3L [μg] | B18R [μg] | eGFP [μg] | GFP replicon [μg] | Luciferase [μg] |
|---|---|---|---|---|---|---|---|
| 1 | 0.5 | | | | 0.75 | — | 1.25 |
| 2 | 0.5 | 0.417 | 0.417 | 0.417 | 0.75 | — | — |
| 3 | 0.5 | 1.25 | | | 0.75 | — | — |
| 4 | 0.5 | | 1.25 | | 0.75 | — | — |
| 5 | 0.5 | 0.625 | 0.625 | | 0.75 | — | — |
| 6 | 0.5 | | | 1.25 | 0.75 | — | — |
| 7 | 0.5 | | | | — | 0.75 | 1.25 |
| 8 | 0.5 | 0.417 | 0.417 | 0.417 | — | 0.75 | — |
| 9 | 0.5 | 1.25 | | | — | 0.75 | — |
| 10 | 0.5 | | 1.25 | | — | 0.75 | — |
| 11 | 0.5 | 0.625 | 0.625 | | — | 0.75 | — |
| 12 | 0.5 | | | 1.25 | — | 0.75 | — |

(A) An increase of IVT RNA expression was detected in all cells, GFP was up to 5-fold increased in presence of cotransfected E3L alone or E3L in combination with K3L and B18R. K3L alone was less effective in human CCD1079Sk cells but still increased IVT RNA expression more than 2-fold. B18R alone had no effect.

(B) Replicon expression was boosted in human fibroblasts and human myoblasts by E3 IVT RNA, K3L had little effects. In mouse cells, expression was also increased, but much less than in human cells. The results obtained with CCD1079SK cells were confirmed with other human fibroblasts (HFF and BJ cells).

Overall, results from FIGS. 16 and 17 indicate that VacV protein might help to overcome species barrier between mouse and human cells.

9.10 VacV Proteins Enhances the Expression of Replicon Expression in Mouse Myotubes Mouse C2C12 derived myotubes were lipofected with replicon coding GFP. IVT RNA coding iRFP or VacV proteins were cotransfected as indicated (refer to table 3 for details); cf. FIG. 18.

Compared to GFP replicon alone, VacV proteins increased GFP expression, with the exception of B18R in mature myotubes.

9.11 Excess of VacV IVT RNA does not Further Enhance Replicon Expression

Mouse C2C12 myoblasts were electroporated with 3 μg replicon RNA encoding luciferase. IVT RNA coding VacV proteins was coelectroporated in different w/w ratios as indicated; cf. FIG. 19. In the first group of samples E3, B18R and K3 (EBK) were mixed 1:1:1, in the second group the same amount of E3 than in the first group was coelectroporated, but K3 and B18R were omitted. Luciferase expression was measured 6 h after electroporation and normalized to the expression obtained without VacV proteins (first column; "1:0").

The mixture EBK and E3 alone increased luciferase replicon expression, but there was no benefit of using high excess of EBK or E3 RNA.

9.12 VacV Proteins Reduce Autophosphorylation of PKR and Substrate Phosphorylation Upon Replicon RNA Transfer Human CCD1079SK fibroblasts were coelectroporated with replicon RNA coding GFP, together with IVT RNA encoding iRFP and the indicated VacV protein (see table 2); cf. FIG. 20. Mock electroporated cells served as negative control. IVT RNA only and IVT RNA coelectroporated with EBK RNA served as reference samples to compare IVT RNA mediated PKR activation to replicon mediated PKR activation. An uncapped replicon was used as control to show the contribution of replication to PKR activation.

PKR-phosphorylation provoqued by replicons is much stronger than by IVT RNA. Uncapped replicon RNA leads to a similar strength of PKR autophosphorylation as non-replicating IVT RNA. E3 and K3 reduce PKR autophosphorylation, B18R does not affect PKR phosphorylation.

9.13 VacV Proteins Enable Efficient Replication of Non-Cytotoxic Mutant Replicons Parental and non-cytotoxic PD vectors (Lundstrom et al., 2003, Histochem. Cell Biol.

115, 83-91) were electroporated into human fibroblasts alongside with IVT NA encoding E3, B18R and K3 (EBK) or not; cf. FIG. 21. (A) Luciferase expression was measured at the indicated time points (B) viability of the cells was assessed 24 h after electroporation using XTT viability staining. Viability was normalized to untransfected samples.

(A) The expression of non-cytotoxic PD-vectors is impaired in human fibroblasts unless EBK is added. Addition of EBK induces a slow increase of PD-vectors expression, which reaches after 72 h a level that is comparable to the expression of parental vector after 24 h. (B) In the presence of EBK, transfected cells showed very high viability scores.

9.14 VacV Proteins Enhance Replicon Expression In Vivo

2 μg Replicon RNA encoding luciferase were coinjected with IVT RNA coding E3, K3 and B18R (EBK) in different w/w ratios as indicated (1- to 6-fold as much EKB as replicon RNA) into the tibialis anterior of Balb/C mice; cf. FIG. 22. The RNA was resuspended in PBS.

A 3-fold and 6-fold excess of EBK RNA increases replicon expression in vivo in a dose dependent fashion.

9.15 VacV Proteins Increase the Expression of IVT RNA in the Spleen

10 μg IVT RNA encoding luciferase was copackaged with 30 μg GFP RNA or 30 μg EBK RNA into liposomes that target the spleen. Luciferase expression was monitored over 4 days; cf. FIG. 23.

EBK enhanced the expression over the whole time course.

Example 10

NS34A and ICP34.5 Enhance Replicon Expression

We have shown that the Vaccinia virus proteins E3, B18R and K3 (EBK) increased replicon expression, especially translation of subgenomic transcripts. We tested further IFN inhibitors: Hepathitis C virus NS34A, which counteracts activation of RIG-I and MDA5, Herpes simplex virus ICP34.5, which actively dephosphorylates eIF2a.

Human fibroblasts were cotransfected with 1, 5 μg replicon RNA encoding a luciferase-GFP fusion and 1 μg mRNA encoding interferon inhibitors, or iRFP as a control. The next day, transgene expression was measured by FACS; cf. FIG. 24.

(A) Percentage of transfected cells determined by GFP expression. NS34A increases transfection rates to the same extend as EBK, while ICP34.5 was more potently increasing transfection rates. (B) Same data as in A, expressed as fold increased transfection rates compared to the sample without inhibitors. (C) Change of GFP translation, expressed as mean fluorescence intensity (MFI). NS34A does not increase translation, while ICP34.4 does. This is most likely due to the fact that NS34A does not inhibit PKR.

Example 11

NS34A Inhibits and ICP34.5 Reduces IFN Response to Synthetic mRNA

We have shown that the Vaccinia virus proteins E3, B18R and K3 (EBK) inhibited IFN-response completely, when used as a mixture. E3 alone was able to reduce the IFN-response. Regarding the induction of IFNβ target genes (OAS1/2), we have found that B18R was required, and that E3 or K3 could only partially prevent upregulation. Here, we tested further IFN inhibitors: Hepathitis C virus NS34A, which counteracts activation of RIG-I and MDA5, Herpes simplex virus ICP34.5, which actively dephosphorylates eIF2a. Human fibroblasts were transfected with 5 μg synthetic mRNA mixtures to induce or prevent IFN response. All mixtures contained 2 μg synthetic mRNA encoding infrared fluorescent protein (iRFP) and 3 μg of either IFN inhibitors (as indicated in FIG. 25) or luciferase as a control. The next day, cells were harvested and lysed to extract RNA for qRT-PCR. The induction of IFNβ and OAS1/2 were normalized to the base line expression in untransfected cells; cf. FIG. 25.

(A) Transcriptional induction of IFNβ. Vaccinia virus proteins EKB abrogated IFNβ and E3 reduced IFNβ induction as we have observed before. NS34A also abrogated IFNβ induction similar to EBK, and ICP34.5 reduced IFNβ induction similar to E3. (B, C) Transcriptional induction of IFNβ target genes OAS1/2. EBK blocked OAS1/2 induction, while E3 alone could only partially prevent OAS1/2 upregulation. This was observed before. Similar to E3, ICP34.5 cannot prevent OAS1/2 induction, but NS34A greatly reduced the induction of both markers.

Thus, NS34A is a potent IFN inhibitor, and ICP34.5 a potent PKR inhibitor when encoded on synthetic mRNA. Both are able to enhance replicon or synthetic mRNA gene transfer and expression.

Example 12

Minimal Lipofection Required for Generation of Ribo-iPS

High efficiency of the reprogramming protocol with unmodified IVT-RNA in combination with unmodified EKB and a miRNA-mixture of mature miRNAs from the cluster 302/367 lead to the question, how many daily lipofections are minimally needed for successful reprogramming.

HFF fibroblasts (System Bioscience) were plated into 6 wells (100,000 cells/well) and lipofected 1 to 6 times as depictured in the scheme using 6 μl RNAiMAX (Invitrogen) and 1.4 μg IVT-RNA; cf. FIG. 26 (A). The IVT-RNA mixtures were thereby composed of 0.8 μg unmodified OSKMNL (1:1:1:1:1:1) with 0.2 μg of each B18R, E3 and K3 (EKB) and 0.4 μg of a miRNA mixture composed of miRNAs 302a-d and 367 [0.4 μM each]. Lipofections in stem cell media (Nutristem media, Stemgent) were performed according to the manufacturer's instructions. From day 9 on, colony formation was observed and representative pictures were taken on d11 by microscopy (B). For further analysis, colonies were stained for the ES surface marker TRA-1-60 using the StainAlive TRA-1-60 antibody (Stemgent) (C) and cells were pelleted afterwards, total RNA isolated and mRNA-expression of the human ES-marker OCT4 (endogenous), NANOG (endogenous), LIN28 (endogenous), TERT and REX1 was quantified by qRT-PCR (D).

(B) It became obvious that 3 daily transfections were required to get a few colonies, but 4 daily transfections were sufficient for robust induction of colony formation. The colonies became visible from d9 on and were fully grown on d11 where they could be stained positive for TRA-1-60 (C). Analysis of the expression levels of several pluripotency markers revealed that consistent with colony formation, induction of ES-marker genes can be achieved with 3 or more lipofections. Nevertheless, robust induction of ES-marker expression was achieved with 4 or more lipofections. It should be mentioned that the expression of ES-marker genes was not further enhanced by more than four lipofections (D).

The reprogramming protocol using unmodified IVT-RNA in combination with unmodified EKB and a miRNA-mixture of mature miRNAs from the cluster 302/367 can be shortened to four daily lipofections leading to a robust induction of Ribo-iPS generation with high inductions of human ES-marker genes and the ES surface marker TRA-1-60. The minimal amount of daily lipofections required for the formation of Ribo-iPS colonies could be determined to 3.

The invention claimed is:

1. A method for providing cells having stem cell characteristics comprising the steps of (i) providing a cell population comprising somatic cells, (ii) preventing engagement of IFN receptor of the somatic cells by extracellular IFN by providing vaccinia virus B18R to the somatic cells in the form of first RNA encoding vaccinia virus B18R, (iii) inhibiting intracellular IFN signaling in the somatic cells by providing vaccinia virus E3 to the somatic cells in the form of second RNA encoding vaccinia virus E3 and by providing vaccinia virus K3 to the somatic cells in the form of third RNA encoding vaccinia virus K3, (iv) providing to the somatic cells further RNA capable of expressing one or more factors allowing the reprogramming of the somatic cells into cells having stem cell characteristics, and (v) allowing the development of cells having stem cell characteristics, wherein the ribonucleotides of the first, second, and third RNAs are simultaneously introduced into the somatic cells and wherein the further RNA comprises naturally occurring nucleotides.

2. The method of claim 1, wherein the one or more factors comprise OCT4 and SOX2.

3. The method of claim 2, wherein the one or more factors further comprise KLF4 and/or c-MYC.

4. The method of claim 3, wherein the one or more factors further comprise NANOG and/or LIN28.

5. The method of claim 1, wherein the one or more factors comprise OCT4, SOX2, KLF4 and c-MYC.

6. The method of claim 4, wherein the one or more factors further comprise LIN28 and optionally NANOG.

7. The method of claim 1, wherein the one or more factors comprise OCT4, SOX2, NANOG and LIN28.

8. The method of claim 1, further comprising the step of culturing the somatic cells in the presence of at least one histone deacetylase inhibitor.

9. The method of claim 8, wherein the at least one histone deacetylase inhibitor comprises valproic acid.

10. The method of claim 1, wherein step (v) comprises culturing the somatic cells under embryonic stem cell culture conditions.

11. The method of claim 1, wherein the stem cell characteristics comprise an embryonic stem cell morphology.

12. The method of claim 1, wherein the cells having stem cell characteristics have normal karyotypes, express telomerase activity, express cell surface markers that are characteristic for embryonic stem cells and/or express genes that are characteristic for embryonic stem cells.

13. The method of claim 1, wherein the cells having stem cell characteristics exhibit a pluripotent state.

14. The method of claim 1, wherein the cells having stem cell characteristics have the developmental potential to differentiate into advanced derivatives of all three primary germ layers.

15. The method of claim 1, wherein the somatic cells are fibroblasts.

16. The method of claim 15, wherein the fibroblasts are lung fibroblasts, foreskin fibroblasts or dermal fibroblasts.

17. The method of claim 1, wherein the somatic cells are human cells.

18. The method of claim 1, wherein the first, second, third and/or further RNA comprises a 5'CAP.

19. The method of claim 1, wherein the RNA capable of expressing one or more factors is repetitively introduced into the cells.

* * * * *